(12) United States Patent
Zhou et al.

(10) Patent No.: US 9,790,537 B2
(45) Date of Patent: Oct. 17, 2017

(54) QUINONE-MASKED PROBES AS LABELING REAGENTS FOR CELL UPTAKE MEASUREMENTS

(71) Applicant: PROMEGA CORPORATION, Madison, WI (US)

(72) Inventors: Wenhui Zhou, San Luis Obispo, CA (US); Poncho Meisenheimer, San Luis Obispo, CA (US); Sarah Duellman, Fitchburg, WI (US); Dongping Ma, Madison, WI (US); James J. Cali, Verona, WI (US); Dana Mustafa, San Luis Obispo, CA (US)

(73) Assignee: Promega Corporation, Madison, WI (US)

( * ) Notice: Subject to any disclaimer, the term of this patent is extended or adjusted under 35 U.S.C. 154(b) by 68 days.

(21) Appl. No.: 14/609,372

(22) Filed: Jan. 29, 2015

(65) Prior Publication Data

US 2015/0307916 A1    Oct. 29, 2015

Related U.S. Application Data

(60) Provisional application No. 61/933,122, filed on Jan. 29, 2014.

(51) Int. Cl.
| | |
|---|---|
| *A61K 31/58* | (2006.01) |
| *A01N 43/58* | (2006.01) |
| *A01N 43/60* | (2006.01) |
| *A61K 31/50* | (2006.01) |
| *A61K 31/495* | (2006.01) |
| *A01N 43/54* | (2006.01) |
| *A61K 31/505* | (2006.01) |
| *A01N 43/78* | (2006.01) |
| *A61K 31/425* | (2006.01) |
| *C07J 43/00* | (2006.01) |
| *C07D 239/02* | (2006.01) |
| *C07D 471/00* | (2006.01) |
| *C07D 487/00* | (2006.01) |
| *C07D 277/82* | (2006.01) |
| *C07D 277/62* | (2006.01) |
| *C07D 277/68* | (2006.01) |
| *C12Q 1/66* | (2006.01) |
| *C07D 417/04* | (2006.01) |
| *C07D 417/12* | (2006.01) |
| *C07D 417/14* | (2006.01) |
| *C07D 487/04* | (2006.01) |
| *C07D 493/10* | (2006.01) |
| *G01N 33/58* | (2006.01) |
| *C07K 7/06* | (2006.01) |
| *C07K 16/28* | (2006.01) |
| *C07K 16/40* | (2006.01) |
| *G01N 33/533* | (2006.01) |
| *C07J 41/00* | (2006.01) |

(52) U.S. Cl.
CPC ............. *C12Q 1/66* (2013.01); *C07D 417/04* (2013.01); *C07D 417/12* (2013.01); *C07D 417/14* (2013.01); *C07D 487/04* (2013.01); *C07D 493/10* (2013.01); *C07J 43/003* (2013.01); *C07K 7/06* (2013.01); *C07K 16/2863* (2013.01); *C07K 16/40* (2013.01); *G01N 33/533* (2013.01); *G01N 33/582* (2013.01); *C07J 41/0088* (2013.01); *G01N 2333/90241* (2013.01)

(58) Field of Classification Search
None
See application file for complete search history.

(56) References Cited

U.S. PATENT DOCUMENTS

| | | | |
|---|---|---|---|
| 4,612,302 A | 9/1986 | Szabo et al. | |
| 4,655,022 A | 4/1987 | Natori | |
| 4,665,022 A | 5/1987 | Schaeffer et al. | |
| 4,684,620 A | 8/1987 | Hruby et al. | |
| 4,826,989 A | 5/1989 | Batz et al. | |
| 4,853,371 A | 8/1989 | Coy et al. | |
| 4,992,531 A | 2/1991 | Patroni et al. | |
| 5,035,999 A | 7/1991 | Geiger et al. | |
| 5,098,828 A | 3/1992 | Geiger et al. | |
| 5,114,704 A | 5/1992 | Spanier et al. | |
| 5,283,179 A | 2/1994 | Wood | |
| 5,283,180 A | 2/1994 | Zomer et al. | |
| 5,290,684 A | 3/1994 | Kelly | |
| 5,374,534 A | 12/1994 | Zomer et al. | |
| 5,498,523 A | 3/1996 | Tabor et al. | |
| 5,641,641 A | 6/1997 | Wood | |
| 5,650,135 A | 7/1997 | Contag et al. | |
| 5,650,289 A | 7/1997 | Wood | |

(Continued)

FOREIGN PATENT DOCUMENTS

| | | |
|---|---|---|
| CN | 1705680 | 12/2005 |
| CN | 101287842 | 10/2008 |

(Continued)

OTHER PUBLICATIONS

Huang, et. al., Biosensors & Bioelectronics (2008), 23(12), 1793-1798.*

(Continued)

*Primary Examiner* — Jeffrey H Murray

(74) *Attorney, Agent, or Firm* — Michael Best & Friedrich LLP

(57) ABSTRACT

Provided are labeling reagents and methods of using the reagents for cell uptake measurements. The labeling reagents can be quinone-masked probes including fluorophores and/or luminophores.

31 Claims, 17 Drawing Sheets

(56) References Cited

U.S. PATENT DOCUMENTS

| | | | |
|---|---|---|---|
| 5,670,356 A | 9/1997 | Sherf et al. | |
| 5,683,888 A | 11/1997 | Campbell | |
| 5,726,041 A | 3/1998 | Chrespi et al. | |
| 5,744,320 A | 4/1998 | Sherf et al. | |
| 5,756,303 A | 5/1998 | Sato et al. | |
| 5,780,287 A | 7/1998 | Kraus et al. | |
| 5,814,471 A | 9/1998 | Wood | |
| 5,837,465 A | 11/1998 | Squirrell et al. | |
| 5,876,946 A | 3/1999 | Burbaum et al. | |
| 5,976,825 A | 11/1999 | Hochman | |
| 5,998,204 A | 12/1999 | Tsien et al. | |
| 6,132,983 A | 10/2000 | Lowe et al. | |
| 6,143,492 A | 11/2000 | Makings et al. | |
| 6,171,808 B1 | 1/2001 | Squirrell et al. | |
| 6,217,847 B1 | 4/2001 | Contag et al. | |
| 6,265,177 B1 | 7/2001 | Squirrell et al. | |
| 6,291,164 B1 | 9/2001 | Blakesley | |
| 6,299,858 B1 | 10/2001 | Serbedzija et al. | |
| 6,376,208 B1 | 4/2002 | Kajiyama | |
| 6,387,675 B1 | 5/2002 | Wood et al. | |
| 6,420,130 B1 | 7/2002 | Makings et al. | |
| 6,514,687 B1 | 2/2003 | Makings et al. | |
| 6,544,754 B2 | 4/2003 | Inouye | |
| 6,552,179 B1 | 4/2003 | Wood et al. | |
| 6,602,677 B1 | 8/2003 | Wood et al. | |
| 6,638,713 B2 | 10/2003 | Makings et al. | |
| 7,078,181 B2 | 7/2006 | Hawkins et al. | |
| 7,108,996 B2 | 9/2006 | Hawkins et al. | |
| 7,118,878 B1 | 10/2006 | Hawkins | |
| 7,125,697 B2 | 10/2006 | Inouye | |
| 7,238,842 B2 | 7/2007 | Wood et al. | |
| 7,241,584 B2 | 7/2007 | Wood et al. | |
| 7,268,229 B2 | 9/2007 | Wood et al. | |
| 7,378,255 B2 | 5/2008 | Horn et al. | |
| 7,416,854 B2 | 8/2008 | Riss et al. | |
| 7,425,436 B2 | 9/2008 | Darzins et al. | |
| 7,429,472 B2 | 9/2008 | Darzins et al. | |
| 7,524,876 B2 | 4/2009 | Takakura et al. | |
| 7,537,912 B2 | 5/2009 | Wood et al. | |
| 7,553,632 B2 | 6/2009 | Niles et al. | |
| 7,692,002 B2 | 4/2010 | Alberto et al. | |
| 7,692,022 B2 | 4/2010 | Cali et al. | |
| 7,728,118 B2 | 6/2010 | Wood et al. | |
| 7,741,067 B2 | 6/2010 | Hawkins et al. | |
| 7,807,402 B2 | 10/2010 | Horn et al. | |
| 7,867,726 B2 | 1/2011 | Wood et al. | |
| 7,879,540 B1 | 2/2011 | Wood et al. | |
| 7,888,086 B2 | 2/2011 | Darzins et al. | |
| 7,906,282 B2 | 3/2011 | Wood et al. | |
| 7,906,298 B1 | 3/2011 | Squirrell et al. | |
| 7,935,803 B2 | 5/2011 | Darzins et al. | |
| 7,951,550 B2 | 5/2011 | Cali et al. | |
| 8,008,006 B2 | 8/2011 | Wood et al. | |
| 8,030,017 B2 | 10/2011 | Wood et al. | |
| RE42,931 E | 11/2011 | Wood et al. | |
| 8,106,052 B2 | 1/2012 | Wood et al. | |
| 8,168,405 B2 | 5/2012 | Darzins et al. | |
| 8,183,007 B2 | 5/2012 | Zegzouti et al. | |
| 8,183,036 B2 | 5/2012 | Fan et al. | |
| 8,202,700 B2 | 6/2012 | Darzins et al. | |
| 8,476,450 B2 | 7/2013 | Cali et al. | |
| 8,557,970 B2 | 10/2013 | Encell et al. | |
| 8,765,969 B2 | 7/2014 | Cali et al. | |
| 8,809,529 B2 | 8/2014 | Klaubert et al. | |
| 9,273,343 B2 * | 3/2016 | Cali | C07D 417/04 |
| 2002/0076777 A1 | 6/2002 | Merkulov et al. | |
| 2003/0068801 A1 | 4/2003 | Wood et al. | |
| 2003/0153090 A1 | 8/2003 | Wood et al. | |
| 2003/0166905 A1 | 9/2003 | Wood et al. | |
| 2003/0211560 A1 | 11/2003 | O'Brien et al. | |
| 2003/0225036 A1 | 12/2003 | Kolesnikov et al. | |
| 2003/0232404 A1 | 12/2003 | Wood et al. | |
| 2003/0237103 A1 | 12/2003 | Jacob et al. | |
| 2004/0002127 A1 | 1/2004 | Inoue et al. | |
| 2004/0096924 A1 | 5/2004 | Hawkins et al. | |
| 2004/0096927 A1 | 5/2004 | Chittock et al. | |
| 2004/0146959 A1 | 7/2004 | Graham et al. | |
| 2004/0171099 A1 | 9/2004 | Cali et al. | |
| 2004/0178545 A1 | 9/2004 | Cates | |
| 2004/0214258 A1 | 10/2004 | Wood et al. | |
| 2004/0224377 A1 | 11/2004 | Hawkins et al. | |
| 2004/0248225 A1 | 12/2004 | Heindl et al. | |
| 2005/0004103 A1 | 1/2005 | Koshio et al. | |
| 2005/0009098 A1 | 1/2005 | Reymonds et al. | |
| 2005/0026171 A1 | 2/2005 | Hawkins et al. | |
| 2005/0118257 A1 | 6/2005 | Bova | |
| 2005/0153306 A1 | 7/2005 | Harris | |
| 2005/0153310 A1 | 7/2005 | Fan et al. | |
| 2005/0164321 A1 | 7/2005 | Riss et al. | |
| 2005/0272114 A1 | 12/2005 | Darzins et al. | |
| 2006/0024808 A1 | 2/2006 | Darzins et al. | |
| 2006/0051827 A1 | 3/2006 | Hawkins et al. | |
| 2006/0068395 A1 | 3/2006 | Wood et al. | |
| 2006/0127988 A1 | 6/2006 | Wood et al. | |
| 2006/0183212 A1 | 8/2006 | Wood et al. | |
| 2007/0015790 A1 | 1/2007 | Cali et al. | |
| 2007/0087400 A1 | 4/2007 | Darzins et al. | |
| 2007/0155806 A1 | 7/2007 | Takakura et al. | |
| 2008/0026407 A1 | 1/2008 | Wood et al. | |
| 2008/0050760 A1 | 2/2008 | Wood et al. | |
| 2008/0070299 A1 | 3/2008 | Wood et al. | |
| 2008/0090291 A1 | 4/2008 | Wood et al. | |
| 2008/0145882 A1 | 6/2008 | Darzins et al. | |
| 2008/0194522 A1 | 8/2008 | Chen et al. | |
| 2008/0248511 A1 | 10/2008 | Daily et al. | |
| 2008/0268482 A1 | 10/2008 | Riss et al. | |
| 2008/0274488 A1 | 11/2008 | Darzins et al. | |
| 2009/0017482 A1 | 1/2009 | Riss et al. | |
| 2009/0098627 A1 | 4/2009 | Darzins et al. | |
| 2009/0137019 A1 | 5/2009 | Wood et al. | |
| 2009/0253131 A1 | 10/2009 | Wigdal et al. | |
| 2009/0275051 A1 | 11/2009 | Niles et al. | |
| 2009/0305280 A1 | 12/2009 | Binkowski et al. | |
| 2009/0311769 A1 | 12/2009 | Wood et al. | |
| 2010/0047839 A1 | 2/2010 | Huang et al. | |
| 2010/0062470 A1 | 3/2010 | Corona et al. | |
| 2010/0075350 A1 | 3/2010 | Zegzouti et al. | |
| 2010/0273186 A1 | 10/2010 | Wood et al. | |
| 2010/0281552 A1 | 11/2010 | Encell | |
| 2011/0003316 A1 | 1/2011 | Cali et al. | |
| 2011/0039257 A1 | 2/2011 | Binkowski et al. | |
| 2011/0081670 A1 | 4/2011 | Hawkins et al. | |
| 2011/0171673 A1 | 7/2011 | Darzins et al. | |
| 2011/0177540 A1 | 7/2011 | Squirrell et al. | |
| 2011/0201024 A1 | 8/2011 | Wood et al. | |
| 2011/0207195 A1 | 8/2011 | Darzins et al. | |
| 2011/0283373 A1 | 11/2011 | Binkowski et al. | |
| 2012/0058505 A1 | 3/2012 | Helms et al. | |
| 2012/0064554 A1 | 3/2012 | Kirkland et al. | |
| 2012/0107849 A1 | 5/2012 | Klaubert et al. | |
| 2012/0117667 A1 | 5/2012 | Klaubert et al. | |
| 2012/0174242 A1 | 7/2012 | Binkowski et al. | |
| 2013/0130289 A1 | 5/2013 | Benink et al. | |
| 2014/0093894 A1 | 4/2014 | Benink et al. | |
| 2014/0154716 A1 | 6/2014 | Cali et al. | |
| 2014/0380514 A1 | 12/2014 | Cali et al. | |
| 2015/0064731 A1 | 3/2015 | Klaubert et al. | |
| 2015/0212078 A1 | 7/2015 | Zhou et al. | |

FOREIGN PATENT DOCUMENTS

| | | | |
|---|---|---|---|
| CN | 102459579 | | 5/2012 |
| EP | 134108 | | 3/1985 |
| EP | 0411912 | | 2/1991 |
| EP | 0751996 | | 1/2003 |
| EP | 1281762 | A2 | 2/2003 |
| EP | 1131441 | B1 | 11/2005 |
| EP | 1630231 | A2 | 3/2006 |
| EP | 1588143 | A4 | 2/2007 |
| EP | 1894933 | A2 | 3/2008 |
| EP | 689587 | B1 | 4/2008 |
| EP | 1935980 | A1 | 6/2008 |
| EP | 1935986 | | 6/2008 |
| EP | 1451155 | B1 | 7/2008 |

(56) References Cited

FOREIGN PATENT DOCUMENTS

| EP | 1978091 A1 | 10/2008 |
|---|---|---|
| EP | 1978092 A1 | 10/2008 |
| EP | 1124944 | 12/2008 |
| EP | 1479763 | 12/2008 |
| EP | 2071023 A2 | 6/2009 |
| EP | 2071023 A8 | 6/2010 |
| EP | 1297337 | 1/2011 |
| EP | 2272972 | 1/2011 |
| EP | 2277872 | 1/2011 |
| EP | 2284271 A2 | 2/2011 |
| EP | 2298902 A1 | 3/2011 |
| EP | 2308978 A1 | 4/2011 |
| EP | 2325328 A1 | 5/2011 |
| EP | 2325329 A1 | 5/2011 |
| EP | 1546162 B1 | 6/2011 |
| EP | 2327768 A2 | 6/2011 |
| EP | 2341134 A2 | 7/2011 |
| EP | 2366777 A1 | 9/2011 |
| EP | 2366778 A1 | 9/2011 |
| EP | 2366779 A1 | 9/2011 |
| EP | 2366780 A1 | 9/2011 |
| EP | 2368976 A1 | 9/2011 |
| EP | 2368977 A1 | 9/2011 |
| EP | 2369006 A1 | 9/2011 |
| EP | 2374875 A2 | 10/2011 |
| EP | 2395078 A2 | 12/2011 |
| EP | 2395358 A2 | 12/2011 |
| EP | 2272973 | 1/2012 |
| EP | 2281046 B1 | 1/2012 |
| JP | 63-501571 | 6/1988 |
| JP | 01-502431 | 8/1989 |
| JP | 08-059686 | 3/1996 |
| JP | H08-294397 | 11/1996 |
| JP | 2000-505086 | 4/2000 |
| JP | 2000-270894 | 10/2000 |
| JP | 2002080476 | 3/2002 |
| JP | 2006219381 | 8/2006 |
| RU | 2242471 | 12/2004 |
| WO | WO 87/02667 | 5/1987 |
| WO | WO 88/05434 | 7/1988 |
| WO | WO 95/18853 | 7/1995 |
| WO | WO 95/25798 | 9/1995 |
| WO | WO 96/07100 | 3/1996 |
| WO | WO 96/22376 | 7/1996 |
| WO | WO 96/31206 | 10/1996 |
| WO | WO 97/36885 | 10/1997 |
| WO | WO 98/46739 | 10/1998 |
| WO | WO 99/14336 | 3/1999 |
| WO | WO 99/60096 | 11/1999 |
| WO | WO 00/16763 | 3/2000 |
| WO | WO 00/34506 | 6/2000 |
| WO | WO 00/35900 | 6/2000 |
| WO | WO 01/20002 | 3/2001 |
| WO | WO 01/31028 | 5/2001 |
| WO | WO 01/96862 | 12/2001 |
| WO | WO 03/040100 | 5/2003 |
| WO | WO 03/066611 | 8/2003 |
| WO | WO 03/096980 | 11/2003 |
| WO | WO 2004/027378 | 4/2004 |
| WO | WO 2004/059294 | 7/2004 |
| WO | WO 2004/072232 | 8/2004 |
| WO | WO 2004/072299 | 8/2004 |
| WO | WO 2005/038029 | 4/2005 |
| WO | WO 2005/073722 | 8/2005 |
| WO | WO 2006/034061 | 3/2006 |
| WO | WO 2006/093529 | 9/2006 |
| WO | WO 2006/130551 | 12/2006 |
| WO | WO 2007/120522 | 10/2007 |
| WO | WO 2008/054821 | 5/2008 |
| WO | WO 2008/086035 | 7/2008 |
| WO | WO 2008/118445 A1 | 10/2008 |
| WO | WO 2008/118445 A9 | 12/2008 |
| WO | WO 2009/061413 | 5/2009 |
| WO | WO 2009/142735 | 11/2009 |
| WO | WO 2010/011607 | 1/2010 |
| WO | WO 2010/021686 | 2/2010 |
| WO | WO 2010/127368 | 11/2010 |
| WO | WO 2011/038219 | 3/2011 |
| WO | WO 2011/143339 | 11/2011 |
| WO | WO 2012/030960 | 3/2012 |
| WO | WO 2012/061477 | 5/2012 |
| WO | WO 2012/061529 | 5/2012 |
| WO | WO 2012/061530 | 9/2012 |
| WO | WO 2013/033515 | 3/2013 |
| WO | WO 2014/052653 | 4/2014 |

OTHER PUBLICATIONS

"5' Labeling—fluorescein and cyanine dyes, biotin," Glen Report, http://www.glenres.com/GlenReports/GR8-2.pdf (Published online by Glen Research, Sterling, VA), (Dec. 1995) 8(2):8 pages.

"Amplex Red monoamine oxidase assay kit (A12214)," Molcular Probes (Oct. 1, 2004) 4 pages, retrieved from the Internet: http://probes.invitrogen.com/media/pis/mp12214.pdf.

Abyshev, A.Z. et al., "Preparation and antiviral effect of benzopyran-2-one derivatives," Khimiko-Farmatsevticheskii Zhurnal (1996) 30(7):17-19; Database CA Accession No. 125:237748.

Allen, T. et al., "Cloning and expression fo the adenine phophoribosyltransferase gene from Leishmania donovani," Mol. Biochem. Parasitology (1995) 74:99-103.

Amess, R. et al., "Synthesis of luciferin glycosides as substrates for novel ultrasensitive enzyme assays," Carbohydrate Research (1990) 205:225-233.

Angelucci, F. et al., "Schistosoma mansoni fatty acid binding protein: specificity and functional control as revealed by crystallographic structure," Biochem. (2004) 43:13000-13011.

Aparna, M.V.L. et al., "Synthesis and 5-HT2A antagonist activity of some 7-(3-aminopropoxy)-4-methyl-chromen-2-ones," Indian J. Pharm. Sci. (2005) 67(4):467-472; Database CA Accession No. 145:62752.

Arnold, K. et al., "The Swiss-Model workspace: a web-based environment for protein structure homology modelling," Bioinformatics (2006) 22(2):195-201.

Banaszynski et al., "Characterization of the FKBP-Rapamycin-FRB Ternary Complex" J. Am. Chem. Soc, 127(13):4715-4721(2005).

Becker, M.M. et al., "Gene cloning, overproduction and purification of a functionally active cytoplasmic fatty acid-binding protein (Sj-FABPc) from the human blood fluke Schistosoma japonicum," Gene (1994) 148:321-325.

Beilstein Registry No. 1007132, Database Crossfire Beilstein, White, E.H. et al., J. Org. Chem. (1966) 31:1484-1488 (2 pages).

Beilstein Registry No. 1034055, Database Crossfire Beilstein, (McCapra, F. et al., Chem. Commun., 1968) 22-23, 1 page).

Beilstein Registry No. 1041968, Database Crossfire Beilstein, White et al., Bioorg. Chem. (1971) 1:92-116 (2 pages).

Beilstein Registry No. 1119094, Database Crossfire Beilstein, Benkoe, et al., Montsh. Chem. (1975) 106:1027-1032 (3 pages).

Beilstein Registry No. 1119095, Database Crossfire Beilstein, Benkoe, A. et al., Monatsh. Chem. (1975) 106:1027-1032 (2 pages).

Beilstein Registry No. 1126922, Databsase Crossfire Beilstein, Benkoe et al., Monatsh. Chem. (1975) 106:1027-1032 (3 pages).

Beilstein Registry No. 1129927, Database Crossfire Beilstein, Benkoe et al., Monatsh. Chem. (1975) 106:1027-1032 ( 2 pages).

Beilstein Registry No. 30484, Database Crossfire Beilstein, White et al., J. Am. Chem. Soc. (1963) 85:337-343 (12 pages).

Beilstein Registry No. 3984932, Database Crossfire Beilstein, White et al., J. Org. Chem. (1965) 30:2344-2348 (2 pages).

Beilstein Registry No. 4240164, Database Crossfire Beilstein, Arness, R. et al., Cathohydr. Res. (1990) 1(1):225-233 (2 pages).

Beilstein Registry No. 926292, Database Crossfire Beilstein, White et al., J. Org. Chem. (1965) 30:2344-2348 (2 pages).

Benet, L.Z. et al., "Pharmacokinetics the Dynamics of drug absorption, distribution and elimination," Introduction and Chapter 1 of the Pharmacological Basis of Therapeutics, 9th Edition, McGraw Hill (1996) 1-27 (was previously listed as: Hardman, J.g. et al., eds. The Pharmacological Basis of Therapeutics, 9th Edition, mcGraw-Hill (1996) 1-27).

(56) References Cited

OTHER PUBLICATIONS

Benezra et al., "The Protein Id: A Negative Regulator of Helix-Loop-Helix DNA Binding Proteins" Cell, 61(1):49-59(1990).
Ben-Shlomo, Y. et al., "Using monoamine oxidase Type B inhibitors in Parkinson's disease," BMJ (2004) 329:581-582.
Berge et al., "Pharmaceutical Salts" J. Pharm. Sci., 66:1-19 (1977).
Binda, C. et al., "Structure-function relationships in flavoenzyme-dependent amine oxidations—a comparison of polyamine oxidase and monoamine oxidase," J. Biol. Chem. (2002) 277(27):23973-23976.
Black, S.D. et al., "P-450 cytochromes: structure and function," Adv. Enzymol. Relat. Areas Mol. Biol. (1987) 60:35-87.
Bowie, L.J. et al., "Synthesis of a new substrate analog of firefly luciferin," Biochemistry (1973) 12(10):1845-1852.
Branchini, B.R., "Naphtyl- and quinolylluciferin: green and red light emitting firefly luciferin analogues," Photochem. Photobiol. (1989) 49(5):689-695.
Burbelo et al., "Antibody-profiling technologies for studying humoral responses to infectious agents" Expert Review of Vaccines 9(6):567-578(2010).
Cali et al., "Characterization of Human Sterol 27-Hydroxylase. A Mitochondrial Cytochrome P-450 That Catalyzes Multiple Oxidation Reactions in Bile Acid Biosynthesis," J. Biol. Chem., 266:12, 7774-7778 (1991).
Cali et al., "Screen for Cytochrome P450 Activity Using a Luminescent Assay," Cell Notes, 13 (2005) pp. 8-10.
Cali, "Bioluminescent P450 assays that use D-luciferin derivatives as substrates for CYPIAI. JA2. JBI, 2C8, 2C9, 2J2, 3A4, 3A7, 4AJ I, 4F3B. 4F1 2 and 19," Proc. 14th Int. Conf Cytochromes P450, Medimond Int. Proc. (2005).
Cali, "Screen for CYP450 Inhibitors Using P450-Glo™ Luminescent Cytochrome P450 Assays," Cell Notes.7: 2-4 (2003).
Carlile, D.J. et al., "In vivo clearrance of ethoxycoumarin and its prediction from in vitro systems," Drug Metabolism and Disposition (1998) 26(3):216-221.
Chandran et al., "Latent Fluorophore Based on the Trimethyl Lock," J. Am. Chem. Soc., 127:1652-1653 (2005).
Charng, Y. et al., "Molecular cloning and expression of the gene encoding ADP-glucose phrophosphorylase from the cyanobacterium anabaena sp. strain PCC 7120," Plant Mol. Biol. (1992) 20:37-47.
Chemistry 2131: organic Chemistry for the Life Sciences (3), http://www.mta.ca/~acockshu/c2131elimination.html (Mount Allison University), observed Dec. 17, 2004 (3 pages).
Chen, K. et al., "R1, a novel repressor of the human monoamine oxidase A," J. Biol. Chem. (2005) 280(12):11552-11559.
Chenna et al., "Multiple sequence alignment with the Clustal series of programs" Nucl. Acids Res. 31(13):3497-3500 (2003).
Chothia et al., "The relation between the divergence of sequence and structure in proteins" EMBO J. 5(4):823-826 (1986).
Cowan, S.W. et al., "Crystallographic studies on a family of cellular lipophillic transport proteins," J. Mol. Biol. (1993) 230;1225-1246.
Craig, F.F. et al., "Membrane-permeable luciferin esters for assay of firefly luciferase in live intact cells," Biochem. J. (1991) 276(3):637-641.
Daughtery, P.S. et al., "Quantitative analysis of the effect of the mutation frequency on the affinity maturation of single chain Fv antibodies," Proc. Natl. Acad. Sci. USA (2000) 97(5):2029-2034.
Demir, B. et al., "Platelet monoamine oxidase activity in alcoholism subtypes: relationship to personality traits and executive functions," Alcohol & Alcoholism (2002) 37(6):597-602.
Dennell, R. et al., "Observations on the luminescence of bathypelagic crustacea decapoda of the Bermuda area," Zool. J. Linn. Soc., London (1955) XLII:393-406.
Dukhovich, A. et al., "Time course of luciferyl adenylate synthesis in the firefly luciferase reaction," FEBS Lett. (1996) 395(2-3):188-190.
Ellis et al., "Evidence That Aspartic Acid 301 Is a Critical Substrate-Contact Residue in the Active Site of Cytochrome P450 2D6," J. Biol Chem., 270:49, 29055-29058 (1995).

Eriksson, J. et al., "Method for real time detectino of inorganic pyrophosphatase activity," Anal. Biochem. (2001) 293(1):67-70.
Esteves and Ehrlich 2006. "Invertebrate Intracellular Fatty Acid Binding Proteins." Comparative Biochemistry and Physiology, Part C 142: 262-274.
Farace, C. et al., "Synthesis and characterization of a new substrate of photinus pyralis luciferase: 4-methyl-D-luciferin," J. Clin. Chem. Clin. Biochem. (1990) 28(7):471-474.
Feldmann, R. et al., "Decreased metabolism and viability of mycoplasma hominis induced by monoclonal antibody-mediated agglutination," Infection and Immunity (1992) 60(1):166-174.
Fieser, L., et al., "Fieser and Fieser's Reagents for Organic Synthesis," John Wiley and Sons (1994).
Flickinger, B., "Using metabolism data in early development," Drug. Disc. Dev. (2001) 4():53-56.
Flower, D.R. et al., "A structural signature characteristic of the calycin protein superfamily," Protein Pept. Lett. (1995) 2(2):341-350.
Flower, D.R. et al., "Structure and sequence relationships in the lipocalins and related proteins," Protein Sci. (1993) 2:753-761.
Flower, D.R. et al., "The lipocalin protein family—structure and function," Biochem. J. (1996) 318:1-14.
Flower, D.R. et al., "The lipocalin protein family-structural and sequence overview," Biochimica et Biophysica Acta (2000) 1482:9-24.
Freifelder et al. "Synthesis of Primary 1,2-Diamines by Hydrogenation of alpha-Aminonitriles" Journal of the American Chemical Society, 82(3):696-698(1960).
Fujii, H. et al., "Increase in bioluminescence intensity of firefly luciferase using genetic modification," Anal. Biochem. (2007) 366:131-136.
Gabelova, A. et al., "Mutagenicity of 7H-dibenzo[c,g]carbazole and its tissue specific derivatives in genetically engineered chinese hamster V79 cell lines stably expressing cytochrome P450," Mutation Research (2002) 517:135-145.
Gandelman, O. et al., "Cytoplasmic factors that affect the intensity and stability of bioluminescence from firefly luciferase in living mammalian cells," J. Biolum. Chemilumin (1994) 9(6):363-371.
Garrido-Hernandez, H. et al., "Design and synthesis of phosphotyrosine peptidomimetic prodrugs," J. Med. Chem. (2006) 49:3368-3376.
Geiger, R. et al., "A new ultrasensitive bioluminogenic enzyme substrate for beta-galactosidase," Biol. Chem. Hoppe-Seyler (1992) 373:1187-1191.
GenBank 1VPR (2009).
GenBank 2021262A (1992).
GenBank AAA68491 (1995).
GenBank AAC36472 (1998).
GenBank AAL40676 (2005).
GenBank AAL40677 (2005).
GenBank AAV35377 (2004).
GenBank AAV35378 (2004).
GenBank AAV35379 (2004).
GenBank AAV35380 (2004).
GenBank AAV35381 (2004).
Gomez-Lechon, M. et al., "Expression and induction of a large set of drug-metabolizing enzymes by the highly differentiated human hepatoma cell line BC2," Eur. J. Biochem. (2001) 268:1448-1459.
Goto, Pure and Applied Chemistry (1968), 17(3-4), pp. 421-441.
Graham-Lorence, S. et al., "P450s: structural similarities and functional differences," FASEB J. (1996) 10:206-214.
Green, T et al., "Protective Groups in Organic Synthesis" Third Edition (1999).
Greenwald et al., "Controlled Release of Proteins from Their Poly(Ethylene Glycol) Conjugates: Drug Delivery Systems Employing 1,6-Elimination," Bioconjugate Chem., 14:395-403 (2003).
Greenwald et al., "Drug Delivery Systems Employing 1,4- or 1,6-Elimination: Poly(ethylene glycol) Prodrugs of Amine-Containing Compounds," J. Med. Chem., 42:3657-3667 (1999).
Gross et al., "Real-time imaging of ligand-induced IKK activation in intact cells and in living mice" Nature Methods 2(8):607-614 (2005).

(56) References Cited

OTHER PUBLICATIONS

Guengerich, F.P., "Common and uncommon cytochrome P-450 reactions related to metabolism and chemical toxicity," Chem. Res. Tox. (2001) 14(6):611-650.
Gunasekaran et al. 2004. "Sequence and Structural Analysis of Cellular Retinoic Acid-Binding Proteins Reveals a Network of Conserved Hydrophobic Interactions." Proteins 54: 179-194.
Gutierrez, M.C. et al., "The first fluorogenic assay for detecting a baeyer-villigerase activity in microbial cells," Org. Biomol. Chem. (2003) 1:3500-3506.
Hagedorn et al., "Darstellung von a.&ungesattigten Isonitrilen, &Keto- und &Chlor-isonitrilen. Synthese des Xanthocillin-dimethylathers" Chem. Ber., 98:193(1965).
Hawkins, E.M. et al., "Coelenterazine derivatives for improved sollution stability," Luminesence, Proceedings of the International Symposium on Bioluminescence and Chemiluminescence, (2002) 17:91-92 (Abstract only).
Hawkins, et al., "Bright Light, No Lysis," Promega, 2005, pp. 10-14.
Head, J.F. et al., "The crystal structure of the photoprotein aequorin at 2.3A resolution," Nature (2000) 405:372-376.
Herring, P.J. et al., "Bioluminescence in crustacea," J. Crust. Biol. (1985) 5(4):557-573.
Herring, P.J. et al., "The spectral characteristics of luminous marine organisms," Proc. Royal Society London Series B. Biological Sciences (1983) 220(1219):183-217.
Herring, P.J., "Bioluminescence in decapod crustacea," J. Mar. Biol. Assoc. UK (1976) 156:1029-1047.
Holt, A., "Imidazoline binding sites on receptors and enzymes: emerging targets for novel antidepressant drugs?" J. Psychiatry Neurosci. (2003) 28(6):409-414.
Huang, S., et al., "Synthesis of a new long-wavelength latent fluorimetric indicator for analytes determination in the DT-Diaphorase coupling dehydrogenase assay system," Bionsensors & Bioelectronics, 2008, 23(12), pp. 1793-1798.
Huffman, et al., "Lithium Alkoxides of Cinchona Alkaloids as Chiral Controllers for Enantioselective Acetylide Addition to Cyclic N-Acyl Ketimines," J. Org. Chem. 1995, 60, 1590-1594.
Hynson, R.M.G. et al., "Conformational changes in monoamine oxidase A in response to ligand binding or reduction," Biochimica et Biophysica Acta (2004) 1672:60-66.
Inoue et al. "Squid bioluminescence. II. Isolation from Watasenia scintillans and synthesis of 2-(p-hydroxybenzyl)-6-(p-hydroxyphenyl)-3,7-dihydroimidazo [1,2-a]pyrazin-3-one" Chem. Lett., 4(2):141-144 (1975).
Inoue et al. Chemical studies of myctophina fish bioluminescence, Chemistry Letters (1987), (2), 417-18.
Inoue, S. et al., "Complete structure of renilla luciferin and luciferyl sulfate," Tetra. Lett (1977) 31:2685-2688.
Inouye, S. et al., "Overexpression, purification and characterization of the catalytic component of oplophorus luciferase in the deep sea shrimp," Protein Exp. Purification (2007) 56(2):261-268.
Inouye, S. et al., "Secretional luciferase of the luminous shrimp oplophorus gracilirostris: cDNA cloning of a novel imidazopyrazinone luciferase," FEBS Letts. (2000) 481:19-25.
Inouye, S. et al., "The use of renilla luciferase, oplophorus luciferase, and apoaequorin as biolumiscent reporter rpotein in the presence of coelenterazine analogues as substrate," Biochem. Biophys. Res. Comm. (1997) 233:349-353.
International Union of Pure and Applied Chemistry "Definitive Rules for Nomenlature of Organic Chemistry" J. Am. Chem. Soc. 1960, 82, 5545-5574.
International Union of Pure and Applied Chemistry, "Definitive Rules for Nomenclature of Organic Chemistry," J. Am. Chem. Soc. 1960, 82, 5566.
Jagadeeswaran, P. et al., "Nucleotide sequence and analysis of deletion mutants of the *Escherichia coli* gpt gene in plasmid pSV2 gpt," Gene (1996) 31:309-313.
Jiang, Y. et al., "Crithidia fasciculata. isolation, sequencing and expression of the hypoxanthine-guanine phosphoribosyltransferase gene," Exp. Parasitology (1996) 82:73-75.
Johnson, F.H. et al., "Introduction to the cypridina system," Meth. Enzym. (1978) 57:331-364.
Kabsch, W. et al., "Dictionary of protein secondary structure: pattern recognition of hydrogen-bonded and geometrical features," Biopolymers (1983) 22:2577-2637.
Kakoi et al., "A New Synthesis of Watasenia Preluciferin by Cyclization of 2-Amino-3-Benzyl-5-(p-Hydroxyphenyl)Pyrazine With p- Hydroxyphenylpyruviacc" Chem. Lett. 11(3):299-300 (1980).
Kakoi, "Synthesis of 2-Amino-3-benzyl-5-(p-hydroxyphenyl)pyrazine" Chem. Pharm. Bull., 50:301 (2002).
Kalmar, G. et al., "Cloning and expression of rat liver CTP:phosphocholine cytidylyltransferase: a ampipathetic protein that controls phophatidylcholine synthesis," Proc. Natl. Acad. Sci. USA (1990) 87:6029-6033.
Karplus, K. et al., "Hidden Markov models for detecting remote protein homologies," Bioinformatics (1998) 14(10):846-856.
Katz, I.R. et al., "Monoamine oxidase, an intracellular probe of oxygen pressure in isolated cardiac myocytes," J. Biol. Chem. (1984) 259(12):7504-7509.
Kelly, J.H. et al., "A fluorescent cell-based assay for cytochrome P-450 isozyme 1A2 induction and inhibition," J. Biomol. Screening (2000) 5(4):249-253.
Kim, D. et al., "Molecular cloning of cucumber phosphoenolpyruvate carboxykinase and development regulation of gene expression," Plant Mol. Biol. (1994) 26:423-434.
Kim, J.J. et al., "Selective enhancement of emotional, but not motor, learning in monoamine oxidase A-deficient mice," Proc. Natl. Acad. Sci. USA (1997) 94:5929-5933.
King, R.D. et al., "Identification and application of the concepts important for accurate and reliable protein secondary structure prediction," Protein Sci. (1996) 5:2298-2310.
Kishi et al., "The structure confirmation of the light-emitting moiety of bioluminescent jellyfish" Tetrahedron Lett. 13(27):2747(1972).
Kunkel, T.A., "Rapid and efficient site-specific mutagenesis without phenotypic selection," Proc. Natl. Acad. Sci. USA (1985) 82(2):488-492.
Kurowski, M.A. et al., "GeneSilico protein structure prediction meta-server," Nucl. Acids. Res. (2003) 31(13):3305-3307.
Ladror, U. et al., "Cloning, sequencing and expressino of pyrophosphate-dependent phosphofructokinase from propionibacterium freudenreichii," J. Biol. Chem. (1991) 266(25):16550-16555.
Langley et al., "Molecular Basis of O-Galactosidase a-Complementation PNAS (protein sequencing/protein conformation/deletion mutant)" 72:1254-1257 (1975).
Larock, R., "Comprehensive Organic Transformations, A Guide to Functional Group Preparation"s VCH Publishers (1989).
Lee et al., "Synthesis of 7'[123I]iodo-d-luciferin for in vivo studies of firefly luciferase gene expression," Bioorg. Med. Chem. Lett. 2004, v.14, pp. 1161-1163.
Leemann, T. et al., "Cytochrome P450TB (CYP2C): a major monooxygenase catalyzing diclofenac 4'-hydroxylation in human liver," Life Sci. (1993) 52(1):29-34.
Lembert, N., "Firefly luciferase can use L-luciferin to produce light," Biochem. J. (1996) 317(Pt. 1):273-277.
Levit et al., "Ribonuclease S-Peptide—A Model for Molecular Recognition" J. Biol. Chem. 251:1333-1339 (1976).
Leyh, T. et al., "The sulfate activation locus of *Escherichia coli* K12: cloning, genetic, and enzymatic characterization," J. Biol. Chem. (1988) 263(5):2409-2416.
Li, A.P., "Evaluation of luciferin-isopropyl acetal as a CYP3A4 substrate for human hepatocytes: effects of organic solvents, cytochrome P450 (P450) inhibitors, and P450 inducers," Drug Metabolism and Disposition (2009) 37(8):1598-1603.
Loening, A.M. et al., "Consensus guided mutagenesis of renilla luciferase yeilds enhanced stability and light output," Protein Eng. Des. Sel. (2006) 19(9):391-400.

(56) References Cited

OTHER PUBLICATIONS

Lorenz, W.W. et al., "Isolation and expression of a cDNA encoding renilla reinformis luciferase," Proc. Natl. Acad. Sci. USA (1991) 88:4438-4442.
Ludin, K. et al., "The Ade4 gene of schizosaccharomyces pombe: cloning, sequence and regulation," Curr. Genet. (1994) 25:465-468.
Madan et al., "Effects of Prototypical Microsomal Enzyme Inducers on Cytochrome P450 Expression in Cultured Human Hepatocytes," Drug Metab. Dispos., 31:421-431 (2003).
Mancy, A. et al., "Diclofenac and its derivatives as tools for studying human cytochromes P450 active sites: particular efficiency and regioselectivity of P450 2Cs," Biochem. (1999) 38:14264-14270.
Marcelino et al. 2006. "Evolutionary Coupling of Structural and Functional Sequence Information in the Intracellular Lipid-Binding Protein Family." Proteins 63: 373-384.
March, "Advanced Organic Chemistry," 4th ed. Wiley-Interscience, John Wiley and Sons, New York, 1992.
Markaglou, N. et al "Immobilized enzyme reactors based upon the flavoenzymes monamine oxidase A and B," J. Chromatog. B (2004) 804:295-302.
Marolda, C. et al., "Identification, expression and DNA sequence of the GDP-mannose biosynthesis genes encoded by the 07 rfb gene cluster of strain VW 187 (*Escherichia coli* 07:k1)," J. Bacteriol. (1993) 175(1):148-158.
Masuda-Nishimura, I. et al., "Development of a rapid postive/ abstent test for coliforms using sensitive bioluminescence assay," Lett. Appl. Microbiol. (2000) 30(2):130-135.
Mazeas et al., "Synthesis of New Melatoninergic Ligands Including Azaindole Moiety," Heterocycles, 50:1065-1080 (1999).
McGuffin, L.J. et al., "The PSIPRED protein structure prediction server," Bioinformatics (2000) 16(4):404-405.
Miller, V.P. et al., "Fluorometric high-throughput screenign for inbitors of cytochrome P450," Ann. NY Acad. Sci. (2000) 919:26-32.
Miska, w. et al., "A new type of ultrasensitive bioluminogenic eynzyme substrates, I. Enzyme substrates with D-luciferin as leaving group," Biol. Chem. Hoppe-Seyler (1998) 369(5):407-411.
Miska, W. et al., "Evaluation of the bioluminescence-enhanced zona binding assay," Biolum. Chemilum.: Mol. Reporting with Protons, Proceedings fo the International Symposium on Bioluminescence and Chemiluminescence, Oct. 4-8, 1996, pp. 315-318.
Miska, W. et al., "Synthesis and characterization of luciferin derivatives for use in bioluminescence enhanced enzyme immunoassays," J. Clin. Chem. Clin. Biochem. (1987) 25:23-30.
Mitani et al., "Enhancement effect of 2, 6-O-dimethyl-cyclodextrin on the chemiluminescent detection of -D-galactosidase using a Cypridina luceferin analog" Analytical Sciences (1995) 11(6), 1013-15.
Mitani, M. et al., "Chemiluminescent assay of beta-D-galactosidase using cypridina luceferin analogue: 3-(Beta-D-galactopyranosyloxy)-6-(4-methoxyphenyl)-2-methyl-imidazol[1,2-alpha]pyrazine," Anal. Sci. (1994) 10(50:813-814.
Monsees, T. et al., "A novel bioluminogenic assay for alpha-chymotrypsin," J. Biolumin Chemilumin (1995) 10(4):213-218.
Monsees, T. et al., "Synthesis and characterization of a bioluminogenic substrate for alpha-chymotrypsin," Anal. Biochem. (1994) 221(2):329-334.
Moroz et al., "Real-Time Imaging of HIF-1a Stabilization and Degradation" Plos One 4(4):e5077 (2009).
Mosrin et al., "Regio- and Chemoselective Multiple Functionalization of Chloropyrazine Derivatives. Application to the Synthesis of Coelenterazine" Organic Letters, 11:3406 (2009).
Muller-Rober, B. et al., "Isolation and expression analysis of cDNA clones encoding a small and a large subunit of ADP-glucose pyrophosphorylase from sugar beet," Plant Mol. Biol. (1995) 27:191-197.
Murray, E.E. et al., "Codon usage in plant genes," Nucl. Acids. Res. (1989) 17(2):477-498.

Nakagawa, S. et al., "Nucleotide sequence of the FAD synthetase gene from corynebacterium ammoniagenes and its expression in *Escherichia coli*," Biosci. Biotech. Biochem. (1995) 59(4):694-702.
Nakamura, H. et al., "Efficient bioluminescence of bisdeoxycoelenterazine with the luciferase of a deep-sea shrimp oplophorus," Tetra. Lett. (1997) 38(36):6405-6406.
Needleman, S.B. et al., "A general method applicable to the search for similarities in the amino acid sequence of two proteins," J. Mol. Biol. (1970) 48:443-453.
Nelson, D.R. et al., "P450 superfamily: update on new sequences, gene mappin, accession numbers and nomenclature," Pharmacogenetics (1996) 6:1-42.
Nicolaus, B.J., "Symbiotic approach to drug design," Decision making in Drug Research (1983) 173-186.
Nowel, M.S. et al., "Cuticular photophores of two decapod crustaceans, oplophorus spinosus and systellaspis debilis," Biol. Bull. (1998) 195:290-307.
Oba et al. 2009. "Biosynthesis of coelenterazine in the deep-sea copepod, Metridia pacifica. Biochem." Biophys. Res. Comm. 390: 684-688.
O'Brien, M.A. et al., "Homogeneous, bioluminescent protein assays: caspase-3 as a model," J. Biomol. Screen. (2005) 10(2):137-148.
Ogbay et al. 2004. "The NMR Structure of a Stable and Compact All β-sheet Variant of Intestinal Fatty-Acid Binding Proteins." Protein Science 13: 1227-1237.
Ohana et al., "HaloTag7: A genetically engineered tag that enhances bacterial expression of soluble proteins and improves protein purification" Protein Expression and Purification, 68:110-120 (2009).
Oxford Dictionary of Biochemistry and Molecular Biology. Diaphorase. Oxford University Press. Second Edition. 2006. The General Editors. New York, New York, p. 178.
Paguio et al., "pGL4 Vectors: A New Generation fo Luciferase Reporter Vectors" Promega Notes, 89:7-10 (2005).
Paquette, L., ed., "Encyclopedia of Reagents for Organic Synthesis," John Wiley and Sons (1995).
Paquette, Leo A.; "Principles of Modem Heterocyclic Chemistry" (W.A. Benjamin, New York, 1968), particularly Chapters 1, 3, 4, 6, 7, 9.
Parsons, M.R. et al., "Crystal structure of a quinoenzyme: copper amine oxidase of *Escherichia coli* at 2 A resolution," Structure (1995) 3:1171-1184.
Pearson, W.R. et al., "Improved tools for biological sequence comparison," Proc. Natl. Acad. Sci. USA (1988) 85:2444-2448.
Phillips, I.R. et al., "Preface: Cytochrome P450 protocols," Methods in Mol. Biol. (1998) 107:v-vi.
Pichler, A. et al., "Imaging reversal of multidrug resistance in living mice with bioluminescence: MDR1 P-glycoprotein transports coelenterazine," Proc. Natl. Acad. Sci. USA (2004) 101(6):1702-1707.
Pla, J. et al., "Cloning of the candida albicans H1S1 gene by direct complementation of a C. albicans histidine auxotroph using an improved double-ARS shuttle vector," Gene (1995) 165:115-120.
Pollastri, G. et al., "Porter: a new, accurate server for protein secondary structure prediction," Bioinformatics (2005) 21(8):1719-1720.
Poupin, J., "Plancton marin bioluminescent," Rapport Scientifique du Leon (Sep. 1999) 1-83.
Promega Corporation, "P450-Glo™ Assays," Technical Bulletin No. 325, Madison, Wisconsin (Jun. 2003) 19 pages.
Rahman, A. et al., "Selective biotransformation of taxol to 6 alpha-hydroxytaxol by human cytochrome P450 2C8," Cancer Res. (1994) 54(21):5543-5546.
Raphael et al., "A novel method for multiple alignment of sequences with repeated and shuffled elements" Genome Res. 14(11):2336-2346 (2004).
Rea et al. 2009. "Mechanism of Ligand-Induced Folding of a Natively Unfolded Helixless Variant of Rabbit I-BABP." Biochemistry 48: 7556-7564.
Rendic, "Summary of Information on Human CYP Enzymes: Human P450 Metabolism Data," Drug Metab. Rev. 34: 83-448 (2002).

(56) References Cited

OTHER PUBLICATIONS

Renwick, A.B. et al., "Evaluation of 7-benzyloxy-4-trifluoromethyl-coumarin, some other 7-hydroxy-4-trifluoro-methylcoumarin derivatives and 7-benzyloxyquinoline as fluorescent substrates for rat hepatic cytochrome P450 enzymes," Xenobiotica (2001) 31(12):861-878.
Richardson and Richardson. 2002. "Natural β-sheet Proteins Use Negative Design to Avoid Edge-to-Edge Aggregation." PNAS 99(5): 2754-2479.
Rose, A. et al., "A phosphoribosylanthranilate transferase gene is defective in blue fluorescent arabidopsis thaliana tryptophan mutants," Plant Physiol. (1992) 100:582-592.
Sai, Y. et al., "Assessment of specificity of eight chemical inhibitors using cDNA-expressed cytochrome P450," Xenobiotica (2000) 30(4):327-343.
Salles, C. et al., "Biochemical characteristics of liver and brain monoamine oxidase from pacu," J. Fish Biol. (2001) 58:1301-1310.
Sasson et al., "From Azides to Nitriles. A Novel Fast Transformation Made Possible by BrF3," Org Lett., 7:11, 2177-2179 (2005).
Schagat, T. et al., "KRX autoinduction protocol: a convenient metod for protein expression," Promega Notes (2008) 98:16-18.
Schultz, L.W. et al., "Crystal structure of a pH-regulated luciferase catalyzing the bioluminescent oxidation of an open tetrapyrrole," Proc. Natl. Acad. Sci. USA (2005) 102(5):1378-1383.
Shanmugam, K. et al., "Purification and characterization of a tRNA nucleotidyltransferase from lipinus albus and fucntional complementation of a yeast mutation by the corresponding cDNA," Plant Mol. Biol. (1996) 30:281-295.
Shimada et al., "Oxidation of Xenobiotics by Recombinant Human Cytochrome P450 1B1," Drug Metab. Dispos., 29:5, 617-622 (1997).
Shimomura et al. 1997. "Membrane Permeability of Coelenterazine Analogs Measured with Fish Eggs." Biochem J. 326: 297-298.
Shimomura, O. et al., "Properties and reaction mechanism of the bioluminescence system of the deep-sea shrimp oplophorus gracilorostris," Biochem. (1978) 17:994-998.
Shimomura, O. et al., "Semi-synthetic aequorin. An improved tool for the measurement of calcium concentration," Biochemical Journal, 1988, vol. 251, No. 2, pp. 405-410.
Shimomura, O. et al., "Semi-synthetic aequorins with improved sensitivity to CA2+ ions," Biochem. J. (1989) 261:913-920.
Shinde, N.D. et al., "Synthesis of some sulfonamido and amino alkanes and their antifungal activity," Asian J. Chem. (1996) 8(1):85-90, Database CA Accession No. 124:232194.
Shou, M. et al., "A kinetic model for the metabolic interaction of two substrates at the active site of cytochrome P450 3A4," J. Biol. Chem. (2001) 276(3):2256-2262.
Sigrist et al., "Prosite, a protein domain database for functional characterization and annotation" Nucleic Acids Res. 38(suppl 1):D161-D166(2010).
Silvers, W.C., et al., "Shedding light by cancer redox—human NAD(P)H: quinone oxidoreductase 1 activation of a cloaked fluorescent dye" Chemical Communications, vol. 47, 2011, 11264-11266.
Skerra, A., "Lipocalins as a scaffold," Biochem et Biophys. Acta (2000) 1482:337-350.
Skolnick, J. et al., "From genes to protein structure and function: novel applications of computational approaches in the genomic era," Trends in Biotech. (2000) 18:34-39.
Smathers and Petersen. 2011. "The Human Fatty Acid-Binding Protein Family: Evolutionary Divergences and Functions." Human Genomics 5(3): 170-191.
Smith, T.F. et al., "Identification of common molecular subsequences," J. Mol. Biol. (1981) 147:195-197.
Stevens et al., "Developmental Expression of the Major Human Hepatic CYP3A Enzymes," J. Pharm. Exp. Ther., 307:2, 573-582 (2003).
Stresser, D.M. et al., "Cytochrome P450 flourometric substrates: identification of isoform-selective probes for rat CYP2D2 and human CYP3A4," Drug and Disposition (2002) 30(7):845-852.

Sussman, H.E. et al., "Choosing the best reporter assay," The Scientist (Jul. 23, 2001) 25-27 (retrieved from the Internet, http:www.the-scientist.com/article/display/12529/profile2_010723.html.
Takahashi et al., "Heteroaromatic N-Oxides. X. 1) Synthesis and Reactions of Benzothiazole 3-Oxide," Chem & Pharm. Bull., 18:6, 1176-1184 (1970).
Takahashi, S. et al., "Benzimidazole N-oxide. VIII. The reactivity of ethyl 1-methyl-2-benzimidazolecarboxylate 3-oxide and related compounds," Chem. Pharm. Bull. (1968) 16(3):527-538.
Tassaneeyakul, W. et al., "Specificity of substrate and inhibitor probes for human cytochromes P450 1A1 and 1A2," J. Pharmacol. Exp. Ther. (1993) 265(1):401-407.
Teranishi et al. 1990. "Synthesis and Chemiluminescence of Coelenterazine (Oplophorus Luciferin) Analogues." Bull. Chem. Soc. Jpn. 63: 3132-3140.
Teranishi, K. et al., "Coelenterazine analogs as chemiluminescent probe for superoxide anion," Anal. Biochem. (1997) 249:37-43.
Thompson et al. 1995. "Crystal Structure of Cellular Retinoic Acid Binding Protein 1 Shows increased Access to the Binding Cavity Due to Formation of an Intermolecular β-sheet." J. Mol. Biol. 252: 433-446.
Thompson, E.M. et al., "Cloning and expression of cDNA for the luciferase from the marine ostracod Vargula hilgendorfii," Proc. Natl. Acad. Sci. USA (1989) 86:6567-6571.
Toya, Y. et al., "Improved synthetic methods of firefly luciferin derivatives for use in bioluminescent analysis of hydrolytic enzymes: carboxylyic esterase and alkaline phosphatase," Bulletin of the Chemical Society of Japan (1992) 65(10):2604-2610.
Tramontano, "Comparative modelling techniques: where are we?" Genomics, 4:402-405 (2003).
Tucker, et al., "Synthesis of a Series of 4-(Arylethynyl)-6-chloro-4-cyclopropyl-3,4-dihydroquinazolilHn-)2-(o nes as Novel Non-nucleoside HIV-1 Reverse Transcriptase Inhibitors," J. Med. Chem. 1994, 37, 2437-2444.
Ubeaud, G. et al., "Estimation of flavin-containing monooxygenase activity in intact hapatoxyte monolayers or rat, hamster, rabbit, dog and human by using N-oxidation of benzydamine," Eur. J. Pharm. Sci. (1999) 8:255-260.
Van Vleet, T. et al., "Metabolism and cytotoxicity of aflatoxin B1 in cytochrome P-450-expressing human lung cells," J. Toxicolog. Environ. Health (2002) 65:853-867.
Vinitsky, A. et al., "Cloning and nucleic acid sequence of the salmonella typhimurium pncB gene and structur of nicotinate phosphoribosyitransferase," J. Bacteriol. (1991) 173(2):536-540.
Vonstein, V. et al., "Molecular cloning of the pyrE gene from the extreme thermophile thermus flavus," J. Bacteriol. (1995) 177(8):4540-4543.
Wada, K. et al., "Codon usage tabulated from the GenBank genetic sequence data," Nucl. Acids Res. (1990) 18(Supp):2367-2411.
Wahler, d. et al., "Enzyme fingerprints of activity, and stereo- and anantionselectivity from fluorogenic and chromogenic substrate arrays," Chem. A European Journal. (2002) 8(14):3211-3228.
Wang et al., "Synthesis of a Novel Esterase-Sensitive Cyclic Prodrug System for Peptides That Utilizes a "Trimethyl Lock"-Facilitated Lactonization Reaction," J. Org. Chem., 62:1363-1367 (1997).
Wei et al., "Activation of Antibacterial Prodrugs by Peptide Deformylase," Bioorg. Med. Chem. Lett., 10, 1073-1076 (2000).
Weissberger, A., ed., "The Chemistry of Heterocyclic Compounds, A Series of Monographs," (John Wiley & Sons, New York, 1950 to present), in particular vols. 13, 14, 16, 19, and 28.
White, E.H. et al, "Analogues of firefly luciferin, III," J. Org. Chem. (1966) 31:1484-1488.
White, E.H. et al., "Amino analogs of firefly luciferin and biological activity thereof," J. Amer. Chem.. Soc. (1966) 88(9):2015-2018.
White, E.H. et al., "Analogs of firefly luciferin," J. Org. Chem. (1965) 30:2344-2348.
Wood, K.A., "Engineering luciferase enzymes and substrates for novel assay capabilities," Proceedings of SPIE—Microarrays and Combinatorial Techniques: Design, Fabrication and Analysis II (Jun. 2004) 5328:69-77.

(56) References Cited

OTHER PUBLICATIONS

Wrighton, S.A. et al., "The human hepatic cytochromes P450 involved in drug metabolism," Crit. Rev. Toxicol. (1992) 22(1):1-21.
Xiao-Hua, L. et al., "Design and Synthesis of a Novel Fluorescein-based Flourescent Probe for Labeling of Histidine in Human Serum" Chemical Journal of Chinese Universities (1986) vol. 24, No. 11 (3 pages with English Abstract).
Yamaguchi et al. 1975. "Oplophorus Oxyluciferin and a Model Luciferin Compound Biologically Active with Oplophorus Luciferase." Biochem. J. 151: 9-15.
Yang, J. et al., "An easily synthesized photolyzable luciferase for in vivo luciferase activity measurement," Biotechniques (1993) 15(5):848-850.
Yang, X. et al., "Homogeneous enzyme immunoassay modified for application to luminescence-based biosensors," Anal. Biochem. (2005) 336:102-107.
Yoshitomi, S. et al., "Establishment of the transformants expressing human cytochrome P450 subtypes in HepG2, and their applications on drug metabolism and toxicology," Toxicology in Vitro (2001) 15:245-256.
Youdin, M.B. et al., "Novel substrates and products of amine oxidase-catalysed reactions," Biochem. Soc. Trans. (1990) 19:224-228.
Yun, B-S et al., "Coumarins with monamine oxidase inhibitory activity and antioxidative coumarino-lignans from hibiscus syriacus," J. Natl. Prod. (2001) 64(9):1238-1240.
Yun, C-H. et al., "Rate-determining steps in phenacetin oxidations by human cytochrome P450 1A2 and selected mutants," Biochem. (2000) 39:11319-11329.
Zapata, G. et al., "Sequence of the cloned *Escherichia coli* K1 CMP-N-acetylneuraminic acid synthetase gene," J. Biol. Chem. (1989) 264(25):14769-14774.
Zhang et al., "A Universal Algorithm for Fast and Automated Charge State Deconvolution of Electrospray Mass-to-Charge Ratio Spectra" J. Am. Soc. Mass Spectrom., 9:225-233 (1998).
Zheng et al., "An efficient one-step site-directed and site-saturation mutagenesis protocol" Nucleic Acids Research, 32:e115 (2004).
Zhou, G. et al., "Platelet monoamine oxidase B and plasma beta-phenylethylamine in Parkinson's disease," J. Neurol. Neurosurg. Psychiatry (2001) 70:229-231.
Zhou, M. et al., "A one-step fluorometric method for the continuous measurement of monoamine oxidase activity," Anal. Biochem. (1997) 253:169-174.
Zhou, M. et al., "A stable nonfluorescent derivative of resorufin for the fluorometric determination of trace hydrogen peroxide: applications in detecting the activity of phagocyte NADPH oxidase and other oxidases," Anal. Biochem. (1997) 253:162-168.
Zhou, W. et al., "New bioluminogenic substrates for monoamine oxidase assays," J. Am. Chem. Soc. (2006) 128(10):3122-3123.
Zuker et al., "Mfold web server for nucleic acid folding and hybridization prediction" Nucleic Acid Res. 31(13):3406-3415(2003).
International Preliminary Examination Report for Application No. PCT/US03/29078 dated Oct. 19, 2006 (6 pages).
International Preliminary Report on Patentability for Application No. PCT/US06/020731 dated Sep. 12, 2007 (8 pages).
International Search Report and Written Opinion for Application No. PCT/US2006/020731 dated Mar. 13, 2007 (17 pages).
International Search Report and Written Opinion for Application No. PCT/US2009/004696 dated Nov. 19, 2009 (13 pages).
International Search Report and Written Opinion for Application No. PCT/US2010/033449 dated Aug. 18, 2010 (12 pages).
International Search Report and Written Opinion for Application No. PCT/US2011/058924 dated Jan. 18, 2012 (8 pages).
International Search Report and Written Opinion for Application No. PCT/US2011/059017 dated Jan. 18, 2012 (8 pages).
International Search Report and Written Opinion for Application No. PCT/US2011/059018 dated Jul. 12, 2012 (15 pages).
International Search Report and Written Opinion for Application No. PCT/US2015/013504 dated Mar. 24, 2015 (12 pages).
International Search Report for Application No. PCT/US03/29078 dated Oct. 8, 2004 (4 pages).
Partial International Search Report for Application No. PCT/US2006/020731 dated Oct. 2, 2006 (6 pages).
PCT/US2012/053310 International Search Report and Written Opinion dated Dec. 18, 2012 (13 pages).
U.S. Appl. No. 10/665,314 Advisory Action dated Jun. 6, 2008 (3 pages).
U.S. Appl. No. 10/665,314 dated Jan. 15, 2009 (6 pages).
U.S. Appl. No. 10/665,314 dated Jul. 18, 2008 (14 pages).
U.S. Appl. No. 10/665,314 dated Mar. 19, 2008 (5 pages).
U.S. Appl. No. 10/665,314 dated May 15, 2009 (6 pages).
U.S. Appl. No. 10/665,314 dated Oct. 11, 2007 (16 pages).
U.S. Appl. No. 11/444,145 dated Apr. 28, 2009 (15 pages).
U.S. Appl. No. 11/444,145 dated Mar. 24, 2008 (16 pages).
U.S. Appl. No. 11/444,145 dated Oct. 15, 2008 (16 pages).
U.S. Appl. No. 12/217,374 dated Dec. 17, 2010 (9 pages).
U.S. Appl. No. 12/217,374 dated Jul. 28, 2010 (8 pages).
U.S. Appl. No. 12/217,374 dated May 24, 2011 (8 pages).
U.S. Appl. No. 12/217,374 dated May 7, 2013 (12 pages).
U.S. Appl. No. 12/217,494 dated Aug. 7, 2012 (17 pages).
U.S. Appl. No. 12/217,494 dated Dec. 16, 2009 (18 pages).
U.S. Appl. No. 12/217,494 dated Jan. 14, 2013 (3 pages).
U.S. Appl. No. 12/217,494 dated Jan. 26, 2012 (14 pages).
U.S. Appl. No. 12/217,494 dated Jun. 28, 2010 (10 pages).
U.S. Appl. No. 12/217,494 dated Nov. 16, 2012 (3 pages).
U.S. Appl. No. 12/543,376 dated Jan. 26, 2012 (7 pages).
U.S. Appl. No. 12/754,164 dated May 13, 2011 (5 pages).
U.S. Appl. No. 12/773,002 dated Dec. 29, 2011 (11 pages).
U.S. Appl. No. 13/287,519 dated Feb. 27, 2015 (8 pages).
U.S. Appl. No. 13/287,519 dated Jul. 2, 2014 (10 pages).
U.S. Appl. No. 13/287,519 dated Nov. 7, 2014 (7 pages).
U.S. Appl. No. 13/287,992 dated Apr. 4, 2013 (9 pages).
U.S. Appl. No. 13/600,579 dated Apr. 28, 2014 (19 pages).
U.S. Appl. No. 13/600,579 dated Jun. 6, 2014 (21 pages).
U.S. Appl. No. 13/600,579 dated Mar. 12, 2015 (12 pages).
U.S. Appl. No. 13/600,579 dated Oct. 24, 2013 (15 pages).
U.S. Appl. No. 13/913,919 dated Mar. 26, 2014 (24 pages).
U.S. Appl. No. 14/032,420 dated Mar. 25, 2015 (19 pages).
United States Patent Office Action for U.S. Appl. No. 14/461,610 dated Feb. 3, 2015 (15 pages).
United States Patent Office Notice of Allowance for U.S. Appl. No. 14/461,610 dated May 15, 2015 (9 pages).
United States Patent Office Final Rejection for U.S. Appl. No. 12/773,002 dated Jun. 1, 2012 (17 pages).
United States Patent Office Final Rejection for U.S. Appl. No. 13/287,519 dated Apr. 24, 2013 (10 pages).
United States Patent Office Final Rejection for U.S. Appl. No. 13/287,519 dated Sep. 6, 2013 (8 pages).
United States Patent Office Final Rejection for U.S. Appl. No. 13/287,992 dated Jul. 11, 2013 (7 pages).
United States Patent Office Final Rejection for U.S. Appl. No. 13/600,579 dated Nov. 14, 2014 (14 pages).
United States Patent Office Notice of Allowance for U.S. Appl. No. 11/444,145 dated Jan. 24, 2011 (19 pages).
United States Patent Office Notice of Allowance for U.S. Appl. No. 12/217,374 dated Nov. 25, 2013 (9 pages).
United States Patent Office Notice of Allowance for U.S. Appl. No. 12/217,494 dated Feb. 21, 2013 (5 pages).
United States Patent Office Notice of Allowance for U.S. Appl. No. 12/543,376 dated Jul. 9, 2012 (10 pages).
United States Patent Office Notice of Allowance for U.S. Appl. No. 12/754,164 dated Sep. 21, 2011 (5 pages).
United States Patent Office Notice of Allowance for U.S. Appl. No. 13/287,992 dated Apr. 1, 2014 (11 pages).
United States Patent Office Notice of Allowance for U.S. Appl. No. 13/287,992 dated Nov. 18, 2013 (12 pages).
United States Patent Office Notice of Allowance for U.S. Appl. No. 13/287,519 dated Jun. 5, 2015 (5 pages).
International Search Report and Written Opinion for Application No. PCT/US2015/013617 dated Mar. 24, 2015 (11 pages).

(56) References Cited

OTHER PUBLICATIONS

Roubinet et al: "New insights into the water-solubilization of thiol-sensitive fluorogenic probes based on long-wavelength 7-hydroxycoumarin scaffolds", Dyes and Pigments, vol. 110, Feb. 12, 2014, pp. 270-284.
United States Patent Office Action for U.S. Appl. No. 14/032,420 dated Aug. 12, 2015 (19 pages).
United States Patent Office Notice of Allowance for U.S. Appl. No. 13/600,579 dated Jun. 26, 2015 (12 pages).
United States Patent Office Action for U.S. Appl. No. 14/553,445 dated Dec. 24, 2015 (12 pages).
United States Patent Office Notice of Allowance for U.S. Appl. No. 13/600,579 dated Oct. 21, 2015 (12 pages).
International Preliminary Examination Report for Application No. PCT/US03/29078 dated Oct. 23, 2006 (5 pages).
United States Patent Office Final Action for U.S. Appl. No. 13/600,579 dated Jun. 26, 2015 (12 pages).
United States Patent Office Action for U.S. Appl. No. 14/608,910 dated Oct. 14, 2016 (16 pages).

\* cited by examiner

```
                              SEQUENCE LISTING

<160> NUMBER OF SEQ ID NOS: 10

<210> SEQ ID NO 1
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 1

Asp Tyr Met Gly Trp Met Asp Phe
1               5

<210> SEQ ID NO 2
<211> LENGTH: 19
<212> TYPE: PRT
<213> ORGANISM: Artificial Sequence
<220> FEATURE:
<223> OTHER INFORMATION: Synthetic Peptide (Name: Ant-20)
<220> FEATURE:
<221> NAME/KEY: MISC_FEATURE
<222> LOCATION: (19)..(19)
<223> OTHER INFORMATION: Modified amino acid attached to SEQ ID NO:3 by
      a disulfide bond

<400> SEQUENCE: 2

Arg Gln Ile Lys Ile Trp Phe Gln Asn Arg Arg Met Lys Trp Lys Lys
1               5                   10                  15

Gly Gly Cys

<210> SEQ ID NO 3
<211> LENGTH: 20
<212> TYPE: DNA
<213> ORGANISM: Artificial Sequence
<220> FEATURE:
<223> OTHER INFORMATION: Synthetic Oligonucleotide (Name: Ant-20)
<220> FEATURE:
<221> NAME/KEY: misc_feature
<222> LOCATION: (1)..(1)
<223> OTHER INFORMATION: Modified nucleotide attached to SEQ ID NO:2 by
      a disulfide bond
<220> FEATURE:
<221> NAME/KEY: misc_feature
<222> LOCATION: (20)..(20)
<223> OTHER INFORMATION: Modified nucleotide attached to quinone label

<400> SEQUENCE: 3
ccatcccgac ctcgcgctcc                                             20

<210> SEQ ID NO 4
<211> LENGTH: 19
<212> TYPE: PRT
<213> ORGANISM: Artificial Sequence
<220> FEATURE:
<223> OTHER INFORMATION: Synthetic Peptide (Name: Ant mismatch)
<220> FEATURE:
<221> NAME/KEY: MISC_FEATURE
<222> LOCATION: (19)..(19)
<223> OTHER INFORMATION: Modified amino acid attached to SEQ ID NO:5 by
      a disulfide bond

<400> SEQUENCE: 4

Arg Gln Ile Lys Ile Trp Phe Gln Asn Arg Arg Met Lys Trp Lys Lys
1               5                   10                  15
```

Gly Gly Cys

<210> SEQ ID NO 5
<211> LENGTH: 20
<212> TYPE: DNA
<213> ORGANISM: Artificial Sequence
<220> FEATURE:
<223> OTHER INFORMATION: Synthetic Oligonucleotide (Name: Ant mismatch)
<220> FEATURE:
<221> NAME/KEY: misc_feature
<222> LOCATION: (1)..(1)
<223> OTHER INFORMATION: Modified nucleotide attached to SEQ ID NO:4 by
      a disulfide bond
<220> FEATURE:
<221> NAME/KEY: misc_feature
<222> LOCATION: (20)..(20)
<223> OTHER INFORMATION: Modified nucleotide attached to quinone label

<400> SEQUENCE: 5
ccataccaac atcacgctcc                                                    20

<210> SEQ ID NO 6
<211> LENGTH: 13
<212> TYPE: PRT
<213> ORGANISM: Artificial Sequence
<220> FEATURE:
<223> OTHER INFORMATION: Synthetic Peptide (Name: Tat-20)
<220> FEATURE:
<221> NAME/KEY: MISC_FEATURE
<222> LOCATION: (13)..(13)
<223> OTHER INFORMATION: Modified amino acid attached to SEQ ID NO:7 by
      a disulfide bond

<400> SEQUENCE: 6

Arg Lys Lys Arg Arg Gln Arg Arg Arg Pro Pro Gln Cys
1               5                   10

<210> SEQ ID NO 7
<211> LENGTH: 20
<212> TYPE: DNA
<213> ORGANISM: Artificial Sequence
<220> FEATURE:
<223> OTHER INFORMATION: Synthetic Oligonucleotide (Name: Tat-20)
<220> FEATURE:
<221> NAME/KEY: misc_feature
<222> LOCATION: (1)..(1)
<223> OTHER INFORMATION: Modified nucleotide attached to SEQ ID NO:6 by
      a disulfide bond
<220> FEATURE:
<221> NAME/KEY: misc_feature
<222> LOCATION: (20)..(20)
<223> OTHER INFORMATION: Modified nucleotide attached to quinone label

<400> SEQUENCE: 7
ccatcccgac ctcgcgctcc                                                    20

<210> SEQ ID NO 8
<211> LENGTH: 13
<212> TYPE: PRT
<213> ORGANISM: Artificial Sequence
<220> FEATURE:
<223> OTHER INFORMATION: Synthetic Peptide (Name: Tat 20mismatch)
<220> FEATURE:
<221> NAME/KEY: MISC_FEATURE
<222> LOCATION: (13)..(13)
<223> OTHER INFORMATION: Modified amino acid attached to SEQ ID NO:9 by
      a disulfide bond

<400> SEQUENCE: 8

Arg Lys Lys Arg Arg Gln Arg Arg Arg Pro Pro Gln Cys

```
<210> SEQ ID NO 9
<211> LENGTH: 20
<212> TYPE: DNA
<213> ORGANISM: Artificial Sequence
<220> FEATURE:
<223> OTHER INFORMATION: Synthetic Oligonucleotide (Name: Tat
      20mismatch)
<220> FEATURE:
<221> NAME/KEY: misc_feature
<222> LOCATION: (1)..(1)
<223> OTHER INFORMATION: Modified nucleotide attached to SEQ ID NO:8 by
      a disulfide bond
<220> FEATURE:
<221> NAME/KEY: misc_feature
<222> LOCATION: (20)..(20)
<223> OTHER INFORMATION: Modified nucleotide attached to quinone label

<400> SEQUENCE: 9
ccataccaac atcacgctcc                                                 20

<210> SEQ ID NO 10
<211> LENGTH: 20
<212> TYPE: DNA
<213> ORGANISM: Artificial Sequence
<220> FEATURE:
<223> OTHER INFORMATION: Synthetic Oligonucleotide (Name: 20)
<220> FEATURE:
<221> NAME/KEY: misc_feature
<222> LOCATION: (20)..(20)
<223> OTHER INFORMATION: Modified nucleotide attached to quinone label

<400> SEQUENCE: 10
caatcccgac ctcgcgctcc                                                 20
```

QUINONE-MASKED PROBES AS LABELING REAGENTS FOR CELL UPTAKE MEASUREMENTS

CROSS-REFERENCE TO RELATED APPLICATIONS

This application claims priority to U.S. Provisional Application 61/933,122, filed Jan. 29, 2014, and is herein incorporated by reference in its entirety.

SEQUENCE LISTING

The sequence listing is filed with the application in electronic format only and is incorporated by reference herein. The sequence listing text file "ASFILED_Sequence-Listing-Text" was created on Jul. 13, 2015 and is 4,133 bytes in size.

TECHNICAL FIELD

The present disclosure relates generally to compounds, compositions, and methods of using the compounds and compositions as labeling reagents. More particularly, the present disclosure relates to quinone-masked probes as labeling reagents for cell uptake measurements.

BACKGROUND

Quantification of the uptake of biomolecules and small molecules of interests in biological samples (i.e., cells, tissues and organs) is becoming a vital part for drug delivery, effectiveness of therapeutic treatments, profiling pharmacokinetics, drug-drug interactions and drug toxicity, but also represents an important indicator for cellular metabolic status, such as fatty acids and glucose, and homeostasis of cholesterol to maintain normal physiological functions. Various techniques such as fluorescent-labeled or isotope-labeled molecules of interests for uptake quantification of cells and tissues already exist, but still needs for new uptake techniques in order to make the uptake measurements simple, reliable and reproducible in high throughput formats.

SUMMARY

In some aspects, disclosed is a compound of formula (I), or a salt thereof, (I)

wherein

A is a reporter moiety;

$R^{14}$ is H, alkyl, hydroxyalkyl, alkoxy, carboxyalkyl, or amidoalkyl;

$R^9$ and $R^{10}$ are independently selected from alkyl;

$R^{11}$, $R^{12}$ and $R^{13}$ are independently selected from H, alkyl, alkoxy, bromo, chloro or amino, or $R^{11}$ and $R^{12}$ can form a fused phenyl ring;

X is O;

L is $-(CH_2)_mC(R^{17})_2(CH_2)_n-Y-C(O)-$;

$R^{17}$ is independently H, alkyl or both $R^{17}$ together can form an alkyl ring having from 3-7 carbons;

m is an integer from 0-2;

n is an integer from 0-2;

Y is O or $NR^{15}$;

$R^{15}$ is H, alkyl, hydroxyalkyl, azidoalkyl, cyanoalkyl, haloalkyl, alkenyl, alkynyl, -alkyl-$N(R^{23})C(O)R^{24}$, -alkyl-$SO_3R^{25}$, -alkyl-$SO_2N(R^{26})(R^{27})$, -alkyl-$COR^{28}$, -alkyl-$CO_2R^{29}$, -alkyl-$OC(O)R^{29}$, -alkyl-$OC(O)N(R^{30})(R^{31})$, -alkyl-$CON(R^{30})(R^{31})$, or polyalkoxyalkyl, wherein the polyalkoxyalkyl is unsubstituted or substituted with one or more suitable substituents; and $R^{23}$, $R^{24}$, $R^{25}$, $R^{26}$, $R^{27}$, $R^{28}$, $R^{29}$, $R^{30}$, and $R^{31}$ are each independently selected from hydrogen, alkyl, aryl, heteroaryl, heterocyclyl, and cycloalkyl.

In certain embodiments, $R^{15}$ is polyalkoxyalkyl, wherein the polyalkoxyalkyl is $-(C_2-C_6\text{-alkoxy})_x$-alkyl, $-(C_2-C_6\text{-alkoxy})_x$-haloalkyl, $-(C_2-C_6\text{-alkoxy})_x$-hydroxyalkyl, $-(C_2-C_6\text{-alkoxy})_x$-aminoalkyl, $-(C_2-C_6\text{-alkoxy})_x$-alkylaminoalkyl, $-(C_2-C_6\text{-alkoxy})_x$di(alkyl)aminoalkyl, $-(C_2-C_6\text{-alkoxy})_x$-azidoalkyl, $-(C_2-C_6\text{-alkoxy})_x$-cyanoalkyl, $-(C_2-C_6\text{-alkoxy})_x$-alkenyl, $-(C_2-C_6\text{-alkoxy})_x$-alkynyl, $-(C_2-C_6\text{-alkoxy})_x$-$N(R^{23})C(O)R^{24}$, $-(C_2-C_6\text{-alkoxy})_x$-$SO_3R^{25}$, $-(C_2-C_6\text{-alkoxy})_x$-alkyl-$SO_2N(R^{26})(R^{27})$, $-(C_2-C_6\text{-alkoxy})_x$-alkyl-$COR^{28}$, $-(C_2-C_6\text{-alkoxy})_x$-alkyl-$OC(O)R^{29}$, $-(C_2-C_6\text{-alkoxy})_x$-alkyl-$OC(O)N(R^{30})(R^{31})$, $-(C_2-C_6\text{-alkoxy})_x$-alkyl-$CO_2R^{29}$, and $-(C_2-C_6\text{-alkoxy})_x$-alkyl-$CON(R^{30})(R^{31})$, wherein $R^{23}$, $R^{24}$, $R^{25}$, $R^{26}$, $R^{27}$, $R^{28}$, $R^{29}$, $R^{30}$, and $R^{31}$ are each independently selected from hydrogen, alkyl, aryl, heteroaryl, heterocyclyl, and cycloalkyl; and x is an integer selected from 1 to 20.

In certain embodiments, $R^{15}$ is polyalkoxyalkyl, wherein the polyalkoxyalkyl is unsubstituted or substituted with 1 to 3 substituents independently selected from the group consisting of alkyl, alkoxyalkyl, haloalkyl, haloalkoxyalkyl, hydroxyalkyl, aminoalkyl, alkylaminoalkyl, di(alkyl)aminoalkyl, azidoalkyl, cyanoalkyl, alkoxy, haloalkoxy, alkoxyalkyl, alkenyl, alkynyl, $-N(R^{23})C(O)R^{24}$, $-SO_3R^{25}$, $-SO_2N(R^{26})(R^{27})$, $-COR^{28}$, $-CO_2R^{29}$ and $-CON(R^{30})(R^{31})$, wherein $R^{23}$, $R^{24}$, $R^{25}$, $R^{26}$, $R^{27}$, $R^{28}$, $R^{29}$, $R^{30}$, and $R^{31}$ are each independently selected from hydrogen, alkyl, aryl, heteroaryl, heterocyclyl, and cycloalkyl.

In certain embodiments, $R^{15}$ is wherein $R^{40}$ is selected from the group consisting of hydrogen, alkyl, alkenyl, alkynyl, aryl, heteroaryl, heterocyclyl, and cycloalkyl, wherein said aryl, heteroaryl, heterocyclyl, and cycloalkyl are unsubstituted or substituted with one or more suitable substituents; and x is an integer selected from 1 to 20.

In certain embodiments, $R^{40}$ is hydrogen.

In certain embodiments, $R^{40}$ is a 5- or 6-membered heterocyclyl, having 1, 2, or 3 heteroatoms independently selected from the group consisting of N, O, and S.

In certain embodiments, $R^{40}$ is

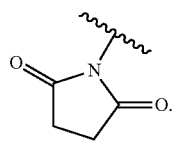 [SMILES: *N1C(=O)CCC1=O]

In certain embodiments, x is 2, 3, or 4.

In certain embodiments, the compound of formula (I) has formula (I-vi), or a salt thereof,

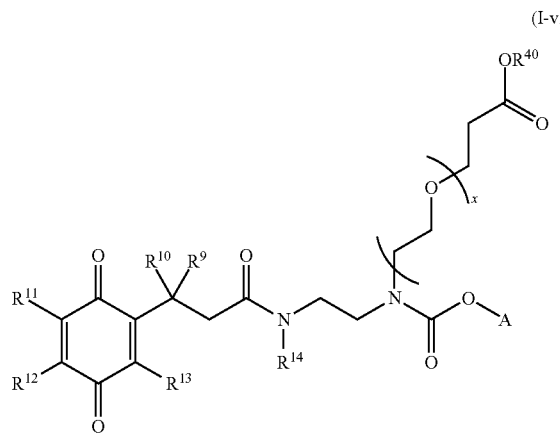

(I-vi)

wherein
$R^9$, $R^{10}$, $R^{11}$, $R^{12}$, $R^{13}$, $R^{14}$, $R^{40}$, x, and A are as defined above.

In some aspects, disclosed is a compound of formula (I), or a salt thereof, A compound of formula (I), or a salt thereof,

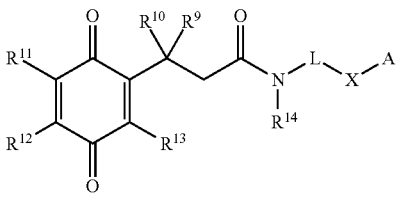

(I)

wherein
A is a reporter moiety;
$R^{14}$ is H, alkyl, hydroxyalkyl, alkoxy, carboxyalkyl, or amidoalkyl;
$R^9$ and $R^{10}$ are independently selected from alkyl;
$R^{11}$, $R^{12}$ and $R^{13}$ are independently selected from H, alkyl, alkoxy, bromo, chloro or amino, or $R^{11}$ and $R^{12}$ can form a fused phenyl ring;
X is O;
L is —$(CH_2)_m C(R^{17})_2 (CH_2)_n$—Y—C(O)—;
$R^{17}$ is independently H, alkyl or both $R^{17}$ together can form an alkyl ring having from 3-7 carbons;
m is an integer from 0-2;
n is an integer from 0-2;
Y is O or $NR^{15}$;
$R^{15}$ is H, alkyl, hydroxyalkyl, azidoalkyl, cyanoalkyl, haloalkyl, alkenyl, alkynyl, -alkyl-$N(R^{23})C(O)R^{24}$, -alkyl-$SO_3R^{25}$, -alkyl-$SO_2N(R^{26})(R^{27})$, -alkyl-$COR^{28}$, -alkyl-$CO_2R^{29}$, -alkyl-$OC(O)R^{29}$, -alkyl-$OC(O)N(R^{30})(R^{31})$, -alkyl-amide, or polyalkoxyalkyl, wherein the polyalkoxyalkyl and -alkyl-amide are unsubstituted or substituted with one or more suitable substituents; and
$R^{23}$, $R^{24}$, $R^{25}$, $R^{26}$, $R^{27}$, $R^{28}$, $R^{29}$, $R^{30}$, and $R^{31}$ are each independently selected from hydrogen, alkyl, aryl, heteroaryl, heterocyclyl, and cycloalkyl.

In certain embodiments, a compound of the invention is selected from the group consisting of:

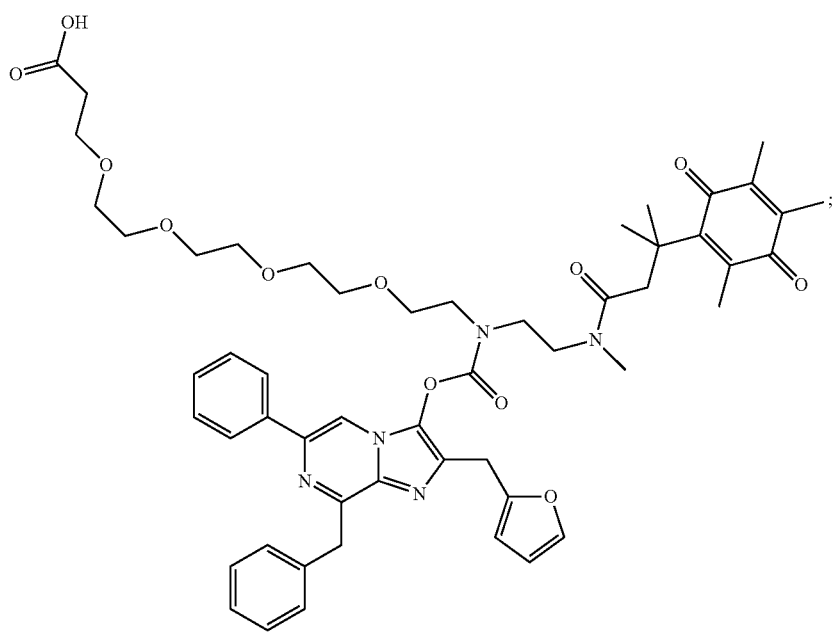

-continued
PBI 5470
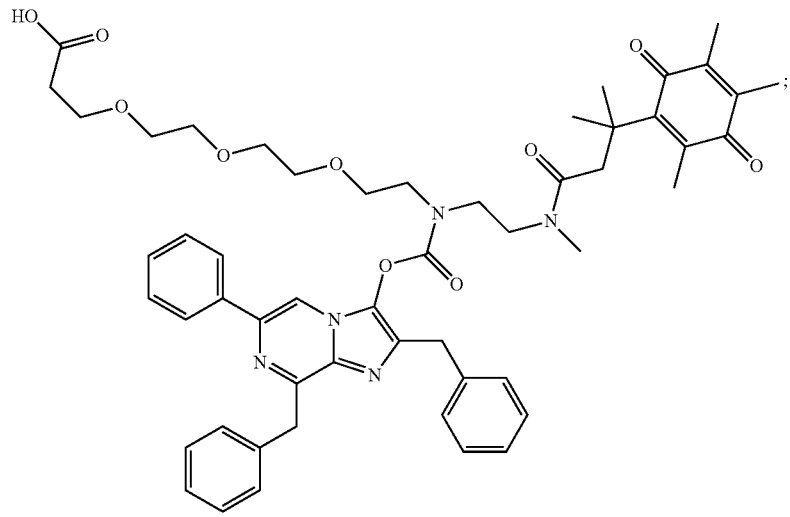
PBI-5471
PBI 5508
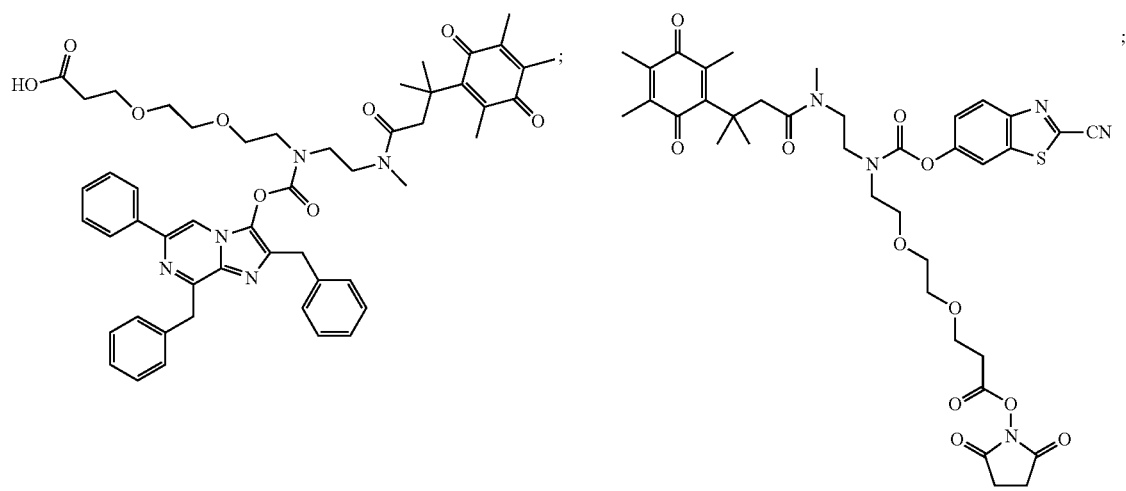
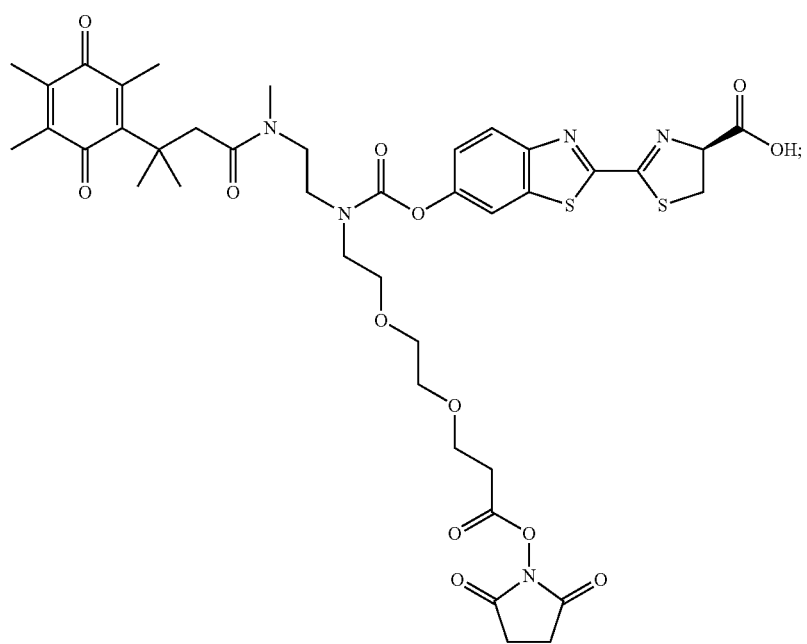

-continued
PBI 5915
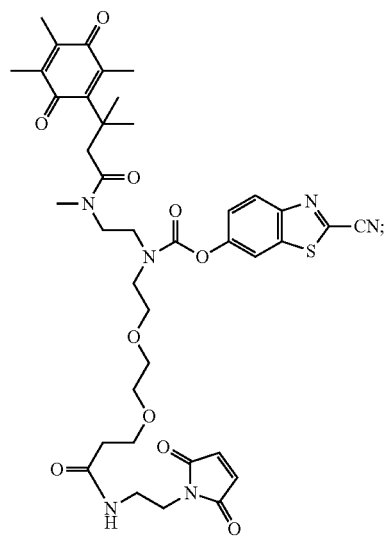
PBI 5916
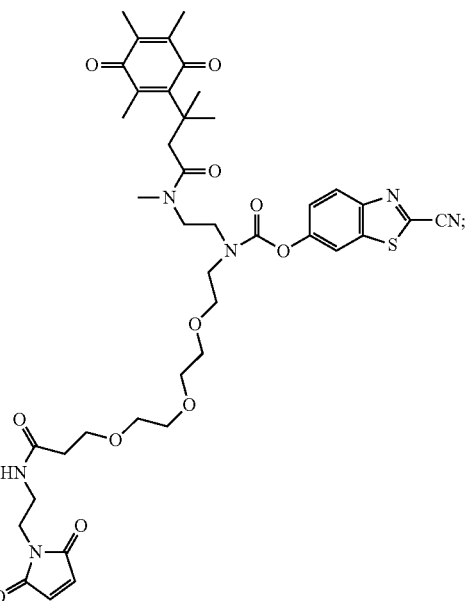
PBI 5917
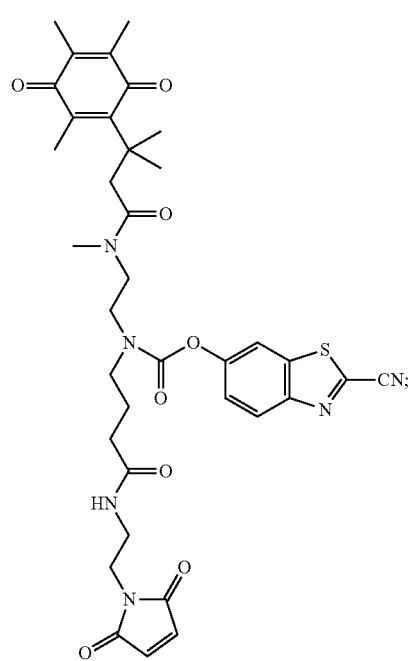
PBI 5918
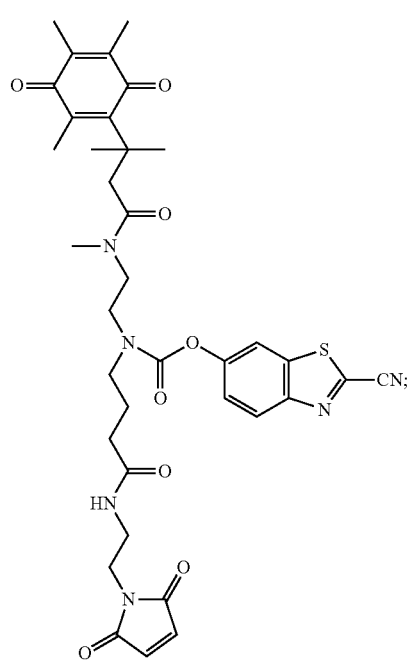

PBI 5651
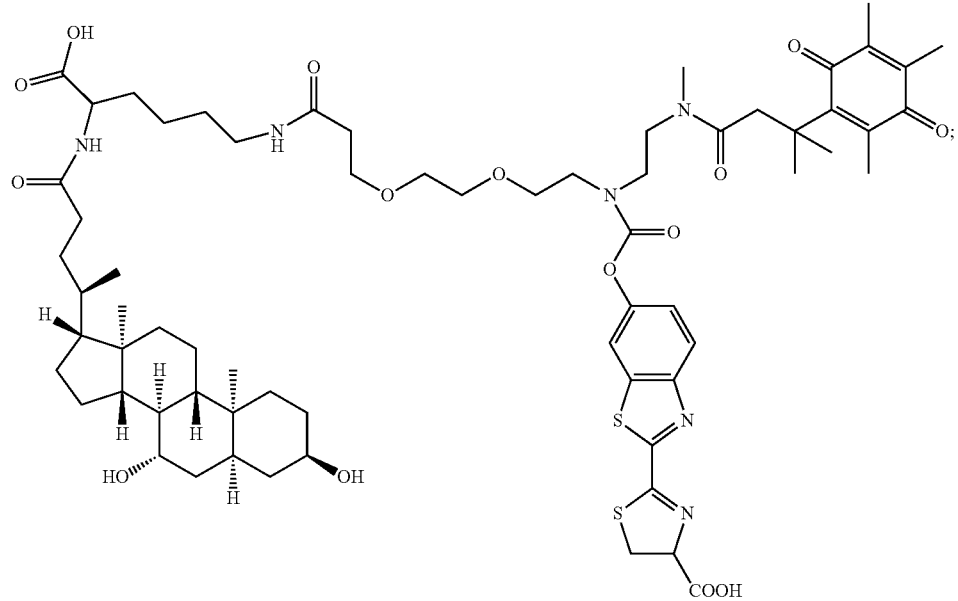
PBI 5648
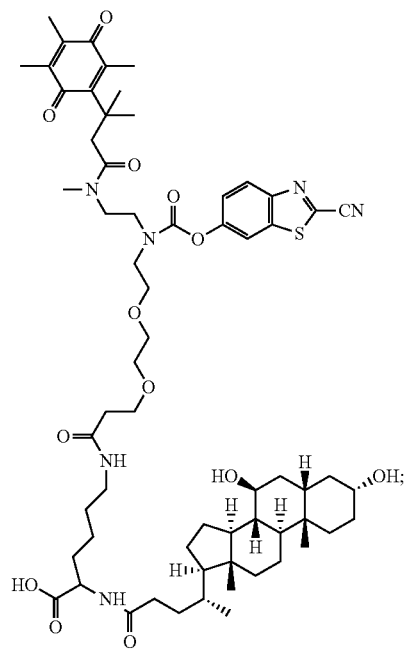

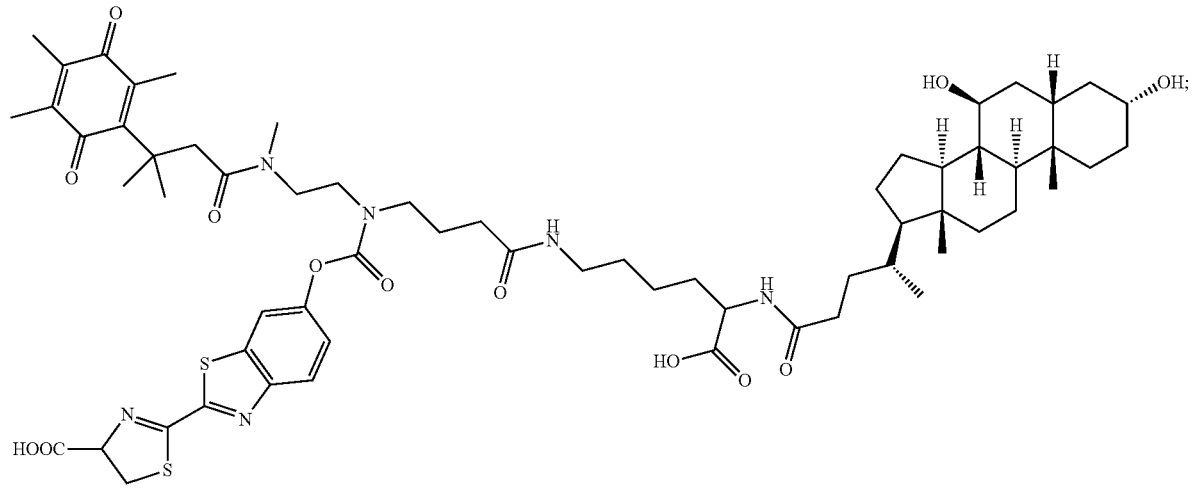
PBI 5657
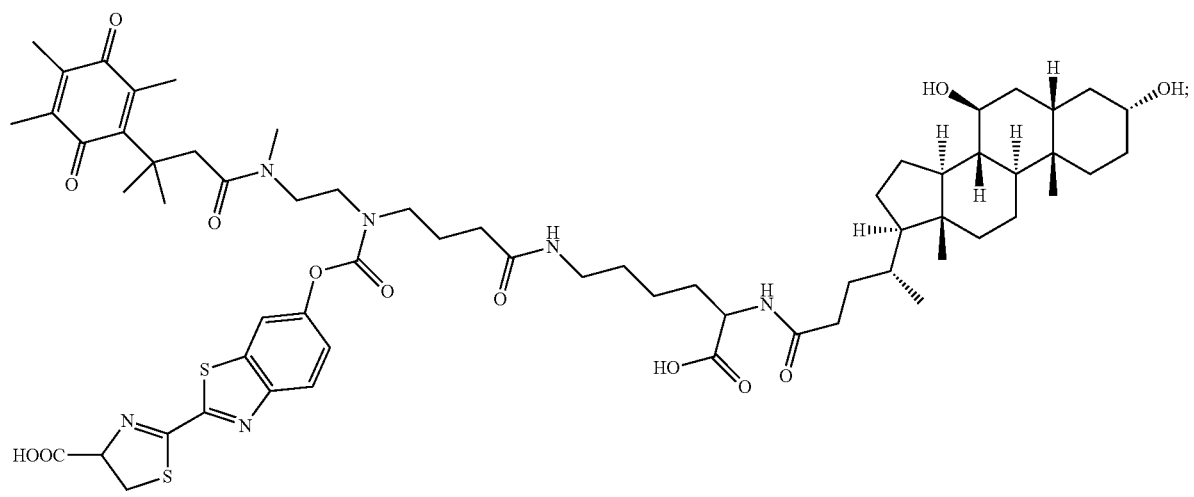
PBI 5658

PBI 5665

-continued
PBI 5666
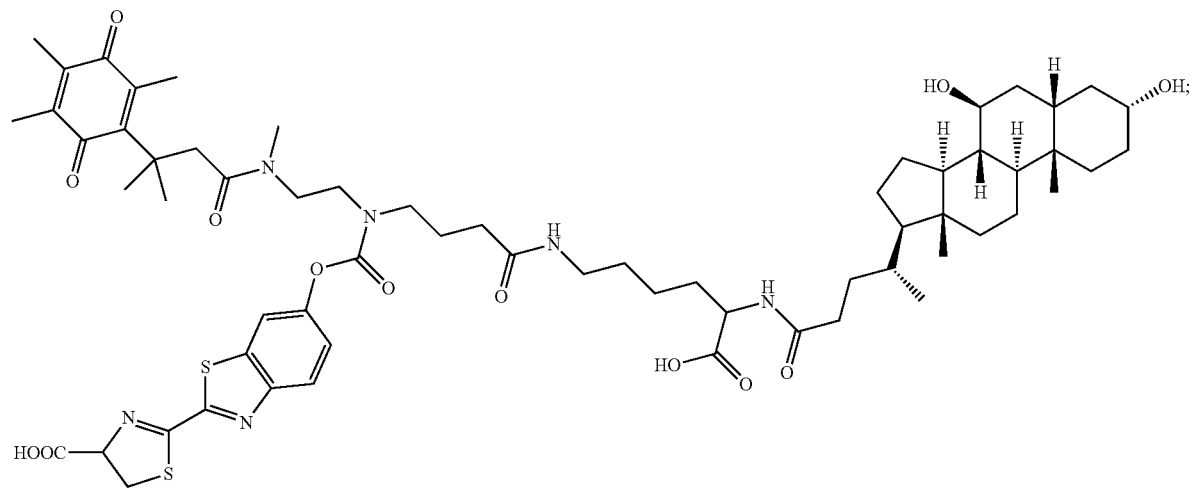
PBI 5684
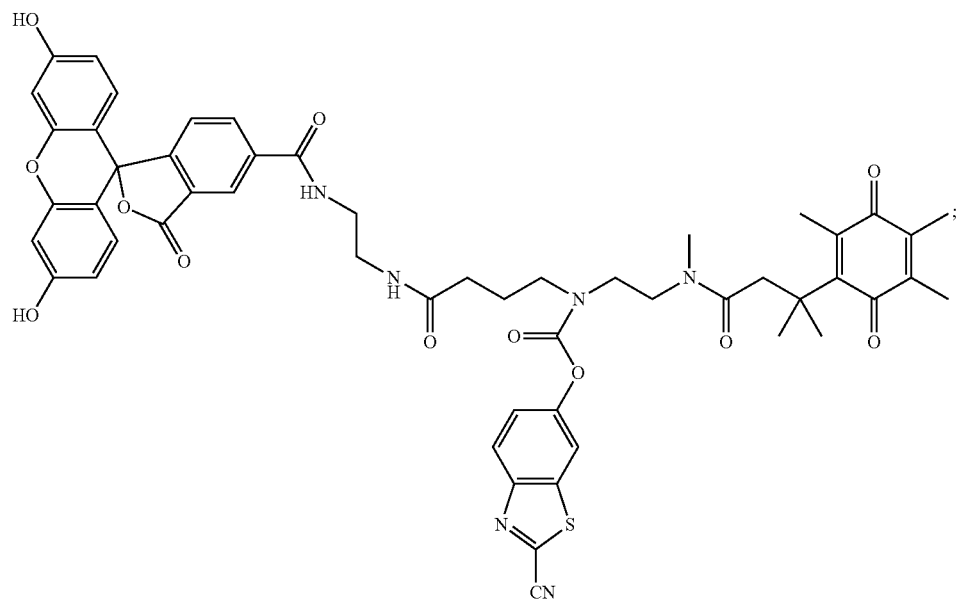

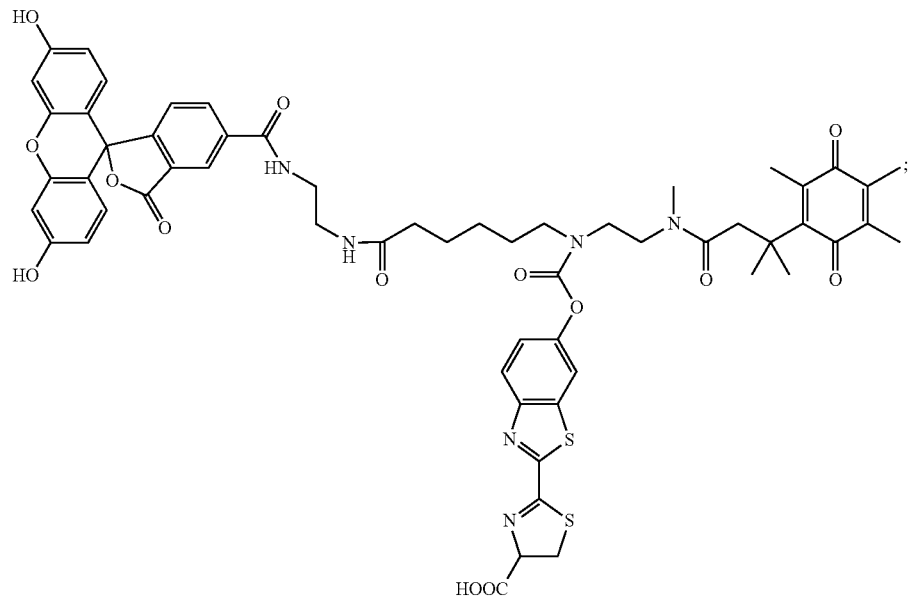
PBI 5825
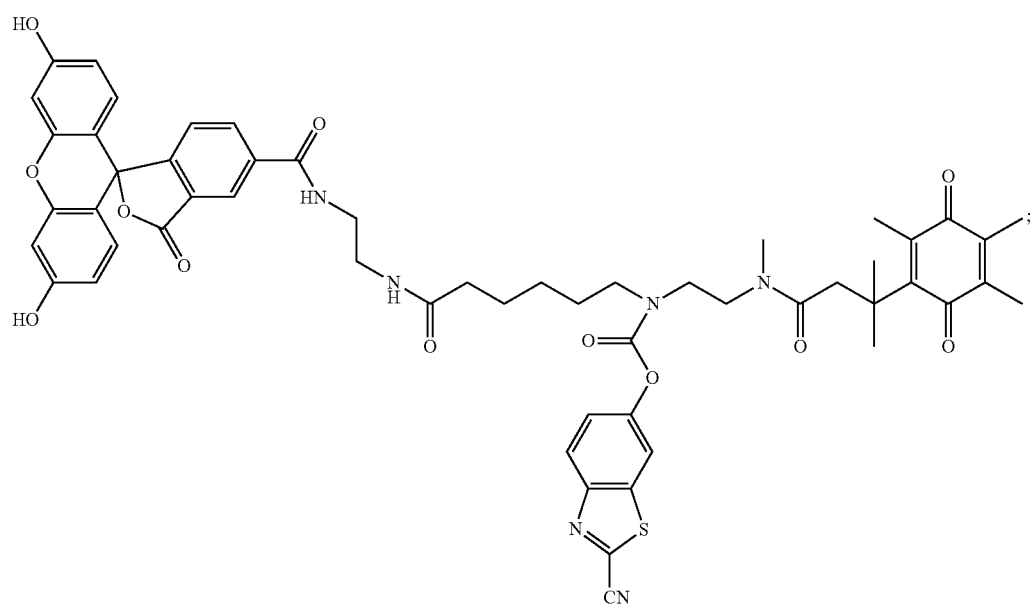
PBI 5683

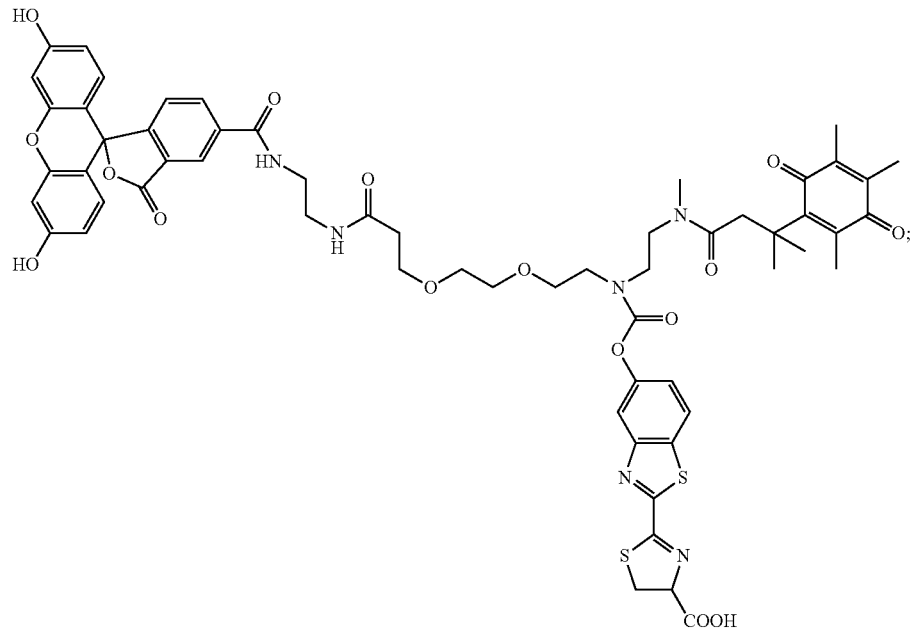
PBI 5826
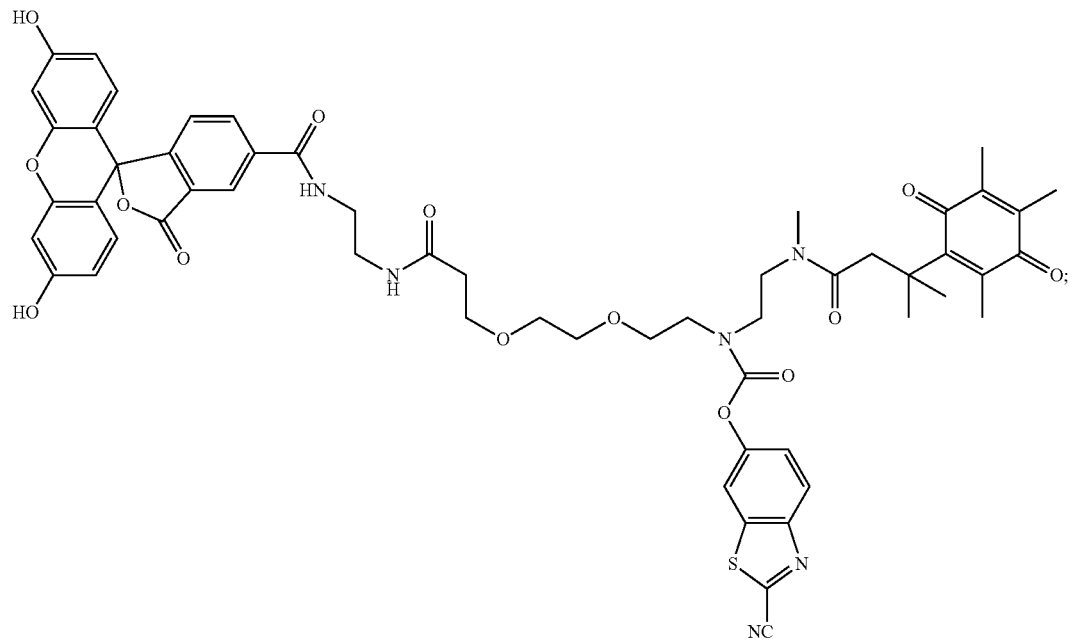
PBI 5682

PBI 5647
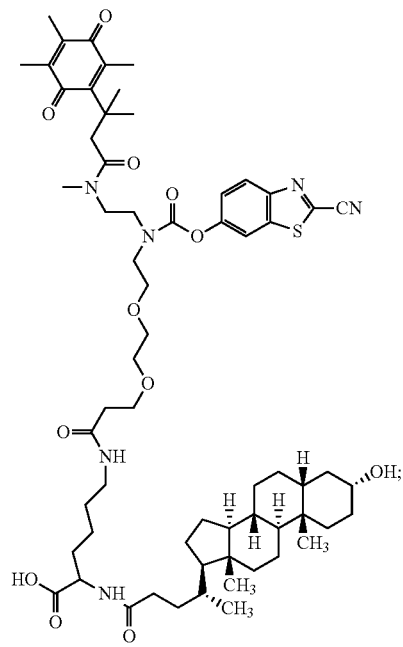
PBI 5668
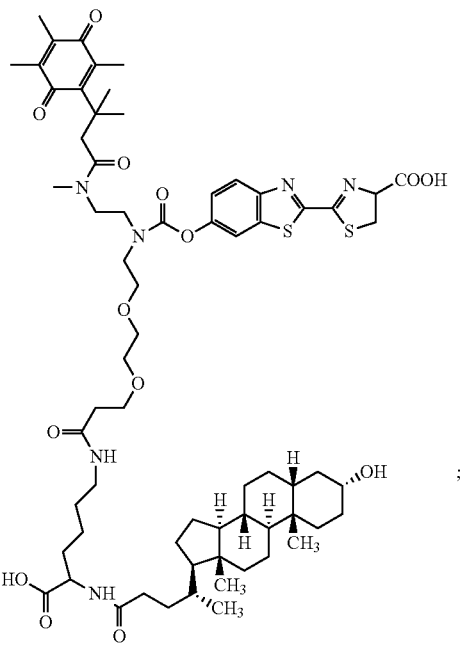
PBI 5625
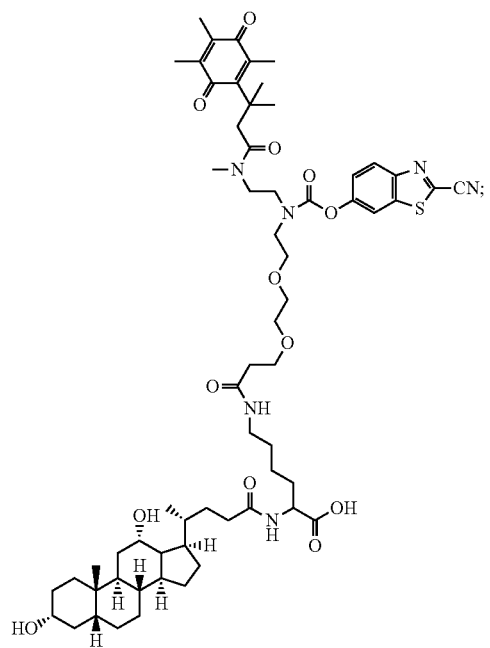
PBI 5649
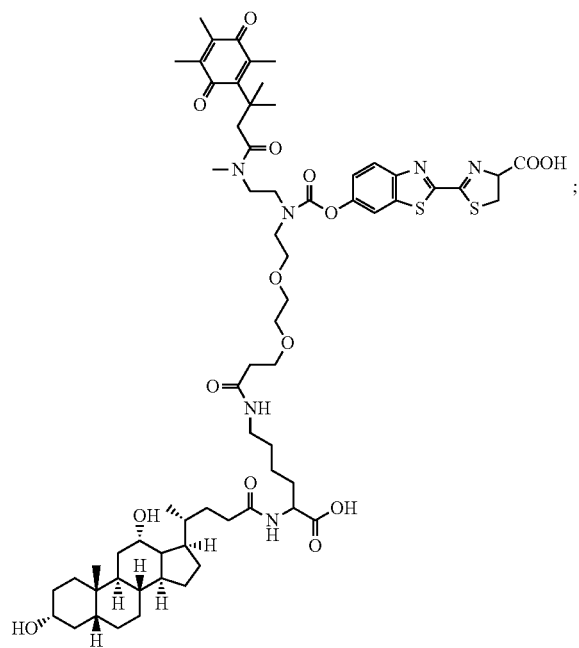

21
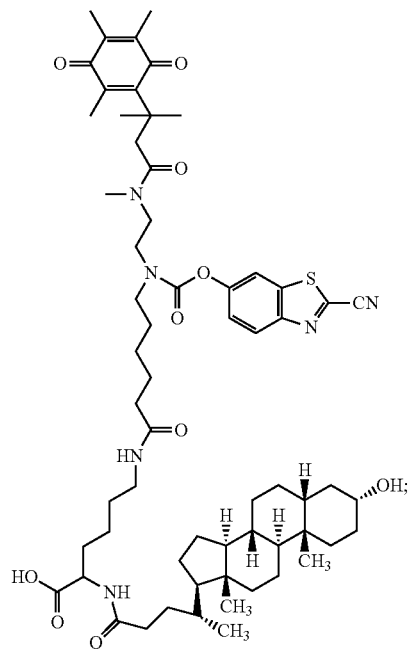
-continued
PBI 5659
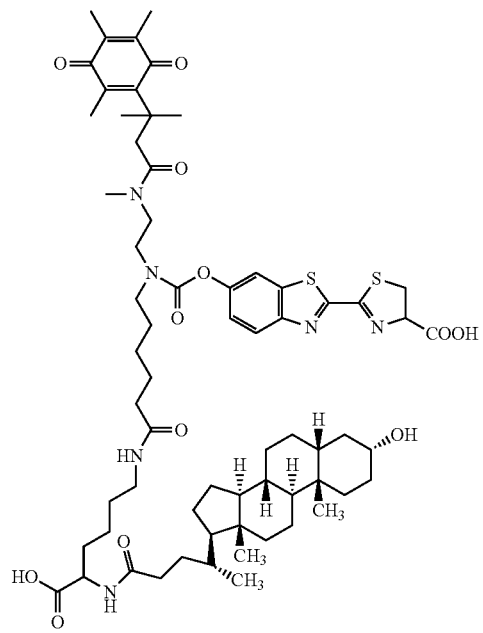
PBI 5663
PBI 5652
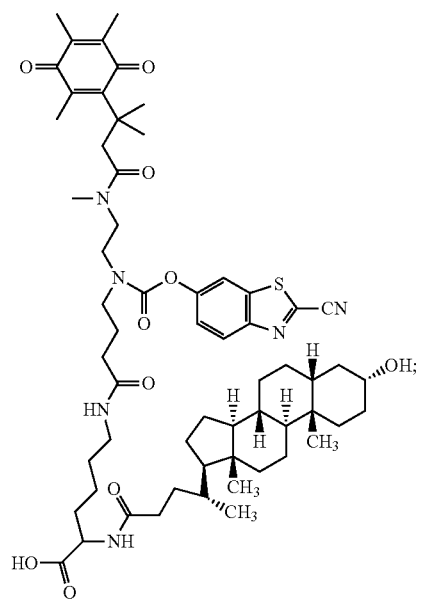
PBI 5669
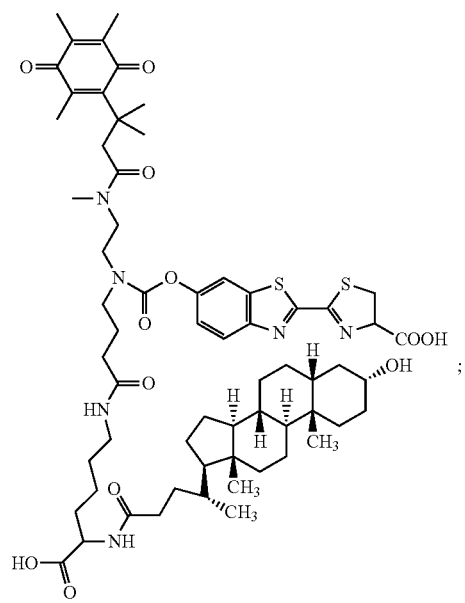

PBI 5653
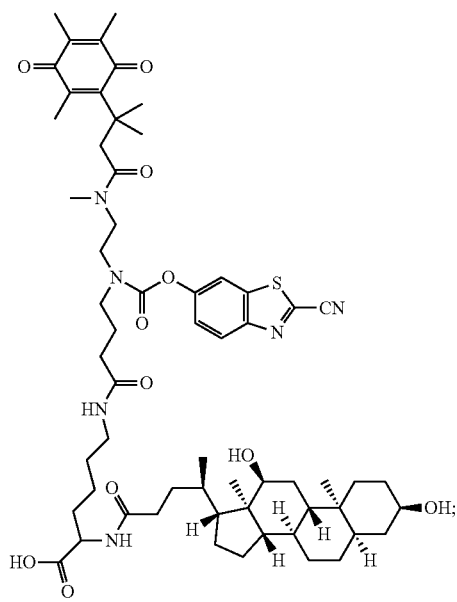
PBI 5656
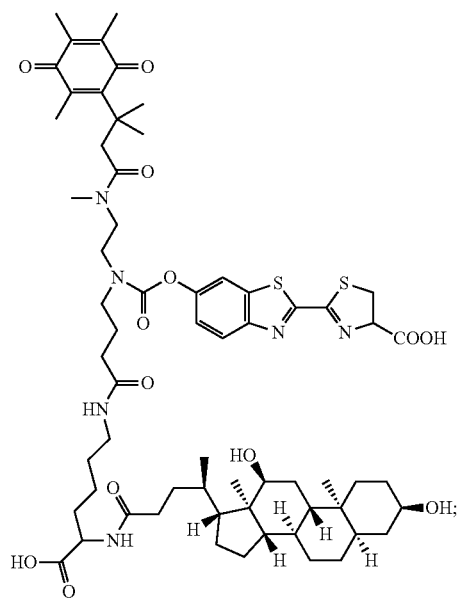
PBI 5660
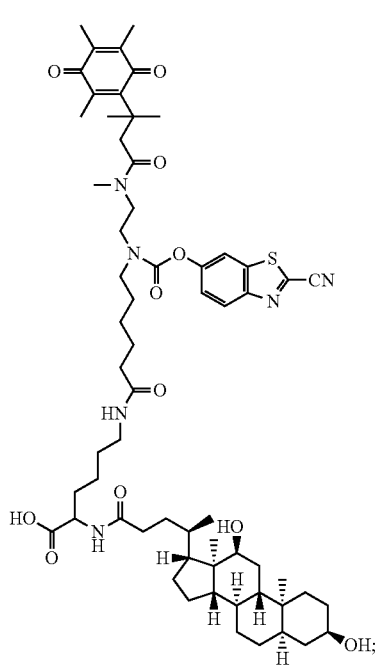
PBI 5664
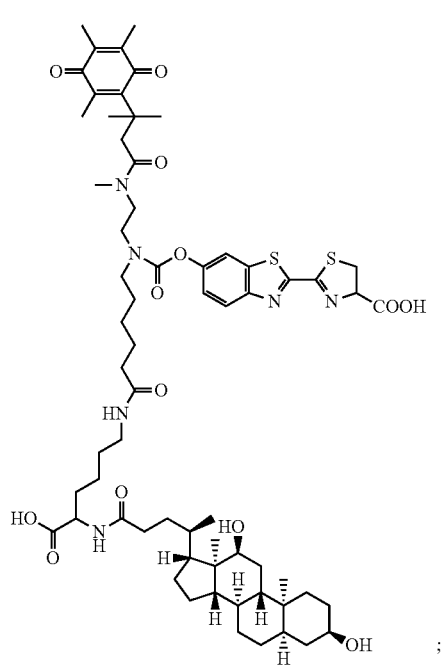

-continued
PBI 5667
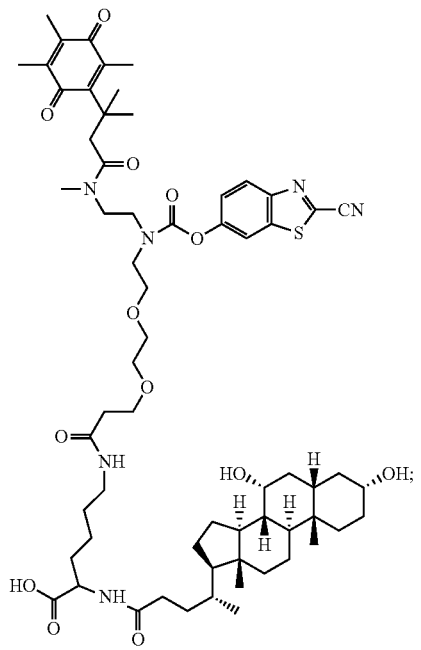
PBI 5650
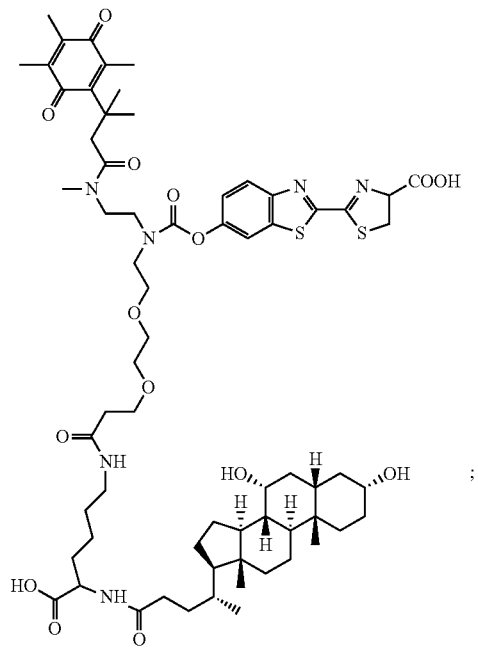
PBI 5654
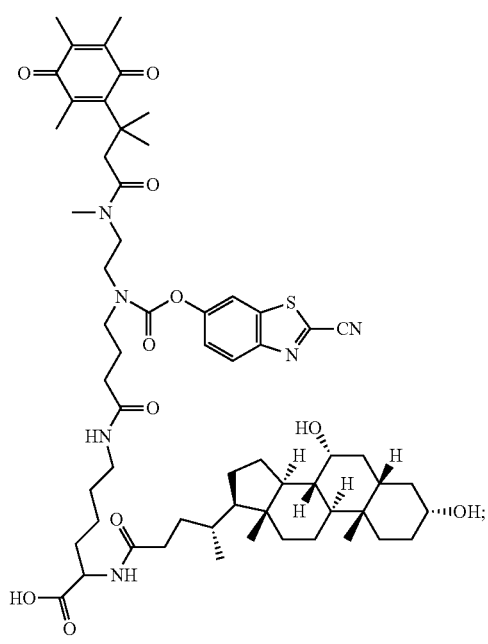
PBI 5655
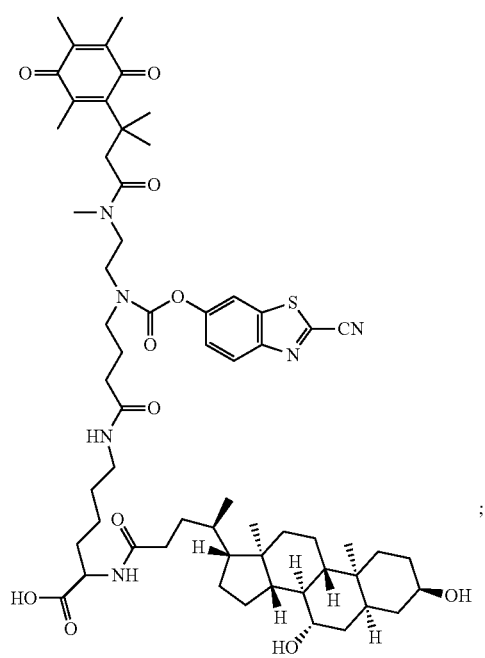

-continued
PBI 5661
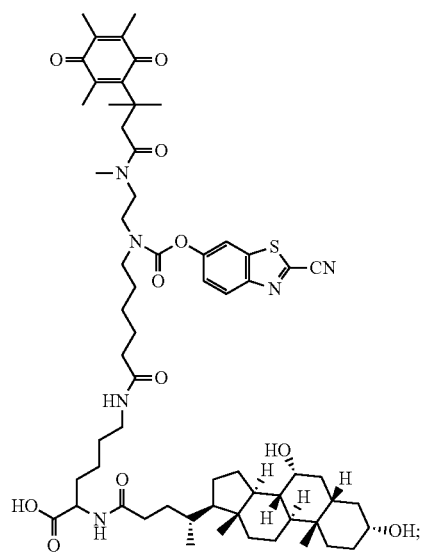
PBI 5662
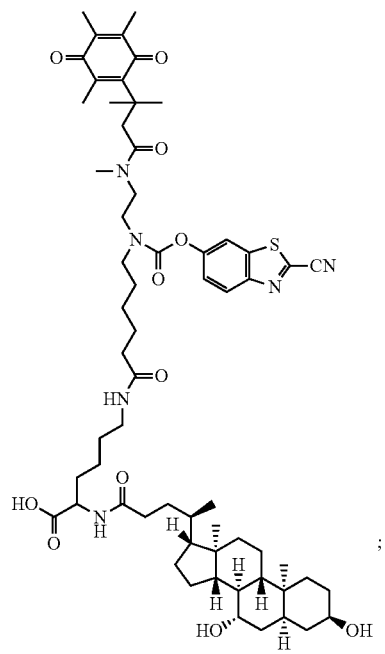
PBI 5824
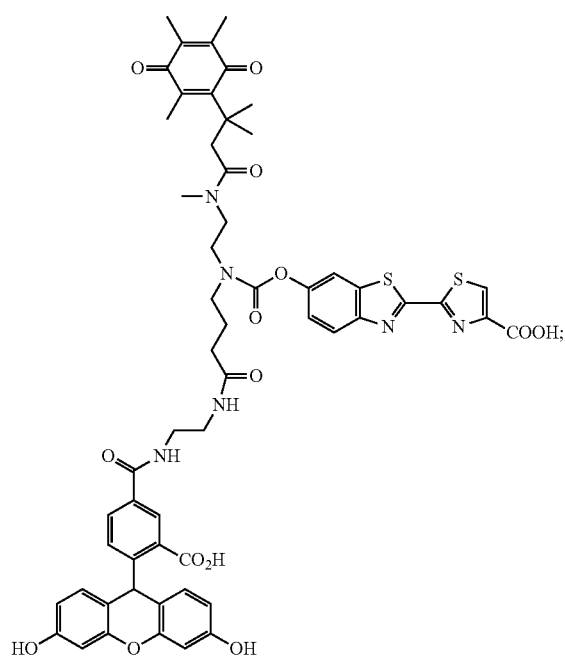
PBI 5830
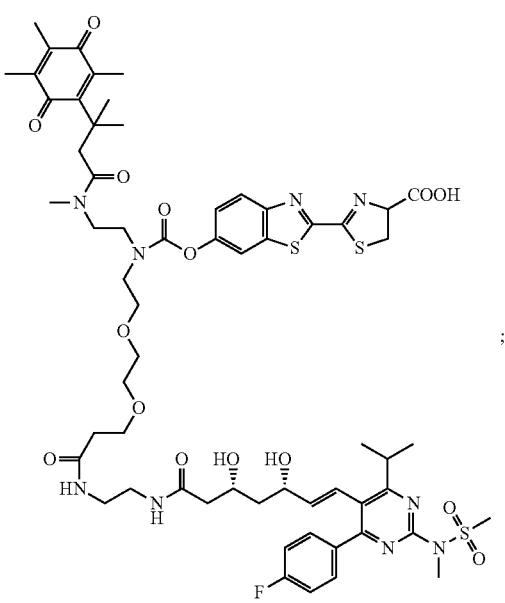

-continued
PBI 5831
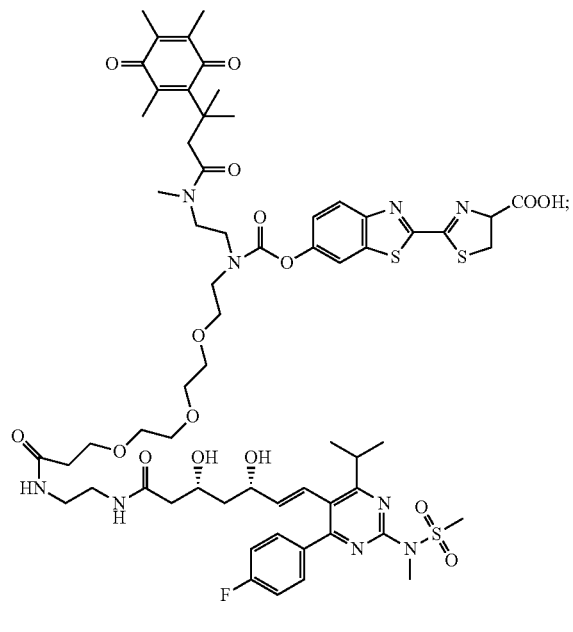
PBI 5827
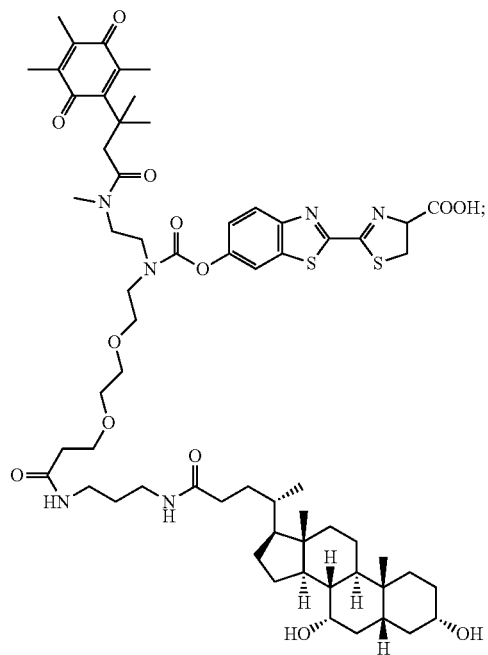
PBI 5828
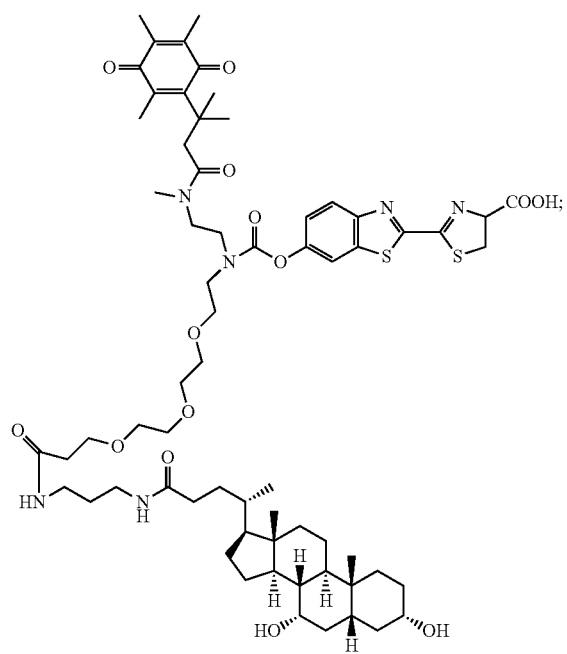

-continued
PBI 5829
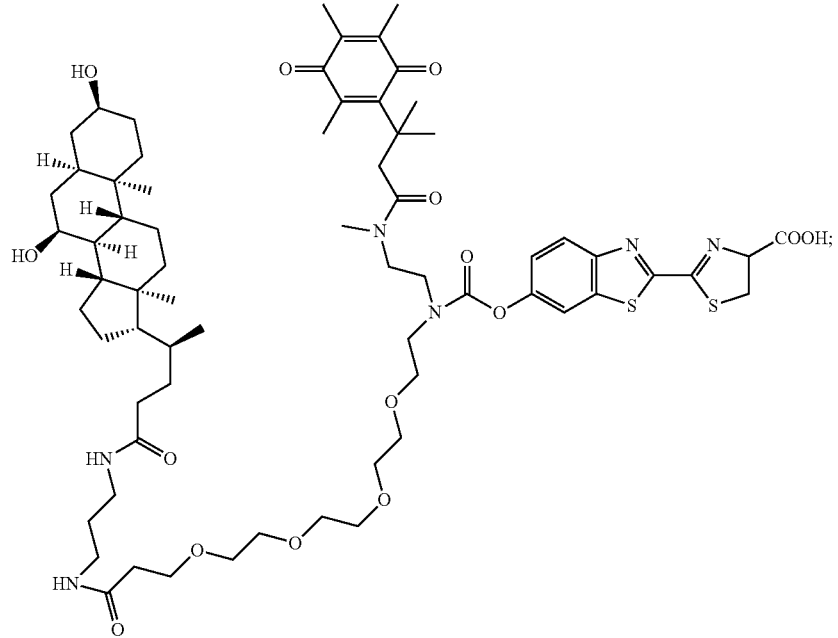
PBI 5832
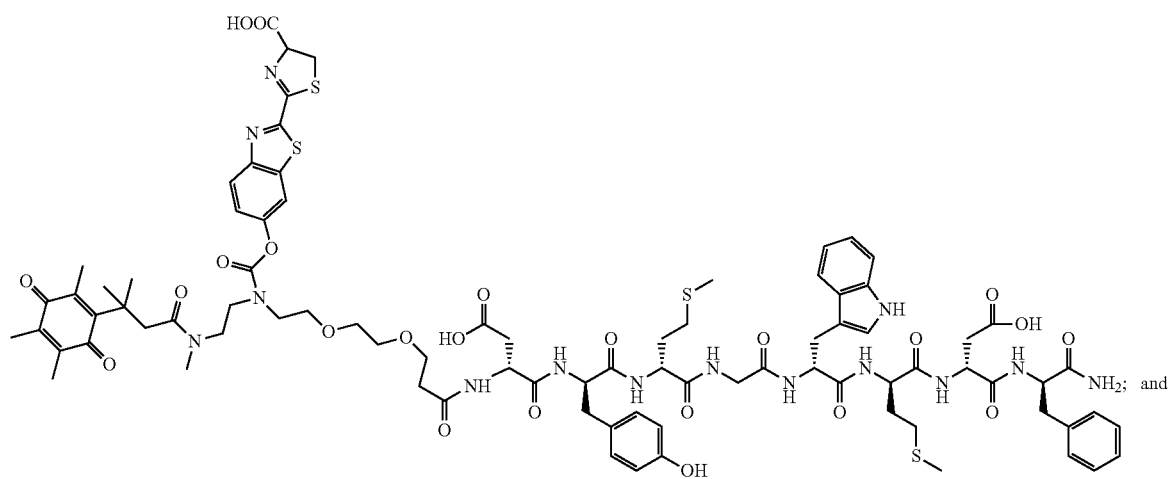

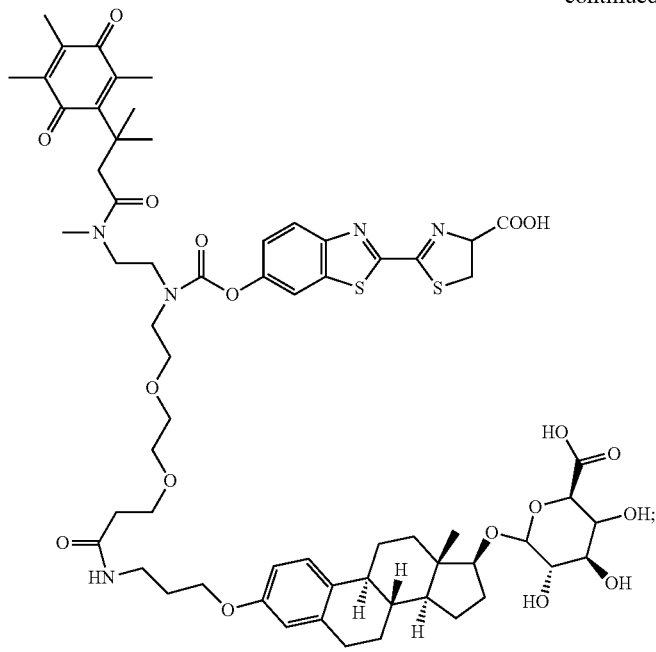

or a salt thereof.

In certain embodiments, the reporter moiety is a bioluminescent or fluorescent reporter moiety. In certain embodiments, the bioluminescent reporter moiety is a luciferin, a luciferin derivative or analog, or a luciferin precursor analog, coelenterazine or a coelenterazine derivative or analog.

In other aspects, disclosed is a method for evaluating cellular uptake of an agent comprising: a) contacting a sample comprising cells with a labeled agent, wherein the labeled agent is derived from an agent and a compound of formula (I); and b) detecting light emission, whereby the detection of light emission indicates cellular uptake of the agent.

In certain embodiments, the compound is a prosubstrate for luciferase or an alternative pre-prosubstrate that does not react with luciferase.

In certain embodiments, the light emission is fluorescence or luminescence.

In certain embodiments, the light emission is luminescence, and the cell comprises a luciferase.

In certain embodiments, the light emission is detected in the cell, outside the cell, e.g., in the cell medium or in a biological fluid, e.g., bodily fluid, e.g., blood, urine, etc.

In certain embodiments, the compound that does not react with luciferase fluoresces in the cell.

In certain embodiments, the agent is a biological agent or a non-biological agent.

In certain embodiments, the agent is selected from the group consisting of a protein, a nucleic acid, a lipid, a sugar, a therapeutic drug, a small molecule, a nanoparticle, antibody, and any combination thereof.

In certain embodiments, the protein is an antibody or a lipoprotein.

In certain embodiments, the cell is a eukaryotic cell.
In certain embodiments, the cell is a prokaryotic cell.
In certain embodiments, the cell is in an animal.
In certain embodiments, the cell is growing in culture medium.
In certain embodiments, the cell is a live cell.

In certain embodiments, the cell expresses a luciferase enzyme.

In another aspect, disclosed is a labeled agent derived from an agent and a compound according to formula (I).

In certain embodiments, the compound in a cell is a substrate for luciferase or an alternative substrate that does not react with luciferase.

In other aspects, disclosed is a kit comprising a compound of formula (I), an agent, a labeled agent derived from an agent and a compound according to formula (I), or any combination thereof.

In certain embodiments, the compound is a prosubstrate for luciferase.

In certain embodiments, the kit further comprises a detection reagent. The detection reagent may comprise a luciferase enzyme.

The compounds, compositions, methods, and processes are further described herein.

DETAILED DESCRIPTION

Figure 1:
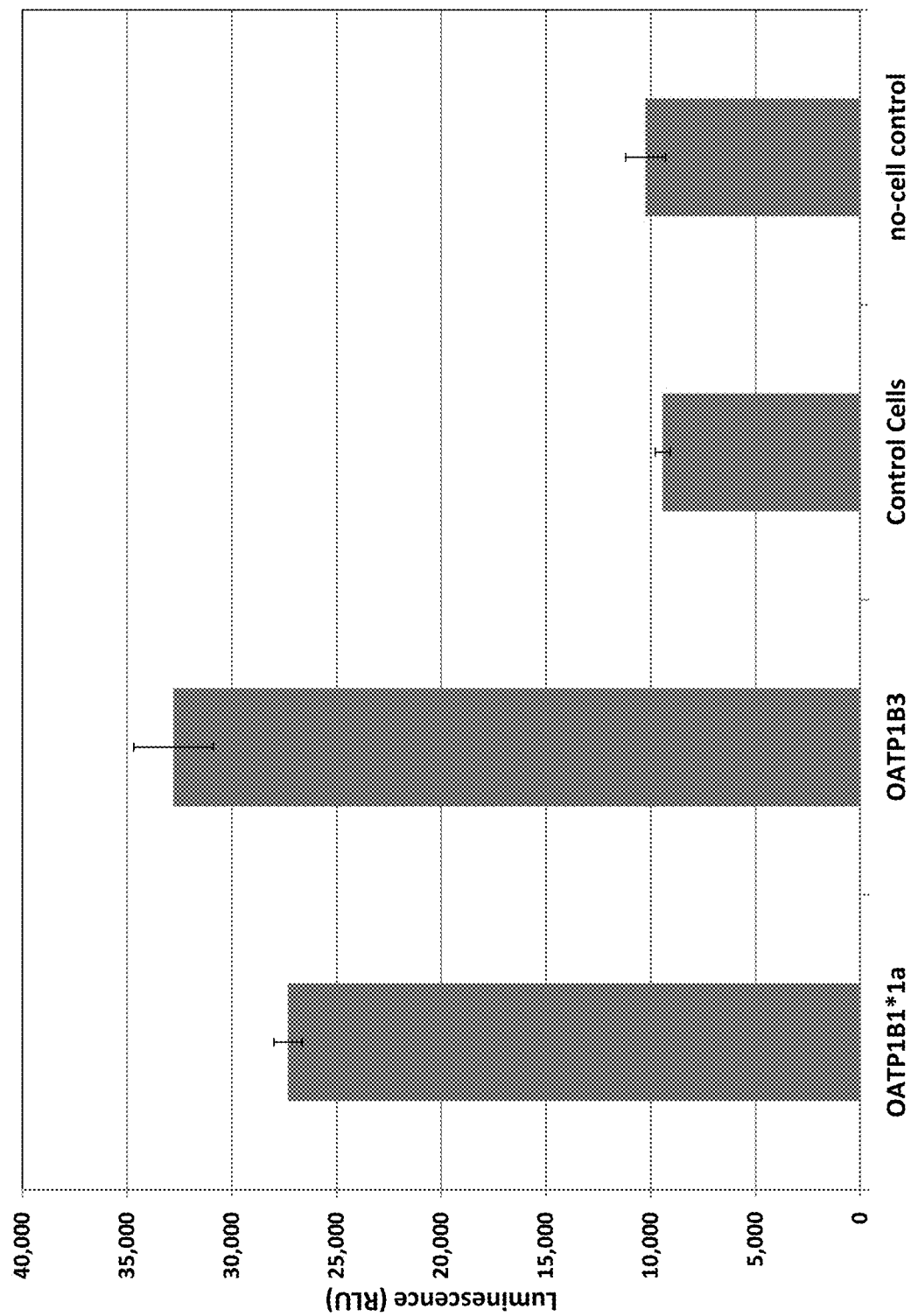
FIG. 1 shows the transporter assay with PBI-5651.
Figure 2:
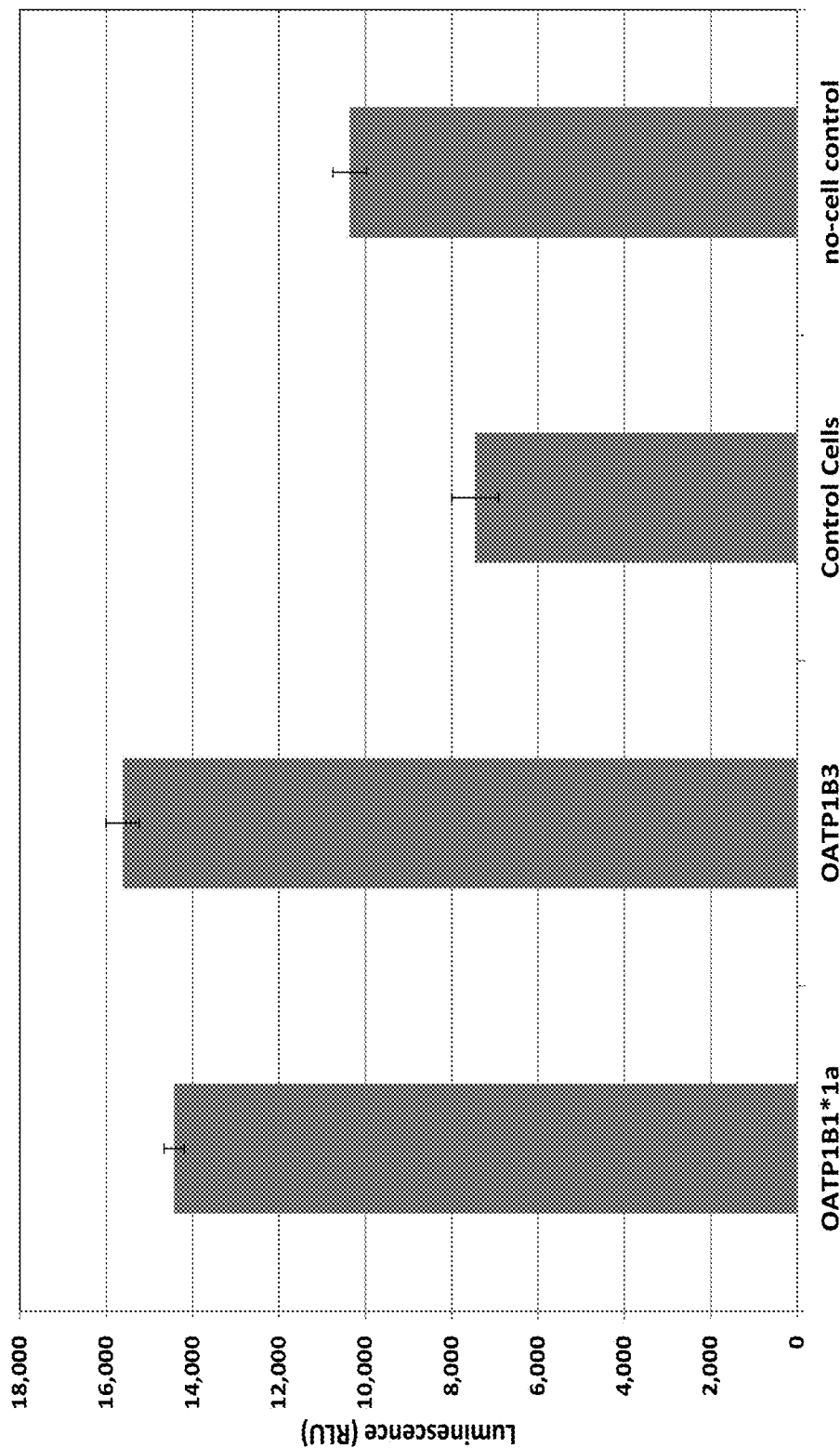
FIG. 2 shows the transporter assay with PBI-5648.
Figure 3:
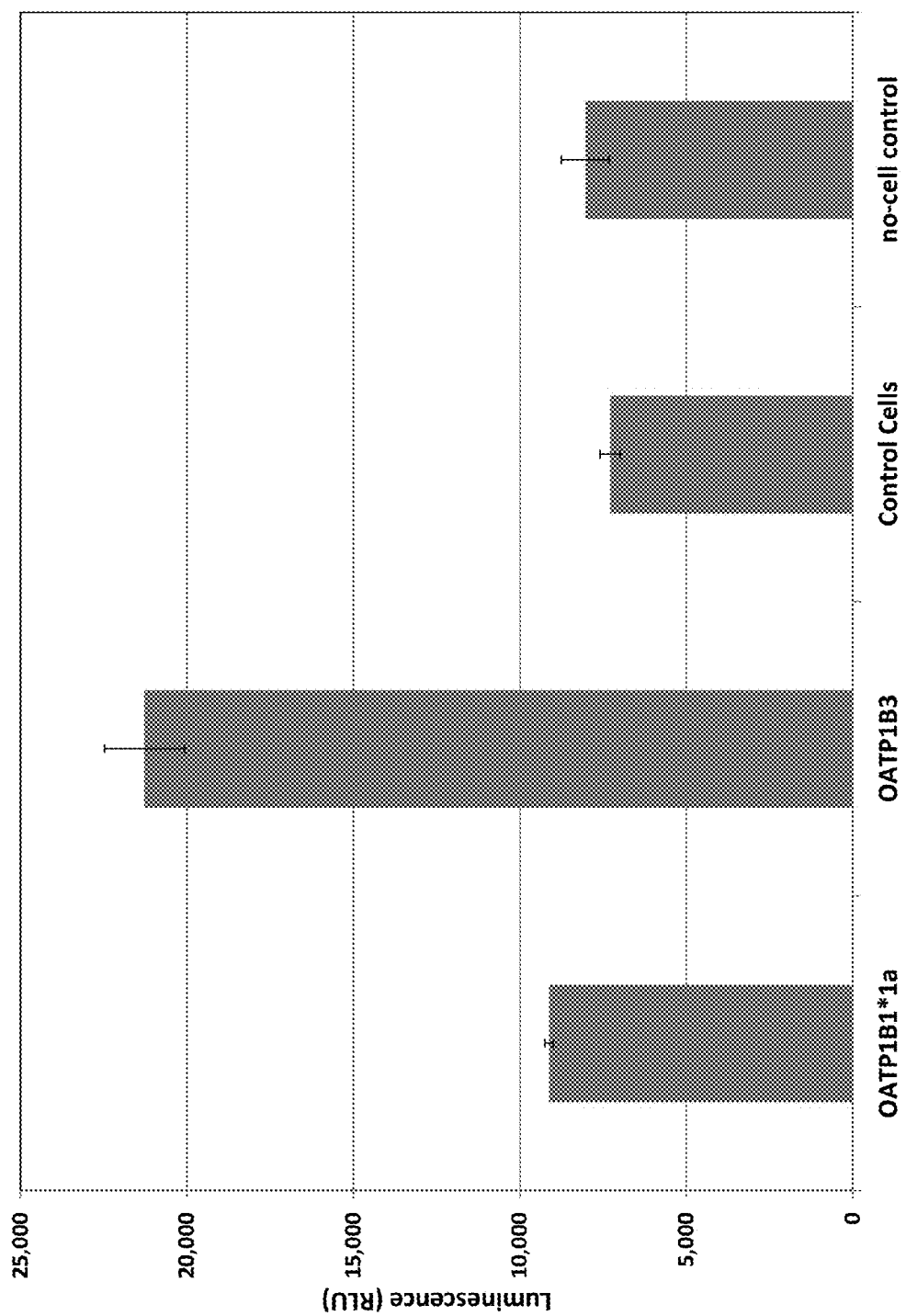
FIG. 3 shows the transporter assay with PBI-5657.
Figure 4:
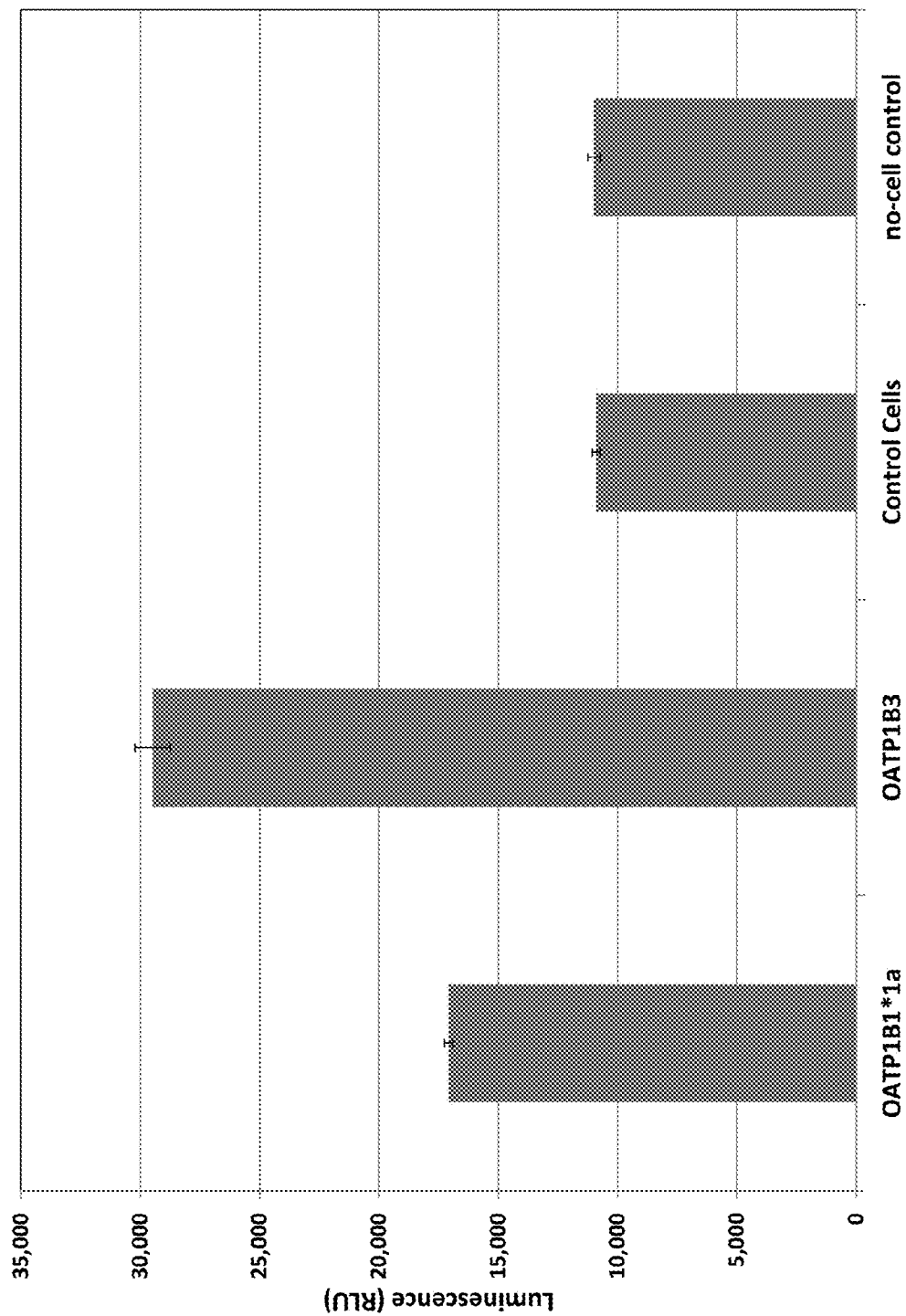
FIG. 4 shows the transporter assay with PBI-5658.
Figure 5:
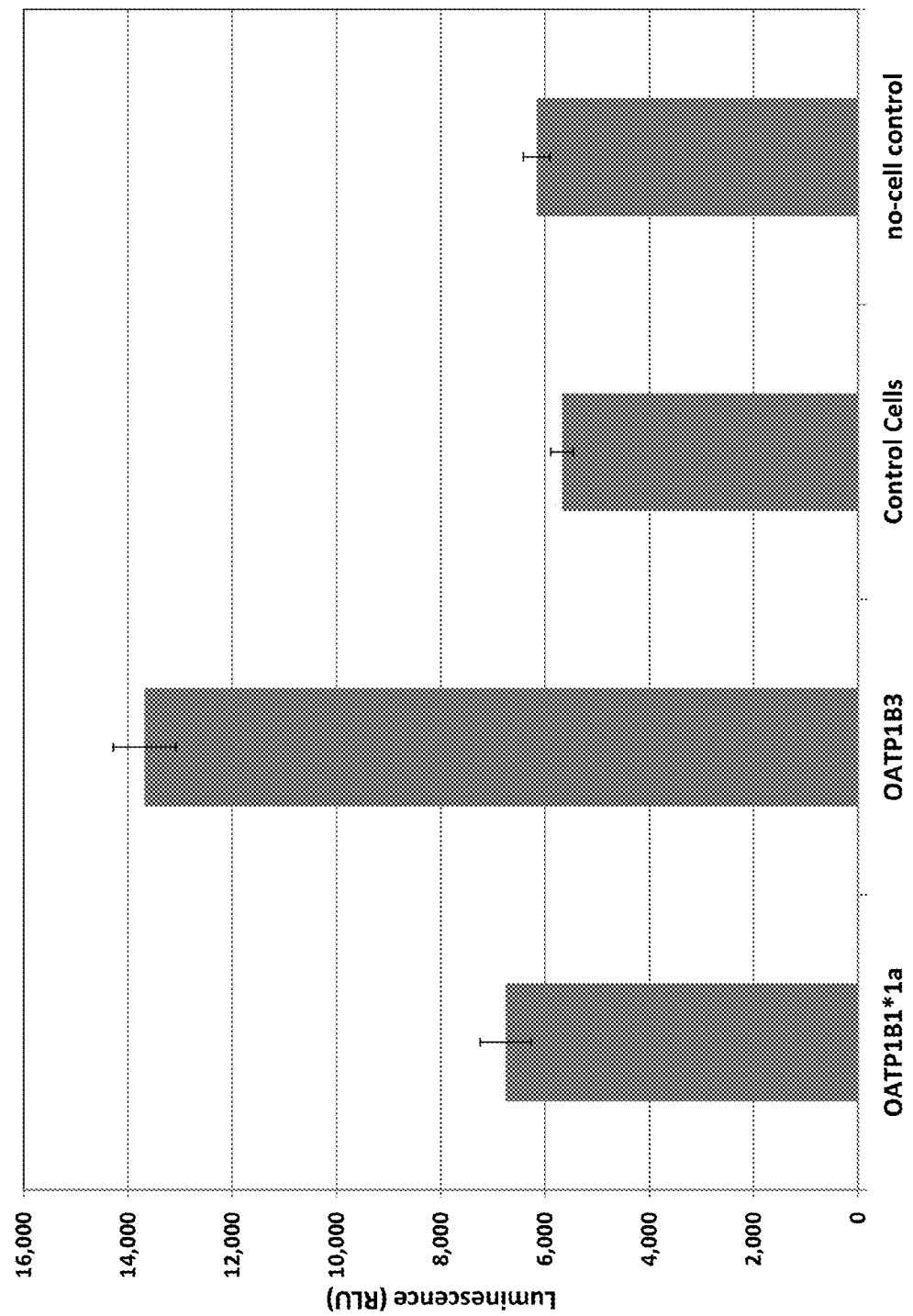
FIG. 5 shows the transporter assay with PBI-5665.
Figure 6:
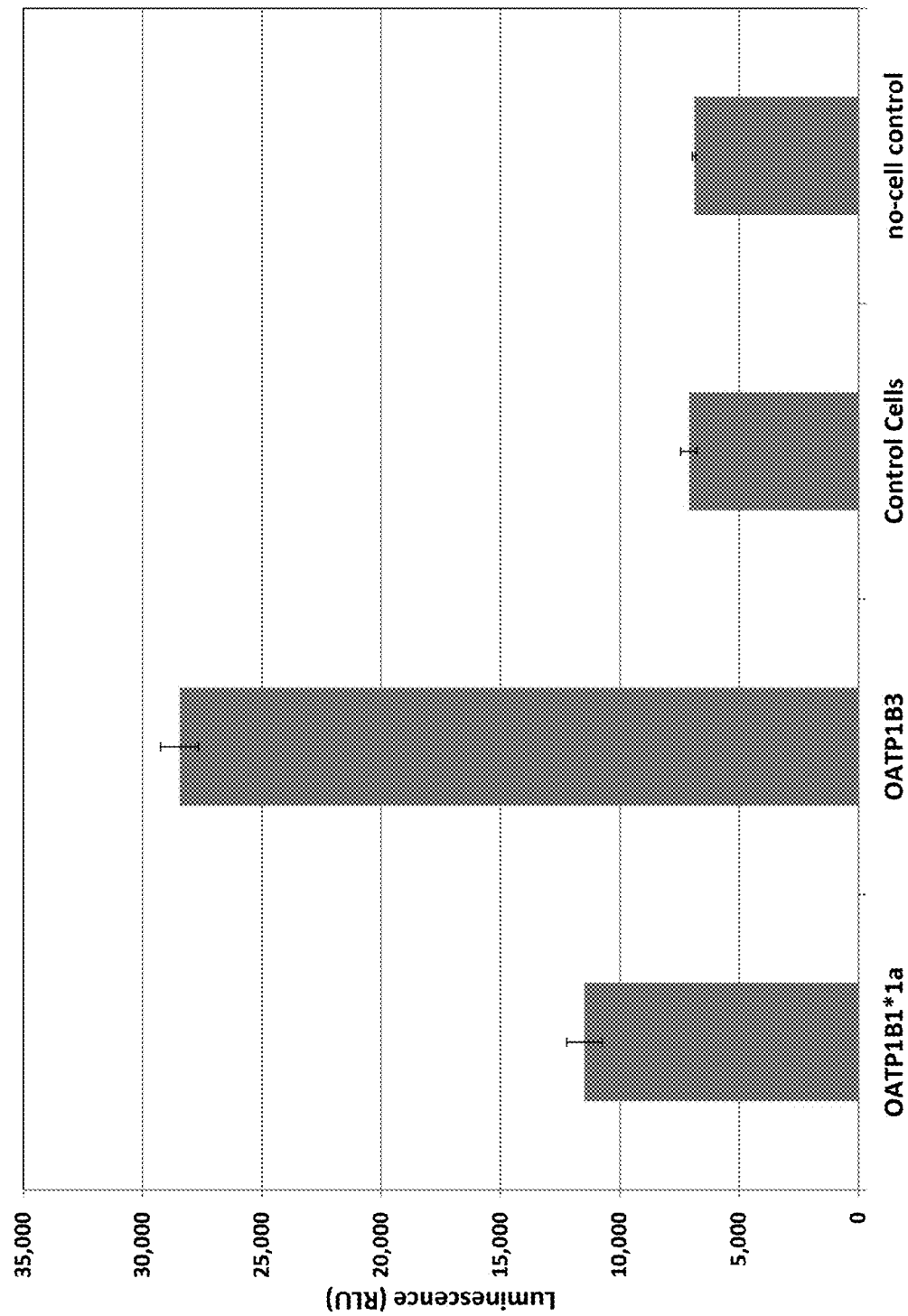
FIG. 6 shows the transporter assay with PBI-5666.
Figure 7:
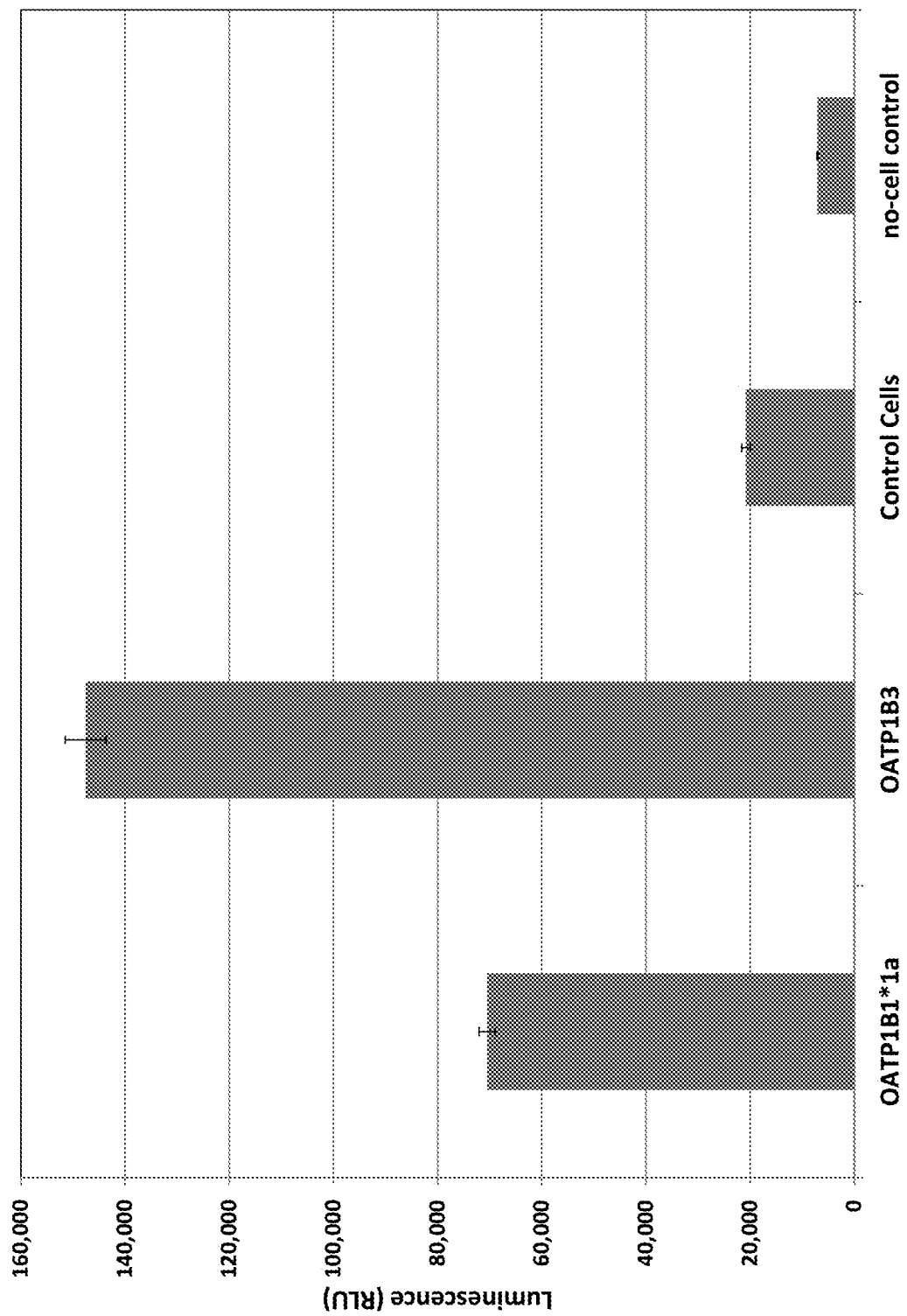
FIG. 7 shows the transporter assay with PBI-5824
Figure 8:
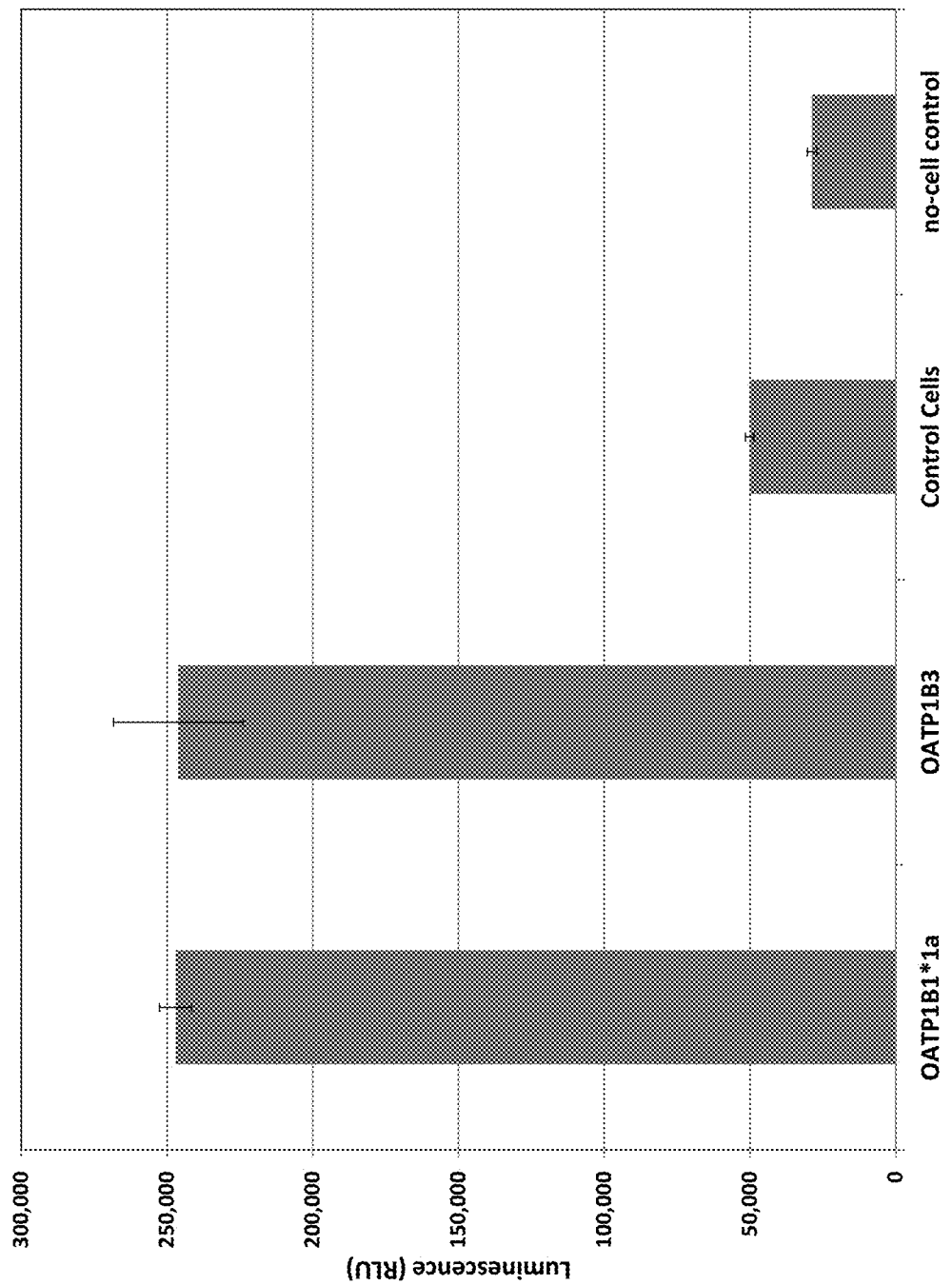
FIG. 8 shows the transporter assay with PBI-5684.
Figure 9:
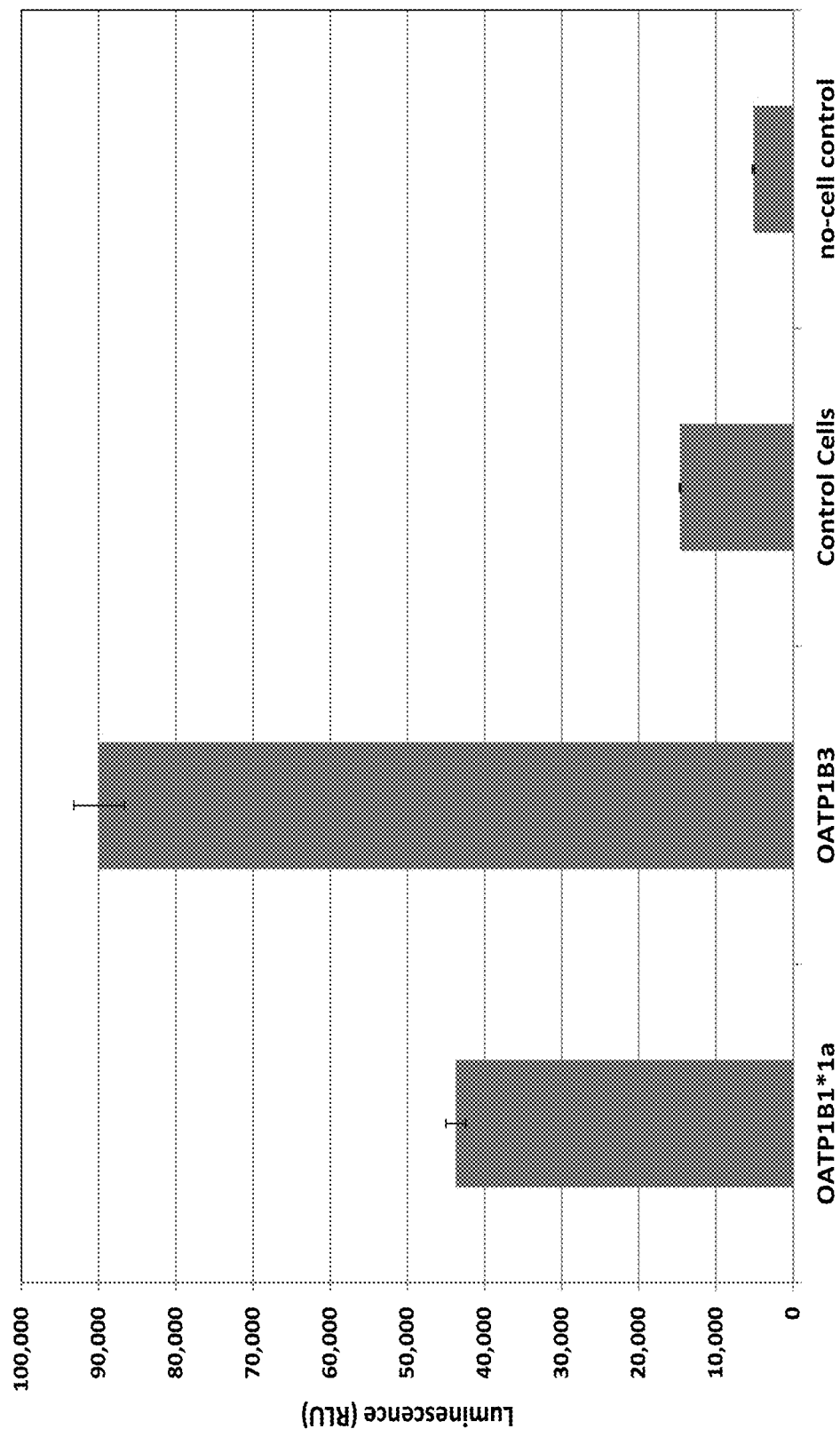
FIG. 9 shows the transporter assay with PBI-5825.
Figure 10:
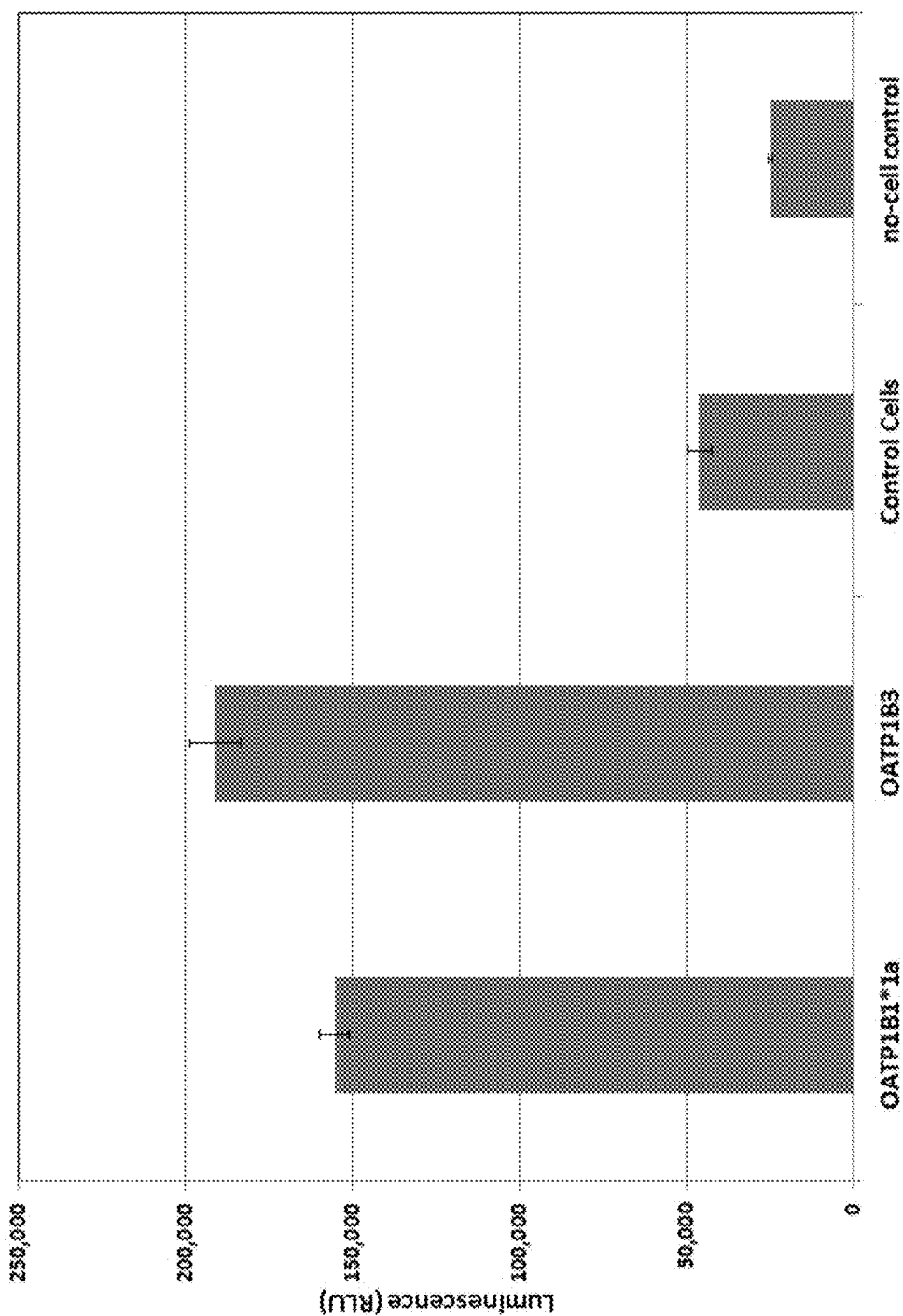
FIG. 10 shows the transporter assay with PBI-5683.
Figure 11:
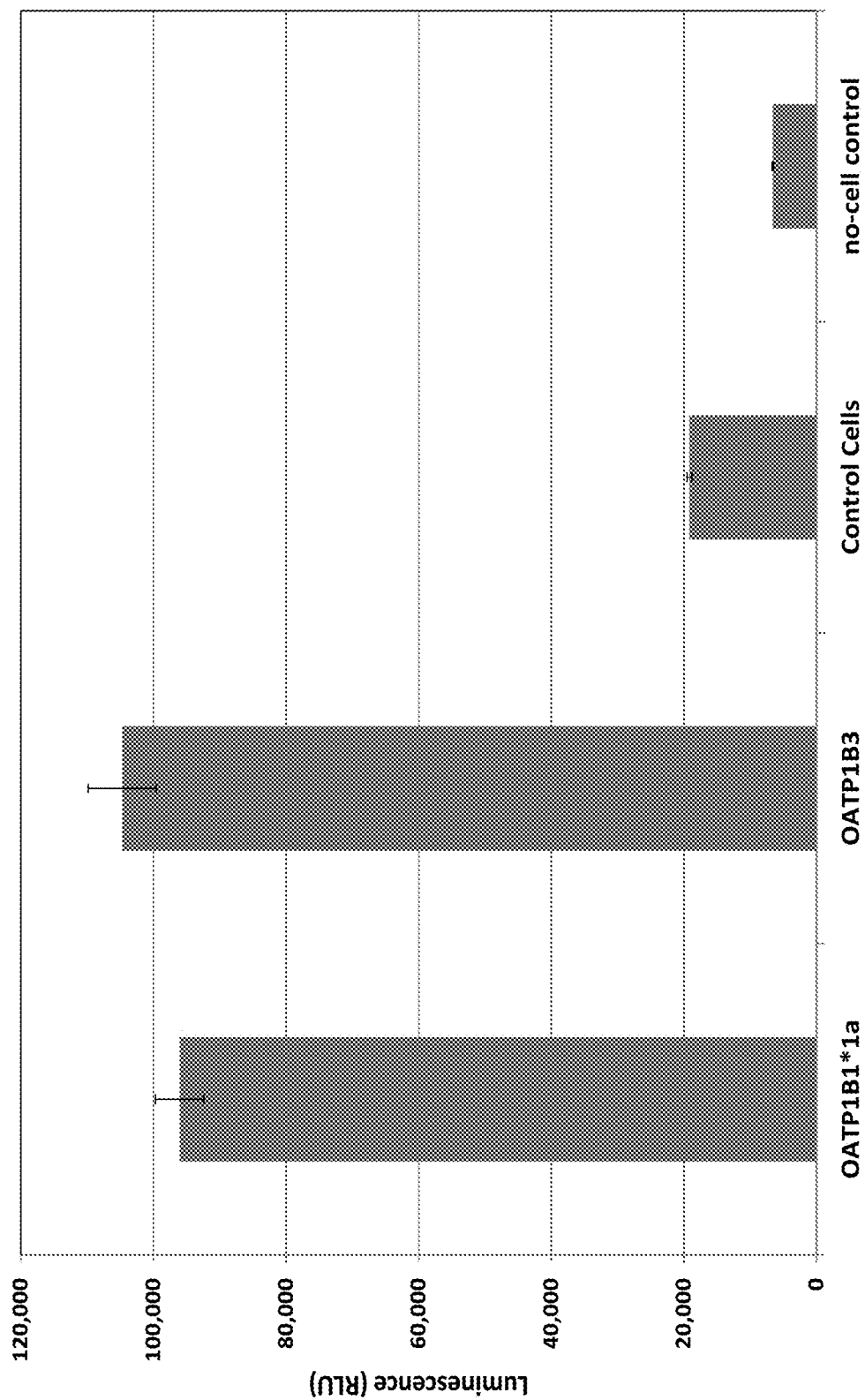
FIG. 11 shows the transporter assay with PBI-5826.
Figure 12:
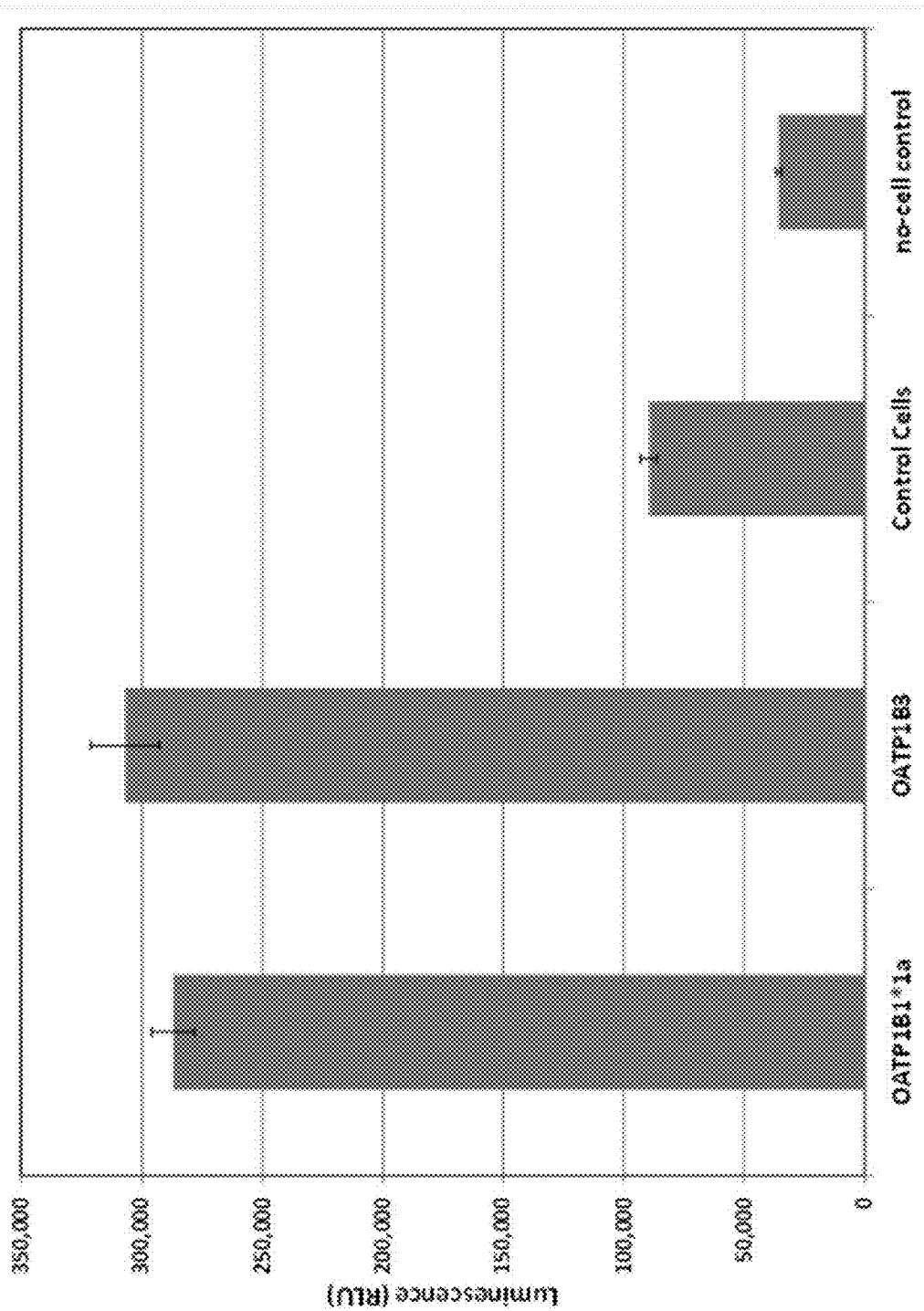
FIG. 12 shows the transporter assay with PBI-5682.

Disclosed herein are quinone-masked probes including fluorophores and/or luminophores. The compounds can be used as labeling reagents for cell uptake measurements. These labeling reagents can be broadly used to label a variety of targets of interest such as peptides, proteins including but not limited to antibodies or low density lipoproteins (LDL), nucleotides, sugars, lipids, specific substrates for transporters, or nanoparticles and microsomes including but not limited to drug carriers. The labeling reagents may also be used to label detergents. Upon uptake of labeled targets of interest by cells, quinone can be reduced by intracellular reduction potential to release the fluorophore or luminophore. The intensity of fluorescence or luminescence can be correlated to the amount of the target(s) of interest taken up by cells. Also disclosed are labeled agents.

The disclosed labeling reagents and labeled agents have multiple advantages over current techniques: they allow for either imaging or plate-based detection; they are less sensitive to extracellular reductants (e.g. free thiols, DTT, GSH); they avoid the need for fixed cells; and no washing step is required opposed to traditional isotope and fluorescence methods.

1. DEFINITION OF TERMS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The present disclosure also contemplates other embodiments "comprising," "consisting of" and "consisting essentially of," the embodiments or elements presented herein, whether explicitly set forth or not.

As used herein, the term "suitable substituent" is intended to mean a chemically acceptable functional group e.g., a moiety that does not negate the activity of the inventive compounds. Illustrative examples of suitable substituents include, but are not limited to halo groups, perfluoroalkyl groups, perfluoroalkoxy groups, alkyl groups, alkenyl groups, alkynyl groups, hydroxy groups, halo groups, oxo groups, mercapto groups, alkylthio groups, alkoxy groups, nitro groups, azidealkyl groups, aryl or heteroaryl groups, aryloxy or heteroaryloxy groups, aralkyl or heteroaralkyl groups, aralkoxy or heteroaralkoxy groups, HO—(C=O)— groups, heterocyclic groups, cycloalkyl groups, amino groups, alkyl- and dialkylamino groups, carbamoyl groups, alkylcarbonyl groups, alkylcarbonyloxy groups, alkoxycarbonyl groups, alkylaminocarbonyl groups, dialkylamino carbonyl groups, arylcarbonyl groups, aryloxycarbonyl groups, alkylsulfonyl groups, arylsulfonyl groups and the like. The substituents can be substituted by additional substituents.

As used herein, the term "alkenyl" refers a straight or branched hydrocarbon chain containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl. Alkenyl groups of the present invention may be unsubstituted or substituted by one or more suitable substituents, preferably 1 to 3 suitable substituents, as defined above.

As used herein, the term "alkoxy" refers to an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

As used herein, the term "alkoxyalkoxy" refers to an alkoxy group, as defined herein, appended to the parent molecular moiety through another alkoxy group, as defined herein. Representative examples of alkoxyalkoxy include, but are not limited to, tert-butoxymethoxy, 2-ethoxyethoxy, 2-methoxyethoxy, and methoxymethoxy.

As used herein, the term "alkoxyalkyl" refers to an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

As used herein, the term "alkoxycarbonyl" refers to an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

As used herein, the term "alkyl" refers to a linear or branched hydrocarbon radical, preferably having 1 to 30 carbon atoms, 1 to 10 carbon atoms, 1 to 6 carbon atoms, or 1 to 4 carbon atoms. The term "$C_1$-$C_6$-alkyl" is defined to include alkyl groups having 1, 2, 3, 4, 5, or 6 carbons in a linear or branched arrangement. For example, "$C_1$-$C_6$-alkyl" specifically includes methyl, ethyl, n-propyl, i-propyl, n-butyl, t-butyl, i-butyl, pentyl, and hexyl. Alkyl groups of the present invention may be unsubstituted or substituted by one or more suitable substituents, preferably 1 to 3 suitable substituents, as defined above.

As used herein, the term "alkylamino" refers to an alkyl group, as defined herein, appended to the parent molecular moiety through an amino group, as defined herein. Representative examples of alkylamino include, but are not limited to, methylamino, ethylamino, and sec-butylamino.

As used herein, the term "alkylaminoalkyl" refers to an alkyl group, as defined herein, appended to the parent molecular moiety through an aminoalkyl group, as defined herein. Representative examples of alkylaminoalkyl groups include, but are not limited to, methylaminoethyl and methylamino-2-propyl.

As used herein, the term "alkylcarbonyl" refers to an alkyl group appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

As used herein, the term "alkylcarbonylalkoxy" refers to an alkylcarbonyl group, as defined herein, appended to the parent molecular moiety through an alkoxy group, as defined herein. Representative examples of alkylcarbonylalkoxy include, but are not limited to, 3-oxopentyloxy, 3-oxobutoxy and 2-oxopropoxy.

As used herein, the term "alkylcarbonylalkoxyalkyl" refers to an alkylcarbonylalkoxy group, as defined herein, appended to the parent molecular moiety through an alkyl group.

As used herein, the term "alkylcarbonyloxy" refers to an alkylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy.

As used herein, the term "alkynyl" refers to a straight or branched hydrocarbon radical having 2, 3, 4, 5, 6, 7, 8, 9 or 10 carbons, and having one or more carbon-carbon triple bonds. Alkynyl groups of the present invention include, but are not limited to, ethynyl, propynyl, and butynyl. Alkynyl groups of the present invention may be unsubstituted or substituted by one or more suitable substituents, preferably 1 to 3 suitable substituents, as defined above.

As used herein, the term "amidoalkyl" refers to an amide group, appended to the parent molecular moiety through an alkyl group as defined herein. The term amidoalkyl includes —CH$_2$CONH$_2$; —CH$_2$CH$_2$CONH$_2$; —CH$_2$CH$_2$CH$_2$CONH$_2$ and the like.

As used herein, the term "amino" refers to an —NH$_2$ group.

As used herein, the term "amino acid" refers to both natural and unnatural amino acids. It also includes protected natural and unnatural amino acids.

As used herein, the term "aminoalkyl" refers to at least one amino group, as defined herein, appended to the parent molecular moiety through an alkyl group, as defined herein. Representative examples of aminoalkyl include, but are not limited to, aminomethyl, 2-aminoethyl, and 2-aminopropyl.

As used herein, the term "aryl" means monocyclic, bicyclic, or tricyclic aromatic radicals. Representative examples of the aryl groups include, but are not limited to, phenyl, dihydroindenyl, indenyl, naphthyl, dihydronaphthalenyl, and tetrahydronaphthalenyl. Aryl groups of the present invention may be optionally substituted by one or more suitable substituents, preferably 1 to 5 suitable substituents, as defined above.

As used herein, the term "arylalkyl" refers to an aryl group, as defined herein, appended to the parent molecular moiety through an alkyl group, as defined herein. Representative examples of arylalkyl include, but are not limited to, phenylmethyl and phenylethyl.

As used herein, the term "arylcarbonyl" refers to an aryl group, as defined herein, appended to the parent molecular moiety through a carbonyl group, as defined herein.

As use herein, the term "azide" refers to an —N=N$^+$=N$^-$(—N$_3$) group.

As used herein, the term "azidealkyl" or "azidoalkyl" refers to an azide group, as defined herein, appended to the parent molecular moiety through an alkyl group, as defined herein. Representative examples of azidealkyl include, but are not limited to, azidemethyl and azideethyl.

As used herein, the term "bioluminescence" or "luminescence" may refer to light produced as a result of a reaction between an enzyme and a substrate that generates light.

Examples of such enzymes (bioluminescent enzymes) include firefly luciferase, e.g. *Photinus pyralis* or *Photuris pennsylvanica*, click beetle luciferase, *Renilla* luciferase, cypridina luciferase, *Oplophorus* luciferase, e.g., *Oplophorous gracilirostris*, Aequorin photoprotein, obelin photoprotein and the like.

As used herein, the term "derivative" may refer to a compound that is derived from a similar compound by some chemical or physical process. The derivative is a compound of similar chemical structure. The derivative may be a structural analogue.

As used herein, the term "reporter moiety" may refer to a moiety that, under appropriate conditions directly or indirectly generates a detectable signal. Exemplary reporter moieties include, but are not limited to, fluorophores, luminescent molecules, dyes, radiolabels and substrates for enzymes such as luciferase. In some embodiments, a reporter moiety may indirectly generate a detectable signal, for example, when the reporter moiety is a substrate for an enzyme. The reaction of the enzyme with the substrate then produces a detectable signal such as fluorescence or luminescence. As used herein, the term "bioluminescent reporter moiety" may refer to a moiety that is a substrate for a luciferase. For example, the bioluminescent reporter moiety can be a luciferin, a luciferin derivative, e.g., pre-luciferin, aminoluciferin, quionolyl-luciferin, napthyl luciferin, fluorolucifeirn, chloroluciferin, precursors of luciferin derivatives, a coelenterazine or a coelenterazine derivative or analog, e.g., furimazine. The luminescent signal generated may be detected using a luminometer. As used herein, the term "fluorescent reporter moiety" may refer to a moiety that fluoresces. For example, the fluorescent reporter moiety may be a flurophore, such as coumarin, R110, fluoroscein, DDAO, resorufin, cresyl violet, sily xanthene, or carbopyronine. Fluorescence may be detected using a fluorometer.

As used herein, the term "carbonyl" or "(C=O)" (as used in phrases such as alkylcarbonyl, alkyl —(C=O)— or alkoxycarbonyl) refers to the joinder of the >C=O moiety to a second moiety such as an alkyl or amino group (i.e. an amido group). Alkoxycarbonylamino (i.e. alkoxy(C=O)—NH—) refers to an alkyl carbamate group. The carbonyl group is also equivalently defined herein as (C=O). Alkylcarbonylamino refers to groups such as acetamide.

As used herein, the term "carboxy" refers to a —C(O)—OH group.

As used herein, the term "carboxyalkoxyalkyl" refers to -alkyl-O-alkyl-CO$_2$H.

As used herein, the term "carboxyalkyl" refers to a carboxy group as defined herein, appended to the parent molecular moiety through an alkyl group as defined herein.

As used herein, the term "cycloalkyl" refers to a mono, bicyclic or tricyclic carbocyclic radical (e.g., cyclopropyl, cyclobutyl, cyclopentyl, cyclohexyl, cycloheptyl, cyclooctyl, cyclononyl, cyclopentenyl, cyclohexenyl, bicyclo[2.2.1]heptanyl, bicyclo[3.2.1]octanyl and bicyclo[5.2.0]nonanyl, etc.); optionally containing 1 or 2 double bonds. Cycloalkyl groups of the present invention may be unsubstituted or substituted by one or more suitable substituents, preferably 1 to 5 suitable substituents, as defined above.

As used herein, the term "di(alkyl)amino" refers to two independently selected alkyl groups, as defined herein, appended to the parent molecular moiety through an amino group, as defined herein. Representative examples of di(alkyl)amino include, but are not limited to, N,N-dimethylamino, N-ethyl-N-methylamino, and N-isopropyl-N-methylamino.

As used herein, the term "di(alkyl)aminoalkyl" refers to a di(alkyl)amino group, as defined herein, appended to the parent molecular moiety through an alkyl group, as defined herein. Representative examples of di(alkyl)aminoalkyl include, but are not limited to, N,N-dimethylaminoethyl and N,N-methyl(2-propyl)aminoethyl.

As used herein, the term "halogen" or "halo" refers to a fluoro, chloro, bromo or iodo radical.

As used herein, the term "haloalkoxy" refers to an alkoxy group, as defined herein, substituted by one, two, three, or four halogen atoms. Representative examples of haloalkoxy include, but are not limited to, chloromethoxy, 2-fluoroethoxy, trifluoromethoxy, and pentafluoroethoxy.

As used herein, the term "haloalkyl" refers to an alkyl group, as defined herein, substituted by one, two, three, or four halogen atoms. Representative examples of haloalkyl include, but are not limited to, chloromethyl, 2-fluoroethyl, trifluoromethyl, pentafluoroethyl, 2-chloro-3-fluoropentyl, and 4,4,4,-trifluorobutyl.

As used herein, the term "heteroaryl" refers to a monocyclic heteroaryl or a bicyclic heteroaryl. The monocyclic heteroaryl is a five- or six-membered ring. The five-membered ring contains two double bonds. The five-membered ring may contain one heteroatom selected from O or S; or one, two, three, or four nitrogen atoms and optionally one oxygen or sulfur atom. The six-membered ring contains three double bonds and one, two, three or four nitrogen atoms. Representative examples of monocyclic heteroaryl include, but are not limited to, furanyl, imidazolyl, isoxazolyl, isothiazolyl, oxadiazolyl, 1,3-oxazolyl, pyridinyl, pyridazinyl, pyrimidinyl, pyrazinyl, pyrazolyl, pyrrolyl, tetrazolyl, thiadiazolyl, 1,3-thiazolyl, thienyl, triazolyl, and triazinyl. The bicyclic heteroaryl includes a monocyclic heteroaryl fused to a phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Representative examples of bicyclic heteroaryl groups include, but are not limited to, benzofuranyl, benzothienyl, benzoxazolyl, benzimidazolyl, benzoxadiazolyl, 6,7-dihydro-1,3-benzothiazolyl, imidazo[1,2-a]pyridinyl, indazolyl, indolyl, isoindolyl, isoquinolinyl, naphthyridinyl, pyridoimidazolyl, quinazolinyl, quinolinyl, thiazolo[5,4-b]pyridin-2-yl, thiazolo[5,4-d]pyrimidin-2-yl, and 5,6,7,8-tetrahydroquinolin-5-yl. Heteroaryl groups of the present invention may be unsubstituted or substituted by one or more suitable substituents, preferably 1 to 5 suitable substituents, as defined above.

As used herein, the term "heterocycle" or "heterocyclyl" refers to a monocyclic heterocycle, a bicyclic heterocycle, or a tricyclic heterocycle. The monocyclic heterocycle is a three-, four-, five-, six-, seven-, or eight-membered ring containing at least one heteroatom independently selected from the group consisting of oxygen, nitrogen, phosphorus and sulfur. The three- or four-membered ring contains zero or one double bond, and one heteroatom selected from the group consisting of oxygen, nitrogen, phosphorus and sulfur. The five-membered ring contains zero or one double bond and one, two or three heteroatoms selected from the group consisting of oxygen, nitrogen, phosphorus and sulfur. The six-membered ring contains zero, one or two double bonds and one, two, or three heteroatoms selected from the group consisting of oxygen, nitrogen, phosphorus and sulfur. The seven- and eight-membered rings contains zero, one, two, or three double bonds and one, two, or three heteroatoms selected from the group consisting of oxygen, nitrogen, phosphorus and sulfur. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, phosphinane, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydropyrimidinyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, trithianyl, and 2,5-dioxo-pyrrolidinyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a bridged monocyclic heterocycle ring system in which two non-adjacent atoms of the ring are linked by an alkylene bridge of 1, 2, 3, or 4 carbon atoms, or an alkenylene bridge of two, three, or four carbon atoms. Representative examples of bicyclic heterocycles include, but are not limited to, benzopyranyl, benzothiopyranyl, chromanyl, 2,3-dihydrobenzofuranyl, 2,3-dihydrobenzothienyl, azabicyclo[2.2.1]heptyl (including 2-azabicyclo[2.2.1]hept-2-yl), 2,3-dihydro-1H-indolyl, isoindolinyl, octahydrocyclopenta[c]pyrrolyl, octahydropyrrolopyridinyl, 9-phosphabicyclo[3.3.1]nonane, 8-phosphabicyclo[3.2.1]octane, and tetrahydroisoquinolinyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non-adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but are not limited to, octahydro-2,5-epoxypentalene, hexahydro-2H-2,5-methanocyclopenta[b]furan, hexahydro-1H-1,4-methanocyclopenta[c]furan, aza-admantane (1-azatricyclo[3.3.1.1$^{3,7}$]decane), oxa-adamantane (2-oxatricyclo[3.3.1.1$^{3,7}$]decane), and 2,4,6-trioxa-8-phosphatricyclo[3.3.1.1$^{3,7}$]decane. Heterocyclic groups of the present invention may be unsubstituted or substituted by one or more suitable substituents, preferably 1 to 3 suitable substituents, as defined above. Heterocyclic groups of the present invention may be can contain one or more oxo groups (=O) or thioxo (=S) groups attached to the ring.

As used herein, the term "hydroxy" refers to an —OH group.

As used herein, the term "hydroxyalkoxy" refers to an alkoxy group, as defined herein, substituted by at least one hydroxy group. Representative examples of hydroxyalkoxy include, but are not limited to, hydroxyethoxy, and 2-hydroxypropoxy.

As used herein, the term "hydroxyalkyl" refers to an alkyl group, as defined herein, substituted by at least one hydroxy group. Representative examples of hydroxyalkyl include, but are not limited to, hydroxymethyl, 2-hydroxyethyl, 3-hydroxypropyl, 2,3-dihydroxypropyl, 2,3-dihydroxypentyl, 4-hydroxybutyl, 2-ethyl-4-hydroxyheptyl, 3,4-dihydroxybutyl, and 5-hydroxypentyl.

As used herein, the term "hydroxycarbonyl" refers to a hydroxy group, as defined herein, appended to the parent molecular moiety through a carbonyl group, as defined herein.

The term "linker" may refer to a chain of 2 to 50 atoms that link a substrate moiety to the parent molecular moiety. Linkers may include one or more heteroatoms. Linkers may also be substituted by oxo groups, amino groups, alkyl groups, halogens and nitro groups. Linkers may also contain aryl groups. The linkers may be "traceless" or "self-immolative" linkers. The term "traceless linker" or "self-immolative linker" refers to a linker wherein cleavage of the substrate moiety from the linker results in spontaneous cleavage of the linker from the parent molecular moiety.

The term "lower cycloalkyl" refers to a monovalent moiety obtained by removing a hydrogen atom from a hydrocarbon compound having from 3 to 6 carbon atoms. Examples of saturated lower cycloalkyl groups include, but are not limited to, groups such as cyclopropyl, cyclobutyl, cyclopentyl and cyclohexyl. Examples of unsaturated lower cycloalkyl groups which have one or more carbon-carbon double bonds include, but are not limited to, groups such as cyclopropenyl, cyclobutenyl, cyclopentenyl and cyclohexenyl.

The term "luminescent enzyme", "bioluminescent enzyme", or "luciferase" as used interchangeably herein refers to a class of oxidative enzymes used in bioluminescence wherein the enzyme produces and emits light when given a substrate. The luciferase may be a naturally occurring, recombinant or mutant luciferase that uses a luciferase substrate. The luciferase substrate may be luciferin, a luciferin derivative or analog, a preluciferin derivative or analog, a coelenterazine, or a coelenterazine derivative or analog. The luminescent enzyme, if naturally occurring, may be obtained easily by the skilled person from an organism. If the luminescent enzyme is one that occurs naturally or is a recombinant or mutant luminescent enzyme, e.g. one which retains activity in a luciferase-coelenterazine or luciferase-luciferin reaction of a naturally occurring luminescent enzyme, it can be obtained readily from a culture of bacteria, yeast, mammalian cells, insect cells, plant cells, or the like, transformed to express a nucleic acid encoding the luminescent enzyme. Further, the recombinant or mutant luminescent enzyme can be derived from an in vitro cell-free system using a nucleic acid encoding the luciferase. Suitable luminescent enzymes include luciferases derived from bioluminescent decapods, such as from the Oplophoroidea (e.g. *Oplophorus*-derived luciferases), beetle luciferases (e.g., *Photinus pyralis, Photuris pennsylvanica*, etc.), marine organisms such as cnidarians (e.g., *Renilla* luciferase), Aristeidae, Solenoceridae, Luciferidae, Sergestidae, Pasipheidae and Thalassocarididae decapoda families, copepod luciferases, such as *Gaussia* luciferase, such as *Gaussia princeps* luciferase, *Metridia* luciferases, such as *Metridia longa* and *Metridia pacifica* luciferases, *Vargula* luciferases, such as *Vargula hilgendorfii* luciferase, *Pleuromamma xiphias* luciferase, and photoproteins, such as Aequorin, and variants, recombinants, and mutants thereof.

A "luminescent reaction mixture" contains materials that will allow the luminescent enzyme to generate a light signal, i.e., luminescence. The mixture may also contain the enzyme, e.g., the luciferase enzyme or luciferase. The materials, and the particular concentrations and/or amounts, needed to generate a luminescent signal will vary depending on the luminescent enzyme used as well as the type of assay being performed. Often other materials will be added to the solution including: a buffer to maintain the reaction at the proper pH, an additive such as PRIONEX or Bovine serum albumin (BSA) to help maintain enzyme activity, reducing agents, detergents, etc.

As used herein, the term "methylenedioxy" refers to a —OCH$_2$O— group wherein the oxygen atoms of the methylenedioxy are attached to the parent molecular moiety through two adjacent carbon atoms.

As used herein, the term "natural amino acid" refers to any one of the common, naturally occurring L-amino acids found in proteins, including glycine (Gly), alanine (Ala), valine (Val), leucine (Leu), isoleucine (Ile), lysine (Lys), arginine (Arg), histidine (His), proline (Pro), serine (Ser), threonine (Thr), phenylalanine (Phe), tyrosine (Tyr), tryptophan (Trp), aspartic acid (Asp), glutamic acid (Glu), asparagine (Asn), glutamine (Gln), cysteine (Cys) and methionine (Met).

As used herein, the term "unnatural amino acid" refers to all amino acids which are not natural amino acids as described above. Such amino acids include the D-isomers of any of the 20 naturally occurring amino acids described above. Unnatural amino acids also include homoserine, ornithine, norleucine, and thyroxine. Additional unnatural amino acids are well known to one of ordinary skill in the art. An unnatural amino acid may be a D- or L-isomer. An unnatural amino acid may also be an alpha amino acid or a beta amino acid. An unnatural amino acid may also be a post-translationally modified amino acid, such as a phosphorylated serine, threonine or tyrosine, an acylated lysine, or an alkylated lysine or arginine. Many forms of post-translationally modified amino acids are known.

As used herein, the term "protected amino acid," refers to an amino acid side chain as described above which additionally contains a protected functional group. Protecting groups are well known in the art and are intended to protect such functional groups as amino, hydroxy, thio or carboxy against undesirable reactions during synthetic procedures. The protecting groups may be removed by a chemical reaction following the synthesis. Examples of protected amino acid side chains include benzyloxymethyl derived from serine, (4-methoxyphenyl)methyl derived from tyrosine, and tert-butylpropanoate derived from glutamate.

As used herein, the term "amino acid side chain," refers to the group attached to the α-carbon of an amino acid. It is the characterizing portion of an amino acid and is derived from a corresponding amino acid by elimination of the NH$_2$CHC(O)OH moiety. For example, the amino acid side chain of alanine is methyl, and the amino acid side chain of phenylalanine is phenylmethyl. An amino acid side chain may be a natural amino acid side chain or an unnatural amino acid side chain. In some embodiments, an amino acid side chain may be a protected amino acid side chain.

As used herein, the term "amino protecting group," refers to a moiety that prevents chemical reactions from occurring on the nitrogen atom to which that protecting group is attached. An amino protecting group must also be removable by a chemical reaction. Such groups are well known in the art and include those described in detail in Protecting Groups in Organic Synthesis, T. W. Greene and P. G. M. Wuts, 3$^{rd}$ edition, John Wiley & Sons, 1999, the entirety of which is incorporated herein by reference. Suitable amino protecting groups include, but are not limited to, carbobenzyloxy (—NHCO—OCH$_2$C$_6$H$_5$ or —NH-Cbz); t-butyloxycarbonyl (—NHCO—OC(CH$_3$)$_3$ or —NH-Boc); 9-fluorenylmethyloxycarbonyl (—NH-Fmoc), 2,2,2-trichloroethyloxycarbonyl (—NH-Troc), and allyloxycarbonyl (—NH-Alloc). (In each of the above, the —NH— represents the nitrogen from the amino group that is being protected.)

As used herein, the term "amino blocking group," refers to a moiety that prevents chemical reactions from occurring on the nitrogen atom to which that blocking group is attached. In contrast to an amino protecting group, an amino blocking group is not intended to be removed by a chemical reaction. Such groups include, for example, acyl groups such as acetyl (—NHCO—CH$_3$), and succinyl (—NH—CO—CH$_2$—CH$_2$—COO$^-$). (In each of the above, the —NH— represents the nitrogen from the amino group that is being blocked.)

As used herein, the term "aminoluciferin" refers to (4S)-2-(6-amino-1,3-benzothiazol-2-yl)-4,5-dihydrothiazole-4-carboxylic acid, or a substituted analog of this molecule.

As used herein, the term "nitrogen protecting group" refers to groups intended to protect an amino group against undesirable reactions during synthetic procedures. Representative nitrogen protecting groups include acetyl, benzoyl, benzyl, benzyloxycarbonyl (Cbz), formyl, phenylsulfonyl, tert-butoxycarbonyl (Boc), tert-butylacetyl, trifluoroacetyl, and triphenylmethyl (trityl).

As used herein, the term "oxo" refers to a double bonded oxygen (═O) radical wherein the bond partner is a carbon atom. Such a radical can also be thought as a carbonyl group.

The term "peptide" or "polypeptide" refers to a sequence of at least two amino acids. In some embodiments, a peptide may contain no more than 80 amino acids, or no more than 35 amino acids, or no more than 10 amino acids.

The term "saccharide" refers to a sugar or other carbohydrate, especially a simple sugar. It includes both the alpha- and the beta-anomers. The saccharide can be a $C_6$-polyhydroxy compound, typically a $C_6$-pentahydroxy, and often a cyclic glycal. It includes the known simple sugars and their derivatives, as well as polysaccharides with two or more monosaccharide residues. The saccharide can include protecting groups on the hydroxyl groups. The hydroxyl groups of the saccharide can be replaced with one or more acetamido, halo or amino groups. Additionally, one or more of the carbon atoms can be oxidized, for example to keto or carbonyl groups. Suitable saccharides include galactose, glucose, glucoronic acid and neurominic acid.

As used herein, the term "sulfonyl" refers to an >S(O)$_2$ group.

A prefix attached to a multi-component substituent only applies to the first component it precedes. To illustrate, the term "cycloalkylalkyl" contains two components: alkyl and cycloalkyl. Thus, the $C_1$-$C_6$-prefix on $C_1$-$C_6$-cycloalkylalkyl means that the alkyl component of the cycloalkylalkyl contains from 1 to 6 carbon atoms; the $C_1$-$C_6$-prefix does not describe the cycloalkyl component. To illustrate further, the term "halo-$C_1$-$C_6$-alkyl" refers to halomethyl, haloethyl, halopropyl, halobutyl, halopentyl, and halohexyl. To illustrate further, the prefix "halo" on haloalkoxyalkyl indicates that only the alkoxy component of the alkoxyalkyl substituent is substituted with one or more halogen radicals. If the halogen substitution may only occur on the alkyl component, the substituent would instead be described as "alkoxy-haloalkyl."

A substituent is "substitutable" if it comprises at least one carbon or nitrogen atom that is bonded to one or more hydrogen atoms. Thus, for example, hydrogen, halogen, and cyano do not fall within this definition. In addition, a sulfur atom in a heterocyclyl containing such atom is substitutable with one or two oxo substituents.

If a substituent is described as being "substituted", a non-hydrogen radical is in the place of hydrogen radical on a carbon or nitrogen of the substituent. Thus, for example, a substituted alkyl substituent is an alkyl substituent in which at least one non-hydrogen radical is in the place of a hydrogen radical on the alkyl substituent. To illustrate, monofluoroalkyl is alkyl substituted with a fluoro radical, and difluoroalkyl is alkyl substituted with two fluoro radicals. It should be recognized that if there is more than one substitution on a substituent, each non-hydrogen radical may be identical or different (unless otherwise stated).

When a substituent is referred to as "unsubstituted" or not referred to as "substituted" or "optionally substituted", it means that the substituent does not have any substituents. If a substituent is described as being "optionally substituted", the substituent may be either (1) not substituted or (2) substituted. If a substituent is described as being optionally substituted with up to a particular number of non-hydrogen radicals, that substituent may be either (1) not substituted; or (2) substituted by up to that particular number of non-hydrogen radicals or by up to the maximum number of substitutable positions on the substituent, whichever is less. Thus, for example, if a substituent is described as a heteroaryl optionally substituted with up to 3 non-hydrogen radicals, then any heteroaryl with less than 3 substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical. To illustrate further, if an amino nitrogen is described as being optionally substituted with up to 2 non-hydrogen radicals, then a primary amino nitrogen will be optionally substituted with up to 2 non-hydrogen radicals, whereas a secondary amino nitrogen will be optionally substituted with up to only 1 non-hydrogen radical.

If substituents are described as being "independently selected" from a group, each substituent is selected independent of the other. Each substituent, therefore, may be identical to or different from the other substituent(s).

2. LABELING REAGENTS

Disclosed are compounds that may be labeling reagents. In certain embodiments, the compounds of formula (I) are labeling reagents. The labeling reagents can be used for cell uptake measurements.

The labeling reagents of the disclosure are compounds of formula (I), or a salt thereof,

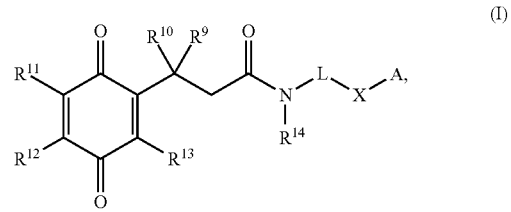

(I)

wherein

A is a reporter moiety;

$R^{14}$ is H, alkyl, hydroxyalkyl, alkoxy, carboxyalkyl, or amidoalkyl;

$R^9$ and $R^{10}$ are independently selected from alkyl;

$R^{11}$, $R^{12}$ and $R^{13}$ are independently selected from H, alkyl, alkoxy, bromo, chloro or amino, or $R^{11}$ and $R^{12}$ can form a fused phenyl ring;

X is O;

L is —$(CH_2)_mC(R^{17})_2(CH_2)_n$—Y—C(O)—;

$R^{17}$ is independently H, alkyl or both $R^{17}$ together can form an alkyl ring having from 3-7 carbons;

m is an integer from 0-2;

n is an integer from 0-2;

Y is O or $NR^{15}$;

$R^{15}$ is H, alkyl, hydroxyalkyl, azidoalkyl, cyanoalkyl, haloalkyl, alkenyl, alkynyl, -alkyl-$N(R^{23})C(O)R^{24}$, -alkyl-$SO_3R^{25}$, -alkyl-$SO_2N(R^{26})(R^{27})$, -alkyl-$COR^{28}$, -alkyl-$CO_2R^{29}$, -alkyl-$OC(O)R^{29}$, -alkyl-$OC(O)N(R^{30})(R^{31})$, -alkyl-$CON(R^{30})(R^{31})$, or polyalkoxyalkyl, wherein the polyalkoxyalkyl is unsubstituted or substituted with one or more suitable substituents; and $R^{23}$, $R^{24}$, $R^{25}$, $R^{26}$, $R^{27}$, $R^{28}$, $R^{29}$, $R^{30}$, and $R^{31}$ are each independently selected from hydrogen, alkyl, aryl, heteroaryl, heterocyclyl, and cycloalkyl.

In certain embodiments, $R^{14}$ is H, $C_1$-$C_{30}$-alkyl, hydroxy-$C_1$-$C_{30}$-alkyl, $C_1$-$C_{30}$-alkoxy, carboxy-$C_1$-$C_{30}$-alkyl, or amido-$C_1$-$C_{30}$-alkyl; $R^9$ and $R^{10}$ are independently selected from $C_1$-$C_4$-alkyl; $R^{11}$, $R^{12}$ and $R^{13}$ are independently selected from H, $C_1$-$C_4$-alkyl, $C_1$-$C_4$-alkoxy, bromo, chloro or amino, or $R^{11}$ and $R^{12}$ can form a fused phenyl ring; X is O; L is —$(CH_2)_mC(R^{17})_2(CH_2)_n$—Y—C(O)—; $R^{17}$ is independently H, $C_1$-$C_4$-alkyl or both $R^{17}$ together can form an alkyl ring having from 3-7 carbons; m is an integer from 0-2; n is an integer from 0-2; Y is O or $NR^{15}$; $R^{15}$ is H, $C_1$-$C_{30}$-alkyl, hydroxy-$C_1$-$C_{30}$-alkyl, azido-$C_1$-$C_{30}$-alkyl, cyano-$C_1$-$C_{30}$-alkyl, halo-$C_1$-$C_{30}$-alkyl, $C_2$-$C_{30}$-alkenyl, $C_2$-$C_{30}$-alkynyl, —$C_1$-$C_{30}$-alkyl-$N(R^{23})C(O)R^{24}$, —$C_1$-$C_{30}$-alkyl-$SO_3R^{25}$, —$C_1$-$C_{30}$-alkyl-$SO_2N(R^{26})(R^{27})$, —$C_1$-$C_{30}$-alkyl-$COR^{28}$, —$C_1$-$C_{30}$-alkyl-$CO_2R^{29}$, —$C_1$-$C_{30}$-alkyl-$OC(O)R^{29}$, —$C_1$-$C_{30}$-alkyl-$OC(O)N(R^{30})(R^{31})$, —$C_1$-$C_{30}$-alkyl-$CON(R^{30})(R^{31})$, or polyalkoxyalkyl, wherein the polyalkoxyalkyl is unsubstituted or substituted with one or more suitable substituents; and $R^{23}$, $R^{24}$, $R^{25}$, $R^{26}$, $R^{27}$, $R^{28}$, $R^{29}$, $R^{30}$, and $R^{31}$ are each independently selected from hydrogen, $C_1$-$C_4$-alkyl, aryl, heteroaryl, heterocyclyl, and cycloalkyl.

In certain embodiments, $R^{14}$ is H, $C_1$-$C_6$-alkyl, hydroxy-$C_1$-$C_6$-alkyl, $C_1$-$C_6$-alkoxy, —$C_1$-$C_6$-alkyl-$CO_2H$, or —$C_1$-$C_6$-alkyl-amide.

In certain embodiments, $R^{14}$ is methyl.

In certain embodiments, $R^{14}$ is carboxyalkyl. In certain embodiments, $R^{14}$ is —$C_2$-$C_{30}$-alkyl-$CO_2H$. In certain embodiments, $R^{14}$ is —$CH_2CO_2H$; —$(CH_2)_2CO_2H$; —$(CH_2)_3CO_2H$; —$(CH_2)_4CO_2H$; —$(CH_2)_5CO_2H$; —$(CH_2)_6CO_2H$; —$(CH_2)_7CO_2H$; —$(CH_2)_8CO_2H$; —$(CH_2)_9CO_2H$; —$(CH_2)_{10}CO_2H$; —$(CH_2)_{11}CO_2H$; —$(CH_2)_{12}CO_2H$; —$(CH_2)_{13}CO_2H$; —$(CH_2)_{14}CO_2H$; —$(CH_2)_{15}CO_2H$; —$(CH_2)_{16}CO_2H$; —$(CH_2)_{17}CO_2H$; —$(CH_2)_{18}CO_2H$; —$(CH_2)_{19}CO_2H$; —$(CH_2)_{20}CO_2H$; —$(CH_2)_{21}CO_2H$; —$(CH_2)_{22}CO_2H$; —$(CH_2)_{23}CO_2H$; —$(CH_2)_{24}CO_2H$; —$(CH_2)_{25}CO_2H$; —$(CH_2)_{26}CO_2H$; —$(CH_2)_{27}CO_2H$; —$(CH_2)_{28}CO_2H$; —$(CH_2)_{29}CO_2H$; or —$(CH_2)_{30}CO_2H$. In certain embodiments, $R^{14}$ is —$(CH_2)_{15}CO_2H$.

In certain embodiments, $R^9$, $R^{10}$, $R^{11}$, $R^{12}$, $R^{13}$, and $R^{14}$ are each methyl.

In certain embodiments, in the variable L, m is 1, $R^{17}$ is hydrogen at each occurrence, and n is 0. In certain embodiments, in the variable L, m is 1, $R^{17}$ is hydrogen at each occurrence, n is 0, and Y is $NR^5$. In certain embodiments, L is —$CH_2CH_2$—$NR^{15}$—C(O)—.

In certain embodiments, A is a bioluminescent reporter moiety. In certain embodiments, A is a luciferin, a luciferin derivative or analog, a preluciferin or analog, coelenterazine or a coelenterazine derivative or analog. In some embodiments, A is luciferin, pro-luciferin, aminoluciferin, quionolyl-luciferin, napthyl luciferin, chloroluciferin, coelenterazine, furimazine, coelenterazine-n, coelenterazine-f, coelenterazine-h, coelenterazine-hcp, coelenterazine-cp, coelenterazine-c, coelenterazine-e, coelenterazine-fcp, bis-deoxycoelenterazine ("coelenterazine-hh"), coelenterazine-i, coelenterazine-icp, coelenterazine-v, and 2-methyl coelenterazine, in addition to those disclosed in WO 2003/040100, U.S. Patent Publication No. 20080248511, and U.S. Patent Publication No. US 20120117667, the disclosures of which are incorporated by reference herein.

In certain embodiments, A is a fluorescent reporter moiety. In certain embodiments, A is a coumarin, R110, fluoroscein, DDAO, resorufin, cresyl violet, sily xanthene, or carbopyronine. In some embodiments, A is rhodamine 123, rhodamine X, Alexa dyes (e.g., Alexa Fluor-350, -430, -488, -and -660), DyLight 594, sulforhodamine B, sulforhodamine 101, sulfonyl chloride derivative of sulforhodamine 101 (Texas Red), fluorescein, 6-carboxyfluorescein (6-FAM), 5-carboxyfluorescein (5-Fam), 5- or 6-carboxy-4,7,2',7'-tetrachlorofluorescein (TET), 5- or 6-carboxy-4'5'2'4'5'7' hexachlorofluorescein (HEX), 5' or 6'-carboxy-4',5'-dichloro-2,'7'-dimethoxyfluorescein (JOE), 6-JOE, 5-carboxy-2',4',5',7'-tetrachlorofluorescein (ZOE) rhodol, fluorescein isothiocyanate, coumarin, 7-amino-4-methylcoumarin, aminocoumarin, hydroxycoumarin, silyl xanthene, or carbopyronine. In certain embodiments, A is a bicyclic aryl or heteroaryl, each of which are independently unsubstituted or substituted with one or more suitable substituents. In certain embodiments, A is a bicyclic aryl or heteroaryl, each of which are independently unsubstituted or substituted with 1, 2, 3, 4, or 5 substituents independently selected from the group consisting of alkyl, haloalkyl, hydroxyalkyl, alkoxyalkyl, haloalkoxyalkyl, aminoalkyl, alkylaminoalkyl, di(alkyl)aminoalkyl, cyanoalkyl, alkoxy, haloalkoxy, cyano, hydroxy, amino, alkylamino, di(alkyl)amino, aryl, heteroaryl, heterocyclyl, cycloalkyl, arylalkyl, heteroarylalkyl, heterocyclylalkyl, and cycloalkylalkyl, wherein the aryl, heteroaryl, heterocyclyl, cycloalkyl, aryl of the arylalkyl, heteroaryl of the heteroarylalkyl, heterocyclyl of the hetercyclylalkyl, and cycloalkyl of the cycloalkylalkyl are each independently unsubstituted or substituted with 1, 2, or 3 substituents independently selected from alkyl, haloalkyl, hydroxyalkyl, alkoxyalkyl, haloalkoxyalkyl, aminoalkyl, alkylaminoalkyl, di(alkyl)aminoalkyl, cyanoalkyl, alkoxy, haloalkoxy, cyano, hydroxy, amino, alkylamino, and di(alkyl)amino.

In certain embodiments, A is a luciferin, luciferin derivative or analog (e.g., luciferin ester), preluciferin, preluciferin derivative or analog, cyanobenzothiazole, coelenterazine, a coelenterazine derivative (e.g., furimazine) or analog, or a fluorophore.

In certain embodiments, A is selected from the group consisting of:

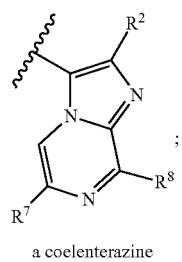

a coelenterazine

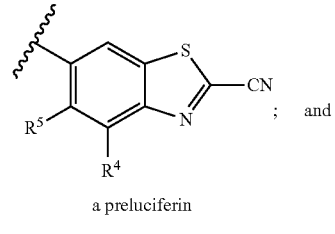

a preluciferin

; and

-continued

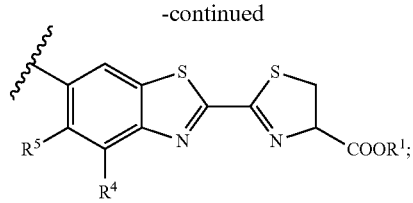

a luciferin wherein $R^1$ is H, $C_1$-$C_4$-alkyl, hydroxy-$C_1$-$C_4$-alkyl, $C_3$-$C_7$-cycloalkyl, aryl, benzyl or substituted benzyl, heterocyclyl, heteroaryl, or —$(CH_2)_q$—$P(Ph)_3$, wherein q is an integer selected from 1, 2, 3, 4, 5, and 6; $R^2$ is —$CH_2$-aryl or —$CH_2$-heteroaryl; $R^4$ is hydrogen, halogen, methyl, or trifluoromethyl; $R^5$ is hydrogen, halogen, methyl, or trifluoromethyl; $R^7$ is aryl (e.g., phenyl), substituted aryl (e.g., 4-hydroxyphenyl), —$CH_2$-aryl, or —$CH_2$-heteroaryl; and $R^8$ is —$CH_2$-aryl or —$CH_2$-heteroaryl. In certain embodiments, the —$CH_2$-aryl is benzyl. In certain embodiments, the —$CH_2$-heteroaryl is furylmethyl.

In certain embodiments, A is selected from the group consisting of:

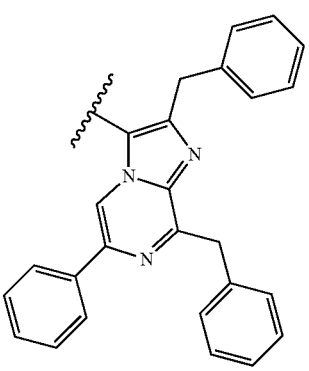

coelenterazine HH

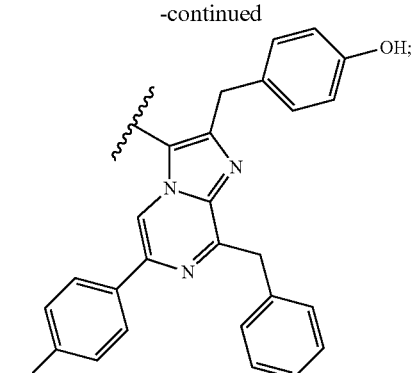

coelenterazine

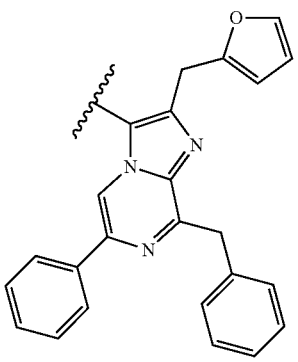

Furimazine

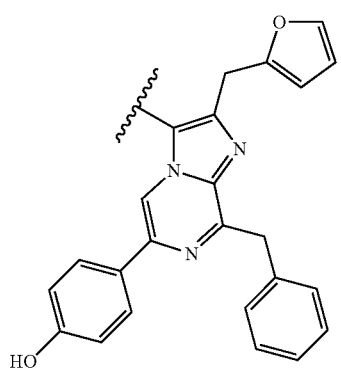

Furimazine H

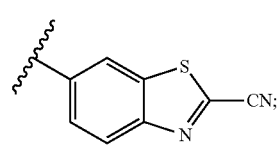

preluciferin

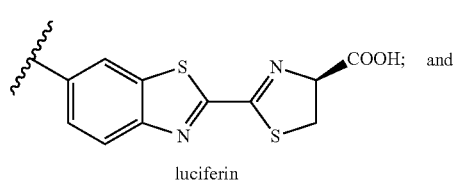

luciferin

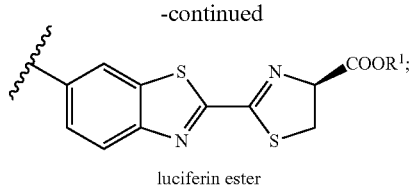

luciferin ester wherein $R^1$ is $C_1$-$C_4$-alkyl, hydroxy-$C_1$-$C_4$-alkyl, $C_3$-$C_7$-cycloalkyl, aryl, benzyl or substituted benzyl, heterocyclyl, heteroaryl, or —$(CH_2)_q$—$P(Ph)_3$, wherein q is an integer selected from 1, 2, 3, 4, 5, and 6.

In certain embodiments, $R^5$ is H, $C_1$-$C_6$-alkyl, hydroxy-$C_1$-$C_6$-alkyl, $C_1$-$C_6$-alkoxy, carboxy-$C_1$-$C_6$-alkyl, amido-$C_1$-$C_6$-alkyl, or polyalkoxyalkyl, wherein the polyalkoxyalkyl is unsubstituted or substituted with one or more suitable substituents.

In certain embodiments, $R^5$ is polyalkoxyalkyl having 1, 2, 3, 4, 5, or 6 repeating alkoxy units.

In certain embodiments, $R^5$ is polyalkoxyalkyl, wherein the polyalkoxyalkyl is —$(C_2$-$C_6$-alkoxy$)_x$-$C_1$-$C_6$-alkyl, —$(C_2$-$C_6$-alkoxy$)_x$-$C_2$-$C_6$-haloalkyl, —$(C_2$-$C_6$-alkoxy$)_x$-hydroxy-$C_2$-$C_6$-alkyl, —$(C_2$-$C_6$-alkoxy$)_x$-amino-$C_2$-$C_6$-alkyl, —$(C_2$-$C_6$-alkoxy$)_x$-$C_1$-$C_6$-alkylamino-$C_2$-$C_6$-alkyl, —$(C_2$-$C_6$-alkoxy$)_x$di($C_1$-$C_6$-alkyl)amino-$C_2$-$C_6$-alkyl, —$(C_2$-$C_6$-alkoxy$)_x$-azido-$C_2$-$C_6$-alkyl, —$(C_2$-$C_6$-alkoxy$)_x$-cyano-$C_1$-$C_6$-alkyl, —$(C_2$-$C_6$-alkoxy$)_x$-$C_2$-$C_6$-alkenyl, —$(C_2$-$C_6$-alkoxy$)_x$-$C_2$-$C_4$-alkynyl, —$(C_2$-$C_6$-alkoxy$)_x$-$N(R^{23})C(O)R^{24}$, —$(C_2$-$C_6$-alkoxy$)_x$-$SO_3R^{25}$, —$(C_2$-$C_6$-alkoxy$)_x$-$C_2$-$C_6$-alkyl-$SO_2N(R^{26})(R^{27})$, —$(C_2$-$C_6$-alkoxy$)_x$-$C_2$-$C_6$-alkyl-$COR^{28}$, —$(C_2$-$C_6$-alkoxy$)_x$-$C_2$-$C_6$-alkyl-$OC(O)R^{29}$, —$(C_2$-$C_6$-alkoxy$)_x$-$C_2$-$C_6$-alkyl-$OC(O)N(R^{30})(R^{31})$, —$(C_2$-$C_6$-alkoxy$)_x$-$C_2$-$C_6$-alkyl-$CO_2R^{29}$, or —$(C_2$-$C_6$-alkoxy$)_x$-$C_2$-$C_6$-alkyl-$CON(R^{30})(R^{31})$, wherein $R^{23}$, $R^{24}$, $R^{25}$, $R^{26}$, $R^{27}$, $R^{28}$, $R^{29}$, $R^{30}$, and $R^{31}$ are each independently selected from hydrogen, $C_1$-$C_4$-alkyl, aryl, heteroaryl, heterocyclyl, and cycloalkyl; and x is an integer selected from 1 to 20.

In certain embodiments, $R^{15}$ is polyalkoxyalkyl, wherein the polyalkoxyalkyl is unsubstituted or substituted with 1 to 3 substituents independently selected from the group consisting of $C_1$-$C_6$-alkyl, $C_1$-$C_6$-alkoxy-$C_1$-$C_6$-alkyl, halo-$C_1$-$C_6$-alkyl, halo-$C_1$-$C_6$-alkoxy-$C_1$-$C_6$-alkyl, hydroxy-$C_1$-$C_6$-alkyl, amino-$C_1$-$C_6$-alkyl, $C_1$-$C_6$-alkylamino-$C_1$-$C_6$-alkyl, di($C_1$-$C_6$-alkyl)amino-$C_1$-$C_6$-alkyl, azido-$C_1$-$C_6$-alkyl, cyano-$C_1$-$C_6$-alkyl, $C_1$-$C_6$-alkoxy, halo-$C_1$-$C_6$-alkoxy, $C_1$-$C_6$-alkoxy-$C_1$-$C_6$-alkoxy, $C_2$-$C_6$-alkenyl, $C_2$-$C_6$-alkynyl, —$N(R^{23})C(O)R^{24}$, —$SO_3R^{25}$, —$SO_2N(R^{26})(R^{27})$, —$COR^{28}$, —$CO_2R^{29}$, and —$CON(R^{30})(R^{31})$, wherein $R^{23}$, $R^{24}$, $R^{25}$, $R^{26}$, $R^{27}$, $R^{28}$, $R^{29}$, $R^{30}$, and $R^{31}$ are each independently selected from hydrogen, $C_1$-$C_4$-alkyl, aryl, heteroaryl, heterocyclyl, and cycloalkyl.

In certain embodiments, $R^{15}$ is a substituted polyalkoxyalkyl of formula:

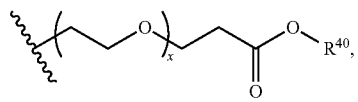

wherein
$R^{40}$ is selected from the group consisting of hydrogen, $C_1$-$C_4$-alkyl, $C_2$-$C_4$-alkenyl, $C_2$-$C_4$-alkynyl, aryl, heteroaryl, heterocyclyl, and cycloalkyl, wherein the aryl, heteroaryl, heterocyclyl, and cycloalkyl are each independently unsubstituted or substituted with one or more suitable substituents; and x is an integer selected from 1 to 20.

In certain embodiments, $R^{40}$ is hydrogen.

In certain embodiments, $R^{40}$ is a 5- or 6-membered heterocyclyl, having 1, 2, or 3 heteroatoms independently selected from the group consisting of N, O, and S, wherein said heterocyclyl is unsubstituted or substituted with 1, 2, or 3 substituents independently selected from alkyl, haloalkyl, hydroxyalkyl, alkoxyalkyl, haloalkoxyalkyl, aminoalkyl, alkylaminoalkyl, di(alkyl)aminoalkyl, cyanoalkyl, alkoxy, haloalkoxy, cyano, hydroxy, amino, alkylamino, di(alkyl)amino. In certain embodiments, $R^{40}$ is

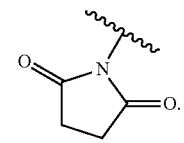 [SMILES: *N1C(=O)CCC1=O]

In certain embodiments, —$OR^{40}$ is defined as a leaving group.

In certain embodiments, x is 2, 3, or 4.

In certain embodiments, $R^{15}$ is a carboxyalkyl selected from the group consisting of: —$CH_2CO_2H$; —$(CH_2)_2CO_2H$; —$(CH_2)_3CO_2H$; —$(CH_2)_4CO_2H$; —$(CH_2)_5CO_2H$; —$(CH_2)_6CO_2H$; —$(CH_2)_7CO_2H$; —$(CH_2)_8CO_2H$; —$(CH_2)_9CO_2H$; —$(CH_2)_{10}CO_2H$; —$(CH_2)_{11}CO_2H$; —$(CH_2)_{12}CO_2H$; —$(CH_2)_{13}CO_2H$; —$(CH_2)_{14}CO_2H$; —$(CH_2)_{15}CO_2H$; —$(CH_2)_{16}CO_2H$; —$(CH_2)_{17}CO_2H$; —$(CH_2)_{18}CO_2H$; —$(CH_2)_{19}CO_2H$; —$(CH_2)_{20}CO_2H$; —$(CH_2)_{21}CO_2H$; —$(CH_2)_{22}CO_2H$; —$(CH_2)_{23}CO_2H$; —$(CH_2)_{24}CO_2H$; —$(CH_2)_{25}CO_2H$; —$(CH_2)_{26}CO_2H$; —$(CH_2)_{27}CO_2H$; —$(CH_2)_{28}CO_2H$; —$(CH_2)_{29}CO_2H$; and —$(CH_2)_{30}CO_2H$. In certain embodiments, $R^{15}$ is —$(CH_2)_{16}CO_2H$.

In certain embodiments, $R^{15}$ is

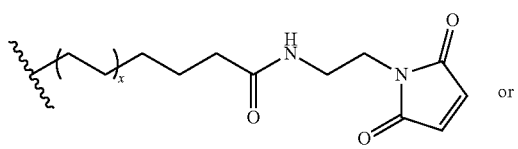 or

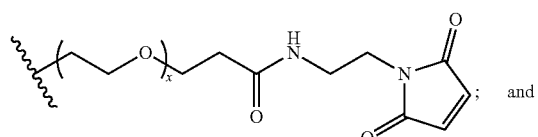; and each x is independently 0 to 20. In certain embodiments, each x is independently 0, 1, 2, 3, or 4.

In certain embodiments, compounds of formula (I) have formula (I-i), or a salt thereof,

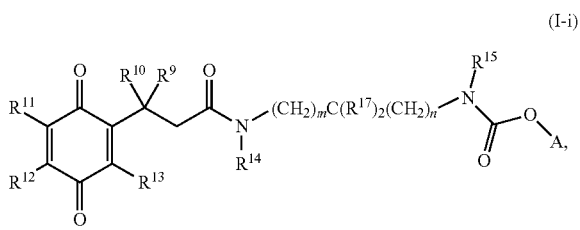

(I-i)

wherein $R^9$, $R^{10}$, $R^{11}$, $R^{12}$, $R^{13}$, $R^{14}$, $R^{15}$, $R^{17}$, m, n, and A are as defined above. In certain embodiments, A is selected from the group consisting of:

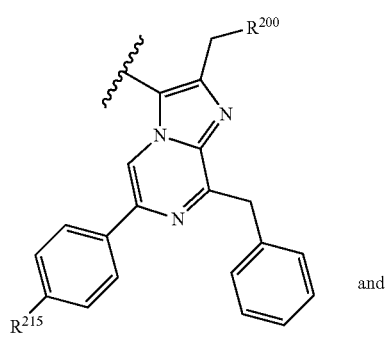

and wherein $R^{200}$ is phenyl, 4-hydroxyphenyl, or furyl; and $R^{215}$ is hydrogen or hydroxy.

In certain embodiments, compounds of formula (I) have formula (I-ii), or a salt thereof,

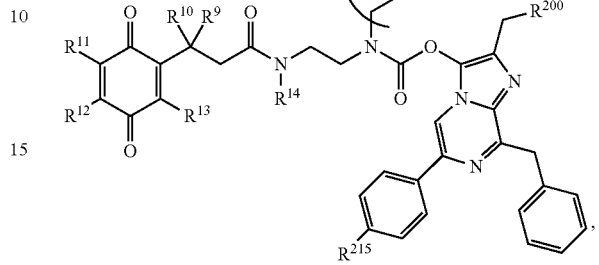

(I-ii)

wherein $R^{200}$ is phenyl, 4-hydroxyphenyl, or furyl; $R^{215}$ is hydrogen or hydroxy; and $R^9$, $R^{10}$, $R^{11}$, $R^{12}$, $R^{13}$, $R^{14}$, and $R^{15}$ are as defined above.

In certain embodiments, compounds of formula (I) have formula (I-iv), or a salt thereof, (I-iv)

wherein $R^{200}$ is phenyl, 4-hydroxyphenyl, or furyl; $R^{215}$ is hydrogen or hydroxy; and $R^9$, $R^{10}$, $R^{11}$, $R^{12}$, $R^{13}$, $R^{14}$, $R^{40}$, and x are as defined above.

In certain embodiments, compounds of formula (I) have formula (I-iii), or a salt thereof,

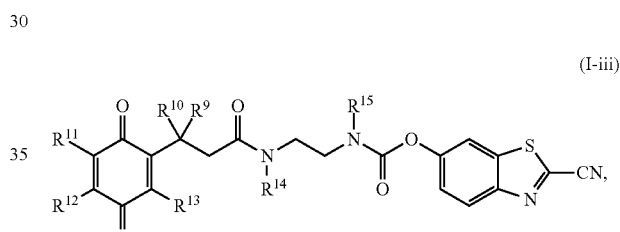

(I-iii)

wherein $R^9$, $R^{10}$, $R^{11}$, $R^{12}$, $R^{13}$, $R^{14}$, and $R^{15}$ are as defined above.

In certain embodiments, compounds of the invention have formula (I-v), or a salt thereof,

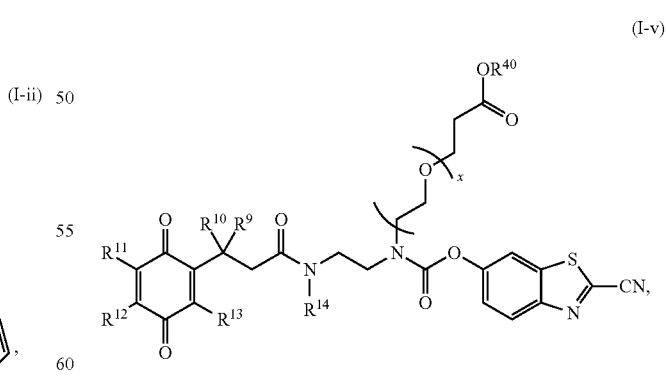

(I-v)

wherein $R^9$, $R^{10}$, $R^{11}$, $R^{12}$, $R^{13}$, $R^{14}$, $R^{40}$, and x are as defined above.

In certain embodiments, compounds of formula (I) have formula (I-vi), or a salt thereof,

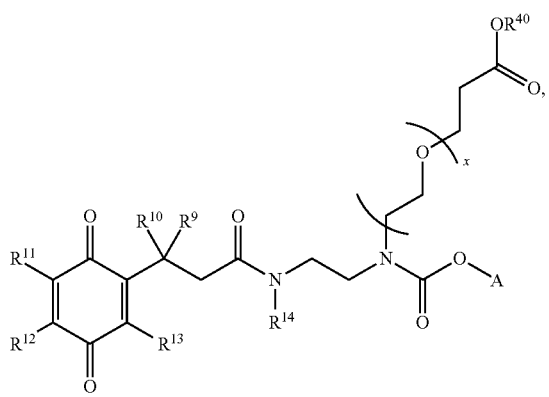

(I-vi)

wherein $R^9$, $R^{10}$, $R^{11}$, $R^{12}$, $R^{13}$, $R^{14}$, $R^{40}$, x, and A are as defined above. In certain embodiments, A is selected from the group consisting of:

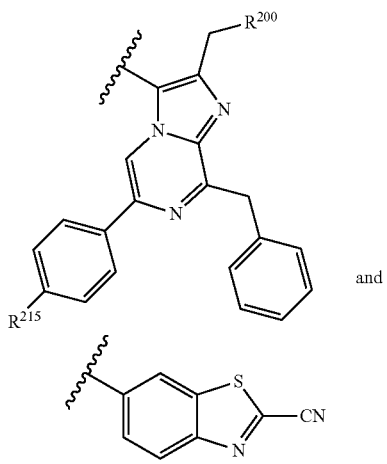

and wherein $R^{200}$ is phenyl, 4-hydroxyphenyl, or furyl; and $R^{215}$ is hydrogen or hydroxy.

In certain embodiments, compounds of formula (I) have formula (I-vii), or a salt thereof,

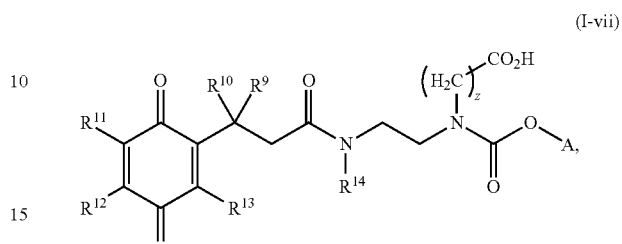

(I-vii)

wherein z is an integer selected from 1 to 30; and $R^9$, $R^{10}$, $R^{11}$, $R^{12}$, $R^{13}$, $R^{14}$, and A are as defined above. In certain embodiments, z is 16.

In certain embodiments, compounds of formula (I) have formula (I-viii), or a salt thereof,

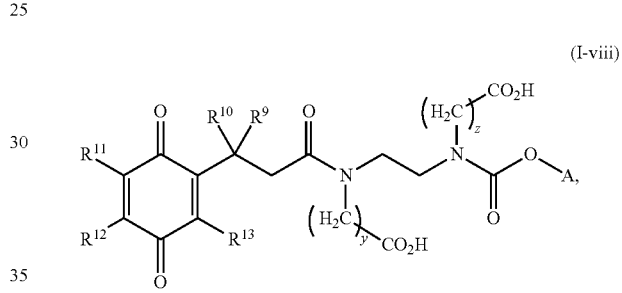

(I-viii)

wherein y and z are each an integer independently selected from 1 to 30; and $R^9$, $R^{10}$, $R^{11}$, $R^{12}$, $R^{13}$, and A are as defined above. In certain embodiments, y is 15 and z is 16.

In certain embodiments, the compound of formula (I) is selected from the group consisting of:

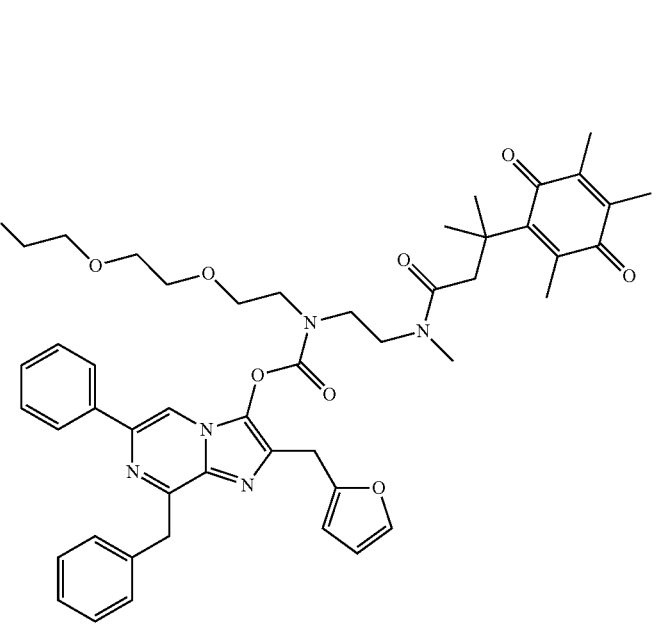

5463: 16-(((8-benzyl-2-(furan-2-ylmethyl)-6-phenylimidazo[1,2-a]pyrazin-3-yl)oxy)carbonyl)-19,22-dimethyl-20-oxo-22-(2,4,5-trimethyl-3,6-dioxocyclohexa-1,4-dien-1-yl)-4,7,10,13-tetraoxa-16,19-diazatricosan-1-oic acid;

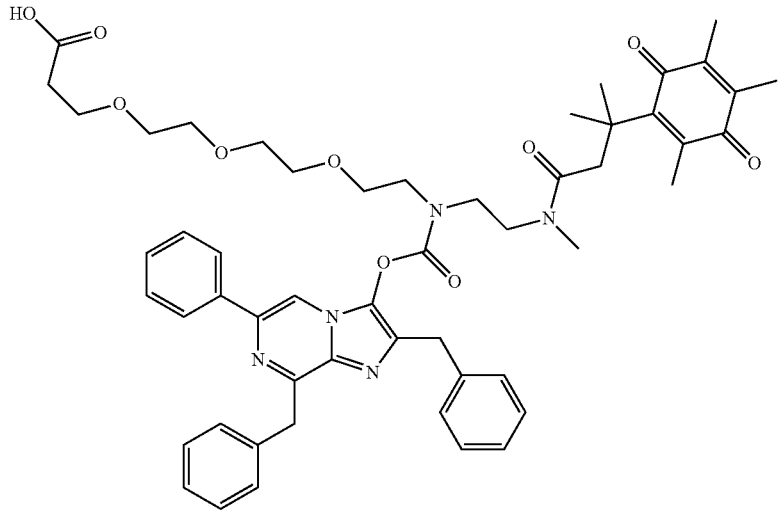 [SMILES: CC1=C(C)C(=O)C(C(C)(C)CC(=O)N(C)CCN(CCOCCOCCOCCC(=O)O)C(=O)Oc2c(Cc3ccccc3)nc3c(Cc4ccccc4)nc(-c4ccccc4)cn23)=C(C)C1=O]

5470: 13-(((2,8-dibenzyl-6-phenylimidazo[1,2-a]pyrazin-3-yl)oxy)carbonyl)-16,19-dimethyl-17-oxo-19-(2,4,5-trimethyl-3,6-dioxocyclohexa-1,4-dien-1-yl)-4,7,10-trioxa-13,16-diazaicosan-1-oic acid;

5471: 10-(((2,8-dibenzyl-6-phenylimidazo[1,2-a]pyrazin-3-yl)oxy)carbonyl)-13,16-dimethyl-14-oxo-16-(2,4,5-trimethyl-3,6-dioxocyclohexa-1,4-dien-1-yl)-4,7-dioxa-10,13-diazaheptadecan-1-oic acid;

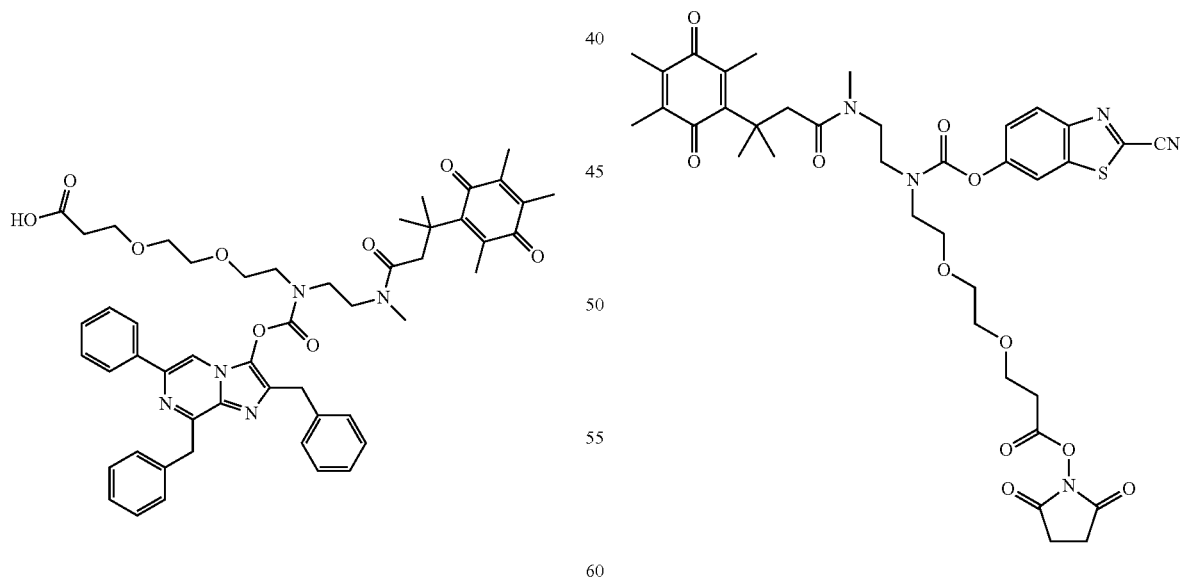

5508: 2,5-dioxopyrrolidin-1-yl 10-(((2-cyanobenzo[d]thiazol-6-yl)oxy)carbonyl)-13,16-dimethyl-14-oxo-16-(2,4,5-trimethyl-3,6-dioxocyclohexa-1,4-dien-1-yl)-4,7-dioxa-10,13-diazaheptadecan-1-oate;

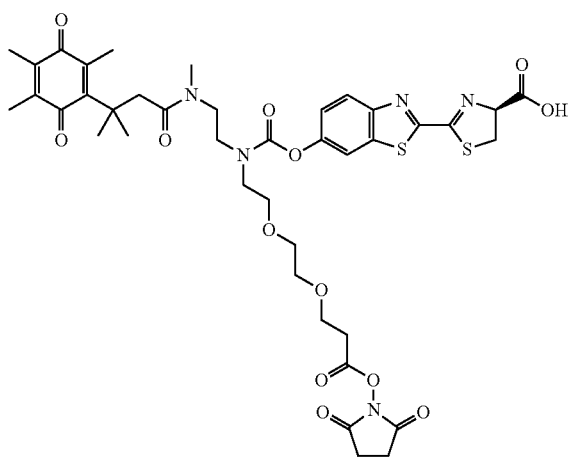 [SMILES: CC1=C(C)C(=O)C(C(C)(C)CC(=O)N(C)CCN(CCOCCOCCC(=O)ON2C(=O)CCC2=O)C(=O)Oc2ccc3nc(C4=N[C@@H](C(=O)O)CS4)sc3c2)=C(C)C1=O]

(S)-2-(6-(((2-(N,3-dimethyl-3-(2,4,5-trimethyl-3,6-dioxo-cyclohexa-1,4-dien-1-yl)butanamido)ethyl)(2-(2-(3-((2,5-dioxopyrrolidin-1-yl)oxy)-3-oxopropoxy)ethoxy)ethyl)carbamoyl)oxy)benzo[d]thiazol-2-yl)-4,5-dihydrothiazole-4-carboxylic acid;

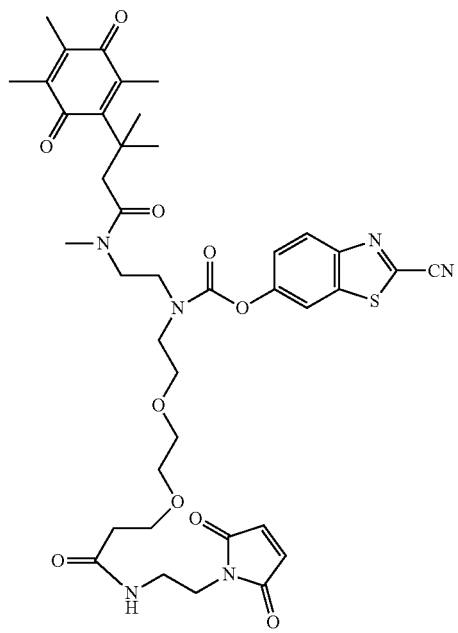 [SMILES: CC1=C(C)C(=O)C(C(C)(C)CC(=O)N(C)CCN(CCOCCOCCC(=O)NCCN2C(=O)C=CC2=O)C(=O)Oc2ccc3nc(C#N)sc3c2)=C(C)C1=O]

5915: 2-cyanobenzo[d]thiazol-6-yl(2-(N,3-dimethyl-3-(2,4,5-trimethyl-3,6-dioxocyclohexa-1,4-dien-1-yl)butanamido)ethyl)(2-(2-(3-((2-(2,5-dioxo-2,5-dihydro-1H-pyrrol-1-yl)ethyl)amino)-3-oxopropoxy)ethoxy)ethyl)carbamate;

17-(((((2-cyanobenzo[d]thiazol-6-yl)oxy)carbonyl)(2-(N,3-dimethyl-3-(2,4,5-trimethyl-3,6-dioxocyclohexa-1,4-dien-1-yl)butanamido)ethyl)amino)heptadecanoic acid;

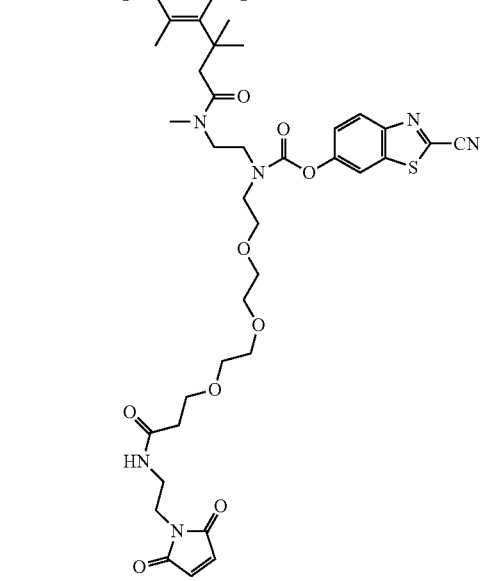

5916: 2-cyanobenzo[d]thiazol-6-yl(2-(N,3-dimethyl-3-(2,4,5-trimethyl-3,6-dioxocyclohexa-1,4-dien-1-yl)butanamido)ethyl)(15-(2,5-dioxo-2,5-dihydro-1H-pyrrol-1-yl)-12-oxo-3,6,9-trioxa-13-azapentadecyl)carbamate;

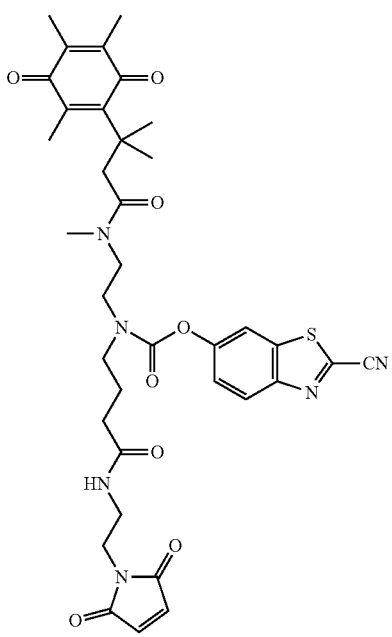 [SMILES: CC1=C(C)C(=O)C(C(C)(C)CC(=O)N(C)CCN(CCCC(=O)NCCN2C(=O)C=CC2=O)C(=O)Oc2ccc3nc(C#N)sc3c2)=C(C)C1=O]

5917: 2-cyanobenzo[d]thiazol-6-yl(2-(N,3-dimethyl-3-(2,4,5-trimethyl-3,6-dioxocyclohexa-1,4-dien-1-yl)butanamido)ethyl)(4-((2-(2,5-dioxo-2,5-dihydro-1H-pyrrol-1-yl)ethyl)amino)-4-oxobutyl)carbamate; and

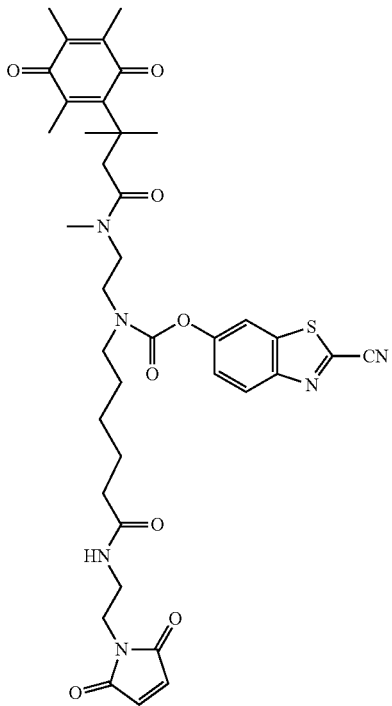 [SMILES: CC1=C(C)C(=O)C(C(C)(C)CC(=O)N(C)CCN(CCCCCC(=O)NCCN2C(=O)C=CC2=O)C(=O)Oc2ccc3nc(C#N)sc3c2)=C(C)C1=O]

5918: 2-cyanobenzo[d]thiazol-6-yl(2-(N,3-dimethyl-3-(2,4,5-trimethyl-3,6-dioxocyclohexa-1,4-dien-1-yl)butanamido)ethyl)(6-((2-(2,5-dioxo-2,5-dihydro-1H-pyrrol-1-yl)ethyl)amino)-6-oxohexyl)carbamate; or a salt thereof.

3. AGENTS

The disclosed compounds may be used as labels that allow for the detection of an agent taken up by cells, tissues or organs. An agent may include a variety of compositions of matter. The disclosed compounds can be used to label a broad range of molecules, including but not limited to, biological agents or biomolecules such as polypeptides, polypeptide-based toxins, amino acids, nucleotides, polynucleotides including nucleic acids such as DNA and RNA, lipids, sugars, carbohydrates, detergents, and enzyme substrates, and any combination thereof. The disclosed compounds can also be used to label biological molecules, including but not limited to, antibodies, nanobodies, haptens, small molecules, drugs, drug compounds, ion-complexing agents, such as metal chelators, microparticles, synthetic or natural polymers, cells, viruses, other fluorescent molecules, such as FAM diamine, or surfaces, and any combination thereof. The drug, or derivative of a drug, may be a bile acid, such as ursodeoxycholic acid (UDCA), chenodeoxycholic acid (CDCA), lithocholic acid (LCA), and deoxycholic acid (DCA), a statin, such as rosuvastatin, or an estradiol, such as estradiol glucuronide. The agent may be an antibody. The resulting labeled agents may be referred to as conjugates or tracers.

The polypeptide may be an antibody, an antibody-like moiety, such as a centyrin (Centyrex), or lipoprotein. The antibody may be a multispecific antibody, a human antibody, a humanized antibody (fully or partially humanized), an animal antibody such as, but not limited to, a bird (for example, a duck or a goose), a shark, a whale, and a mammal, including a non-primate (for example, a cow, a pig, a camel, a llama, a horse, a goat, a rabbit, a sheep, a hamster, a guinea pig, a cat, a dog, a rat, a mouse, etc.) or a non-human primate (for example, a monkey, a chimpanzee, etc.), a recombinant antibody, a chimeric antibody, a single-chain Fv ("scFv"), a single chain antibody, a single domain antibody, a Fab fragment, a F(ab') fragment, a F(ab')2 fragment, a disulfide-linked Fv ("sdFv"), and an anti-idiotypic ("anti-Id") antibody, a dual-domain antibody, a dual variable domain (DVD) or a triple variable domain (TVD) antibody (dual-variable domain immunoglobulin, and functionally active epitope-binding fragment of any of the above. In particular, an antibody includes an immunoglobulin molecule and an immunologically active fragment of an immunoglobulin molecule, namely, a molecule that contain an analyte-binding site. Immunoglobulin molecules can be of any type (for example, IgG, IgE, IgM, IgD, IgA, and IgY), class (for example, IgG1, IgG2, IgG3, IgG4, IgA1, and IgA2), or subclass. The antibody may be a therapeutic antibody such as Trastuzumab (Herceptin), Abciximab (ReoPro), Adalimumab (Humira), Alemtuzumab (Campath), Basiliximab (Simulect), Belimumab (Benlysta), Bevacizumab (Avastin), Brentuximab vedotin (Adcetris), Canakinumab (Ilaris), Cetuximab (Erbitux), Certolizumab pegol (Cimzia), Daclizumab (Zenapax), Denosumab (Prolia, Xgeva), Eculizumab (Soliris), Efalizumab (Raptiva), Gemtuzumab (Mylotarg), Golimumab (Simponi), Ibritumomab tiuxetan (Zevalin), Infliximab (Remicade), Ipilimumab (MDX-101; Yervoy), Muromonab-CD3 (Orthoclone OKT3), Natalizumab (Tysabri), Ofatumumab (Arzerra), Omalizumab (Xolair), Palivizumab (Synagis), Panitumumab (Vectibix), Ranibizumab (Lucentis), Rituximab (Rituxan, Mabthera), Tocilizumab (or Atlizumab) (Actemra and RoActemra), and Tositumomab (Bexxar). Further example antibodies are also found in Table 1.

TABLE 1

| Antigens | Antibodies |
| --- | --- |
| CD30 | Ch IgG1 |
| CD22 | Hz IgG4 |
| CD33 | Hz IgG4 |
| CD19 | Hz IgG1 |
| CD138 | Ch IgG4 |
| CD22 | Hz IgG1 |
| CD79b | Hz IgG1 |
| CD74 | Hz IgG1 |
| HER2 | Hz IgG1 |
| GPNMB | Hu IgG2 |
| PSMA | Hu IgG1 |
| CD56 | Hz IgG1 |
| SLC44A4 | Hu IgG2 |
| CA6 | Hu IgG1 |
| CA-IX | Hu IgG1 |
| Mesothelin | Hu IgG1 |
| CD70 | Hu IgG1 |
| CD66e/CEACAM5 | Hz IgG1 |
| Nectin-4 | Hu IgG1 |

Ch: chimeric; Hz: humanized; Hu: fully human; GPNMB: Glycoprotein NMB; PSMA: prostate specific membrane antigen.

The polypeptide may be Cholecystockinin (CCK), such as herring CCK-8, i.e., DYMGWMDF (SEQ ID NO: 1).

The lipoprotein may be high-density lipoprotein (HDL), low-density lipoprotein (LDL), intermediate-density lipoprotein, oxidized LDL, very low-density lipoprotein (VLDL), chylomicrons, chylomicron remnants, and non-natural lipoproteins.

Additionally, the compounds may be used to label non-biological agents, including but not limited to, solid supports/surfaces, nanoparticles, such as [60]fullerene, core-shell nanoparticles, liposome, dendrimer, and gold nanoparticles, and detergents. The detergent may be comprised within a liposome and/or solid-lipid nanoparticle (SLN) that may optionally be used to test drug delivering efficiency. The detergent may be a transfecting reagent, such as Lipofectamine® 2000 or Fugene 6.

a. Methods of Labeling an Agent

The disclosed compounds may be used to label an agent. In some aspects, the compounds can be conjugated with a nucleoside, nucleotide, or a polynucleotide. The compounds of the invention may be conjugated with a nucleoside, nucleotide, or polynucleotide in any way known to one of ordinary skill in the art such as through a phosphoramidite, an activated ester or a reactive platinum complex. In certain embodiments, the labeling compounds may be conjugated to an agent using an activated carboxylic acid such as an NHS ester, pentafluorobenzene ester, an anhydride, an acetyl chloride; or using direct carboxylic acid and amine coupling reactions, or click chemistry, or maleimide, or activated carbonate, or phosphoramidite.

For example, as shown in Scheme 1, a labeling reagent can be attached to dU allylamine phosphoamidite and further incorporated in oligomers of interest by a traditional phosphoamidite chemistry. Alternatively, dU allylamine modified oligomers of interest can be labeled with the labeling reagent through an activated ester by post labeling. If those labeled oligos are primers of interest, they can also be used to amplify a sequence of interest through PCR.

Scheme 1

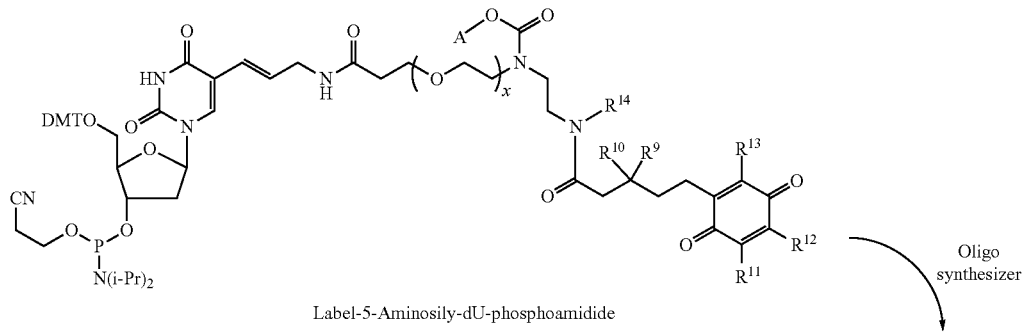

Label-5-Aminosily-dU-phosphoamidite

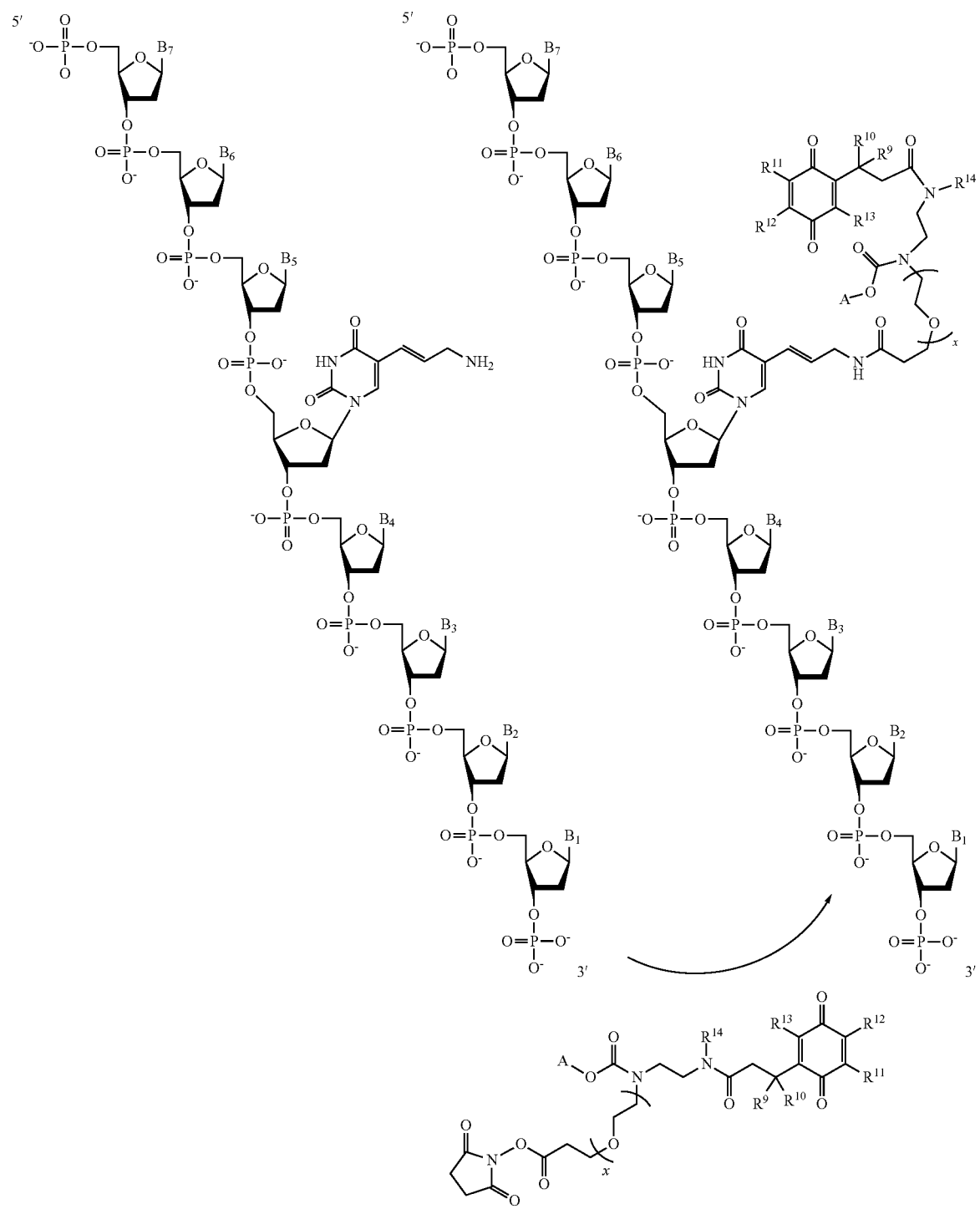

In certain embodiments, a labeled agent may have formula (II), or a salt thereof,

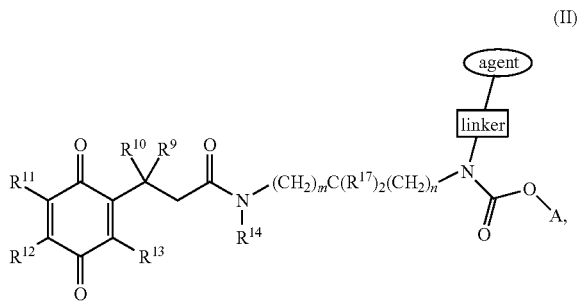

(II)

wherein the linker is a bond or a carbon chain that covalently attaches the parent molecular moiety to the agent, wherein the carbon chain is optionally interrupted by one or more nitrogen atoms, oxygen atoms, carbonyl groups, (substituted) aromatic rings, or peptide bonds; the agent is a target of interest; and $R^9$, $R^{10}$, $R^{11}$, $R^{12}$, $R^{13}$, $R^{14}$, $R^{17}$, and A are as defined above.

In certain embodiments, the labeled agent of formula (II) may have formula (II-i), or a salt thereof,

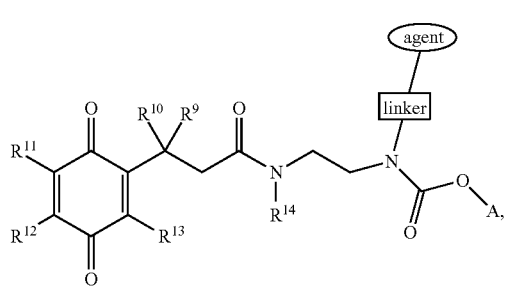

(II-i)

wherein the linker, the agent, $R^9$, $R^{10}$, $R^{11}$, $R^{12}$, $R^{13}$, $R^{14}$, $R^{17}$, and A are as defined above.

In certain embodiments, the labeled agent of formula (II) may have formula (II-ii), or a salt thereof,

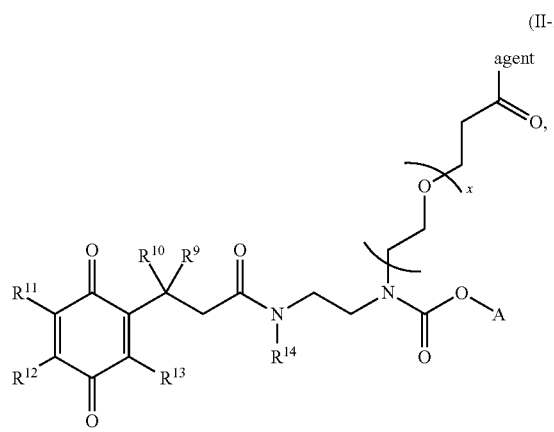

(II-ii)

wherein the agent, $R^9$, $R^{10}$, $R^{11}$, $R^{12}$, $R^{13}$, $R^{14}$, x, and A are as defined above.

In certain embodiments, the labeled agent of formula (II) may have formula (II-iii),

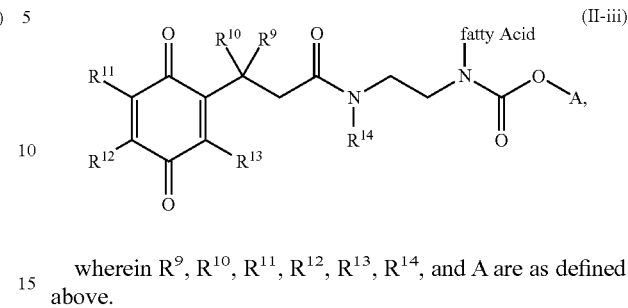

(II-iii)

wherein $R^9$, $R^{10}$, $R^{11}$, $R^{12}$, $R^{13}$, $R^{14}$, and A are as defined above.

In certain embodiments, the labeled agent may have formula (III),

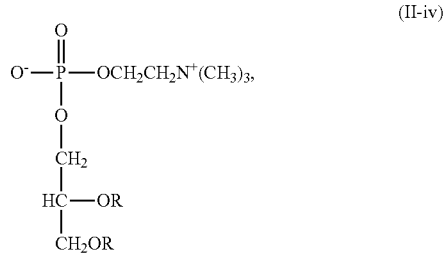

(II-iv)

wherein each R is independently selected from hydrogen, alkyl, alkenyl, and a group of formula (a):

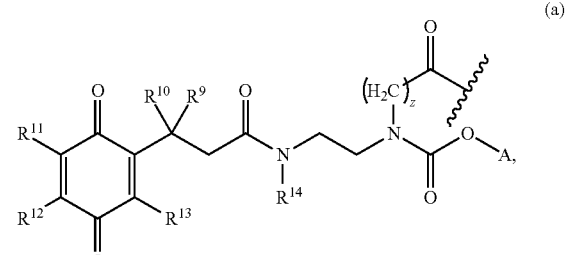

(a)

wherein $R^9$, $R^{10}$, $R^{11}$, $R^{12}$, $R^{13}$, $R^{14}$, z, and A are as defined above; wherein at least one R group is formula (a).

In certain embodiments, the agent in the above formulas is selected from the group consisting of: a polypeptide, a polypeptide-based toxin, an amino acid, a nucleotide, a polynucleotide, including nucleic acids such as DNA and RNA, a lipid, a carbohydrate, and an enzyme substrate, or any combination thereof. In certain embodiments, the agent is a peptide, an antibody, a lipoprotein, a protein, a nucleotide, a sugar, a fatty acid, a detergent, or a lipid. In certain embodiments, the agent is an antibody. In certain embodiments, the agent in the above formulas is selected from the group consisting of: a therapeutic drug, a small molecule, and a nanoparticle, or any combination thereof.

In other aspects, the disclosed labeling reagents can be conjugated with an amino acid, an amino acid analog, or a polypeptide. In other aspects, the disclosed labeling reagents can be conjugated with a small molecule, e.g., a drug or drug compound. In some aspects, the conjugated small molecule can be used as a fluorescent tracer.

4. LABELED AGENTS

In certain embodiments, the compounds of the present disclosure are labeled agents. The labeled agents are compounds of formula (I), or a salt thereof,

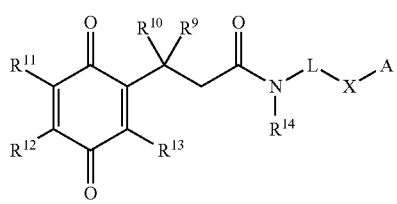

(I)

wherein

A is a reporter moiety;

$R^{14}$ is H, alkyl, hydroxyalkyl, alkoxy, carboxyalkyl, or amidoalkyl;

$R^9$ and $R^{10}$ are independently selected from alkyl;

$R^{11}$, $R^{12}$ and $R^{13}$ are independently selected from H, alkyl, alkoxy, bromo, chloro or amino, or $R^{11}$ and $R^{12}$ can form a fused phenyl ring;

X is O;

L is $-(CH_2)_m C(R^{17})_2 (CH_2)_n-Y-C(O)-$;

$R^{17}$ is independently H, alkyl or both $R^{17}$ together can form an alkyl ring having from 3-7 carbons;

m is an integer from 0-2;

n is an integer from 0-2;

Y is O or $NR^{15}$;

$R^{15}$ is H, alkyl, hydroxyalkyl, azidoalkyl, cyanoalkyl, haloalkyl, alkenyl, alkynyl, -alkyl-$N(R^{23})C(O)R^{24}$, -alkyl-$SO_3R^{25}$, -alkyl-$SO_2N(R^{26})(R^{27})$, -alkyl-$COR^{28}$, -alkyl-$CO_2R^{29}$, -alkyl-$OC(O)R^{29}$, -alkyl-$OC(O)N(R^{30})(R^{31})$, -alkyl-amide, or polyalkoxyalkyl, wherein the polyalkoxyalkyl and -alkyl-amide are unsubstituted or substituted with one or more suitable substituents; and $R^{23}$, $R^{24}$, $R^{25}$, $R^{26}$, $R^{27}$, $R^{28}$, $R^{29}$, $R^{30}$, and $R^{31}$ are each independently selected from hydrogen, alkyl, aryl, heteroaryl, heterocyclyl, and cycloalkyl.

In certain embodiments, the agent being labeled is selected from aryl, arylalkyl, cycloalkylalkyl, heteroaryl, heteroarylalkyl, heterocycle, hydroxyalkyl, protein, polypeptide, polypeptide-based toxin, amino acid, nucleotide, polynucleotide, lipid, sugar, carbohydrate, enzyme substrate, drug, derivative of a drug, polymer-linked nanoparticle, antibody, detergent, and a dye, or a combination thereof.

In certain embodiments, Y is $NR^{15}$.

In certain embodiments, $R^{15}$ comprises the agent.

In certain embodiments, $R^{15}$ is H, alkyl, hydroxyalkyl, azidoalkyl, cyanoalkyl, haloalkyl, alkenyl, alkynyl, -alkyl-$N(R^{23})C(O)R^{24}$, -alkyl-$SO_3R^{25}$, -alkyl-$SO_2N(R^{26})(R^{27})$, -alkyl-$COR^{28}$, -alkyl-$CO_2R^{29}$, -alkyl-$OC(O)R^{29}$, -alkyl-$OC(O)N(R^{30})(R^{31})$, -alkyl-amide, or polyalkoxyalkyl, wherein the polyalkoxyalkyl and -alkyl-amide are unsubstituted or substituted with one or more suitable substituents; and $R^{23}$, $R^{24}$, $R^{25}$, $R^{26}$, $R^{27}$, $R^{28}$, $R^{29}$, $R^{30}$, and $R^{31}$ are each independently selected from hydrogen, alkyl, aryl, heteroaryl, heterocyclyl, and cycloalkyl.

In certain embodiments, $R^{15}$ is polyalkoxyalkyl, wherein the polyalkoxyalkyl is selected from the group consisting of $-(C_2-C_6$-alkoxy$)_x$-alkyl, $-(C_2-C_6$-alkoxy$)_x$-haloalkyl, $-(C_2-C_6$-alkoxy$)_x$-hydroxyalkyl, $-(C_2-C_6$-alkoxy$)_x$-aminoalkyl, $-(C_2-C_6$-alkoxy$)_x$-alkylaminoalkyl, $-(C_2-C_6$-alkoxy$)_x$di(alkyl)aminoalkyl, $-(C_2-C_6$-alkoxy$)_x$-azidoalkyl, $-(C_2-C_6$-alkoxy$)_x$-cyanoalkyl, $-(C_2-C_6$-alkoxy$)_x$-alkenyl, $-(C_2-C_6$-alkoxy$)_x$-alkynyl, $-(C_2-C_6$-alkoxy$)_x$-$N(R^{23})C(O)R^{24}$, $-(C_2-C_6$-alkoxy$)_x$-$SO_3R^{25}$, $-(C_2-C_6$-alkoxy$)_x$-alkyl-$SO_2N(R^{26})(R^{27})$, $-(C_2-C_6$-alkoxy$)_x$-alkyl-$COR^{28}$, $-(C_2-C_6$-alkoxy$)_x$-alkyl-$OC(O)R^{29}$, $-(C_2-C_6$-alkoxy$)_x$-alkyl-$OC(O)N(R^{30})(R^{31})$, $-(C_2-C_6$-alkoxy$)_x$-alkyl-$CO_2R^{29}$, $-(C_2-C_6$-alkoxy$)_x$-alkyl-$CON(R^{32})(R^{33})$ and $-(C_2-C_6$-alkoxy$)_x$-alkyl-$(CO)-NR^{34}-(CR^aR^b)_p-NR^{35}(CO)$-T, wherein $R^{23}$, $R^{24}$, $R^{25}$, $R^{26}$, $R^{27}$, $R^{28}$, $R^{29}$, $R^{30}$, and $R^{31}$ are each independently selected from hydrogen, alkyl, aryl, heteroaryl, heterocyclyl, and cycloalkyl;

x is an integer selected from 1 to 20;

$R^{32}$ and $R^{33}$ are each independently selected from hydrogen, alkyl, carboxy, a peptide, a drug, a biologically active moiety, and a dye;

$R^{34}$ and $R^{35}$ are each independently selected from hydrogen, and alkyl;

$R^a$ and $R^b$ are each independently selected from hydrogen, alkyl, and carboxy;

p is 0 to 6; and

T is selected from aryl, arylalkyl, cycloalkylalkyl, heteroaryl, heteroarylalkyl, heterocycle, hydroxyalkyl, protein, polypeptide, polypeptide-based toxin, amino acid, nucleotide, polynucleotide, lipid, sugar, carbohydrate, enzyme substrate, drug, derivative of a drug, polymer-linked nanoparticle, antibody, detergent, and a dye, or a combination thereof.

In certain embodiments, $R^{15}$ is polyalkoxyalkyl, wherein the polyalkoxyalkyl is $-(C_2-C_6$-alkoxy$)_x$-alkyl-$CON(R^{32})(R^{33})$ or $-(C_2-C_6$-alkoxy$)_x$-alkyl-$(CO)-NR^{34}-(CR^aR^b)-NR^{35}(CO)$-T;

x is an integer selected from 1 to 20;

$R^{32}$ and $R^{33}$ are each independently selected from hydrogen, alkyl, carboxy, aryl, arylalkyl, cycloalkylalkyl, heteroaryl, heteroarylalkyl, heterocycle, hydroxyalkyl, protein, polypeptide, polypeptide-based toxin, amino acid, nucleotide, polynucleotide, lipid, sugar, carbohydrate, enzyme substrate, drug, derivative of a drug, polymer-linked nanoparticle, antibody, detergent, and a dye, or a combination thereof;

$R^{34}$ and $R^{35}$ are each independently selected from hydrogen, and alkyl;

$R^a$ and $R^b$ are each independently selected from hydrogen, alkyl, and carboxy;

p is 0 to 6; and

T is selected from aryl, arylalkyl, cycloalkylalkyl, heteroaryl, heteroarylalkyl, heterocycle, hydroxyalkyl, protein, polypeptide, polypeptide-based toxin, amino acid, nucleotide, polynucleotide, lipid, sugar, carbohydrate, enzyme substrate, drug, derivative of a drug, polymer-linked nanoparticle, antibody, detergent, and a dye, or a combination thereof.

In certain embodiments, $R^{15}$ is

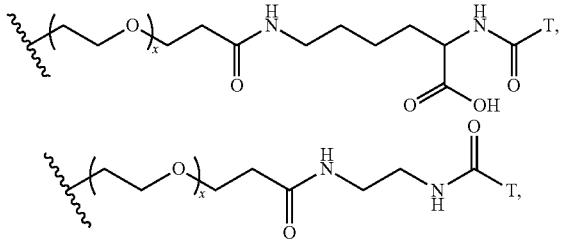

-continued

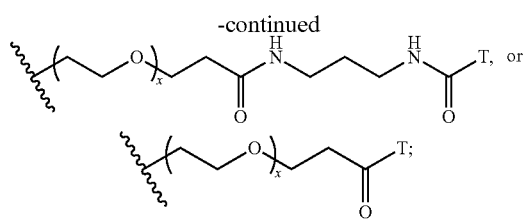

wherein

T is selected from aryl, arylalkyl, cycloalkylalkyl, heteroaryl, heteroarylalkyl, heterocycle, hydroxyalkyl, protein, polypeptide, polypeptide-based toxin, amino acid, nucleotide, polynucleotide, lipid, sugar, carbohydrate, enzyme substrate, drug, derivative of a drug, polymer-linked nanoparticle, antibody, detergent, and a dye, or a combination thereof; and x is an integer selected from 1 to 20.

In certain embodiments, x is 1 to 10, 1 to 8, 1 to 6, 1 to 5, 1 to 4, 1 to 3, or 1 to 2. In certain embodiments, x is 1, 2, 3, 4, 5, 6, 7, 8, 9, 10, 11, 12, 13, 14, 15, 16, 17, 18, 19 or 20.

In certain embodiments, $R^{15}$ is -alkyl-amide, wherein the -alkyl-amide is -alkyl-CON($R^{32}$)($R^{33}$) or -alkyl-(CO)—$NR^{34}$—$(CR^aR^b)_p$—$NR^{35}$(CO)-T, wherein $R^{32}$ and $R^{33}$ are each independently selected from hydrogen, alkyl, carboxy, aryl, arylalkyl, cycloalkylalkyl, heteroaryl, heterocycle, alkene, polyol, alkenylpolyol, a peptide, a drug, a derivative of a drug, a biologically active moiety, and a dye;

$R^{34}$ and $R^{35}$ are each independently selected from hydrogen, and alkyl;

$R^a$ and $R^b$ are each independently selected from hydrogen, alkyl, and carboxy;

p is 0 to 6; and

T is selected from aryl, arylalkyl, cycloalkylalkyl, heteroaryl, heteroarylalkyl, heterocycle, hydroxyalkyl, protein, polypeptide, polypeptide-based toxin, amino acid, nucleotide, polynucleotide, lipid, sugar, carbohydrate, enzyme substrate, drug, derivative of a drug, polymer-linked nanoparticle, antibody, detergent, and a dye, or a combination thereof.

In certain embodiments, $R^{15}$ is

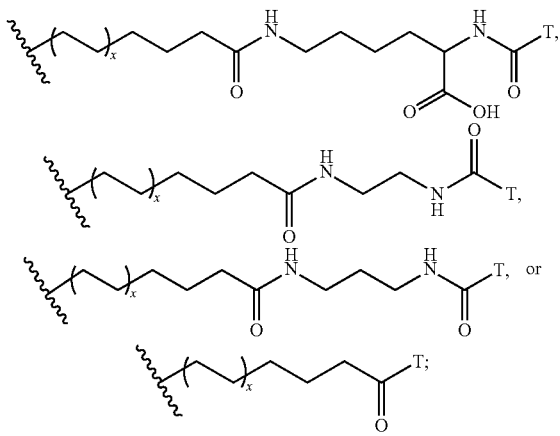

wherein

T is selected from aryl, arylalkyl, cycloalkylalkyl, heteroaryl, heteroarylalkyl, heterocycle, hydroxyalkyl, protein, polypeptide, polypeptide-based toxin, amino acid, nucleotide, polynucleotide, lipid, sugar, carbohydrate, enzyme substrate, drug, derivative of a drug, polymer-linked nanoparticle, antibody, detergent, and a dye, or a combination thereof; and x is 0 to 20.

In certain embodiments, x is 0 to 10, 0 to 8, 0 to 6, 0 to 5, 0 to 4, 0 to 3, or 0 to 2. In certain embodiments, x is 0, 1, 2, 3, 4, 5, 6, 7, 8, 9, 10, 11, 12, 13, 14, 15, 16, 17, 18, 19 or 20.

In certain embodiments, $R^{15}$ is

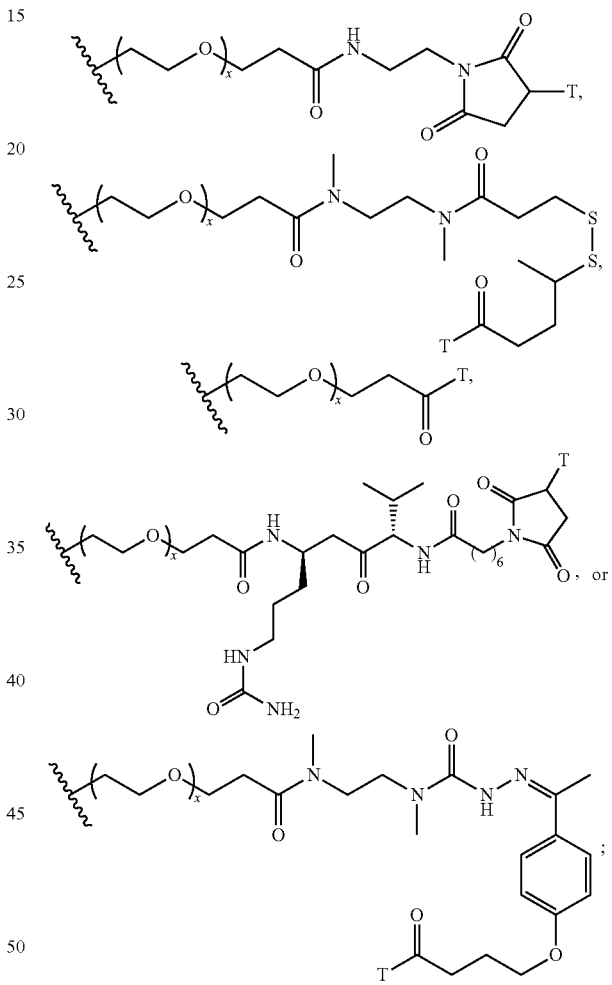

wherein x is 1 to 20 and T is an antibody.

In certain embodiments, when T is a monoclonal antibody, examples of antibodies include those in Table 1.

In certain embodiments, $R^{15}$ is

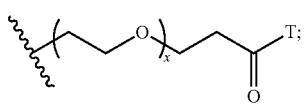

wherein T comprises a $C_{60}$ fullurene. For example, T may be

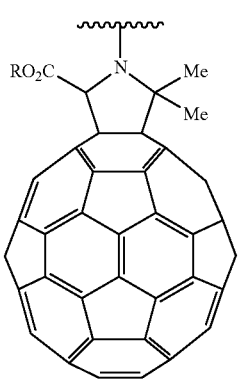

In certain embodiments, $R^{15}$ is -alkyl-T, wherein T is a solid-liquid nanoparticle (SLN). SLNs mainly comprise lipids that are in solid phase at room temperature and surfactant for emulsification, the mean diameters of which range from 50 nm to 1000 nm for colloid drug delivery application. Solid lipids that utilized in SLN include fatty acids, triglycerides, steroids and waxes. Several types of surfactants are commonly used as emulsifiers to stabilize lipid dispersion.

In certain embodiments, $R^{15}$ is

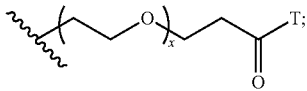

wherein T is —NH-PEG$_{3000}$-gold nanoparticle, a PAMAM dendrimer, an oligonucleotide, or a peptide-oligonucleotide conjugate. The oligonucleotide or peptide-oligonucleotide conjugate may be one from Table 2.

TABLE 2

| Name | Sequence |
|---|---|
| Ant-20 | NH2RQIKIWFQNRRMKWKKGGC(COOH)S-S-5'CCA-TCC-CGA-CCT-CGC-GCT-CC-3'-NH-Quinone-label |
| Ant mismatch | NH2RQIKIWFQNRRMKWKKGGCCOOHSS5'CCA-TAC-CAA-CAT-CAC-GCT-CC-3'-NH-Quinone-label |
| Tat-20 | NH2RKKRRQRRRPPQC(COOH)-S-S-5'CCA-TCCCGA-CCT-CGC-GCT-CC-3'NH-Quinone-label |
| Tat 20mismatch | NH2RKKRRQRRRPPQC(COOH)-S-S-5'CCA-TAC-CAA-CAT-CAC-GCT-CC-3-'NH-Quinone-label |
| 20 | 5'CAA-TCC-CGA-CCT-CGC-GCT-CC-3'-NH-Quinone-label |

In certain embodiments, $R^{14}$ is H, $C_1$-$C_{30}$-alkyl, hydroxy-$C_1$-$C_{30}$-alkyl, $C_1$-$C_{30}$-alkoxy, carboxy-$C_1$-$C_{30}$-alkyl, or amido-$C_1$-$C_{30}$-alkyl; $R^9$ and $R^{10}$ are independently selected from $C_1$-$C_4$-alkyl; $R^{11}$, $R^{12}$ and $R^{13}$ are independently selected from H, $C_1$-$C_4$-alkyl, $C_1$-$C_4$-alkoxy, bromo, chloro or amino, or $R^{11}$ and $R^{12}$ can form a fused phenyl ring; X is O; L is —(CH$_2$)$_m$C(R$^{17}$)$_2$(CH$_2$)$_n$—Y—C(O)—; $R^{17}$ is independently H, $C_1$-$C_4$-alkyl or both $R^{17}$ together can form an alkyl ring having from 3-7 carbons; m is an integer from 0-2; n is an integer from 0-2; Y is O or $NR^{15}$; $R^{15}$ is H, $C_1$-$C_{30}$-alkyl, hydroxy-$C_1$-$C_{30}$-alkyl, azido-$C_1$-$C_{30}$-alkyl, cyano-$C_1$-$C_{30}$-alkyl, halo-$C_1$-$C_{30}$-alkyl, $C_2$-$C_{30}$-alkenyl, $C_2$-$C_{30}$-alkynyl, —$C_1$-$C_{30}$-alkyl-N(R$^{23}$)C(O)R$^{24}$, —$C_1$-$C_{30}$-alkyl-SO$_3$R$^{25}$, —$C_1$-$C_{30}$-alkyl-SO$_2$N(R$^{26}$)(R$^{27}$), —$C_1$-$C_{30}$-alkyl-COR$^{28}$, —$C_1$-$C_{30}$-alkyl-CO$_2$R$^{29}$, —$C_1$-$C_{30}$-alkyl-OC(O)R$^{29}$, —$C_1$-$C_{30}$-alkyl-OC(O)N(R$^{30}$)(R$^{31}$), —$C_1$-$C_{30}$-alkyl-CON(R$^{30}$)(R$^{31}$), or polyalkoxyalkyl, wherein the polyalkoxyalkyl is unsubstituted or substituted with one or more suitable substituents; and $R^{23}$, $R^{24}$, $R^{25}$, $R^{26}$, $R^{27}$, $R^{28}$, $R^{29}$, $R^{30}$, and $R^{31}$ are each independently selected from hydrogen, $C_1$-$C_4$-alkyl, aryl, heteroaryl, heterocyclyl, and cycloalkyl.

In certain embodiments, $R^{14}$ is H, $C_1$-$C_6$-alkyl, hydroxy-$C_1$-$C_6$-alkyl, $C_1$-$C_6$-alkoxy, —$C_1$-$C_6$-alkyl-CO$_2$H, or —$C_1$-$C_6$-alkyl-amide.

In certain embodiments, $R^{14}$ is methyl.

In certain embodiments, $R^{14}$ is carboxyalkyl. In certain embodiments, $R^{14}$ is —$C_2$-$C_{30}$-alkyl-CO$_2$H. In certain embodiments, $R^{14}$ is —CH$_2$CO$_2$H; —(CH$_2$)$_2$CO$_2$H; —(CH$_2$)$_3$CO$_2$H; —(CH$_2$)$_4$CO$_2$H; —(CH$_2$)$_5$CO$_2$H; —(CH$_2$)$_6$CO$_2$H; —(CH$_2$)$_7$CO$_2$H; —(CH$_2$)$_8$CO$_2$H; —(CH$_2$)$_9$CO$_2$H; —(CH$_2$)$_{10}$CO$_2$H; —(CH$_2$)$_{11}$CO$_2$H; —(CH$_2$)$_{12}$CO$_2$H; —(CH$_2$)$_{13}$CO$_2$H; —(CH$_2$)$_{14}$CO$_2$H; —(CH$_2$)$_{15}$CO$_2$H; —(CH$_2$)$_{16}$CO$_2$H; —(CH$_2$)$_{17}$CO$_2$H; —(CH$_2$)$_{18}$CO$_2$H; —(CH$_2$)$_{19}$CO$_2$H; —(CH$_2$)$_{20}$CO$_2$H; —(CH$_2$)$_{21}$CO$_2$H; —(CH$_2$)$_{22}$CO$_2$H; —(CH$_2$)$_{23}$CO$_2$H; —(CH$_2$)$_{24}$CO$_2$H; —(CH$_2$)$_{25}$CO$_2$H; —(CH$_2$)$_{26}$CO$_2$H; —(CH$_2$)$_{27}$CO$_2$H; —(CH$_2$)$_{28}$CO$_2$H; —(CH$_2$)$_{29}$CO$_2$H; or —(CH$_2$)$_{30}$CO$_2$H. In certain embodiments, $R^{14}$ is —(CH$_2$)$_{15}$CO$_2$H.

In certain embodiments, $R^9$, $R^{10}$, $R^{11}$, $R^{12}$, $R^{13}$, and $R^{14}$ are each methyl.

In certain embodiments, in the variable L, m is 1, $R^{17}$ is hydrogen at each occurrence, and n is 0. In certain embodiments, in the variable L, m is 1, $R^{17}$ is hydrogen at each occurrence, n is 0, and Y is $NR^{15}$. In certain embodiments, L is —CH$_2$CH$_2$—NR$^{15}$—C(O)—.

In certain embodiments, A is a bioluminescent reporter moiety. In certain embodiments, A is a luciferin, a luciferin derivative or analog, a prelucifern or analog, coelenterazine or a coelenterazine derivative or analog. In some embodiments, A is luciferin, pro-luciferin, aminoluciferin, quionolyl-luciferin, napthyl luciferin, chloroluciferin, coelenterazine, furimazine, coelenterazine-n, coelenterazine-f, coelenterazine-h, coelenterazine-hcp, coelenterazine-cp, coelenterazine-c, coelenterazine-e, coelenterazine-fcp, bis-deoxycoelenterazine ("coelenterazine-hh"), coelenterazine-i, coelenterazine-icp, coelenterazine-v, and 2-methyl coelenterazine, in addition to those disclosed in WO 2003/040100, U.S. Patent Publication No. 20080248511, and U.S. Patent Publication No. US 20120117667, the disclosures of which are incorporated by reference herein.

In certain embodiments, A is a fluorescent reporter moiety. In certain embodiments, A is a coumarin, R110, fluoroscein, DDAO, resorufin, cresyl violet, sily xanthene, or carbopyronine. In some embodiments, A is rhodamine 123, rhodamine X, Alexa dyes (e.g., Alexa Fluor-350, -430, -488, -and -660), DyLight 594, sulforhodamine B, sulforhodamine 101, sulfonyl chloride derivative of sulforhodamine 101 (Texas Red), fluorescein, 6-carboxyfluorescein (6-FAM), 5-carboxyfluorescein (5-Fam), 5- or 6-carboxy-4,7,2',7'-tetrachlorofluorescein (TET), 5- or 6-carboxy-4'5'2'4'5'7' hexachlorofluorescein (HEX), 5' or 6'-carboxy-4',5'-dichloro-2',7'-dimethoxyfluorescein (JOE), 6-JOE, 5-carboxy-2',4',5',7'-tetrachlorofluorescein (ZOE) rhodol, fluorescein isothiocyanate, coumarin, 7-amino-4-methylcoumarin, aminocoumarin, hydroxycoumarin, silyl xanthene, or carbopyronine. In certain embodiments, A is a bicyclic aryl or heteroaryl, each of which are independently unsubstituted or substituted with one or more suitable substituents. In certain embodiments, A is a bicyclic aryl or heteroaryl, each of which are independently unsubstituted or substituted with 1, 2, 3, 4, or 5 substituents independently selected from the group consisting of alkyl, haloalkyl, hydroxyalkyl, alkoxyalkyl, haloalkoxyalkyl, aminoalkyl, alkylaminoalkyl, di(alkyl)aminoalkyl, cyanoalkyl, alkoxy, haloalkoxy, cyano, hydroxy, amino, alkylamino, di(alkyl)amino, aryl, heteroaryl, heterocyclyl, cycloalkyl, arylalkyl, heteroarylalkyl, hetercyclylalkyl, and cycloalkylalkyl, wherein the aryl, heteroaryl, heterocyclyl, cycloalkyl, aryl of the arylalkyl, heteroaryl of the heteroarylalkyl, heterocyclyl of the hetercyclylalkyl, and cycloalkyl of the cycloalkylalkyl are each independently unsubstituted or substituted with 1, 2, or 3 substituents independently selected from alkyl, haloalkyl, hydroxyalkyl, alkoxyalkyl, haloalkoxyalkyl, aminoalkyl, alkylaminoalkyl, di(alkyl)aminoalkyl, cyanoalkyl, alkoxy, haloalkoxy, cyano, hydroxy, amino, alkylamino, and di(alkyl)amino.

In certain embodiments, A is a luciferin, luciferin derivative or analog (e.g., luciferin ester), preluciferin, preluciferin derivative or analog, cyanobenzothiazole, coelenterazine, a coelenterazine derivative or analog, or a fluorophore.

In certain embodiments, A is selected from the group consisting of:

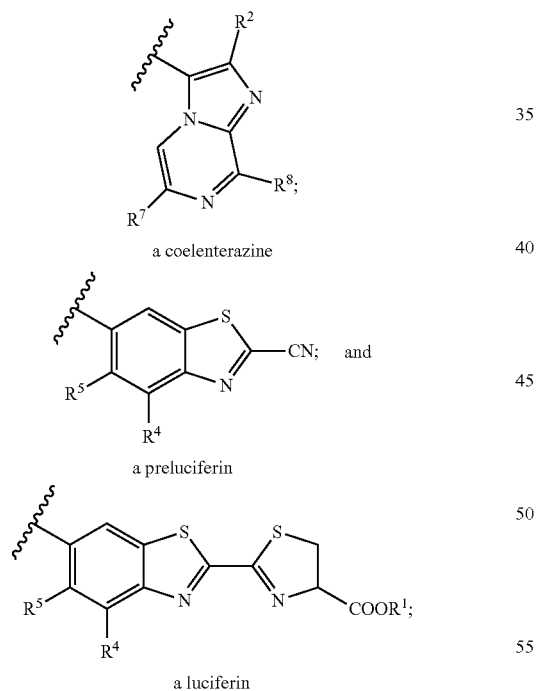

a coelenterazine a preluciferin a luciferin wherein $R^1$ is H, $C_1$-$C_4$-alkyl, hydroxy-$C_1$-$C_4$-alkyl, $C_3$-$C_7$-cycloalkyl, aryl, benzyl or substituted benzyl, heterocyclyl, heteroaryl, or —$(CH_2)_q$—$P(Ph)_3$, wherein q is an integer selected from 1, 2, 3, 4, 5, and 6; $R^2$ is —$CH_2$-aryl or —$CH_2$-heteroaryl; $R^4$ is hydrogen, halogen, methyl, or trifluoromethyl; $R^5$ is hydrogen, halogen, methyl, or trifluoromethyl; $R^7$ is aryl (e.g., phenyl), substituted aryl (e.g., 4-hydroxyphenyl), —$CH_2$-aryl, or —$CH_2$-heteroaryl; and $R^8$ is —$CH_2$-aryl or —$CH_2$-heteroaryl. In certain embodiments, the —$CH_2$-aryl is benzyl. In certain embodiments, the —$CH_2$-heteroaryl is furylmethyl.

In certain embodiments, A is selected from the group consisting of:

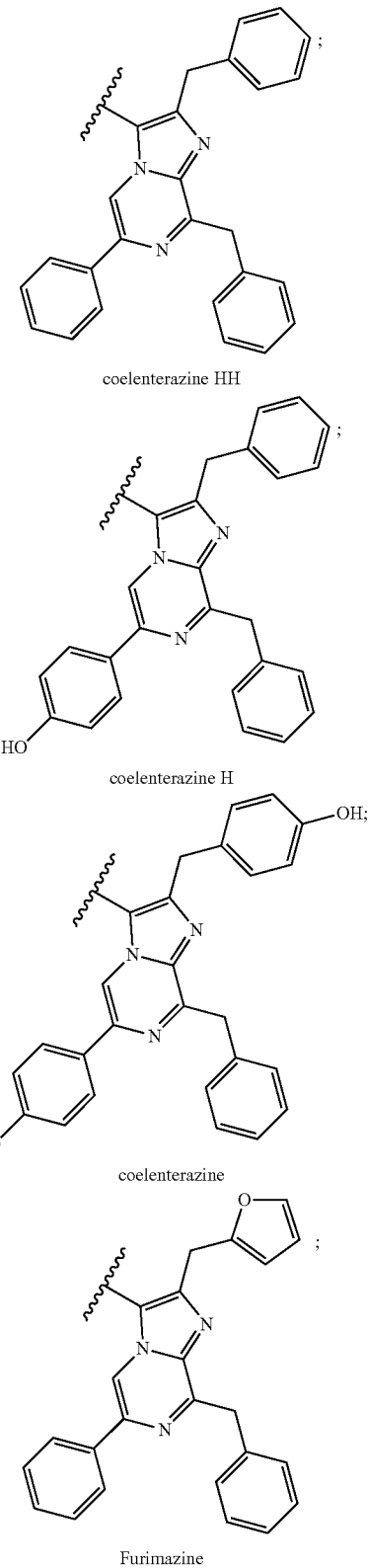

coelenterazine HH coelenterazine H coelenterazine

Furimazine

-continued

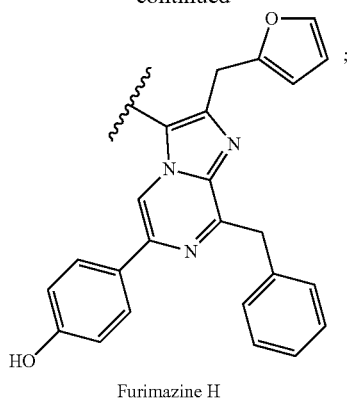

Furimazine H

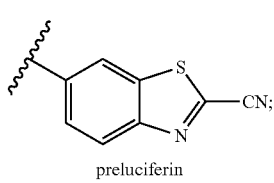

preluciferin

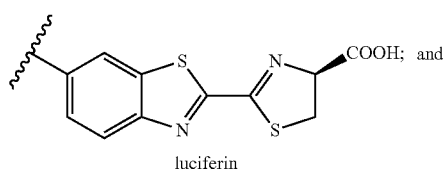

luciferin

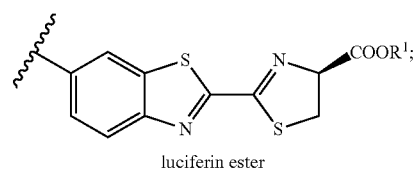

luciferin ester wherein R$^1$ is C$_1$-C$_4$-alkyl, hydroxy-C$_1$-C$_4$-alkyl, C$_3$-C$_7$-cycloalkyl, aryl, benzyl or substituted benzyl, heterocyclyl, heteroaryl, or —(CH$_2$)$_q$—P(Ph)$_3$, wherein q is an integer selected from 1, 2, 3, 4, 5, and 6.

In certain embodiments, compounds of formula (I) have formula (I-i), or a salt thereof, (I-i)

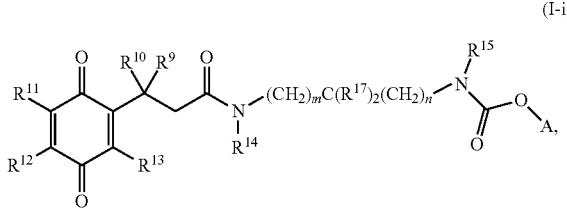

wherein R$^9$, R$^{10}$, R$^{11}$, R$^{12}$, R$^{13}$, R$^{14}$, R$^{15}$, R$^{17}$, m, n, and A are as defined above. In certain embodiments, A is selected from the group consisting of:

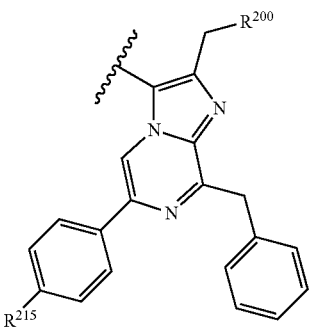

and

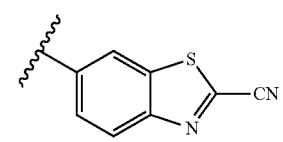

wherein R$^{200}$ is phenyl, 4-hydroxyphenyl, or furyl; and R$^{215}$ is hydrogen or hydroxy.

In certain embodiments, compounds of formula (I) have formula (I-ii), or a salt thereof, (I-ii)

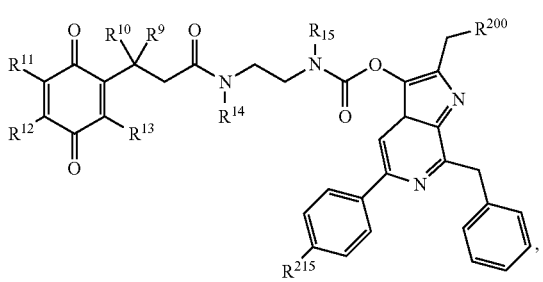

wherein R$^{200}$ is phenyl, 4-hydroxyphenyl, or furyl; R$^{215}$ is hydrogen or hydroxy; and R$^9$, R$^{10}$, R$^{11}$, R$^{12}$, R$^{13}$, R$^{14}$, and R$^{15}$ are as defined above.

In certain embodiments, compounds of formula (I) have formula (I-iv), or a salt thereof, (I-iii)

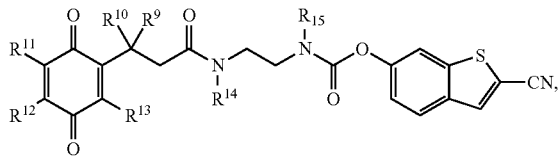

wherein R$^9$, R$^{10}$, R$^{11}$, R$^{12}$, R$^{13}$, R$^{14}$, and R$^{15}$ are as defined above.

In certain embodiments, the compound of formula (I) is selected from the group consisting of:

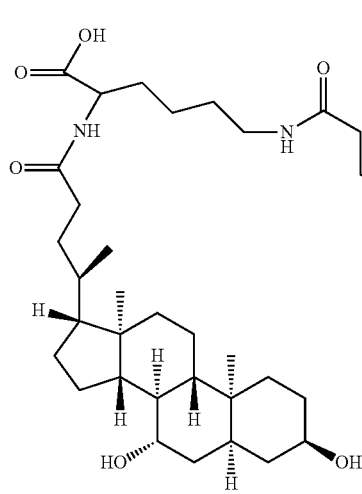
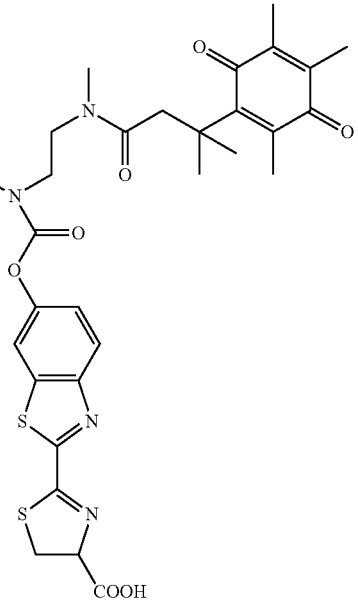

5651: 2-(6-((((20R)-15-carboxy-20-((3R,5S,7S,8R,9S,10S,13R,14S,17R)-3,7-dihydroxy-10,13-dimethylhexadecahydro-1H-cyclopenta[a]phenanthren-17-yl)-9,17-dioxo-3,6-dioxa-10,16-diazahenicosyl)(2-(N,3-dimethyl-3-(2,4,5-trimethyl-3,6-dioxocyclohexa-1,4-dien-1-yl)butanamido)ethyl)carbamoyl)oxy)benzo[d]thiazol-2-yl)-4,5-dihydrothiazole-4-carboxylic acid;

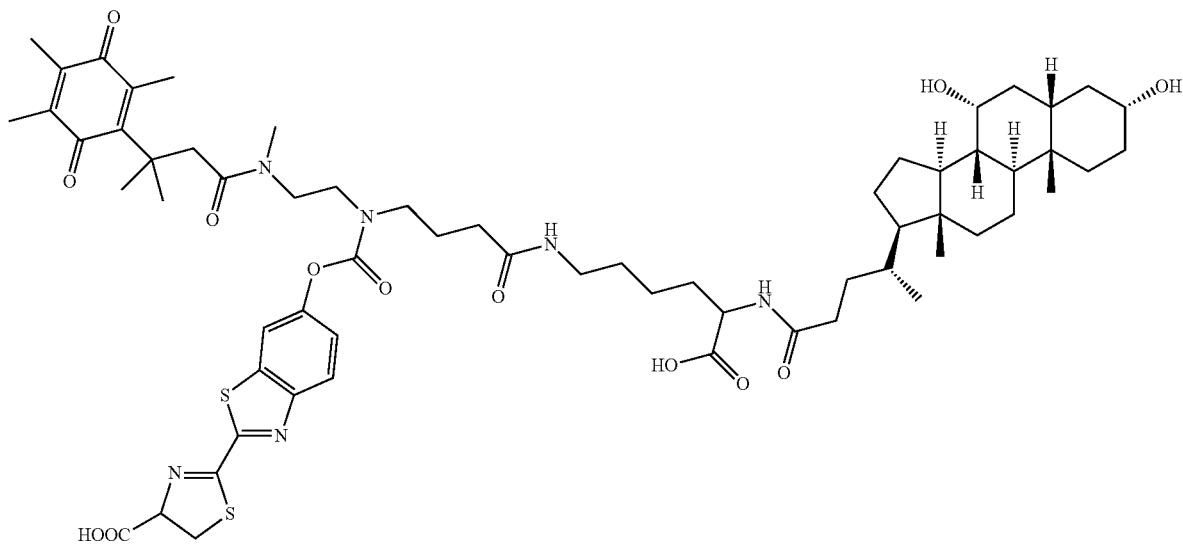

5657: 2-(6-(((4-((5-carboxy-5-((R)-4-((3R,5S,7R,8R,9S,10S,13R,14S,17R)-3,7-dihydroxy-10,13-dimethylhexadecahydro-1H-cyclopenta[a]phenanthren-17-yl)pentanamido)pentyl)amino)-4-oxobutyl)(2-(N,3-dimethyl-3-(2,4,5-trimethyl-3,6-dioxocyclohexa-1,4-dien-1-yl)butanamido)ethyl)carbamoyl)oxy)benzo[d]thiazol-2-yl)-4,5-dihydrothiazole-4-carboxylic acid;

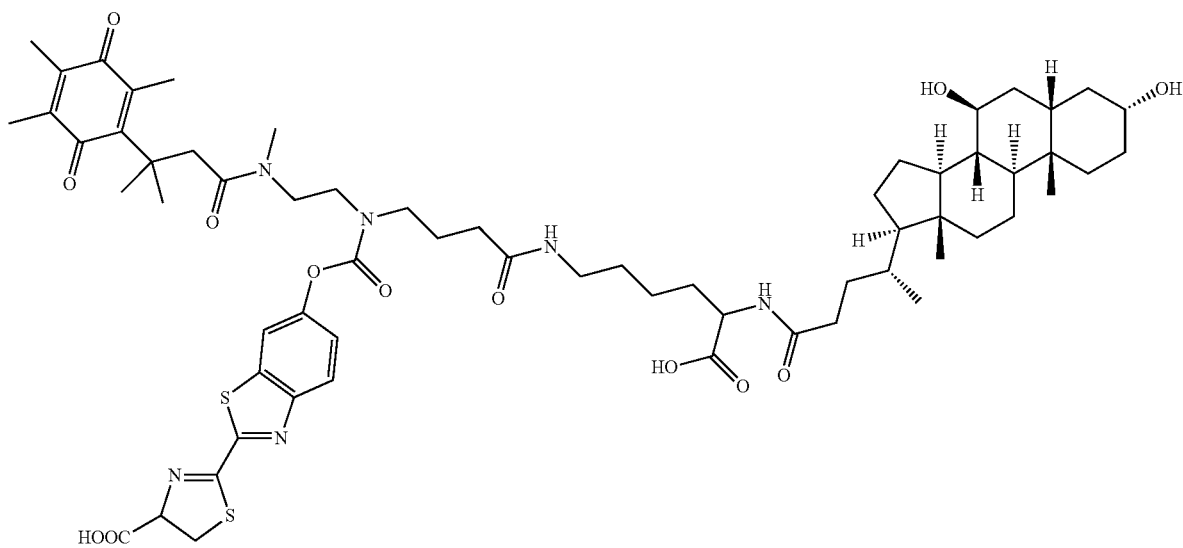

5658: 2-(6-(((4-((5-carboxy-5-((R)-4-((3R,5S,7S,8R,9S,10S,13R,14S,17R)-3,7-dihydroxy-10,13-dimethylhexadecahydro-1H-cyclopenta[a]phenanthren-17-yl)pentanamido)pentyl)amino)-4-oxobutyl)(2-(N,3-dimethyl-3-(2,4,5-trimethyl-3,6-dioxocyclohexa-1,4-dien-1-yl)butanamido)ethyl)carbamoyl)oxy)benzo[d]thiazol-2-yl)-4,5-dihydrothiazole-4-carboxylic acid;

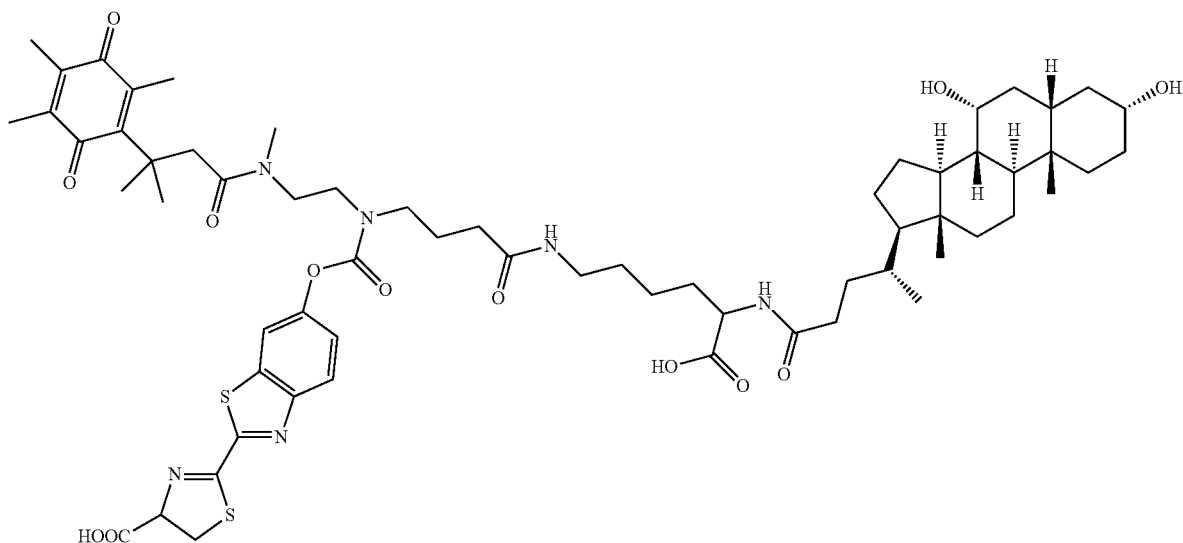

5665: 2-(6-(((4-((5-carboxy-5-((R)-4-((3R,5S,7R,8R,9S,10S,13R,14S,17R)-3,7-dihydroxy-10,13-dimethylhexadecahydro-1H-cyclopenta[a]phenanthren-17-yl)pentanamido)pentyl)amino)-4-oxobutyl)(2-(N,3-dimethyl-3-(2,4,5-trimethyl-3,6-dioxocyclohexa-1,4-dien-1-yl)butanamido)ethyl)carbamoyl)oxy)benzo[d]thiazol-2-yl)-4,5-dihydrothiazole-4-carboxylic acid;

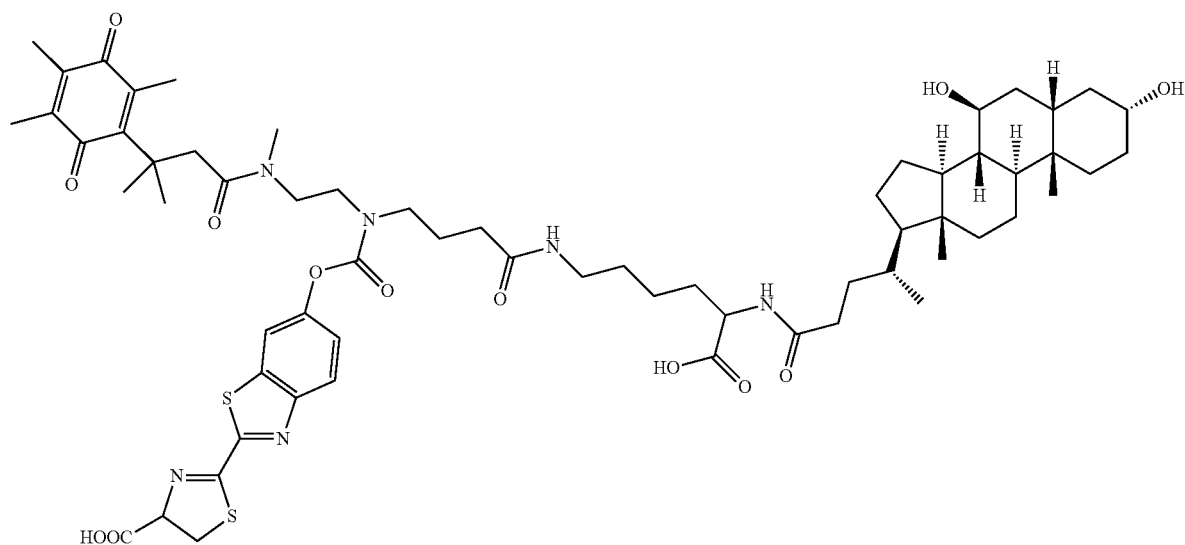

5666: 2-(6-(((4-((5-carboxy-5-((R)-4-((3R,5S,7S,8R,9S,10S,13R,14S,17R)-3,7-dihydroxy-10,13-dimethylhexadecahydro-1H-cyclopenta[a]phenanthren-17-yl)pentanamido)pentyl)amino)-4-oxobutyl)(2-(N,3-dimethyl-3-(2,4,5-trimethyl-3,6-dioxocyclohexa-1,4-dien-1-yl)butanamido)ethyl)carbamoyl)oxy)benzo[d]thiazol-2-yl)-4,5-dihydrothiazole-4-carboxylic acid;

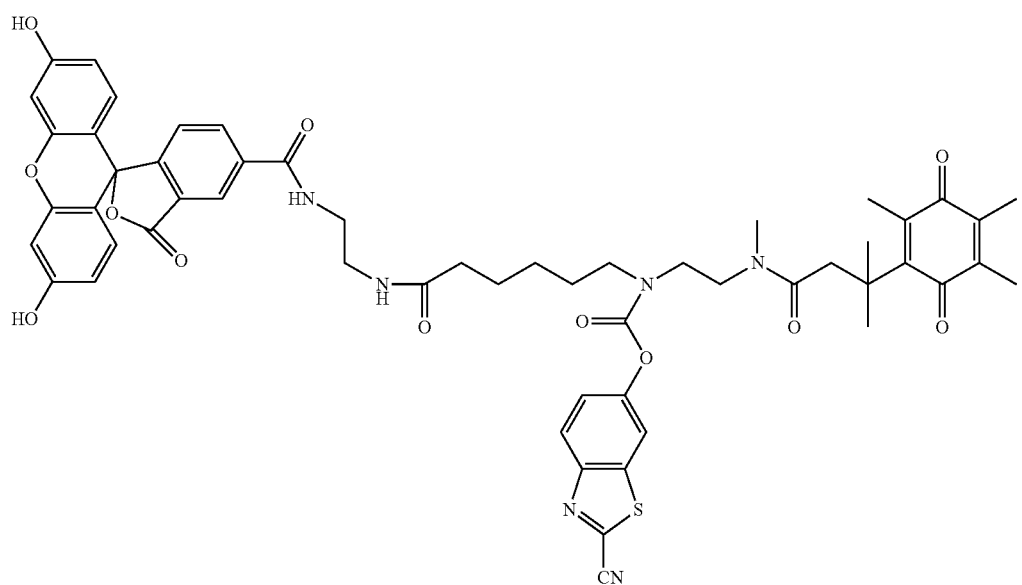 [SMILES: CC1=C(C)C(=O)C(C(C)(C)CC(=O)N(C)CCN(CCCCCC(=O)NCCNC(=O)c2ccc3c(c2)C(=O)OC32c3ccc(O)cc3Oc3cc(O)ccc32)C(=O)Oc2ccc3nc(C#N)sc3c2)=C(C)C1=O]

5683: 2-cyanobenzo[d]thiazol-6-yl(6-((2-(3',6'-dihydroxy-3-oxo-3H-spiro[isobenzofuran-1,9'-xanthen]-5-ylcarboxamido)ethyl)amino)-6-oxohexyl)(2-(N,3-dimethyl-3-(2,4,5-trimethyl-3,6-dioxocyclohexa-1,4-dien-1-yl)butanamido)ethyl)carbamate;

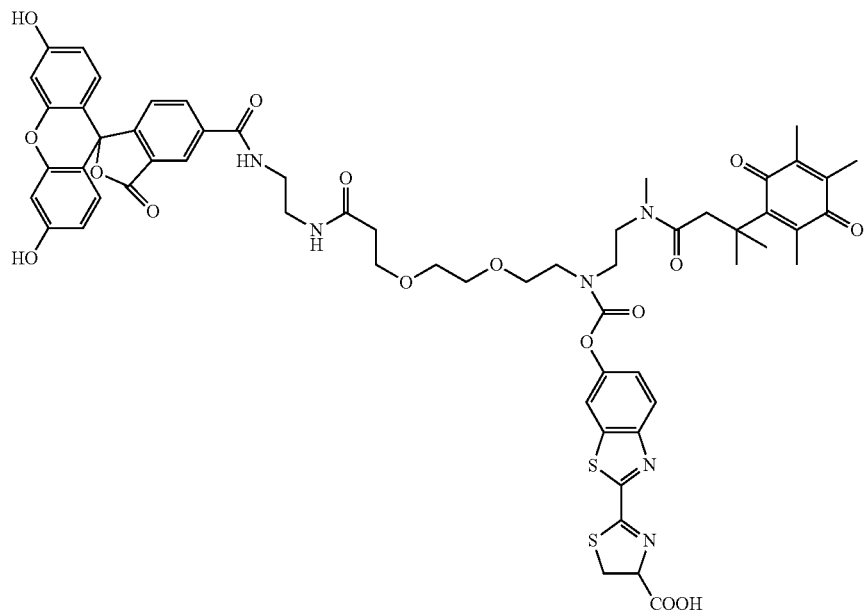 [SMILES: CC1=C(C)C(=O)C(C(C)(C)CC(=O)N(C)CCN(CCOCCOCCC(=O)NCCNC(=O)c2ccc3c(c2)C(=O)OC32c3ccc(O)cc3Oc3cc(O)ccc32)C(=O)Oc2ccc3nc(C4=NC(C(=O)O)CS4)sc3c2)=C(C)C1=O]

5826: 2-(6-(((1-(3',6'-dihydroxy-3-oxo-3H-spiro[isobenzofuran-1,9'-xanthen]-5-yl)-1,6-dioxo-9,12-dioxa-2,5-diazatetradecan-14-yl)(2-(N,3-dimethyl-3-(2,4,5-trimethyl-3,6-dioxocyclohexa-1,4-dien-1-yl)butanamido)ethyl)carbamoyl)oxy)benzo[d]thiazol-2-yl)-4,5-dihydrothiazole-4-carboxylic acid;

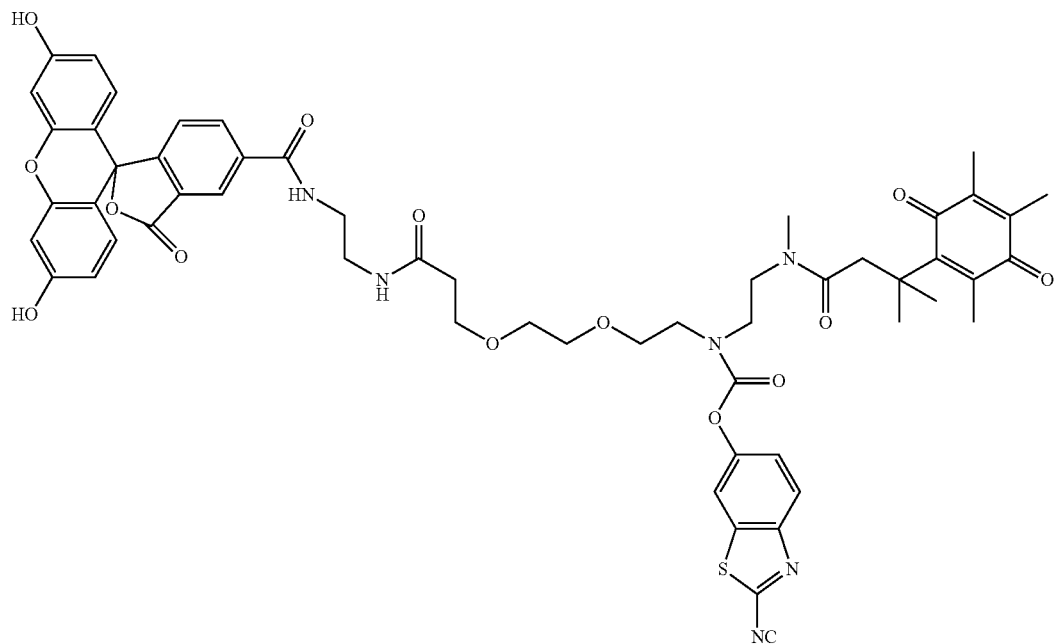

5682: 2-cyanobenzo[d]thiazol-6-yl(1-(3',6'-dihydroxy-3-oxo-3H-spiro[isobenzofuran-1,9'-xanthen]-5-yl)-1,6-dioxo-9,12-dioxa-2,5-diazatetradecan-14-yl)(2-(N,3-dimethyl-3-(2,4,5-trimethyl-3,6-dioxocyclohexa-1,4-dien-1-yl)butanamido)ethyl)carbamate;

85

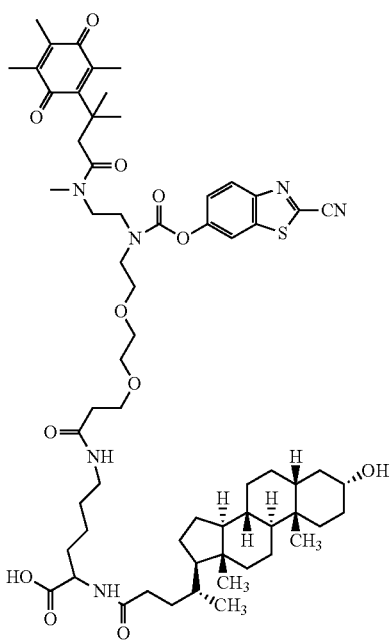

5647: 8-(((2-cyanobenzo[d]thiazol-6-yl)oxy)carbonyl)-23-((R)-4-((3R,5R,8R,9S,10S,13R,14S,17R)-3-hydroxy-10,13-dimethylhexadecahydro-1H-cyclopenta[a]phenanthren-17-yl)pentanamido)-2,5-dimethyl-4,17-dioxo-2-(2,4,5-trimethyl-3,6-dioxocyclohexa-1,4-dien-1-yl)-11,14-dioxa-5,8,18-triazatetracosan-24-oic acid;

86

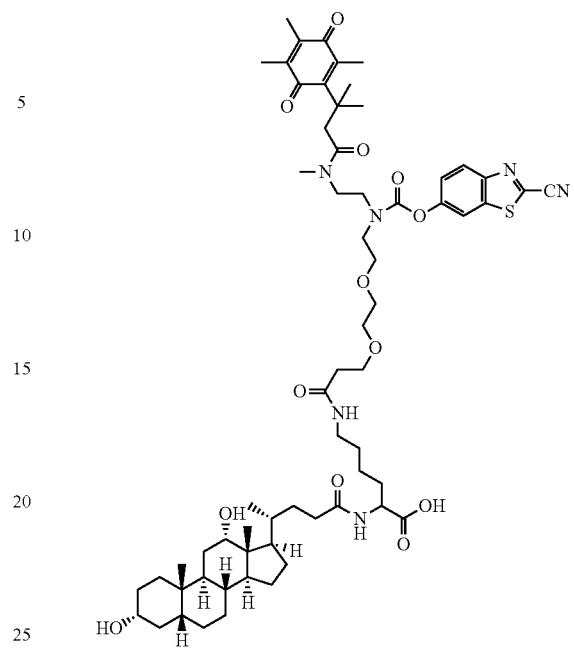

5625: 8-(((2-cyanobenzo[d]thiazol-6-yl)oxy)carbonyl)-23-((R)-4-((3R,5R,8R,9S,10S,12S,13R,14S,17R)-3,12-dihydroxy-10,13-dimethylhexadecahydro-1H-cyclopenta[a]phenanthren-17-yl)pentanamido)-2,5-dimethyl-4,17-dioxo-2-(2,4,5-trimethyl-3,6-dioxocyclohexa-1,4-dien-1-yl)-11,14-dioxa-5,8,18-triazatetracosan-24-oic acid;

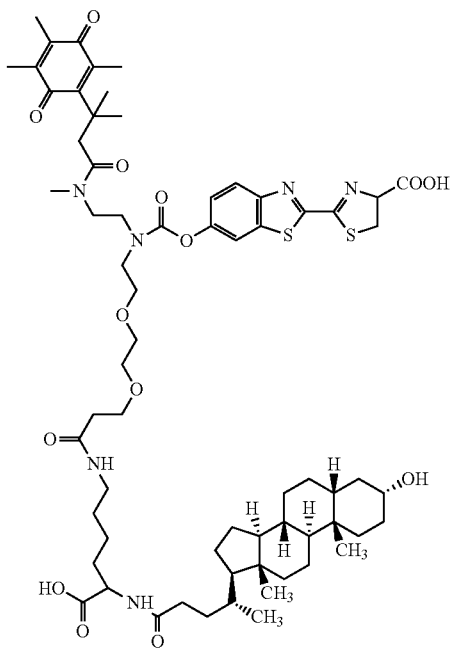

5668: 2-(6-(((((20R)-15-carboxy-20-((3R,5R,8R,9S,10S,13R,14S,17R)-3-hydroxy-10,13-dimethylhexadecahydro-1H-cyclopenta[a]phenanthren-17-yl)-9,17-dioxo-3,6-dioxa-10,16-diazahenicosyl)(2-(N,3-dimethyl-3-(2,4,5-trimethyl-3,6-dioxocyclohexa-1,4-dien-1-yl)butanamido)ethyl)carbamoyl)oxy)benzo[d]thiazol-2-yl)-4,5-dihydrothiazole-4-carboxylic acid;

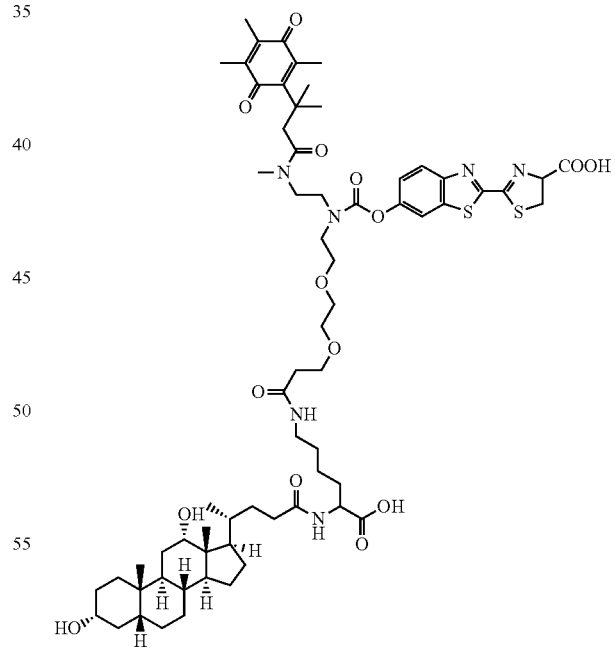

5649: 2-(6-(((((20R)-15-carboxy-20-((3R,5R,8R,9S,10S,12S,13R,14S,17R)-3,12-dihydroxy-10,13-dimethylhexadecahydro-1H-cyclopenta[a]phenanthren-17-yl)-9,17-dioxo-3,6-dioxa-10,16-diazahenicosyl)(2-(N,3-dimethyl-3-(2,4,5-trimethyl-3,6-dioxocyclohexa-1,4-dien-1-yl)butanamido)ethyl)carbamoyl)oxy)benzo[d]thiazol-2-yl)-4,5-dihydrothiazole-4-carboxylic acid;

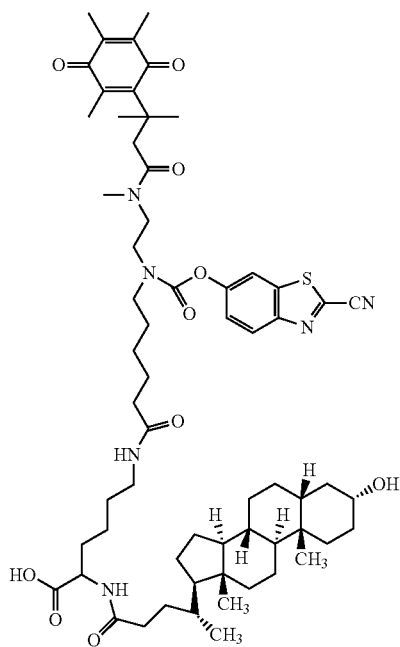

5659: 6-(6-((((2-cyanobenzo[d]thiazol-6-yl)oxy)carbonyl)(2-(N,3-dimethyl-3-(2,4,5-trimethyl-3,6-dioxocyclohexa-1,4-dien-1-yl)butanamido)ethyl)amino)hexanamido)-2-((R)-4-((3R,5R,8R,9S,10S,13R,14S,17R)-3-hydroxy-10,13-dimethylhexadecahydro-1H-cyclopenta[a]phenanthren-17-yl)pentanamido)hexanoic acid;

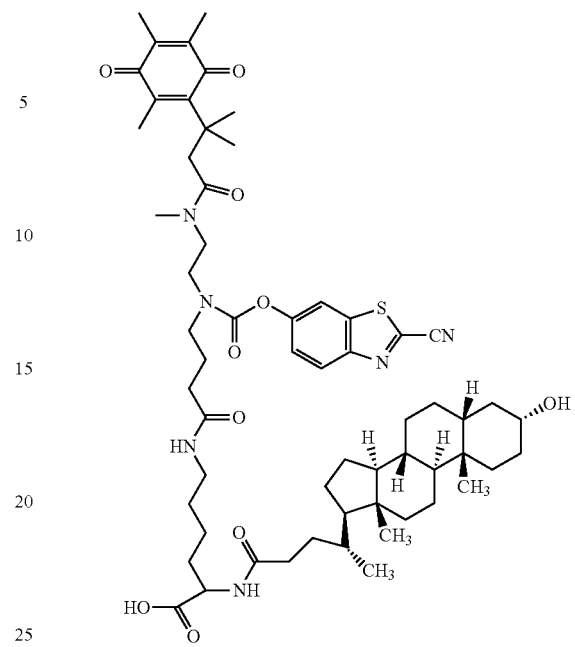

5652: 6-(4-((((2-cyanobenzo[d]thiazol-6-yl)oxy)carbonyl)(2-(N,3-dimethyl-3-(2,4,5-trimethyl-3,6-dioxocyclohexa-1,4-dien-1-yl)butanamido)ethyl)amino)butanamido)-2-((R)-4-((3R,5R,8R,9S,10S,13R,14S,17R)-3-hydroxy-10,13-dimethylhexadecahydro-1H-cyclopenta[a]phenanthren-17-yl)pentanamido)hexanoic acid;

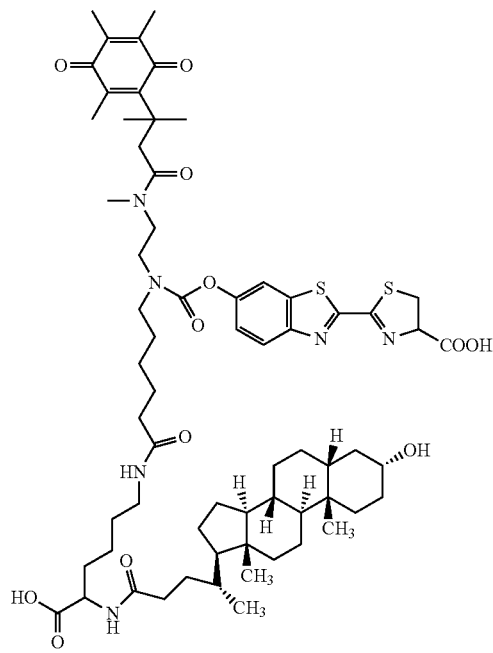

5663: 2-(6-(((6-((5-carboxy-5-((R)-4-((3R,5R,8R,9S,10S,13R,14S,17R)-3-hydroxy-10,13-dimethylhexadeca-hydro-1H-cyclopenta[a]phenanthren-17-yl)pentanamido)pentyl)amino)-6-oxohexyl)(2-(N,3-dimethyl-3-(2,4,5-trimethyl-3,6-dioxocyclohexa-1,4-dien-1-yl)butanamido)ethyl)carbamoyl)oxy)benzo[d]thiazol-2-yl)-4,5-dihydrothiazole-4-carboxylic acid;

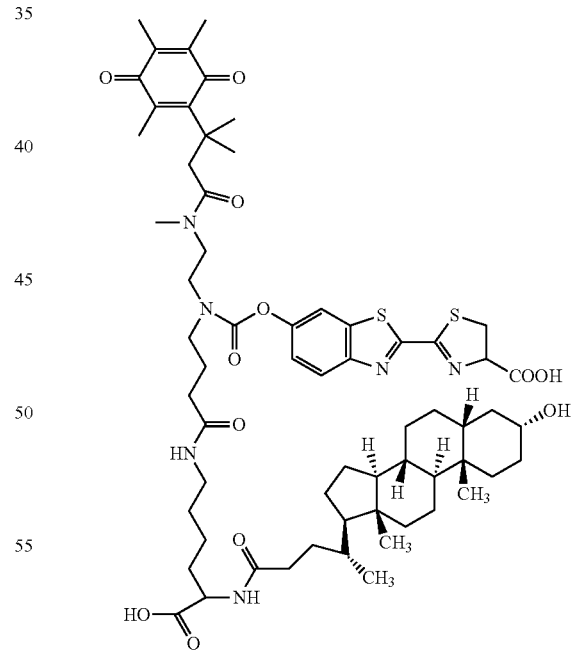

5669: 2-(6-(((4-((5-carboxy-5-((R)-4-((3R,5R,8R,9S,10S,13R,14S,17R)-3-hydroxy-10,13-dimethylhexadeca-hydro-1H-cyclopenta[a]phenanthren-17-yl)pentanamido)pentyl)amino)-4-oxobutyl)(2-(N,3-dimethyl-3-(2,4,5-trimethyl-3,6-dioxocyclohexa-1,4-dien-1-yl)butanamido)ethyl)carbamoyl)oxy)benzo[d]thiazol-2-yl)-4,5-dihydrothiazole-4-carboxylic acid;

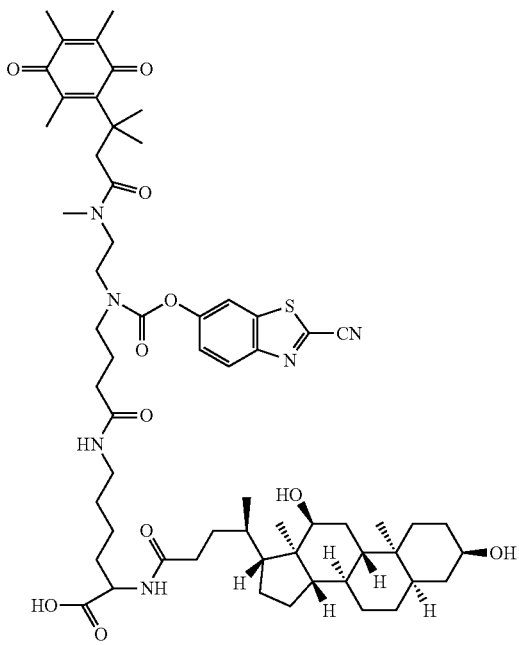

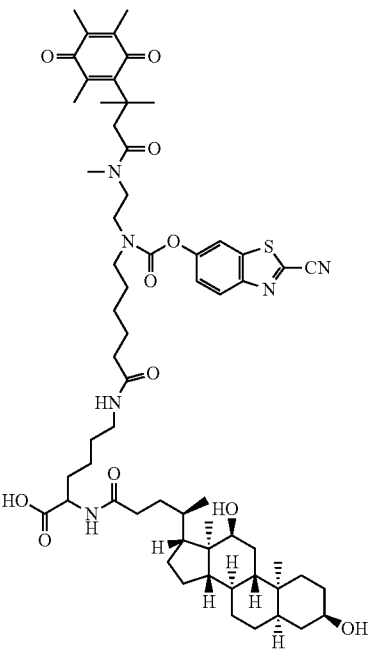

5653: 6-(4-((((2-cyanobenzo[d]thiazol-6-yl)oxy)carbonyl)
(2-(N,3-dimethyl-3-(2,4,5-trimethyl-3,6-dioxocyclohexa-
1,4-dien-1-yl)butanamido)ethyl)amino)butanamido)-2-
((R)-4-((3R,5R,8R,9S,10S,12S,13R,14S,17R)-3,12-
dihydroxy-10,13-dimethylhexadecahydro-1H-cyclopenta
[a]phenanthren-17-yl)pentanamido)hexanoic acid;

5660: 6-(6-((((2-cyanobenzo[d]thiazol-6-yl)oxy)carbonyl)
(2-(N,3-dimethyl-3-(2,4,5-trimethyl-3,6-dioxocyclohexa-
1,4-dien-1-yl)butanamido)ethyl)amino)hexanamido)-2-
((R)-4-((3R,5R,8R,9S,10S,12S,13R,14S,17R)-3,12-
dihydroxy-10,13-dimethylhexadecahydro-1H-cyclopenta
[a]phenanthren-17-yl)pentanamido)hexanoic acid;

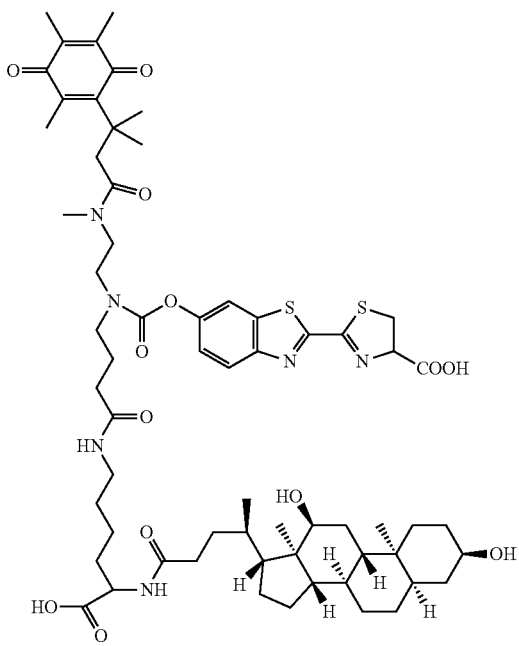

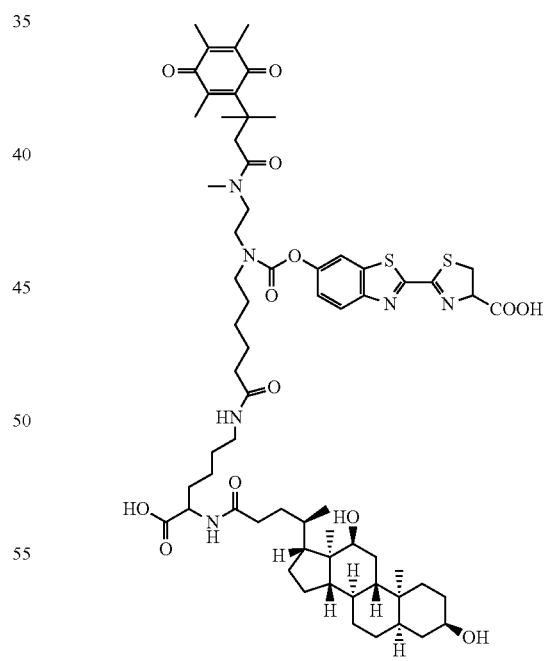

5656: 2-(6-(((4-((5-carboxy-5-((R)-4-((3R,5R,8R,9S,10S,
12S,13R,14S,17R)-3,12-dihydroxy-10,13-dimethylhexa-
decahydro-1H-cyclopenta[a]phenanthren-17-yl)pentana-
mido)pentyl)amino)-4-oxobutyl)(2-(N,3-dimethyl-3-(2,4,
5-trimethyl-3,6-dioxocyclohexa-1,4-dien-1-yl)
butanamido)ethyl)carbamoyl)oxy)benzo[d]thiazol-2-yl)-
4,5-dihydrothiazole-4-carboxylic acid;

5664: 2-(6-(((6-((5-carboxy-5-((R)-4-((3R,5R,8R,9S,10S,
12S,13R,14S,17R)-3,12-dihydroxy-10,13-dimethylhexa-
decahydro-1H-cyclopenta[a]phenanthren-17-yl)pentana-
mido)pentyl)amino)-6-oxohexyl)(2-(N,3-dimethyl-3-(2,
4,5-trimethyl-3,6-dioxocyclohexa-1,4-dien-1-yl)
butanamido)ethyl)carbamoyl)oxy)benzo[d]thiazol-2-yl)-
4,5-dihydrothiazole-4-carboxylic acid;

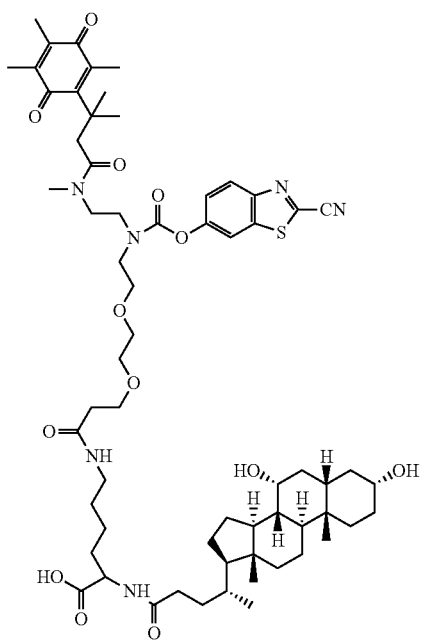

5667: 8-(((2-cyanobenzo[d]thiazol-6-yl)oxy)carbonyl)-23-((R)-4-((3R,5S,7R,8R,9S,10S,13R,14S,17R)-3,7-dihydroxy-10,13-dimethylhexadecahydro-1H-cyclopenta[a]phenanthren-17-yl)pentanamido)-2,5-dimethyl-4,17-dioxo-2-(2,4,5-trimethyl-3,6-dioxocyclohexa-1,4-dien-1-yl)-11,14-dioxa-5,8,18-triazatetracosan-24-oic acid;

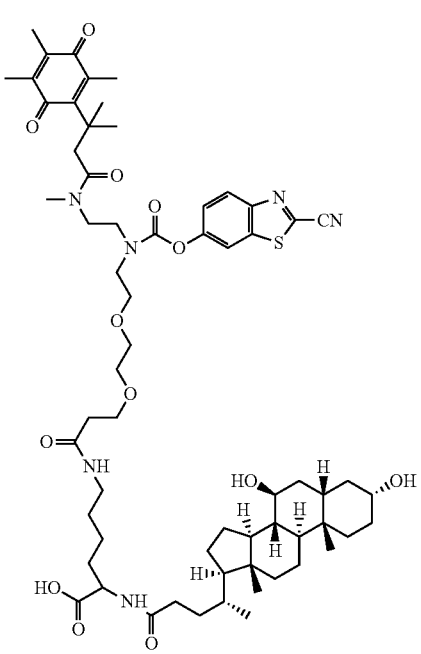

5648: 8-(((2-cyanobenzo[d]thiazol-6-yl)oxy)carbonyl)-23-((R)-4-((3R,5S,7S,8R,9S,10S,13R,14S,17R)-3,7-dihydroxy-10,13-dimethylhexadecahydro-1H-cyclopenta[a]phenanthren-17-yl)pentanamido)-2,5-dimethyl-4,17-dioxo-2-(2,4,5-trimethyl-3,6-dioxocyclohexa-1,4-dien-1-yl)-11,14-dioxa-5,8,18-triazatetracosan-24-oic acid;

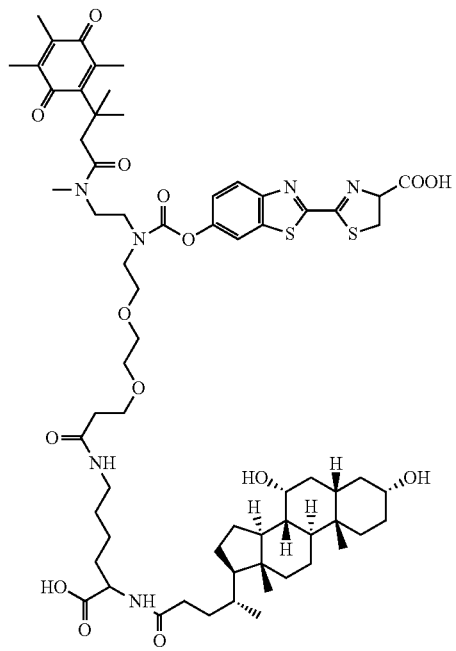

5650: 2-(6-((((20R)-15-carboxy-20-((3R,5S,7R,8R,9S,10S,13R,14S,17R)-3,7-dihydroxy-10,13-dimethylhexadecahydro-1H-cyclopenta[a]phenanthren-17-yl)-9,17-dioxo-3,6-dioxa-10,16-diazahenicosyl)(2-(N,3-dimethyl-3-(2,4,5-trimethyl-3,6-dioxocyclohexa-1,4-dien-1-yl)butanamido)ethyl)carbamoyl)oxy)benzo[d]thiazol-2-yl)-4,5-dihydrothiazole-4-carboxylic acid;

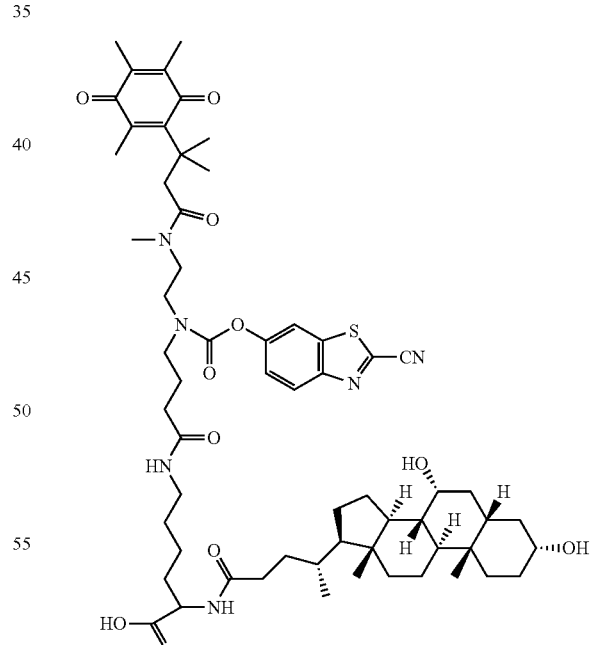

5654: 6-(4-(((((2-cyanobenzo[d]thiazol-6-yl)oxy)carbonyl)(2-(N,3-dimethyl-3-(2,4,5-trimethyl-3,6-dioxocyclohexa-1,4-dien-1-yl)butanamido)ethyl)amino)butanamido)-2-((R)-4-((3R,5S,7R,8R,9S,10S,13R,14S,17R)-3,7-dihydroxy-10,13-dimethylhexadecahydro-1H-cyclopenta[a]phenanthren-17-yl)pentanamido)hexanoic acid;

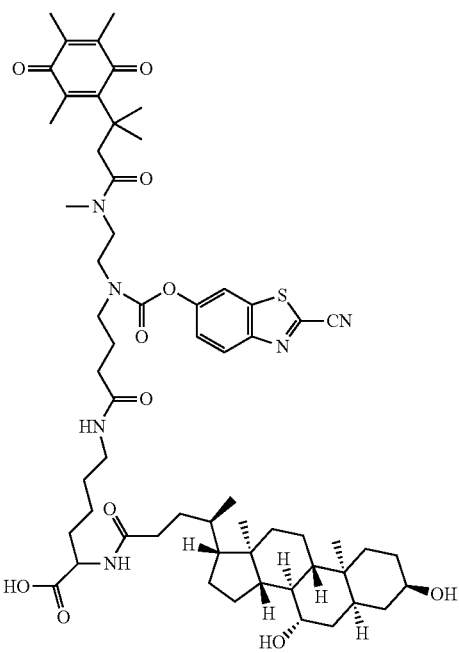

5655: 6-(4-((((2-cyanobenzo[d]thiazol-6-yl)oxy)carbonyl)
(2-(N,3-dimethyl-3-(2,4,5-trimethyl-3,6-dioxocyclohexa-
1,4-dien-1-yl)butanamido)ethyl)amino)butanamido)-2-
((R)-4-((3R,5S,7S,8R,9S,10S,13R,14S,17R)-3,7-
dihydroxy-10,13-dimethylhexadecahydro-1H-cyclopenta
[a]phenanthren-17-yl)pentanamido)hexanoic acid;

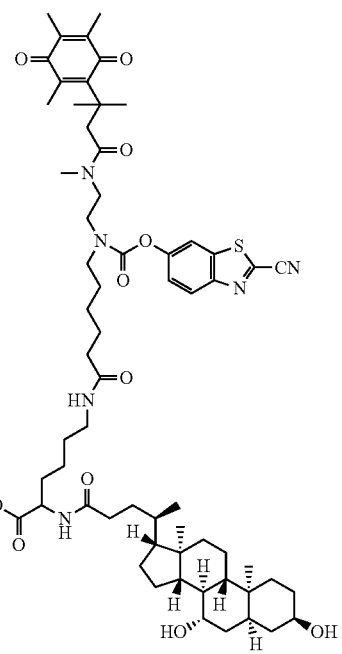

5662: 6-(6-((((2-cyanobenzo[d]thiazol-6-yl)oxy)carbonyl)
(2-(N,3-dimethyl-3-(2,4,5-trimethyl-3,6-dioxocyclohexa-
1,4-dien-1-yl)butanamido)ethyl)amino)hexanamido)-2-
((R)-4-((3R,5S,7S,8R,9S,10S,13R,14S,17R)-3,7-
dihydroxy-10,13-dimethylhexadecahydro-1H-cyclopenta
[a]phenanthren-17-yl)pentanamido)hexanoic acid;

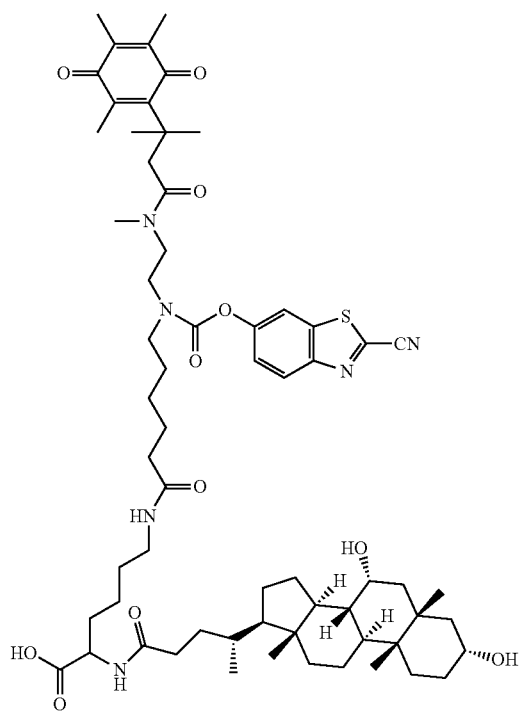

5661: 6-(6-((((2-cyanobenzo[d]thiazol-6-yl)oxy)carbonyl)
(2-(N,3-dimethyl-3-(2,4,5-trimethyl-3,6-dioxocyclohexa-
1,4-dien-1-yl)butanamido)ethyl)amino)hexanamido)-2-
((R)-4-((3R,5S,7R,8R,9S,10S,13R,14S,17R)-3,7-
dihydroxy-10,13-dimethylhexadecahydro-1H-cyclopenta
[a]phenanthren-17-yl)pentanamido)hexanoic acid;

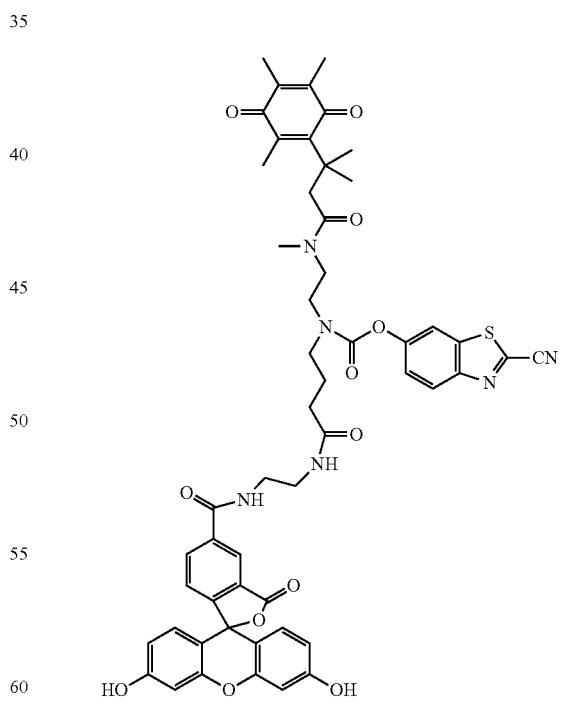

5684: 2-cyanobenzo[d]thiazol-6-yl(4-((2-(3',6'-dihydroxy-
3-oxo-3H-spiro[isobenzofuran-1,9'-xanthene]-5-carbox-
amido)ethyl)amino)-4-oxobutyl)(2-(N,3-dimethyl-3-(2,4,
5-trimethyl-3,6-dioxocyclohexa-1,4-dien-1-yl)
butanamido)ethyl)carbamate;

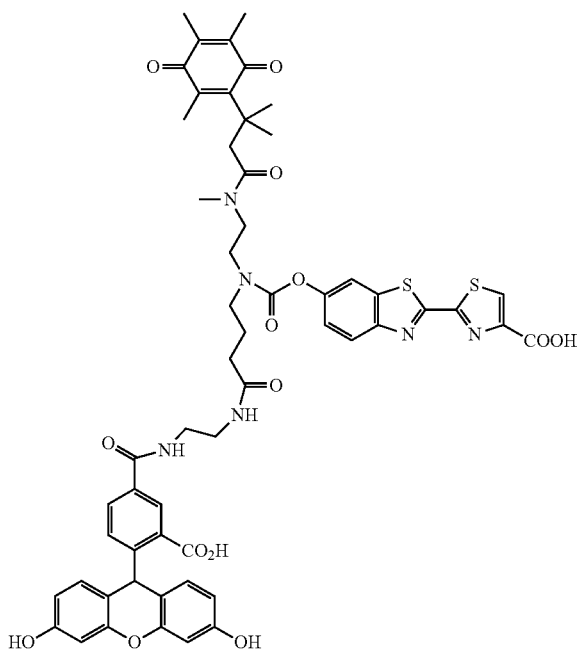 [SMILES: CC1=C(C)C(=O)C(C(C)(C)CC(=O)N(C)CCN(CCCC(=O)NCCNC(=O)c2ccc(C3c4ccc(O)cc4Oc4cc(O)ccc43)c(C(=O)O)c2)C(=O)Oc2ccc3nc(-c4nc(C(=O)O)cs4)sc3c2)=C(C)C1=O]

5824: 2-(6-(((4-((2-(3-carboxy-4-(3,6-dihydroxy-9H-xanthen-9-yl)benzamido)ethyl)amino)-4-oxobutyl)(2-(N,3-dimethyl-3-(2,4,5-trimethyl-3,6-dioxocyclohexa-1,4-dien-1-yl)butanamido)ethyl)carbamoyl)oxy)benzo[d]thiazol-2-yl)thiazole-4-carboxylic acid;

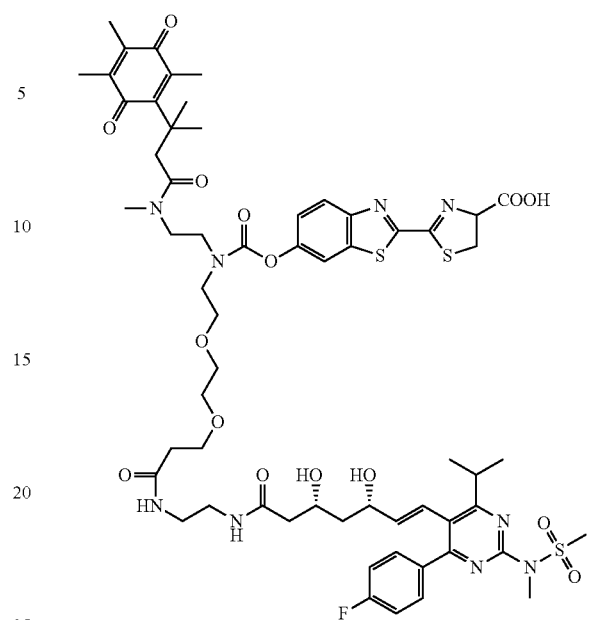

5830: 2-(6-(((2-(N,3-dimethyl-3-(2,4,5-trimethyl-3,6-dioxocyclohexa-1,4-dien-1-yl)butanamido)ethyl)((16R,18S,E)-20-(4-(4-fluorophenyl)-6-isopropyl-2-(N-methylmethylsulfonamido)pyrimidin-5-yl)-16,18-dihydroxy-9,14-dioxo-3,6-dioxa-10,13-diazaicos-19-en-1-yl)carbamoyl)oxy)benzo[d]thiazol-2-yl)-4,5-dihydrothiazole-4-carboxylic acid;

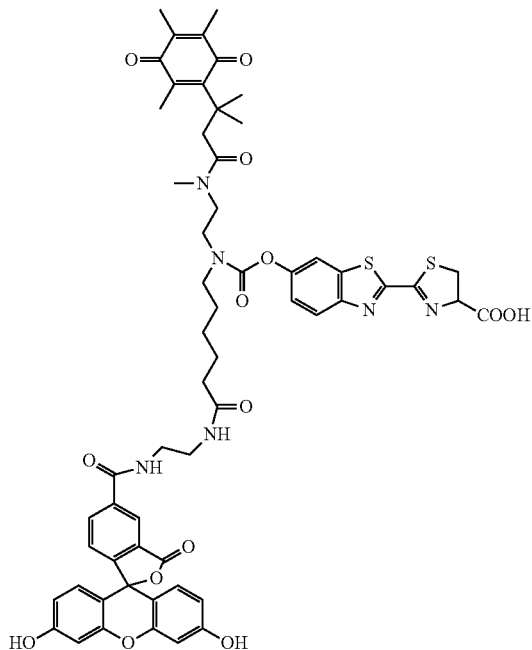 [SMILES: CC1=C(C)C(=O)C(C(C)(C)CC(=O)N(C)CCN(CCCCCC(=O)NCCNC(=O)c2ccc3c(c2)C(=O)OC32c3ccc(O)cc3Oc3cc(O)ccc32)C(=O)Oc2ccc3nc(C4=NC(C(=O)O)CS4)sc3c2)=C(C)C1=O]

5825: 2-(6-(((6-((2-(3',6'-dihydroxy-3-oxo-3H-spiro[isobenzofuran-1,9'-xanthen]-5-ylcarboxamido)ethyl)amino)-6-oxohexyl)(2-(N,3-dimethyl-3-(2,4,5-trimethyl-3,6-dioxocyclohexa-1,4-dien-1-yl)butanamido)ethyl)carbamoyl)oxy)benzo[d]thiazol-2-yl)-4,5-dihydrothiazole-4-carboxylic acid;

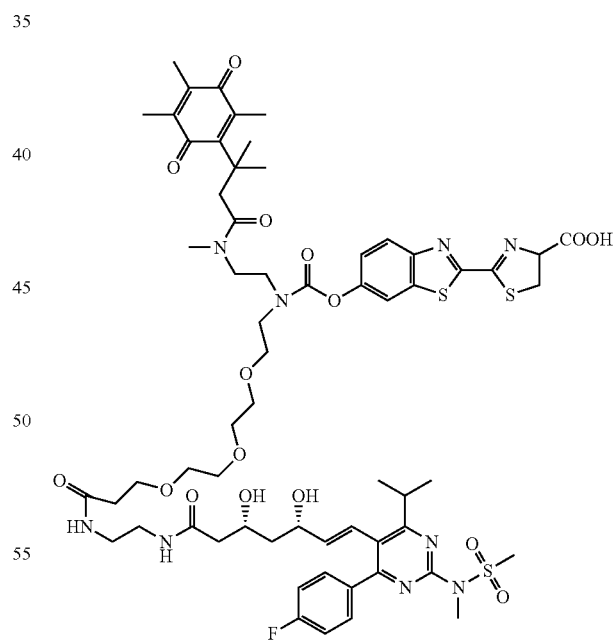

5831: 2-(6-(((2-(N,3-dimethyl-3-(2,4,5-trimethyl-3,6-dioxocyclohexa-1,4-dien-1-yl)butanamido)ethyl)((19R,21S,E)-23-(4-(4-fluorophenyl)-6-isopropyl-2-(N-methylmethylsulfonamido)pyrimidin-5-yl)-19,21-dihydroxy-12,17-dioxo-3,6,9-trioxa-13,16-diazatricos-22-en-1-yl)carbamoyl)oxy)benzo[d]thiazol-2-yl)-4,5-dihydrothiazole-4-carboxylic acid;

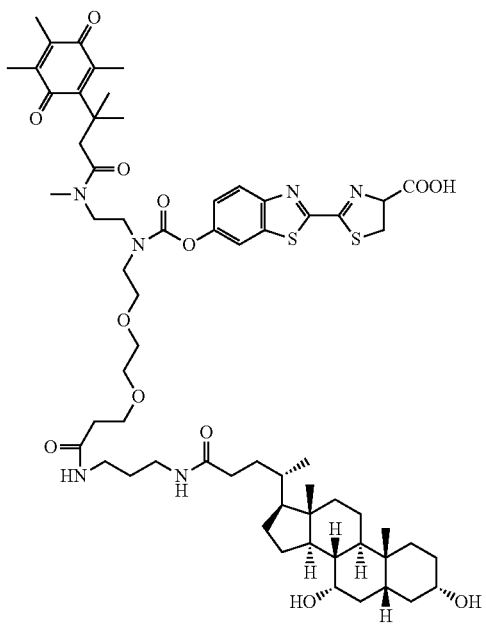

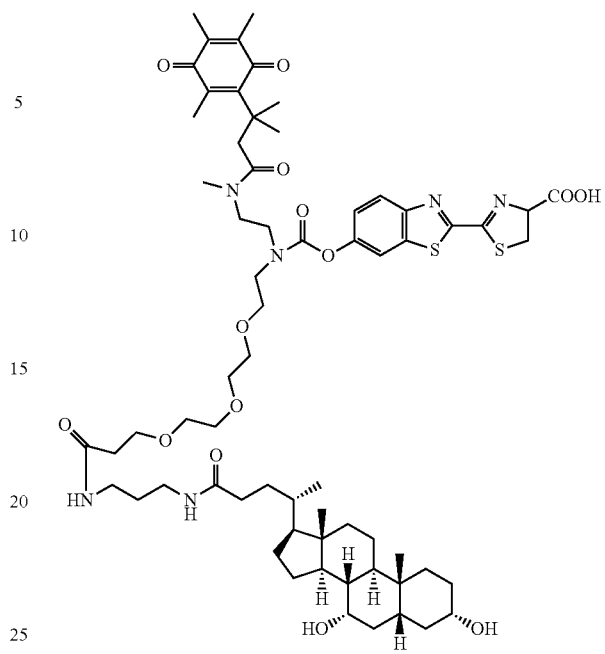

5827: 2-(6-(((((S)-18-((3S,5R,7S,8S,9R,10R,13S,14R,17S)-3,7-dihydroxy-10,13-dimethylhexadecahydro-1H-cyclopenta[a]phenanthren-17-yl)-9,15-dioxo-3,6-dioxa-10,14-diazanonadecyl)(2-(N,3-dimethyl-3-(2,4,5-trimethyl-3,6-dioxocyclohexa-1,4-dien-1-yl)butanamido)ethyl)carbamoyl)oxy)benzo[d]thiazol-2-yl)-4,5-dihydrothiazole-4-carboxylic acid;

5828: 2-(6-(((((S)-21-((3S,5R,7S,8S,9R,10R,13S,14R,17S)-3,7-dihydroxy-10,13-dimethylhexadecahydro-1H-cyclopenta[a]phenanthren-17-yl)-12,18-dioxo-3,6,9-trioxa-13,17-diazadocosyl)(2-(N,3-dimethyl-3-(2,4,5-trimethyl-3,6-dioxocyclohexa-1,4-dien-1-yl)butanamido)ethyl)carbamoyl)oxy)benzo[d]thiazol-2-yl)-4,5-dihydrothiazole-4-carboxylic acid;

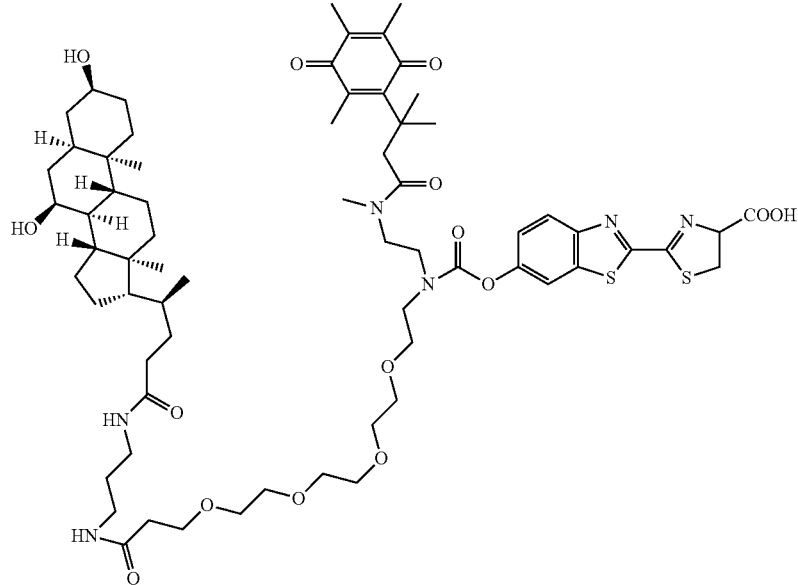

5829: 2-(6-((((S)-24-((3S,5R,7S,8S,9R,10R,13S,14R,17S)-3,7-dihydroxy-10,13-dimethylhexadecahydro-1H-cyclopenta[a]phenanthren-17-yl)-15,21-dioxo-3,6,9,12-tetraoxa-16,20-diazapentacosyl)(2-(N,3-dimethyl-3-(2,4,5-trimethyl-3,6-dioxocyclohexa-1,4-dien-1-yl)butanamido)ethyl)carbamoyl)oxy)benzo[d]thiazol-2-yl)-4,5-dihydrothiazole-4-carboxylic acid;

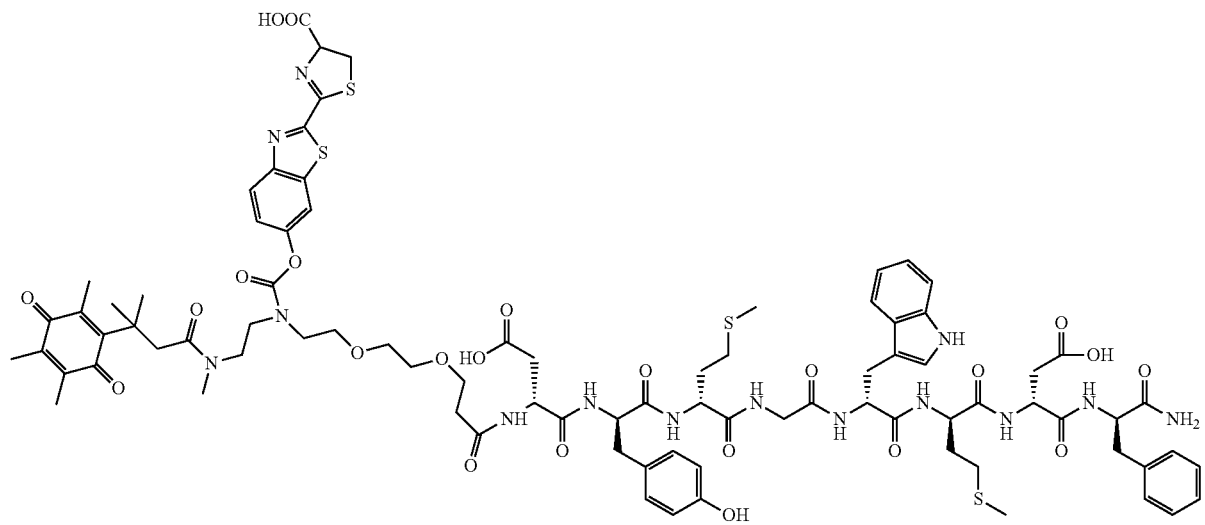 [SMILES: CSCC[C@@H](NC(=O)[C@@H](Cc1ccc(O)cc1)NC(=O)[C@@H](CC(=O)O)NC(=O)CCOCCOCCN(CCN(C)C(=O)CC(C)(C)C1=C(C)C(=O)C(C)=C(C)C1=O)C(=O)Oc1ccc2nc(C3=NC(C(=O)O)CS3)sc2c1)C(=O)NCC(=O)N[C@H](Cc1c[nH]c2ccccc12)C(=O)N[C@H](CCSC)C(=O)N[C@H](CC(=O)O)C(=O)N[C@H](Cc1ccccc1)C(N)=O]

5832: (3R,6R,9R,15R,18R,21R)-9-((1H-indol-3-yl)methyl)-3-(((R)-1-amino-1-oxo-3-phenylpropan-2-yl)carbamoyl)-21-(10-(((2-(4-carboxy-4,5-dihydrothiazol-2-yl)benzo[d]thiazol-6-yl)oxy)carbonyl)-13,16-dimethyl-14-oxo-16-(2,4,5-trimethyl-3,6-dioxocyclohexa-1,4-dien-1-yl)-4,7-dioxa-10,13-diazaheptadecanamido)-18-(4-hydroxybenzyl)-6,15-bis(2-(methylthio)ethyl)-5,8,11,14,17,20-hexaoxo-4,7,10,13,16,19-hexaazatricosane-1,23-dioic acid;

2-(6-(((2-(2-(3-((3-(((8R,9S,13S,14S,17S)-17-(((3S,4R,6R)-6-carboxy-3,4,5-trihydroxytetrahydro-2H-pyran-2-yl)oxy)-13-methyl-7,8,9,11,12,13,14,15,16,17-decahydro-6H-cyclopenta[a]phenanthren-3-yl)oxy)propyl)amino)-3-oxopropoxy)ethoxy)ethyl)(2-(N,3-dimethyl-3-(2,4,5-trimethyl-3,6-dioxocyclohexa-1,4-dien-1-yl)butanamido)ethyl)carbamoyl)oxy)benzo[d]thiazol-2-yl)-4,5-dihydrothiazole-4-carboxylic acid;

5907

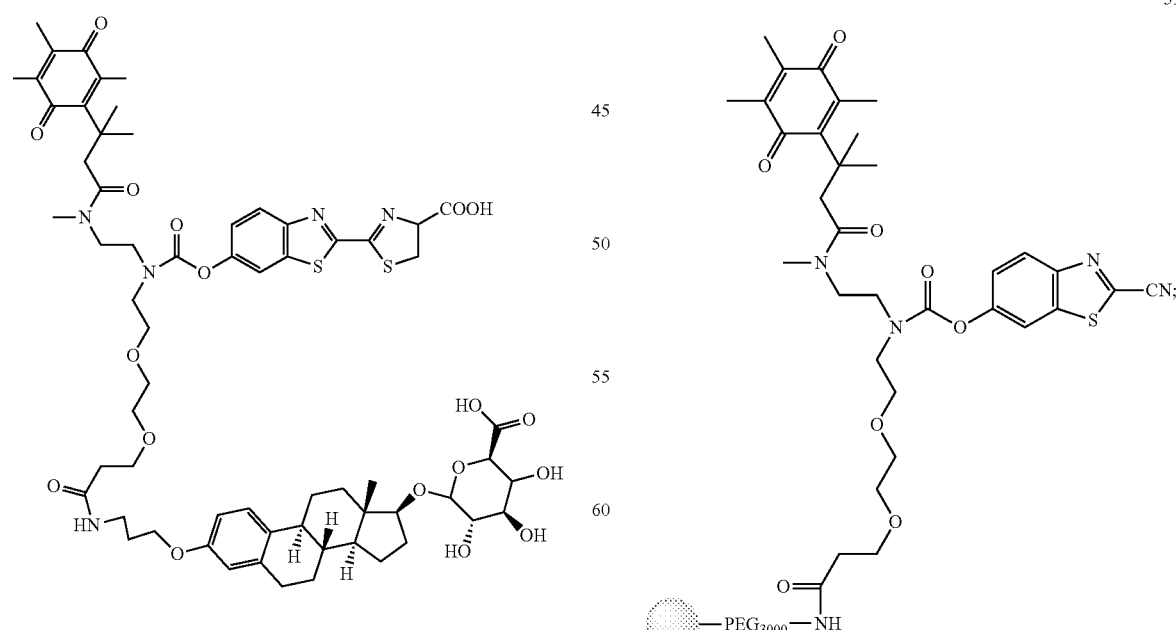

101
-continued
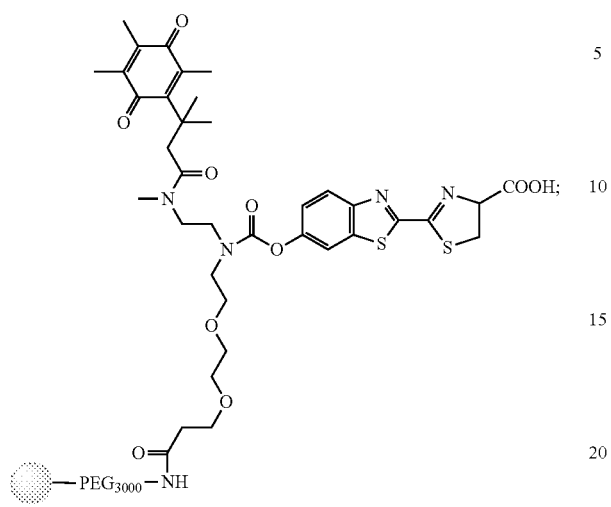
5908
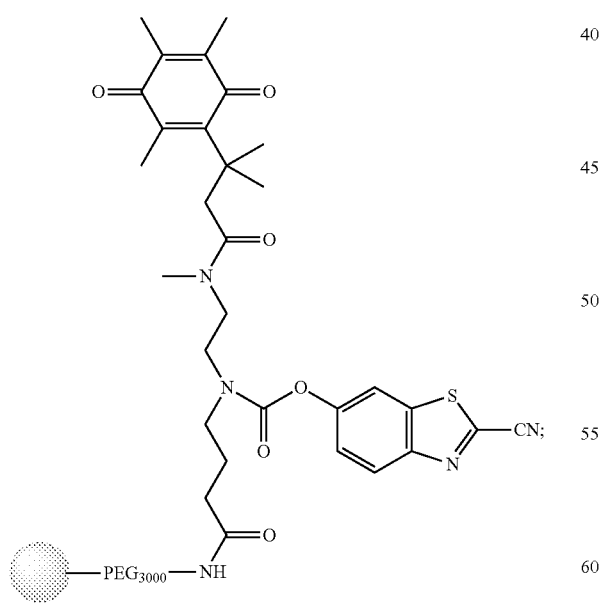
5909
102
-continued
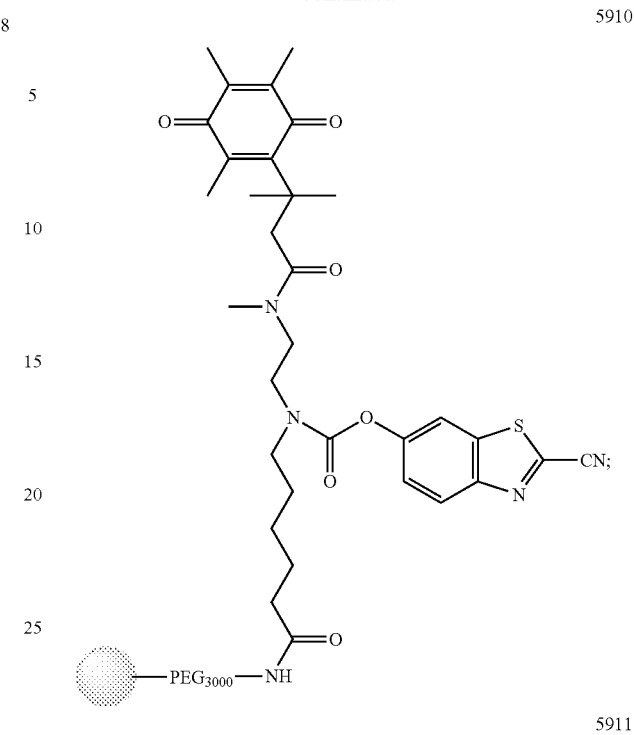
5910
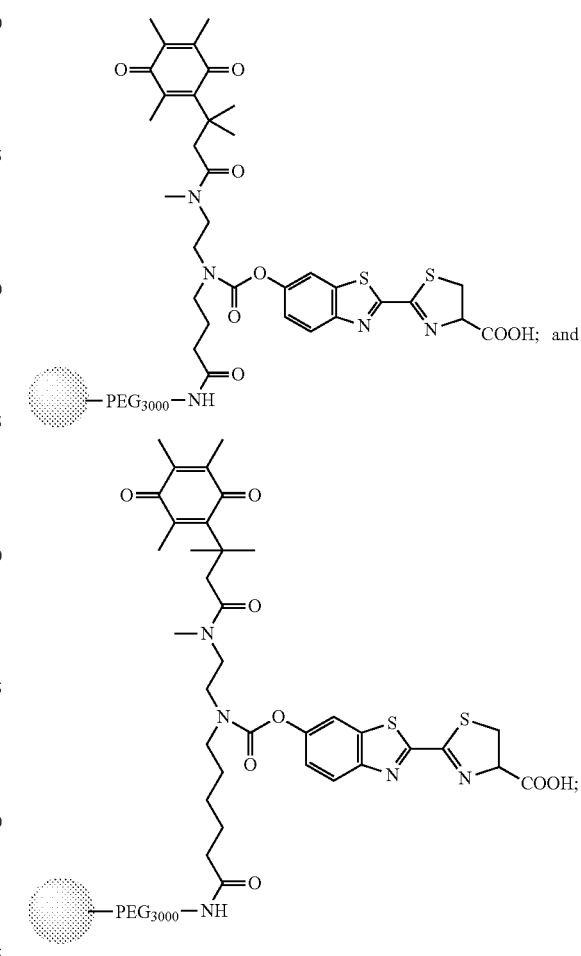
5911
or a salt thereof.

Figure 14:
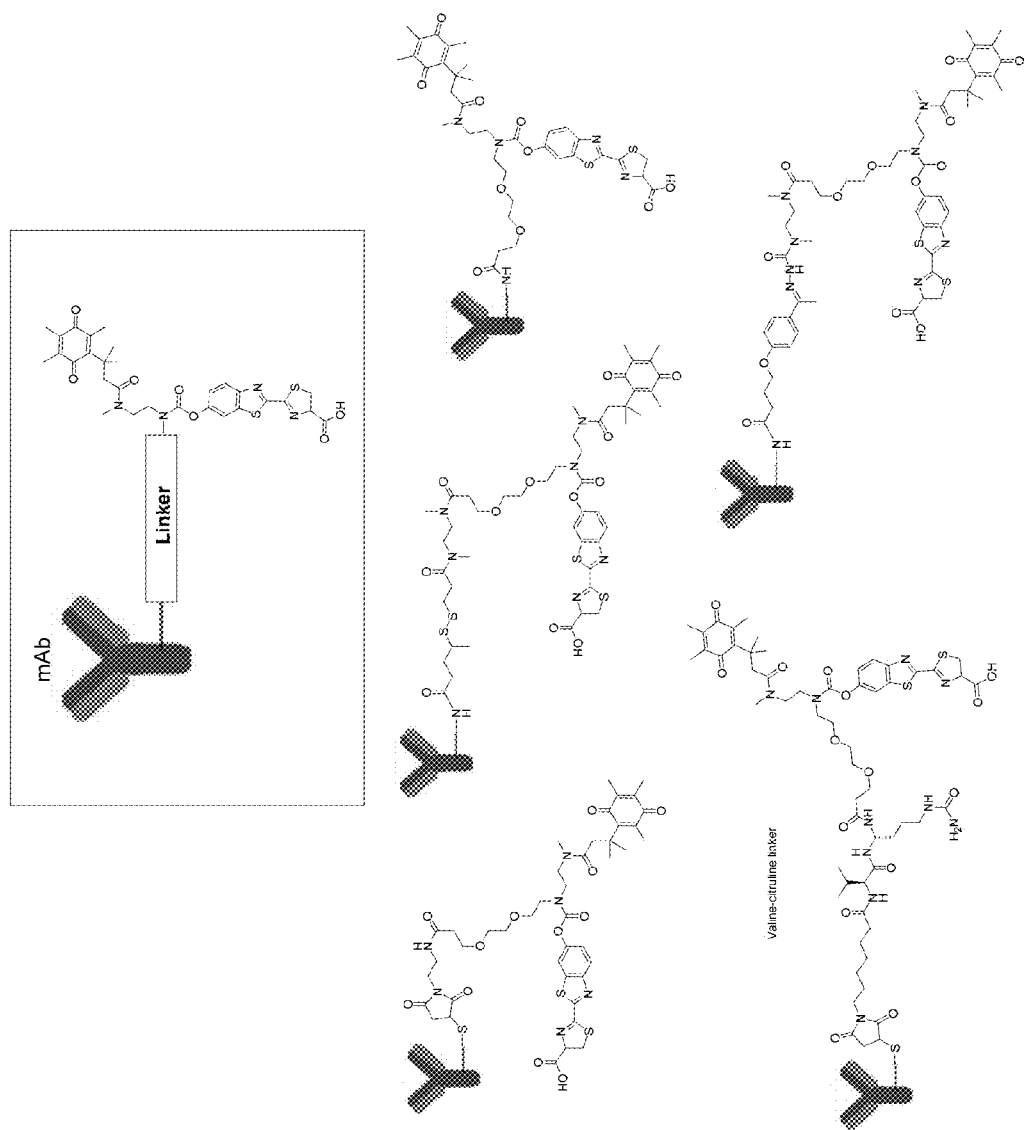
FIG. 14 shows examples of monoclonal antibody (mAb) quinone-luciferin conjugates.

In certain embodiments, the labeled agent may be a labeled antibody. The labeled antibody may be a labeled monoclonal antibody (mAb) (see FIG. 14). The labeled antibody may be a Herceptin labeled with PBI-5508.

In certain embodiments, the labeled agent may be a labeled therapeutic drug. The labeled therapeutic drug may be a labeled bile acid. The labeled bile acid may be a labeled UDCA, such as PBI-5651, PBI-5658, PBI-5666, PBI-5648, PBI-5655, or PBI-5662, a labeled CDCA such as PBI-5657, PBI-5665, PBI-5667, PBI-5650, PBI-5654, PBI-5661, PBI-5827, PBI-5828, or PBI-5829, a labeled LCA, such as PBI-5647, PBI-5668, PBI-5659, PBI-5663, PBI-5652, or PBI-5669, or a labeled DCA such as PBI-5625, PBI-5649, PBI-5653, PBI-5656, PBI-5660, or PBI-5664. The labeled drug may be a labeled statin. The labeled statin may be a labeled rosuvastatin, such as PBI-5830 or PBI-5831. The labeled drug may be a labeled estradiol. The labeled estradiol may be a labeled estradiol glucuronide, such as

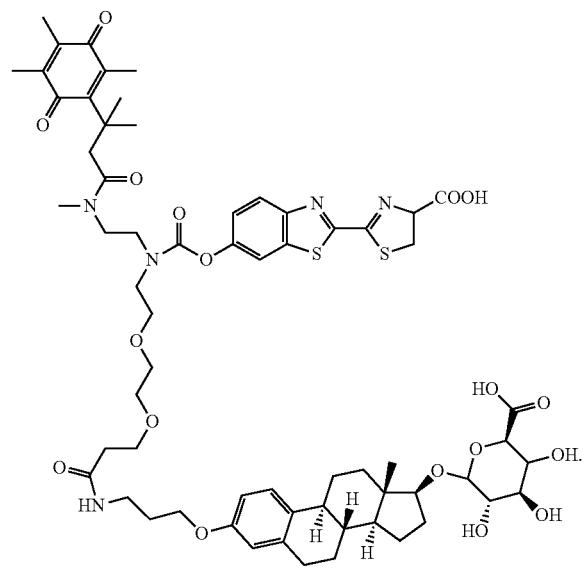

In certain embodiments, the labeled agent may be a solid-liquid nanoparticle. For example, the labeled agent may be a labeled gold nanoparticle (see e.g., FIG. 15). The labeled gold nanoparticle may be PBI-5907, PBI-5908, PBI-5909, PBI-5910, PBI-5911, or PBI-5912.

In certain embodiments, the labeled agent may be a labeled peptide. The peptide may be cholecystockinin (CCK), such as CCK-8. The labeled peptide may be PBI-5832.

In certain embodiments, the labeled agent may be a labeled fluorescent molecule. The labeled fluorescent molecule may be a labeled FAM diamine, such as PBI-5683, PBI-5826, PBI-5682, PBI-5684, PBI-5824, or PBI-5825.

Figure 16:
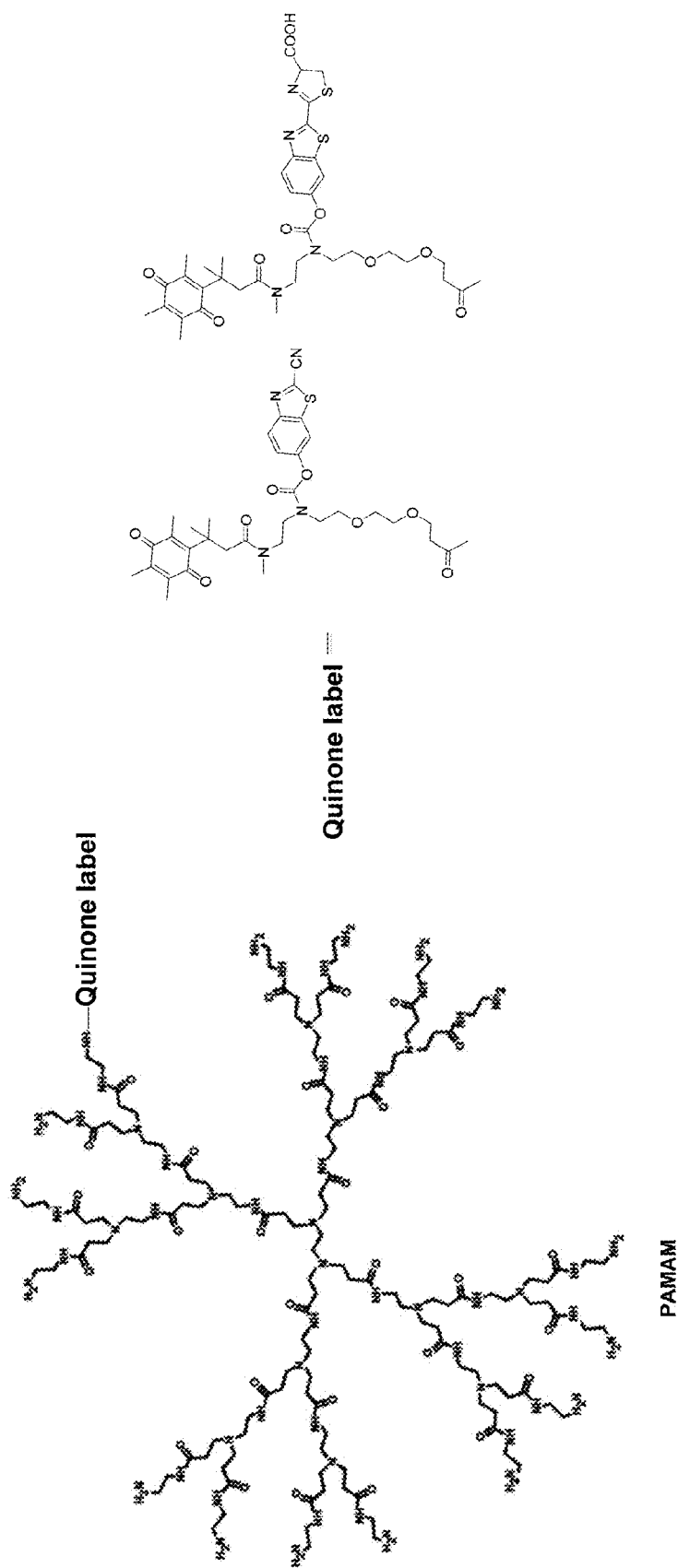
FIG. 16 shows an example of labeled Poly(amido amine) (PAMAM) dendrimer.
Figure 17:
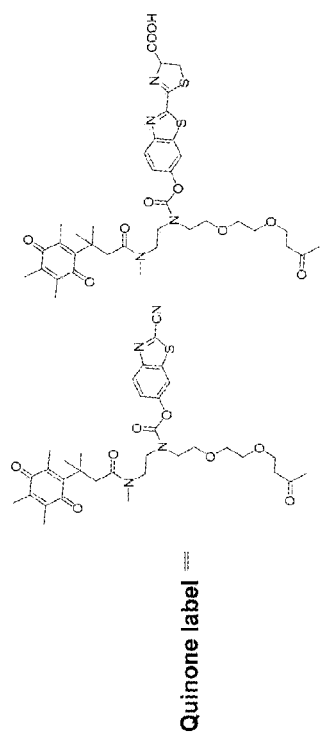
FIG. 17 shows an example of labeled oligonucleotide (20 (SEQ ID NO: 10)) and peptide-oligonucleotide conjugates (Ant-20 (SEQ ID NO: 2), Ant mismatch (SEQ ID NO: 4), Tat-20 (SEQ ID NO: 6), and Tat 20mismatch (SEQ ID NO: 8)) for antisense inhibition of P-glycoprotein expression.

In certain embodiments, the labeled agent may be a labeled PAMAM dendrimer (see e.g., FIG. 16). In certain embodiments, the labeled agent may be a labeled oligonucleotide or a labeled peptide-oligonucleotide conjugate. For example, the labeled agent may be a labeled oligonucleotide or a peptide-oligonucleotide conjugate for antisense inhibition of P-glycoprotein expression (see e.g., FIG. 17).

5. METHODS

The compounds of the present invention provide an effective tool for covalently labeling agents for a wide variety of cell uptake applications. The labeled agents allow quantification of the uptake of a biomolecule(s) of interest in biological samples (i.e., cells, tissues, and organs), monitoring effectiveness for drug delivery, effectiveness of therapeutic treatments, profiling pharmacokinetics, drug-drug interactions and drug toxicity, monitoring cellular metabolic status, such as fatty acids and glucose, and detecting homeostasis of cholesterol.

The cell uptake measurement is often a significant part of scientific research and development, drug design, screening and optimization, phylogenetic classification, genotyping individuals, parental and forensic identification, environmental studies, diagnosis, prognosis, and/or treatment of disease conditions.

a. Methods of Evaluating Cellular Uptake

In some aspects, provided are methods for evaluating cellular uptake of an agent. The methods may comprise contacting a sample comprising a cell with a labeled agent as detailed above and detecting light emission, whereby the detection of light emission indicates cellular uptake of the agent. The cellular uptake of the agent results in the reduction of the compound and the generation of a released reporter moiety.

(1) Fluorescent Reporter Moiety

In some embodiments, the reporter moiety may include a fluorescent reporter moiety. The fluorescent reporter moiety may include a fluorophore. Light emission is detected by exposing the sample to a wavelength of light and detecting the fluorescence generated by the released reported moiety. An increase in fluorescence or a change in fluorescence wavelength as compared to the fluorescence or fluorescence wavelength of a control sample indicates cellular uptake of the agent. The control sample may be sample medium only, without cells, a sample with cells but without experimental treatment, or a sample not contacted with labeled agent. Fluorescence may be detected inside or outside the cell. Non-reducible analogues of the disclosed quinone labeling moieties may be used as control labels.

(2) Bioluminescent Reporter Moiety

In some aspects, the reporter moiety may include a bioluminescent reporter moiety. The bioluminescent reporter moiety may include a prosubstrate for a luciferase. In some embodiments, the cell includes a luciferase. The luciferase may be expressed in the cell. Light emission is detected by detecting luminescence produced by the luciferase utilizing the released reporter moiety. The detection of any light emission may indicate the cellular uptake of the agent. Alternatively, luminescence of the sample may be compared to the luminescence of a control sample, wherein cellular uptake of the agent is indicated if the luminescence of the sample is higher than the luminescence of the control sample. The control sample may be a sample that is not contacted with a labeled agent. Luminescence may be detected inside or outside the cell.

In some embodiments, the cell does not include or express a luciferase, and luciferase is added to the sample. Light emission is detected by detecting luminescence produced by the luciferase utilizing the released reporter moiety that may exit the cell or be present in a cell lysate. The detection of any light emission may indicate the cellular uptake of the agent. Alternatively, luminescence of the sample may be compared to the luminescence of a control sample, wherein cellular uptake of the agent is indicated if the luminescence of the sample is higher than the luminescence of the control sample. The control sample may be sample medium only, without cells, a sample with cells but without experimental treatment, or a sample not contacted with labeled agent.

Luminescence may be detected inside or outside the cell. Non-reducible analogues of the disclosed quinone labeling moieties may be used as control labels.

(3) Sample

The labeled agents may be used with samples containing biological components. The sample may comprise cells, tissues, or organs in vitro or in vivo. The compounds are generally non-toxic to living cells and other biological components within the concentrations of use.

Cells may include eukaryotic cells, e.g., yeast, avian, plant, insect or mammalian cells, including but not limited to human, simian, murine, canine, bovine, equine, feline, ovine, caprine or swine cells, or prokaryotic cells, or cells from two or more different organisms, or cell lysates or supernatants thereof. The cells may not have been genetically modified via recombinant techniques (non-recombinant cells), or may be recombinant cells which are transiently transfected with recombinant DNA and/or the genome of which is stably augmented with a recombinant DNA, or which genome has been modified to disrupt a gene, e.g., disrupt a promoter, intron or open reading frame, or replace one DNA fragment with another. The recombinant DNA or replacement DNA fragment may encode a molecule to be detected by the methods of the invention, a moiety which alters the level or activity of the molecule to be detected, and/or a gene product unrelated to the molecule or moiety that alters the level or activity of the molecule. The cell may or may not express a luciferase.

(4) Contact

The labeled agents may be combined with the sample in a way that facilitates contact between the compound and the sample components of interest. Typically, the labeled agent or a solution containing the labeled agent is simply added to the sample.

The cell uptake levels for selected labeled agents can be monitored with/without treatments that permeabilize the plasma membrane, such as electroporation, shock treatments or high extracellular ATP. Alternatively, selected labeled agents can be monitored physically inserted into cells, e.g., by pressure microinjection, scrape loading, patch clamp methods, or phagocytosis.

An additional detection reagent typically produces a detectable response due to the presence of a specific cell component, intracellular substance, or cellular condition, according to methods generally known in the art. When the additional detection reagent has, or yields a product with, spectral properties that differ from those of the subject labeled agents, multi-color applications are possible. This is particularly useful where the additional detection reagent is a dye or dye conjugate having spectral properties that are detectably distinct from those of the labeled agents.

In certain embodiments, washing steps are unnecessary when using the disclosed labeling reagents and labeled agents.

(5) Light Detection

The labeled agents are generally utilized by combining a labeled agent as described above with a sample of interest comprising a cell under conditions selected to yield a detectable optical response or light output. Typically, a specified characteristic of the sample is determined by comparing the optical response with a standard or expected response. The sample may be illuminated at a wavelength selected to elicit the optical response. Alternatively, the light emission from the sample may be measured in a reading device that can measure the light output (luminescence) generated by the luciferase and bioluminescent reporter moiety, e.g., using a luminometer or photomultiplier. The optical response or light output may also be measured over time, for example in the same reaction chamber for a period of seconds, minutes, hours, etc.

A detectable optical response means a change in, or occurrence of, an optical signal that is detectable either by observation or instrumentally. Typically, the detectable response is a change in fluorescence or luminescence, such as a change in the intensity, excitation or emission wavelength distribution of fluorescence or luminescence, fluorescence or luminescence lifetime, fluorescence or luminescence polarization, or a combination thereof. The degree and/or location of the signal, compared with a standard or expected response, indicates whether, and to what degree, the sample possesses a given characteristic.

At any time after or during contact with the labeled agent, the sample is illuminated with a wavelength of light selected to give a detectable optical response and observed with a means for detecting the optical response. Equipment that is useful for illuminating the compounds of the invention includes, but is not limited to, hand-held ultraviolet lamps, mercury arc lamps, xenon lamps, lasers and laser diodes. These illumination sources are optionally integrated into laser scanners, fluorescence microplate readers, standard or minifluorometers, or chromatographic detectors.

The optical response or light output may be optionally detected by visual inspection or by use of any of the following devices: CCD cameras, video cameras, photographic film, laser-scanning devices, fluorometers, photodiodes, quantum counters, epifluorescence microscopes, scanning microscopes, flow cytometers, fluorescence microplate readers, or by means for amplifying the signal such as photomultiplier tubes. Where the sample is examined using a flow cytometer, examination of the sample optionally includes sorting portions of the sample according to their fluorescence response.

6. KITS

One aspect of the invention is the formulation of kits that facilitate the practice of various assays using any of the compounds of the invention, as described above. The kits of the invention may comprise a labeling reagent, an agent, a labeled agent, or any combination thereof. The kit optionally further comprises one or more buffering agents, typically present as an aqueous solution. The kits of the invention optionally further comprise at least one component for detecting the released labeled reagent, such as a detection reagent. The detection reagent may contain a luciferase, as described above, and/or other reagents required to conduct the detection assay such as buffers, salts, enzymes, enzyme co-factors, such as D-cysteine, and the like buffers. For example, the detection reagent may be Luciferin Detection Reagent (Promega Corporation). The kits of the invention optionally further comprise a purification medium for purifying the resulting labeled agent, luminescence and/or fluorescence standards, enzymes, enzyme inhibitors, organic solvent, constructs for expression of fusion proteins, e.g., fusion proteins comprising a luciferase protein fused to a protein or target of interest, fusion proteins, or instructions for carrying out an assay of the invention. In other embodiments, the kit also includes a genetically-modified cell or a vector for gene fusion, e.g., fusion comprising a luciferase protein fused to a protein or target of interest. Instructions for use optionally may be included.

7. EXAMPLES

The foregoing may be better understood by reference to the following examples, which are presented for purposes of illustration and are not intended to limit the scope of the invention.

Example 1
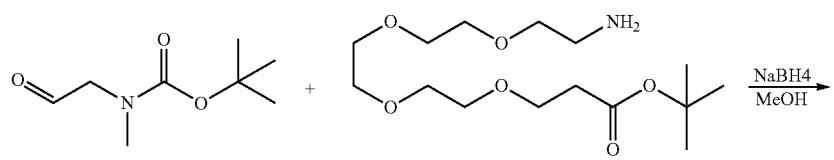
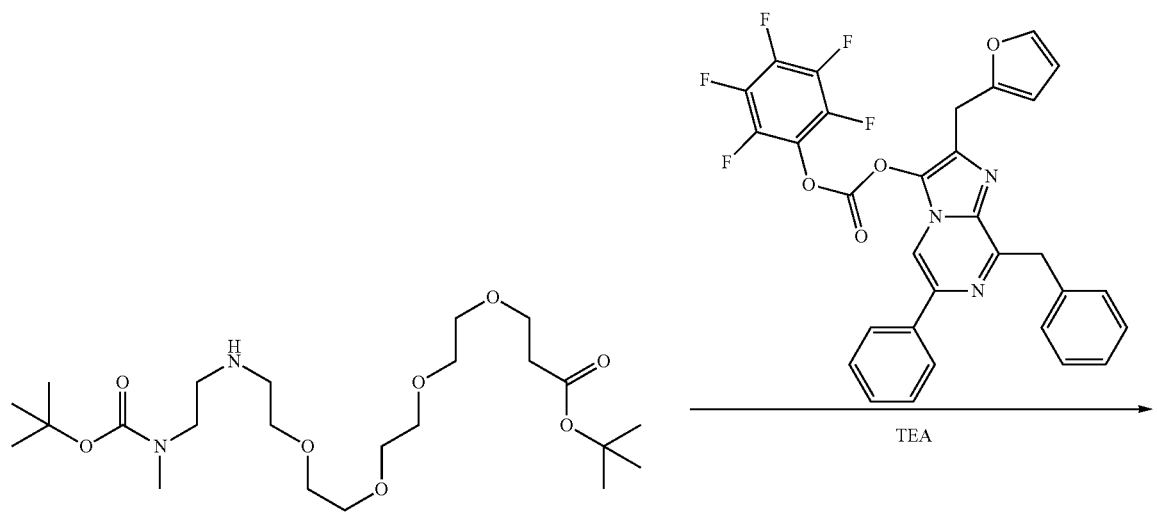
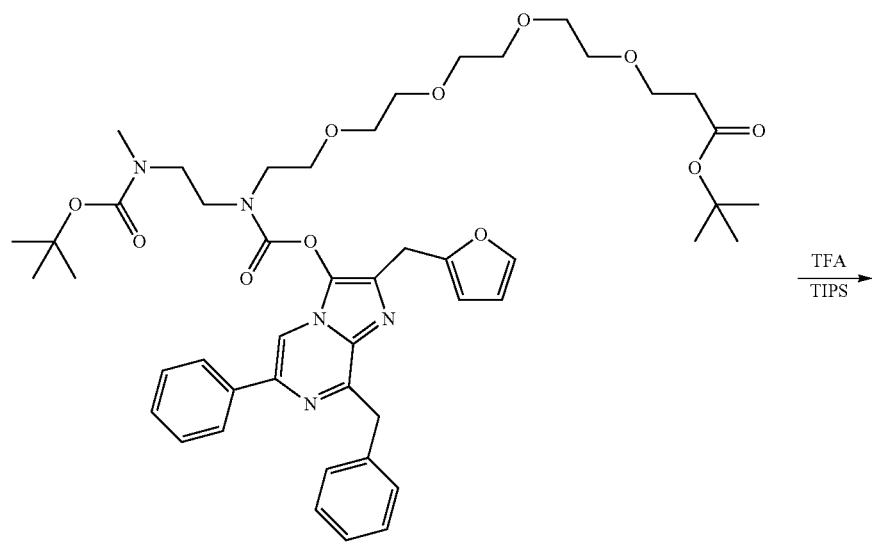

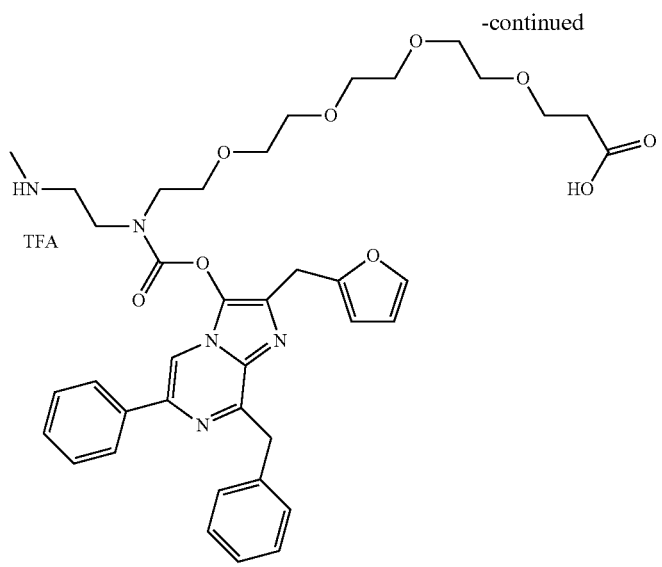
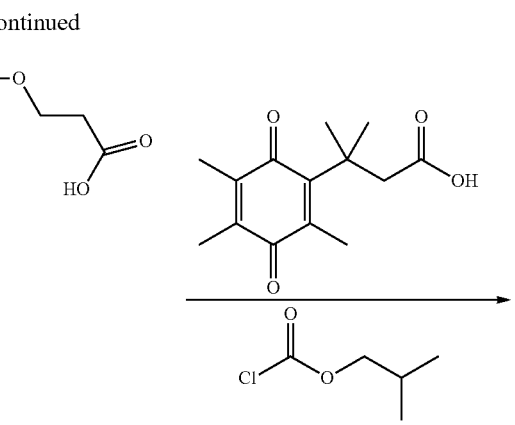
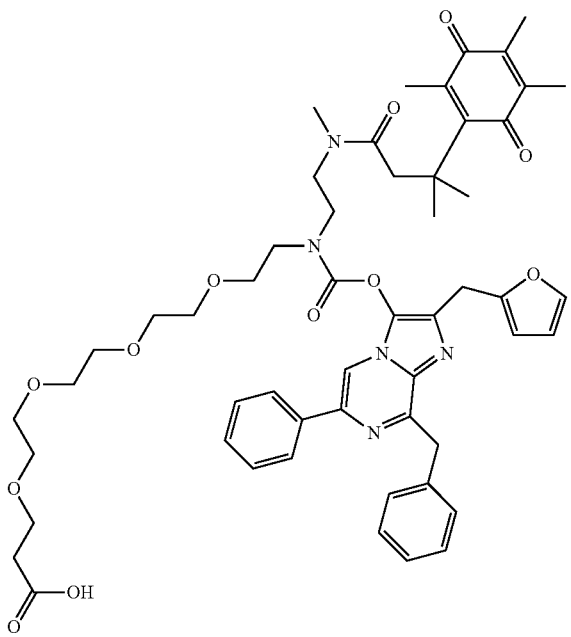

5463

Synthesis of N—[(PEG)$_4$-COO-t-Bu]-N'—Boc-N'-methyl-ethylenediamine

To the solution of N-t-BuOOC—(PEG)$_4$-amine (0.557 g, 1.73 mmol) in 20 ml of methanol, (N-methyl)-N-Boc acetaldehyde (0.3 g, 1.73 mmol) was added. The mixture was stirred at room temperature for 3 hours. NaBH$_4$ (0.196 g, 5.2 mmol) was added to the mixture at 0° C., and the resultant mixture was stirred at 0° C. for 1 hour and 1 hour at room temperature. The reaction was quenched by adding 5 ml of water. After removal of solvent, 5 ml of water was added, and the mixture was extracted three times with methylene chloride. The combined organic layer was dried over Na$_2$SO$_4$, and the product was purified by flash silica chromatography using heptane/ethyl acetate to methylene chloride/methanol to give a yield of 64.5% (0.535 g). $^1$H NMR (300 MHz, CD$_2$Cl$_2$) δ ppm: 3.5-3.8 (m, 18H, CH$_2$), 3.45 (br, 2H, CH$_2$), 2.98 (br, 2H, CH$_2$), 2.83 (s, 3H, NCH$_3$), 2.46 (t, 2H, COCH$_2$), 1.42 (s, 18H, CH$_3$); MS-ESI (m/e): 479.6 [M+H].

Synthesis of N—[(PEG)$_4$COO-t-Bu]-N'—Boc-N'-methyl-ethylene-diamine furimazine carbamate To the mixture of furimazine (0.20 g, 0.526 mmol) and bis(pentafluorophenyl) dicarbonate (0.276 g, 0.630 mmol) in 10 ml of dry THF, TEA (0.106 mg, 1.05 mmol) was added at room temperature under argon. The mixture was stirred for 2-3 minutes, and N—[(PEG)$_4$COO-t-Bu]-N'—Boc-N'-methyl-ethylene diamine (0.553 mg, 1.16 mmol) was added. The resulted mixture was stirred at room temperature for 30 minutes. The compound was purified by flash column chromatography using heptane/ethyl acetate as eluent to give the product in a yield of 25.8% (0.12 g). MS-ESI (m/e): 886.6 [M+H].

Synthesis of N—[(PEG)$_4$COOH]—(N'-methyl)-ethylenediamine furimazine carbamate

N—[(PEG)$_4$COO-t-Bu]-N'—Boc-N-methyl-ethylenediamine furimazine carbamate (0.12 g, 0.136 mmol) and triisopropylsilane (50 ul) were dissolved in 10 ml of methylene chloride and TFA (1:1 in volume), and the mixture was stirred at room temperature for 2 hours. After removal of the solvent, the residue was dried under high vacuum overnight, and the product was used directly in next step.

Synthesis of #5463

To the solution of 3-methyl-3-(2,4,5-trimethyl-3,6-dioxo-cyclohexa-1,4-dien-1-yl)butanoic acid (107 mg, 0.428 mmol) and isobutyl chloroformate (58.4 mg, 0.427 mmol) in 10 ml dry THF, N-methyl morpholine (86.5 mg, 0.855 mmol) was added at 0° C. The resultant mixture was stirred 30 minutes at 0° C., and N'-methyl-N-[(PEG)$_4$COOH]ethylene-diamine]furimazine carbamate in 5 ml of CH$_2$Cl$_2$ was added, and the resultant mixture was stirred for 1 hour. The compound was directly purified with flash silica column chromatography using heptane and ethyl acetate as eluent to give the product in a yield of 76.6% (105 mg). MS-ESI (m/e): 962.5 [M+H].

Example 2

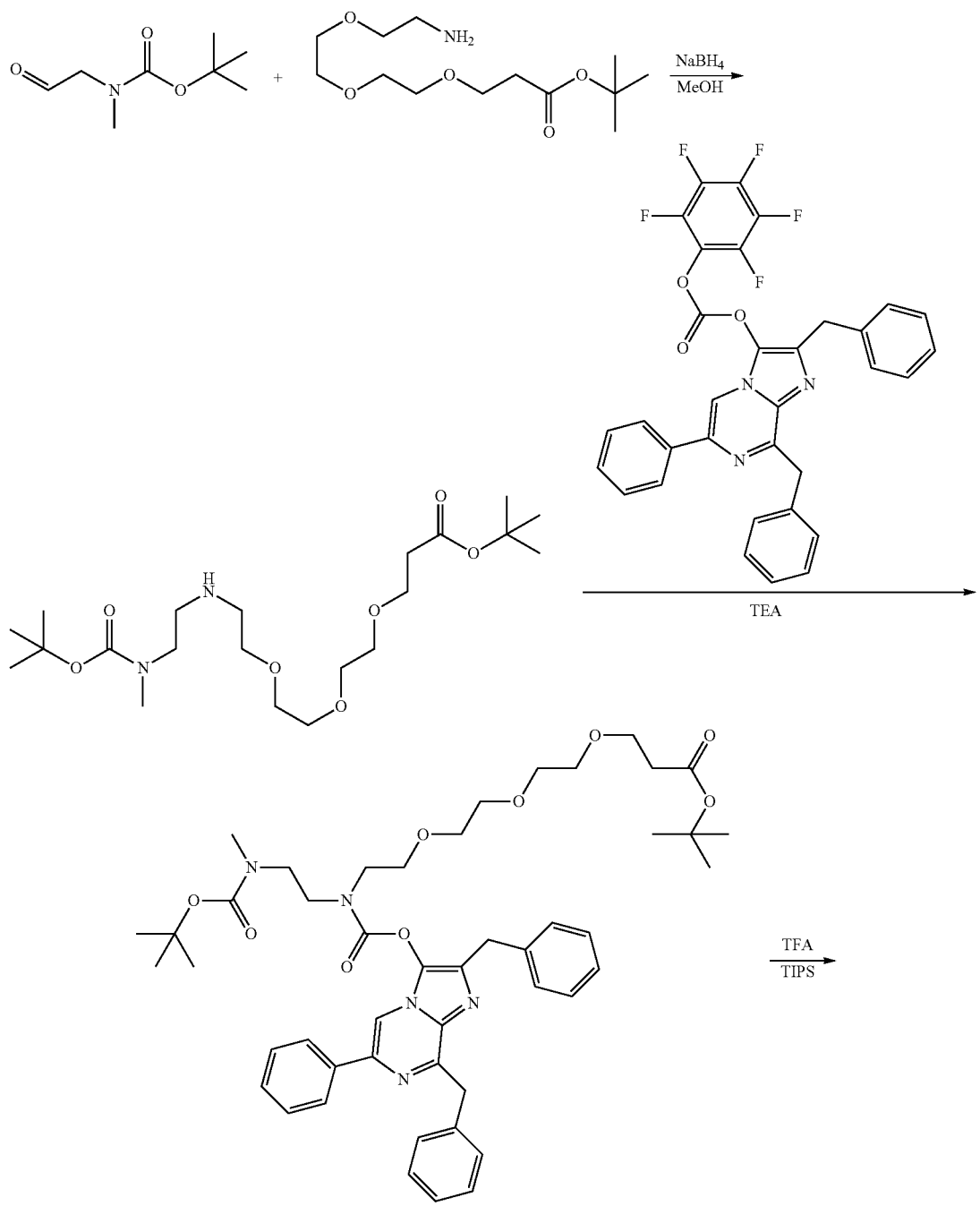

113

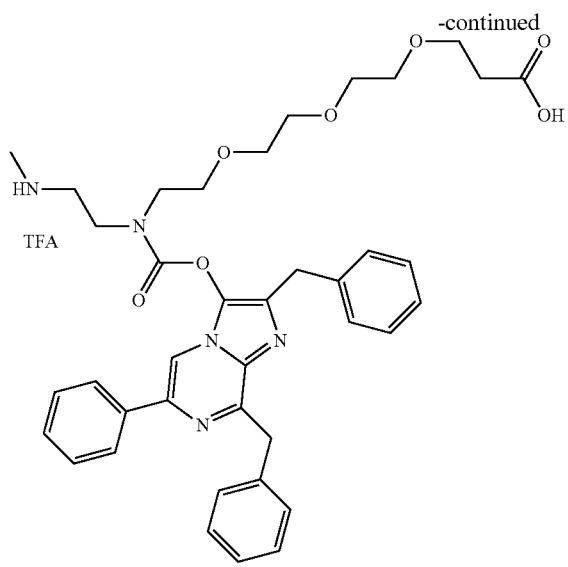

-continued

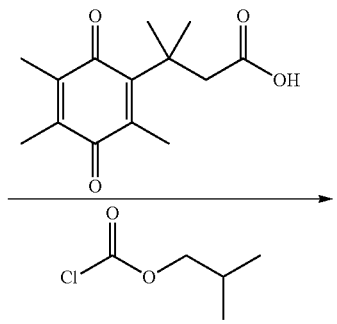

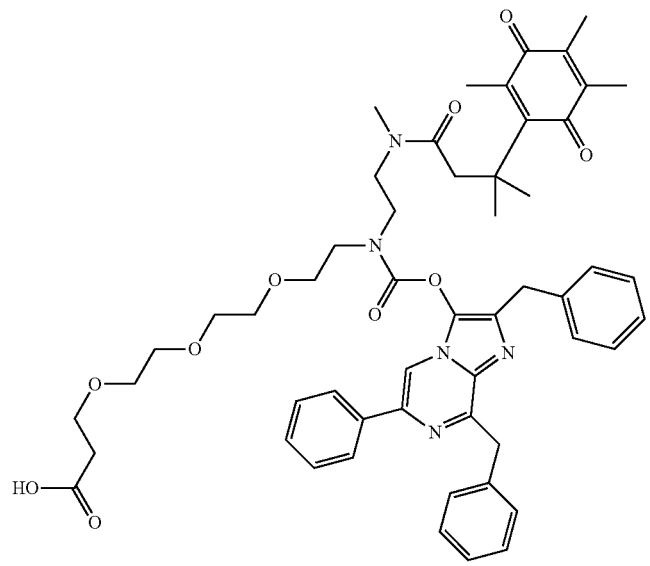

5470

Synthesis of N—[(PEG)₃-COO-t-Bu]-N'—Boc-N'-methyl-ethylene-diamine

To the solution of t-Bu-(PEG)₃-amine (1.01 g, 3.64 mmol) in 20 ml of methanol, (N-methyl)-N-Boc acetaldehyde (0.63 g, 3.64 mmol) was added. The mixture was stirred at room temperature for 3 hours. NaBH₄ (0.412 g, 10.9 mmol) was added to the mixture at 0° C., and the resultant mixture was stirred at 0° C. for 1 hour and 1 hour at room temperature. The reaction was quenched by adding 5 ml of water. After removal of solvent, 5 ml of water was added, and the mixture was extracted three times with methylene chloride. The combined organic layer was dried over Na₂SO₄, and the product was purified by flash silica chromatography using heptane/ethyl acetate to methylene chloride/methanol to give a yield of 72% (1.14 g). $^1$H NMR (300 MHz, CD$_2$Cl$_2$) δ ppm: 3.68 (t, 2H, OCH$_2$), 3.56-3.60 (br, 10H, CH$_2$), 3.53 (t, 2H, OCH$_2$), 3.29 (t, 2H, CH2), 2.85 (s, 3H, NCH$_3$), 2.7-2.8 (m, 4H, NCH2), 2.47 (t, 2H, COCH$_2$), 1.44 (s, 18H, CH$_3$); MS-ESI (m/e): 435.5 [M+H].

Synthesis of N—[(PEG)₃COO-t-Bu]-N'—Boc-N'-methyl-ethylene-diamine coelenterazine-H,H-carbamate To the mixture of coelenterazine H,H (0.60 g, 1.54 mmol) and bis(penta-fluorophenyl) dicarbonate (0.74 g, 1.69 mmol) in 30 ml of dry THF, TEA (0.311 g, 3.07 mmol) was added at room temperature under argon. The mixture was stirred for 2-3 minutes, and N—[(PEG)₃COO-t-Bu]-N'—Boc-N'-methyl ethylenediamine (1.34 g, 3.07 mmol) was added. The resulted mixture was stirred at room temperature for 30 minutes. The compound was purified by flash column chromatography using heptane/ethyl acetate as eluent to give the product in a yield of 70.3% (0.92 g). MS-ESI (m/e): 852.7 [M+H].

Synthesis of N—(PEG)₃COOH—N'-methyl-ethylenediamine coelenterazine H,H-carbamate N—[(PEG)₃COO-t-Bu]-N'—Boc-N-methyl-ethylenediamine coelenterazine H,H-carbamate (0.92 g, 0.136 mmol)

and triisopropylsilane (100 ul) were dissolved in 30 ml of methylene chloride and TFA (1:1 in volume), and the mixture was stirred at room temperature for 2 hours. After removal of the solvent, the residue was dried under high vacuum overnight, and the product was used directly in next step.

Synthesis of #5470

To the solution of 3-methyl-3-(2,4,5-trimethyl-3,6-dioxo-cyclohexa-1,4-dien-1-yl)butanoic acid (810 mg, 3.24 mmol) and isobutyl chloroformate (442 mg, 3.24 mmol) in 30 ml dry THF, N-methyl morpholine (655 mg, 6.48 mmol) was added at 0° C. The resultant mixture was stirred 30 minutes at 0° C., and N'-methyl-N-[(PEG)$_3$COOH]ethylenediamine coelenterazine H,H-carbamate (0.92 g) in 10 ml of CH$_2$Cl$_2$ was added, and the resultant mixture was stirred for 1 hour. The compound was directly purified with flash silica column chromatography using heptane and ethyl acetate as eluent to give the product in a yield of 61% (611 mg). MS-ESI (m/e): 928.7 [M+H]; HPLC 98.2% at 254 nm.

Example 3

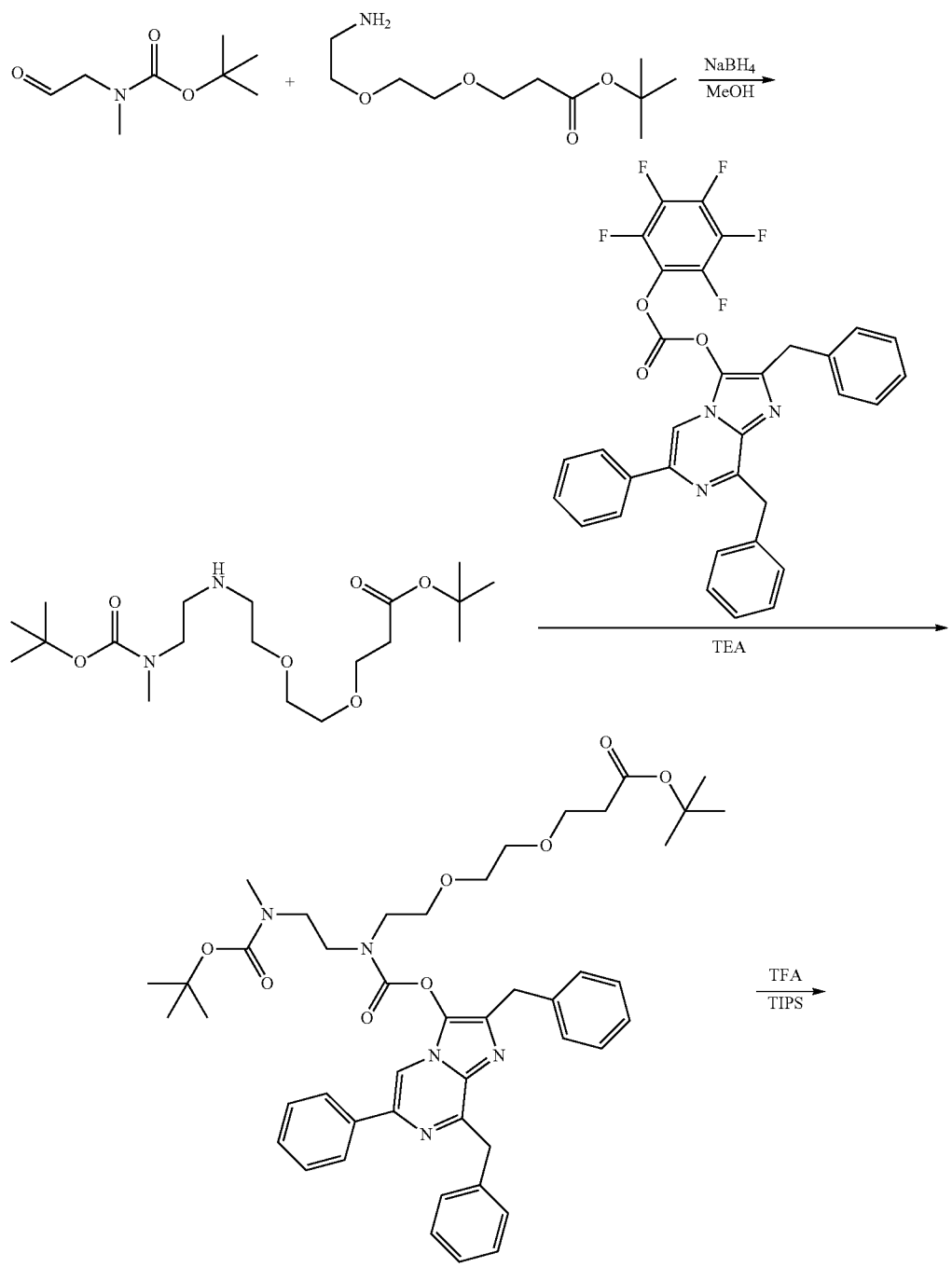

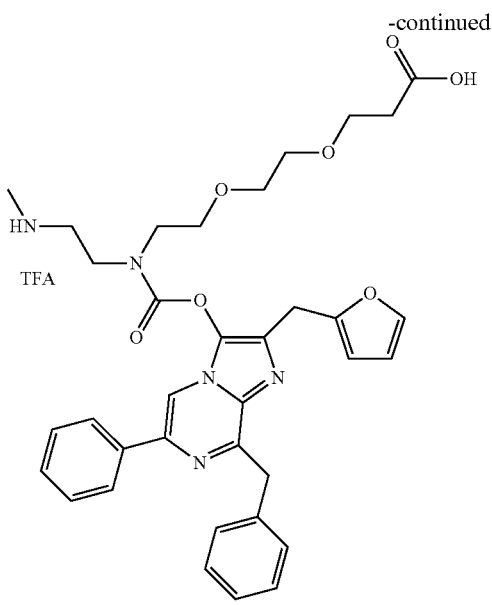
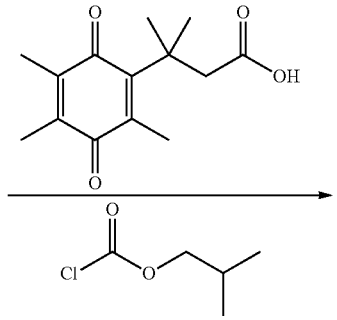

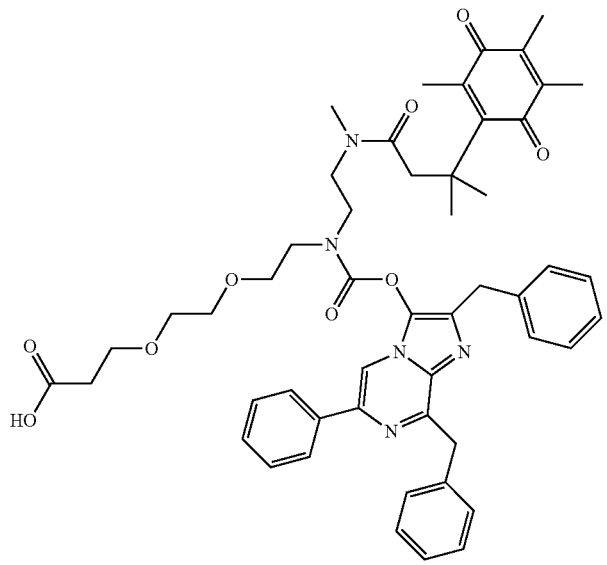

5471

Synthesis of N—[(PEG)₂-COO-t-Bu]-N'—Boc-N'-methyl-ethylenediamine

To the solution of N—(PEG)₂COO-t-Bu-amine (1.08 g, 4.62 mmol) in 50 ml of methanol, (N-methyl)-N-Boc acetaldehyde (0.8 g, 4.62 mmol) was added. The mixture was stirred at room temperature for 3 hours. NaBH₄ (0.524, 13.9 mmol) was added to the mixture at 0° C., and the resultant mixture was stirred at 0° C. for 1 hour and 1 hour at room temperature. The reaction was quenched by adding 5 ml of water. After removal of solvent, 5 ml of water was added, and the mixture was extracted three times with methylene chloride. The combined organic layer was dried over Na₂SO₄, and the product was purified by flash silica chromatography using heptane/ethyl acetate to methylene chloride/methanol to give a yield of 77.6% (1.40 g). ¹H NMR (300 MHz, CD₂Cl₂) δ ppm: 3.67 (t, 2H, OCH₂), 3.56-3.60 (br, 6H, OCH₂), 3.29 (t, 2H, CH₂), 2.85 (s, 3H, NCH₃), 2.7-2.8 (m, 4H, NCH2), 2.46 (t, 2H, COCH₂), 1.45 (s, 18H, CH₃); MS-ESI (m/e): 391.4 [M+H].

Synthesis of N—[(PEG)₂COO-t-Bu]-N'—Boc-N'-methyl-ethylene-diamine coelenterazine-H,H-carbamate To the mixture of coelenterazine H,H (0.60 g, 1.54 mmol) and bis(penta-fluorophenyl) dicarbonate (0.74 g, 1.69 mmol) in 30 ml of dry THF, TEA (0.311 g, 3.07 mmol) was added at room temperature under argon. The mixture was stirred for 2-3 minutes, and N—[(PEG)₂COOtBu]-N'—BOC—N'-methyl ethylenediamine (1.20 g, 3.07 mmol) was added. The resulted mixture was stirred at room temperature for 30 minutes. The compound was purified by flash column chromatography using heptane/ethyl acetate as eluent to give the product in a yield of 72.8% (0.92 g). MS-ESI (m/e): 808.7 [M+H].

Synthesis of N—[(PEG)$_2$COOH]—N'-methyl-ethyl-enediamine coelenterazine H,H-carbamate N—[(PEG)$_2$COO-t-Bu]-N'—Boc-N-methyl-ethylenediamine coelenterazine H,H-carbamate (0.92 g, 0.136 mmol) and triisopropylsilane (100 ul) were dissolved in 30 ml of methylene chloride and TFA (1:1 in volume), and the mixture was stirred at room temperature for 2 hours. After removal of the solvent, the residue was dried under high vacuum overnight, and the product was used directly in next step.

Synthesis of #5471

To the solution of 3-methyl-3-(2,4,5-trimethyl-3,6-dioxo-cyclohexa-1,4-dien-1-yl)butanoic acid (855 mg, 3.42 mmol) and isobutyl chloroformate (466 mg, 3.42 mmol) in 40 ml dry THF, N-methyl morpholine (691 mg, 6.83 mmol) was added at 0° C. The resultant mixture was stirred 30 minutes at 0° C., and N'-methyl-N[(PEG)$_2$COOH]ethylene-diamine] coelenterazine H,H-carbamate (0.92 g) in 10 ml of CH$_2$Cl$_2$ was added and the resultant mixture was stirred for 1 hour. The compound was directly purified with flash silica column chromatography using heptane and ethyl acetate as eluent to give the product in a yield of 68.5% (690 mg). MS-ESI (m/e): 884.7 [M+H]; HPLC 92.2% at 254 nm.

Example 4

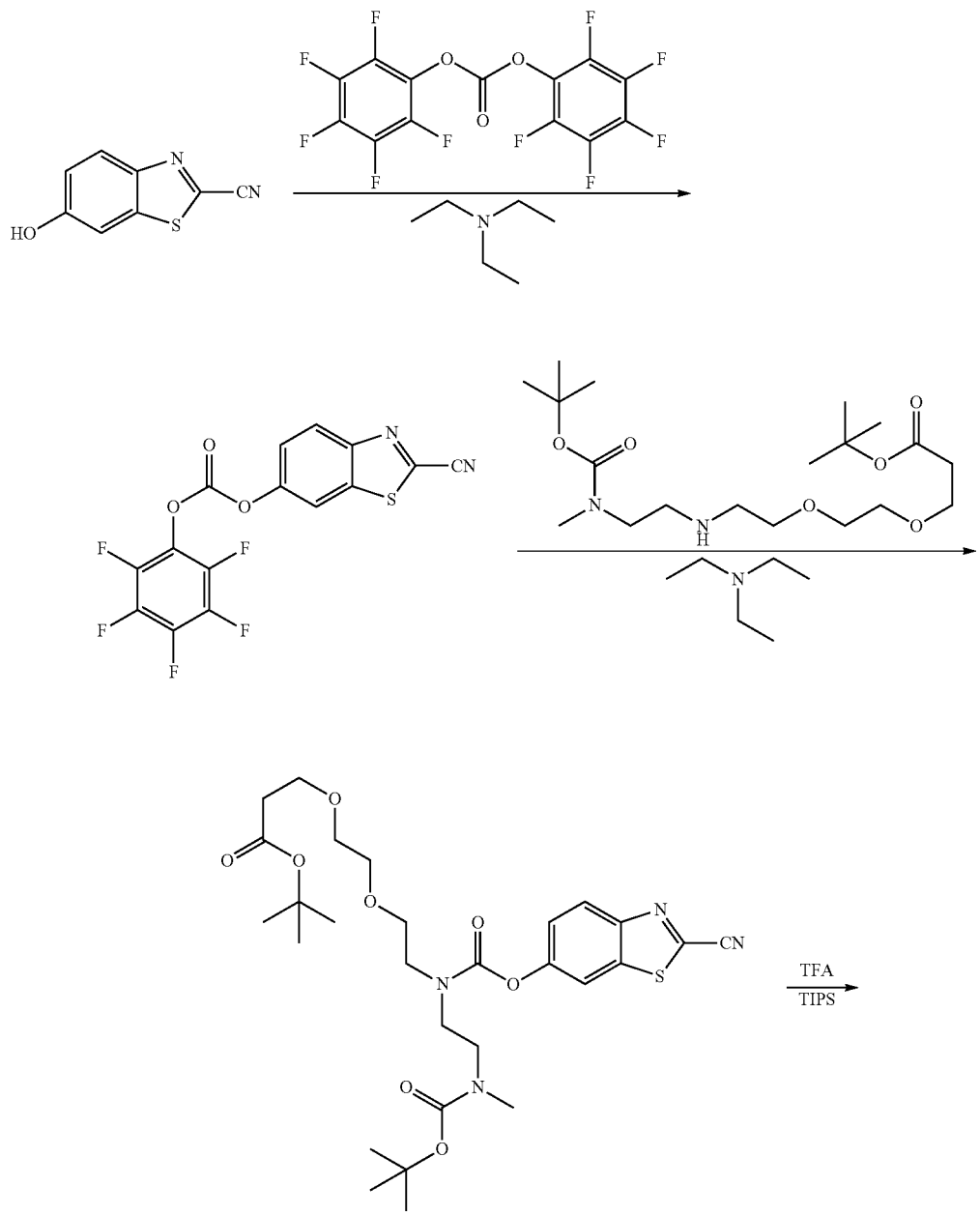

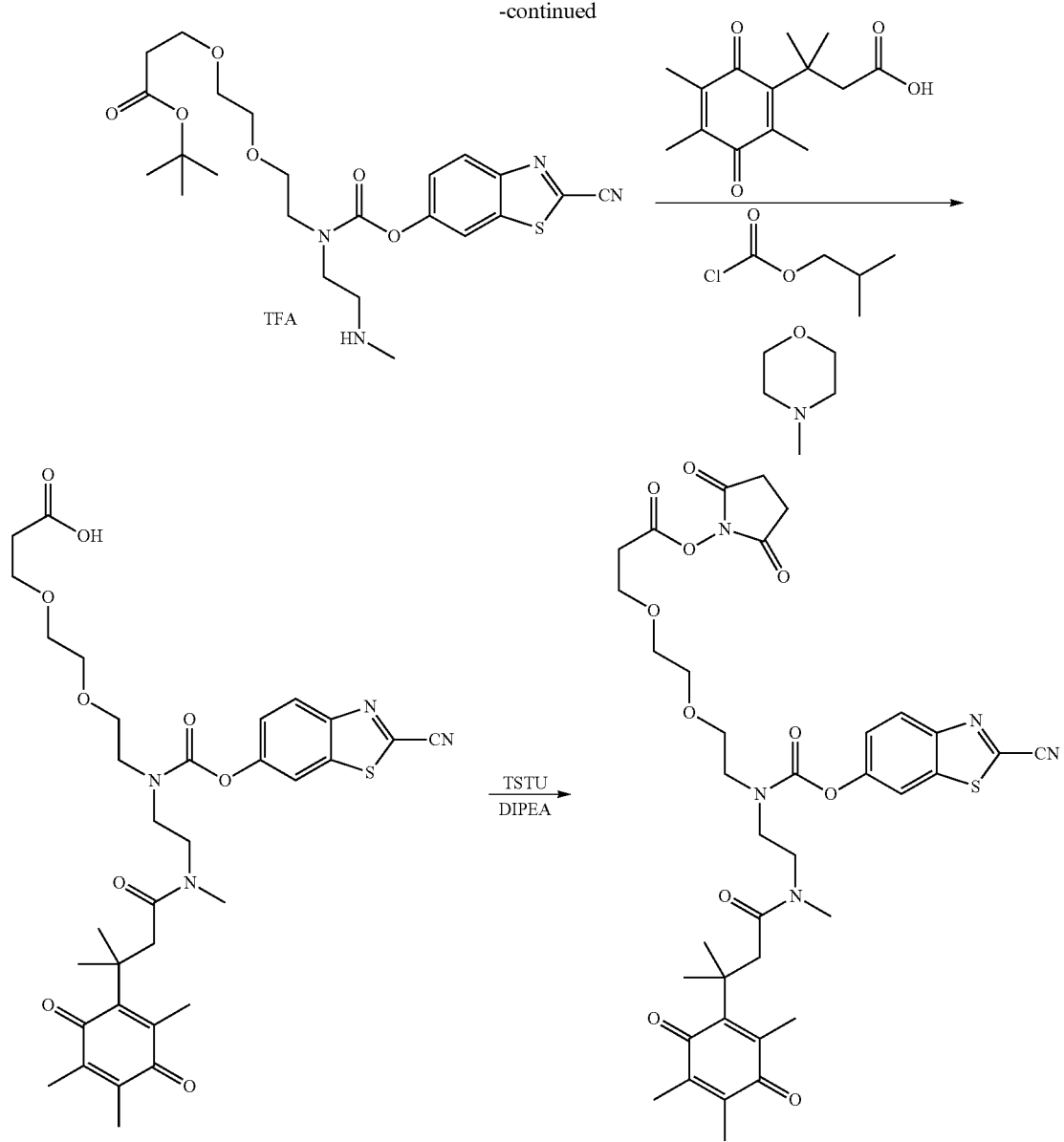

5508

Synthesis of N—[(PEG)₂COO-t-Bu]-N'—Boc-N'-methyl-ethylene-diamine-2-cyanobenzothiazole-6-carbamate To the mixture of 6-hydroxyl-2-cyanobenzothiazole (1.0 g, 5.68 mmol) and bis(penta-fluorophenyl) dicarbonate (2.68 g, 1.69 mmol) in 100 ml of dry THF, TEA (2.22 g, 5.68 mmol) was added at room temperature. The mixture was stirred for 10 minutes, and N—[(PEG)2COOtBu]-N'—BOC—N'-methyl ethylenediamine (2.22 g, 5.68 mmol) was added. The resultant mixture was stirred at room temperature for 30 minutes. The compound was purified by flash column chromatography using heptane/ethyl acetate as eluent to give the product in a yield of 100% (3.4 g). MS-ESI (m/e): 593.3 [M+H].

Synthesis of N—[(PEG)₂COOH]—N'-methyl-ethylenediamine-2-cyanobenzothiazole-6-carbamate N-t-BuOOC—(PEG)₂-N'—Boc-N-methyl-ethylenediamine-2-cyanobenzothiazole-6-carbamate (2.0 g) and triisopropylsilane (100 ul) were dissolved in 60 ml of methylene chloride and TFA (1:1 in volume), and the mixture was stirred at room temperature for 4 hours. After removal of the solvent, the residue was dried under high vacuum overnight, and the product was used directly in next step.

Synthesis of N—[(PEG)₂COOH]—N'-methyl-N'-[3-methyl-3-(2,4,5-trimethyl-3,6-dioxocyclohexa-1,4-dien-1-yl)butanoic amido]-ethylenediamine-2-cyanobenzothiazole-6-carbamate. To the solution of 3-methyl-3-(2,4,5-trimethyl-3,6-dioxocyclohexa-1,4-dien-1-yl)butanoic acid (1.27 g, 5.07 mmol) and isobutyl chloroformate (691 mg, 5.07 mmol) in 50 ml dry THF was added N-methyl morpholine (932 mg, 9.21 mmol) at 0° C. The resultant mixture was stirred 30 minutes at 0° C., and N'-methyl-N[(PEG)2COOH] ethylenediamine]-2-cyanobenzothiazole-6-carbamate (1.07 g, 4.61 mmol) in 15 ml of $CH_2Cl_2$ was added and the resultant mixture was stirred for 1 hour. The compound was directly purified with flash silica column chromatography using heptane and ethyl acetate as eluent and further purified by HPLC using 0.1% of formic acid/acetonitrile as eluent. MS-ESI (m/e): 668.7 [M+H]; HPLC 92.6% at 330 nm.

Synthesis of #5508

To the solution of N—[(PEG)$_2$COOH]—N'-methyl-N'-[3-methyl-3-(2,4,5-trimethyl-3,6-dioxocyclohexa-1,4-dien-1-yl)butanoic amido]-ethylenediamine-2-cyanobenzothiazole-6-carbamate (210 mg, 0.314 mmol) and TSTU (473 mg, 1.57 mmol) in 20 ml acetonitrile and methylene chloride (1:1), DIPEA (325 mg, 2.51 mmol) was added at room temperature. The mixture was stirred for 30 minutes. 120 ml of methylene chloride was added, and the resultant mixture was washed three times with citric acid (30%) solution and twice with water. The organic layer was dried over $Na_2SO_4$. The compound was purified with heptane and ethyl acetate to give a yield of 87.3% (210 mg). MS-ESI (m/e): 593.3 [M+H]; HPLC 92.6% at 330 nm. MS-ESI (m/e): 766.3 [M+H]; HPLC 98.2% at 254 nm.

Example 5

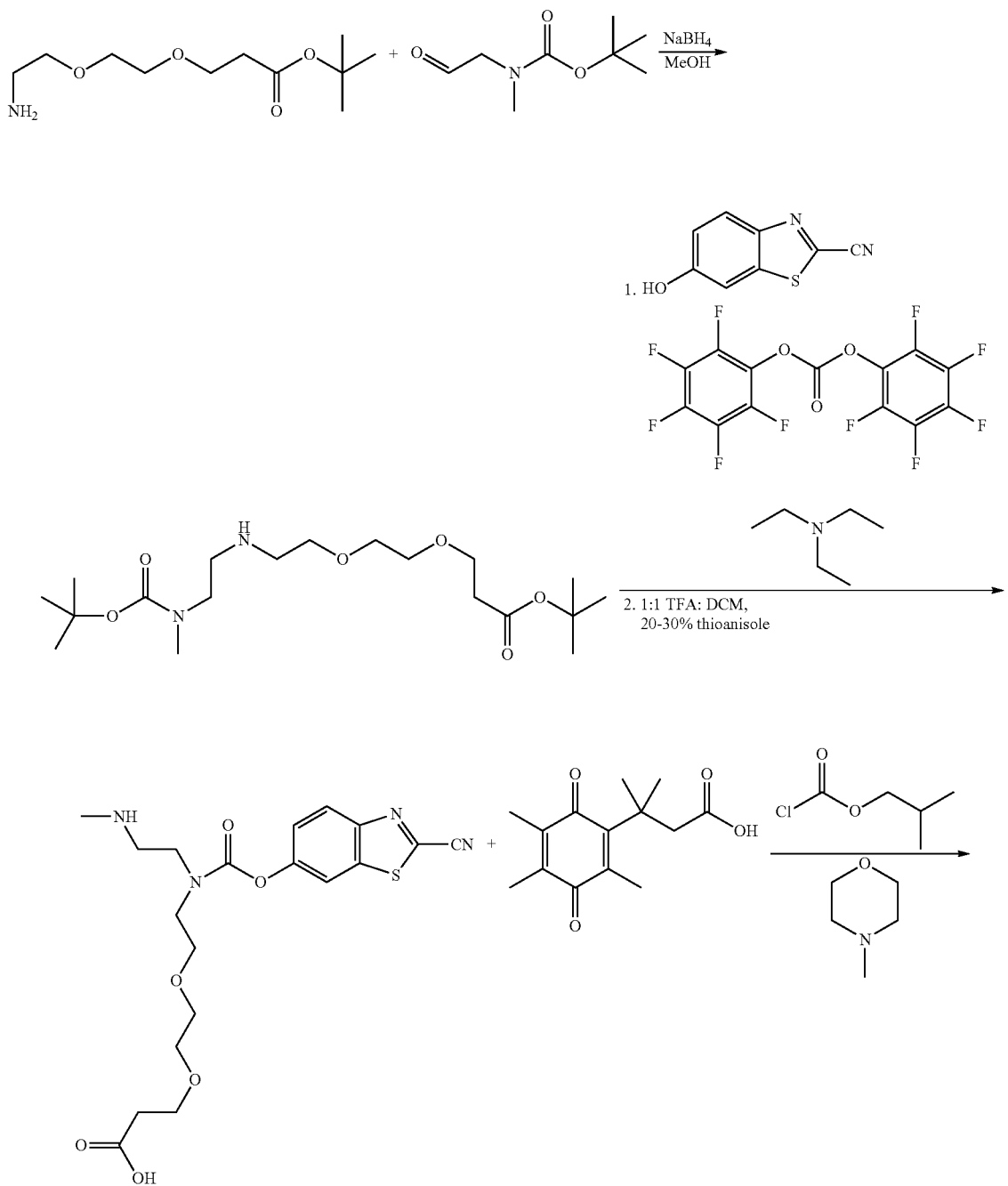

-continued
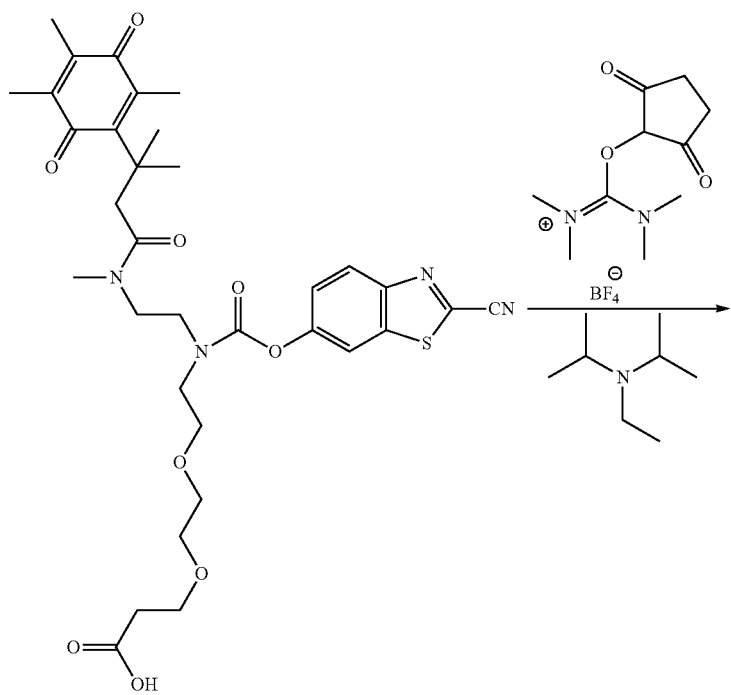
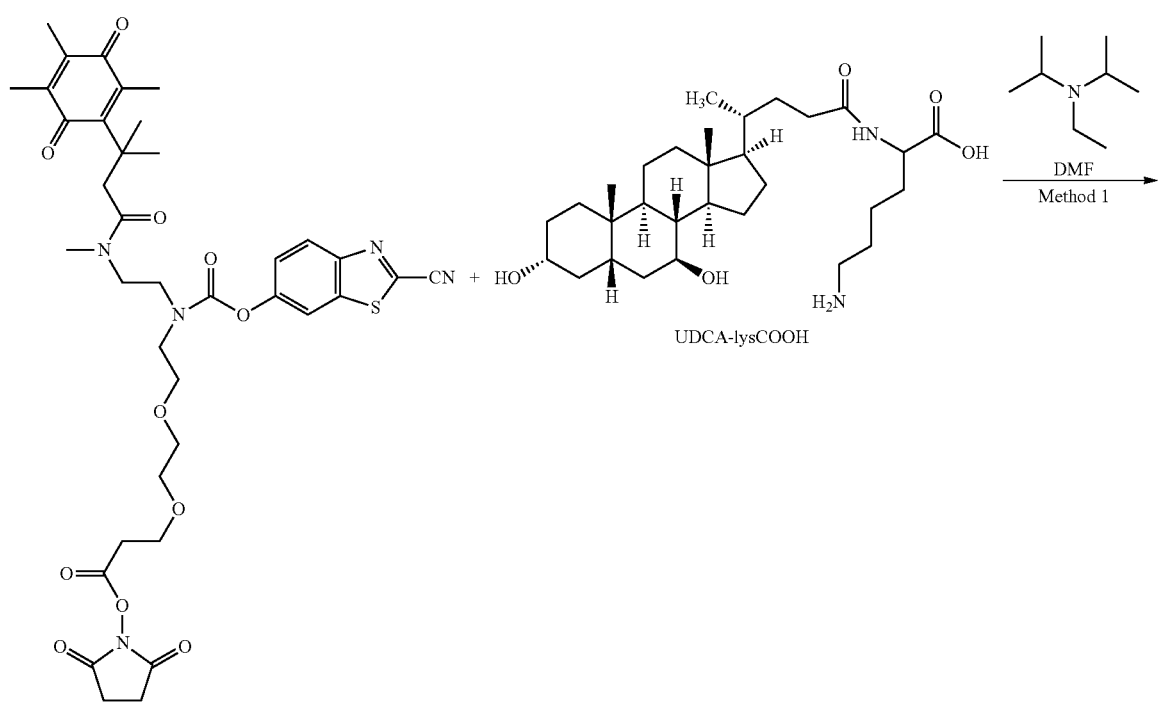

-continued
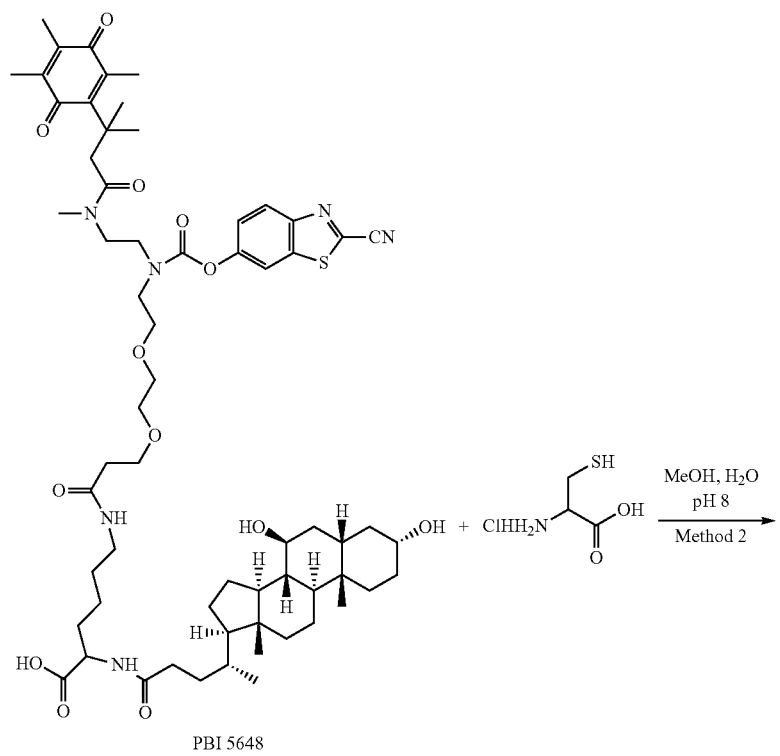
PBI 5648
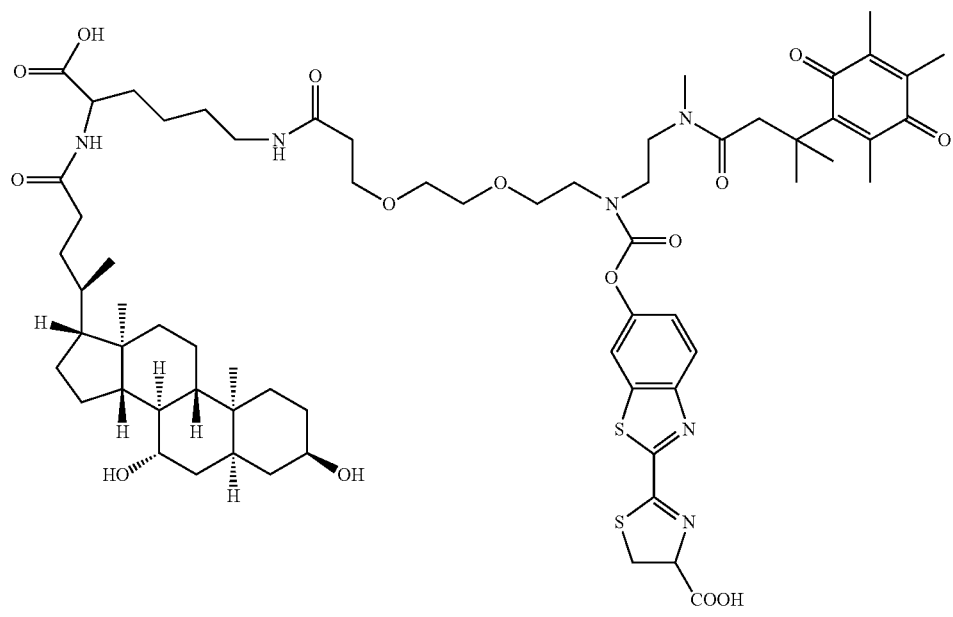
PBI 5651
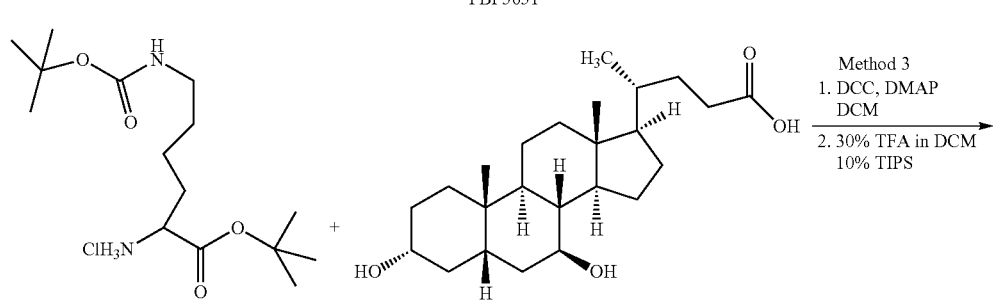

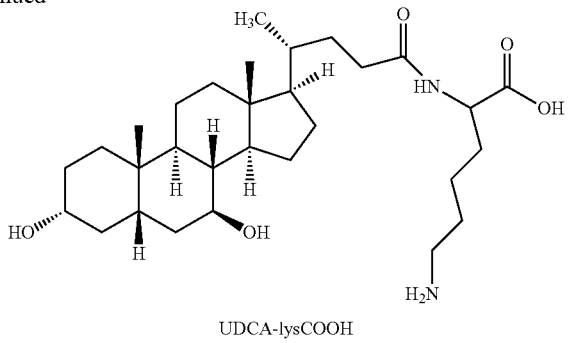

UDCA-lysCOOH

Method 3: Synthesis of UDCA-lysCOOH

To a mixture of lysine (2.44 g, 7.20 mmol) and UDCA (1.13 g, 2.88 mmol), 120 mL methylene chloride and 4-dimethylaminopyridine (1.06 g, 8.64 mmol) was added. Lastly, N,N'-dicyclohexylcarbodiimide (1.78 g, 8.64 mmol) was added and stirred at room temperature for several days. The reaction mixture was then filtered, and the solvent was removed. The product was then purified by flash silica column chromatography using a heptane/ethyl acetate gradient to give a yield of 90% (1.76 g) of the intermediate with protected lysine. This compound was then dissolved in a mixture of 40 mL methylene chloride and 30 mL TFA together with 10% triisoproypylsilane (TIPS), and the mixture was stirred at room temperature for 5 hours. The solvents were co-evaporated with toluene, and the product was purified by flash silica column chromatography using a gradient of methylene chloride/methanol to give UDCA-lysCOOH in a 67% yield (901 mg). MS-ESI (m/e): 521.5 [M+H].

Synthesis of N—[(PEG)$_2$-COO-t-Bu]-N'—Boc-N'-methyl-ethylenediamine

To the solution of N—(PEG)$_2$COO-t-Bu-amine (3.16 g, 13.54 mmol) in 100 ml of methanol, (N-methyl)-N-Boc acetaldehyde (2.35 g, 13.54 mmol) was added. The mixture was stirred at room temperature for 3 hours. NaBH$_4$ (1.54 g, 40.63 mmol) was added to the mixture at 0° C., and the resultant mixture was stirred at 0° C. for 1 hour and 1 hour at room temperature. The reaction was quenched by adding 15 ml of water. After removal of solvent, 15 ml of water was added, and the mixture was extracted three times with methylene chloride. The combined organic layer was dried over Na$_2$SO$_4$, and the product was purified by flash silica chromatography using heptane/ethyl acetate to methylene chloride/methanol to give a yield of 67% (3.56 g).

Synthesis of N—[(PEG)$_2$COO-t-Bu]-N'—Boc-N'-methyl-ethylene-diamine 6-hydroxybenzo[d]thiazole-2-carbonitrile-carbamate To the mixture of 2-cyano-6-hydroxybenzothiazole (0.803 g, 4.56 mmol) and bis(pentafluorophenyl) carbonate (1.98 g, 5.02 mmol) in 40 ml of dry THF, TEA (0.293 g, 2.89 mmol) was added at room temperature under nitrogen. The mixture was stirred for 1 hour, and N-t-butylCOO (PEG)3-N'—BOC—N'-methyl ethylenediamine (3.56 g, 9.12 mmol) in 18 mL dry THF was added. The resulting mixture was stirred at room temperature for over 30 minutes after which the solvent was removed. The product mixture was dissolved in methylene chloride and washed with sat K$_2$CO$_3$ solution three times and once with water, then the organic layer was dried over Na$_2$SO$_4$. The compound was purified by flash column chromatography using heptane/ethyl acetate as eluent to give the product in a yield of 70% (1.90 g).

Synthesis of N—[(PEG)$_2$COO-t-Bu]-N'-methyl-ethylene-diamine-2-cyanobenzothiazole-6-carbamate N—[(PEG)$_2$COO-t-Bu]-N'—Boc-N'-methyl-ethylene-diamine 6-hydroxybenzo[d]thiazole-2-carbonitrile-carbamate (1.90 g, 3.21 mmol) in 30 mL CH$_2$Cl$_2$ was dissolved over ice and then 26 mL (30%)thioanisole was added. TFA (30 mL) was slowly added over 10-15 min while on ice. The mixture was then stirred on ice for 20 min and then at room temperature for 5 hours. After the reaction, the solvent was removed, and the product was purified by flash column chromatography using a gradient of heptane/ethyl acetate followed by methylene chloride/methanol to give a yield of 57% (0.797 g).

Synthesis of N—[(PEG)$_2$COOH]—N'-methyl-N'-[3-methyl-3-(2,4,5-trimethyl-3,6-dioxocyclohexa-1,4-dien-1-yl)butanoic amido]-ethylenediamine-2-cyanobenzothiazole-6-carbamate To the solution of 3-methyl-3-(2,4,5-trimethyl-3,6-dioxo-cyclohexa-1,4-dien-1-yl)butanoic acid (1.37 g, 5.48 mmol) and isobutyl chloroformate (719 uL, 5.48 mmol) in 40 ml dry THF, N-methyl morpholine (1.53 mL, 10.96 mmol) was added at 0° C. The resultant mixture was stirred for 1 hour at 0° C., N—[(PEG)$_2$COO-t-Bu]-N'-methyl-ethylene-di-amine-2-cyanobenzothiazole-6-carbamate (0.797 g, 1.83 mmol) in 20 ml of dry THF added, and the resultant mixture was stirred for 2 hours. The reaction mixture was then acidified with acetic acid, dried down, then dissolved in methylene chloride and washed twice with water. The organic layer was dried over Na$_2$SO4, and then the solvent was removed. The compound was directly purified with flash silica column using heptane and ethyl acetate as eluent, followed by 100% THF, to give the product in a yield of 48.8% (0.596 g).

Synthesis of N—[(PEG)$_2$COOH]—N'-methyl-N'-[3-methyl-3-(2,4,5-trimethyl-3,6-dioxocyclohexa-1,4-dien-1-yl)butanoic amido]-ethylenediamine-2-cyanobenzothiazole-6-carbamate NHS ester To a solution of N—[(PEG)$_2$COOH]—N'-methyl-N'-[3-methyl-3-(2,4,5-trimethyl-3,6-dioxocyclohexa-1,4-dien-1-yl)butanoic amido]-ethylenediamine-2-cyanobenzothiazole-6-carbamate (0.315 g, 0.471 mmol) in 70 mL acetonitrile, 709 mg (2.36 mmol) of TSTU and 660 uL of DIPEA was added and then stirred for 1 hour at room temperature. The product mixture was diluted in a large volume of methylene chloride, and the product mixture washed twice with 30% citric acid solution and then once with water. The organic layer was dried with Na₂SO₄, filtered, and the solvent was removed. The product was then purified by flash column chromatography using a heptane/ethyl acetate gradient to give the product in 109% yield (394 mg).

Method 1: Synthesis of #5648

Dissolved NHS ester (100 mg, 0.130 mmol) in 2 mL DMF and added UDCA-lysCOOH synthesized by Method 3 (~136 mg, 0.261 mmol), followed by 45 uL of DIPEA and 3 more mL of DMF. The reaction was stirred at room temperature for 1 hour and then acidified with acetic acid and dried down. The product was purified by flash column chromatography using a gradient of heptane/ethyl acetate, switched to methylene chloride/methanol to give product in a yield of 40% (61 mg). MS-ESI (m/e): 1172.09 [M+H].

Method 2: Synthesis of #5651

Dissolved 12 mg of d-cysteine (0.077 mmol) in 1 mL of water and adjusted pH to 8-8.5 with TEA and then added 30 mg (0.025 mmol) of #5648 in 1 mL methanol and stirred for an hour at room temperature. The product was acidified with acetic acid and then extracted into methylene chloride. The solvent was removed, and the product was purified by flash column chromatography using a gradient of heptane/THF followed by methylene chloride/methanol to give the product in a yield of 70% (22.8 mg). MS-ESI (m/e): 1276.93 [M+H].

Example 6

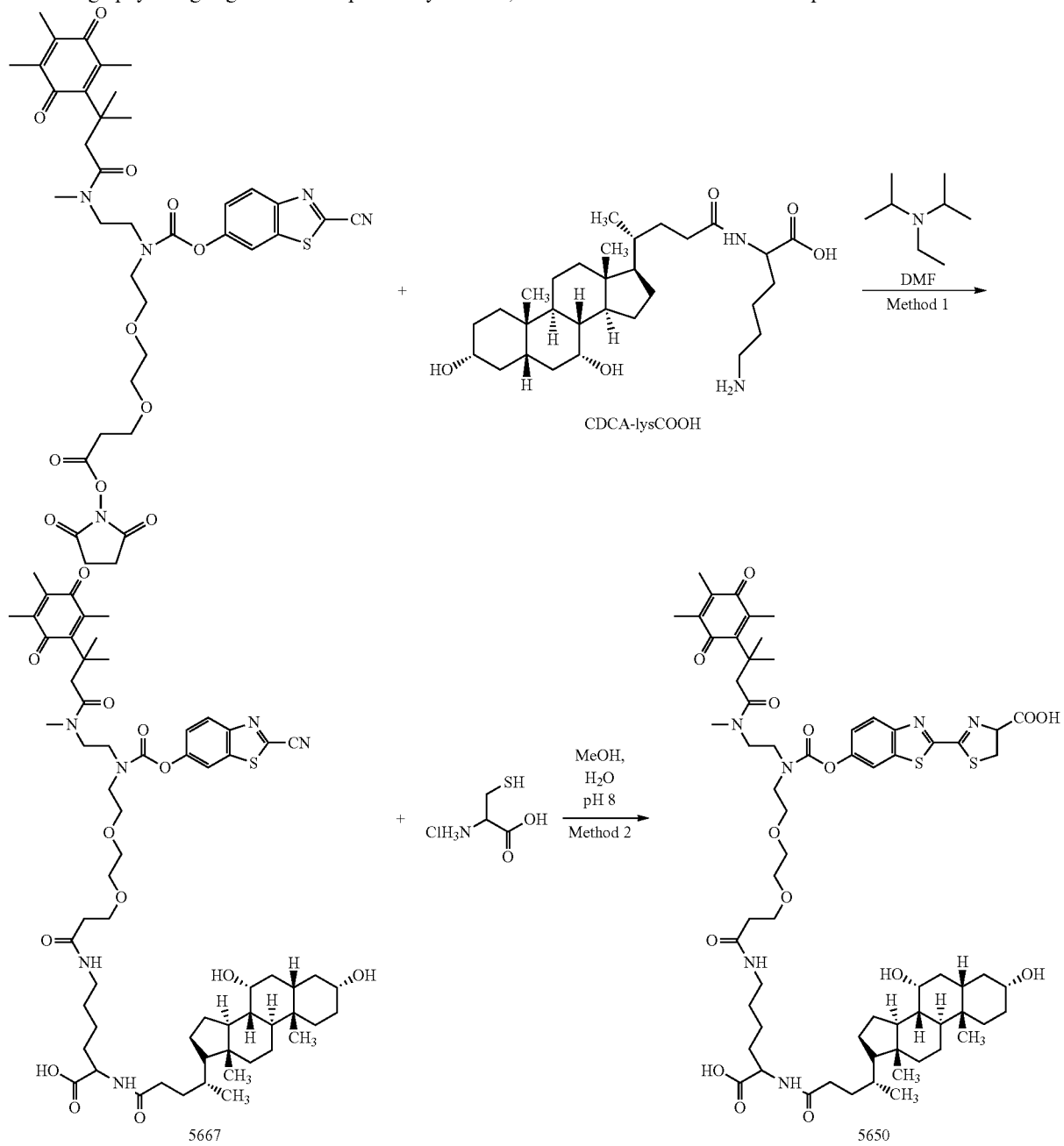

133
Synthesis of #5667
Coupled the NHS ester in Example 9 and CDCA-lysCOOH (synthesized by Method 3) utilizing Method 1 to give product in a yield of 25% (19 mg). MS-ESI (m/e): 1172.10 [M+H].
134
Synthesis of #5650
Synthesized the luciferin version of #5667 utilizing Method 2 to give the product in a yield of 55% (8.40 mg). MS-ESI (m/e): 1275.77 [M+H].
Example 7
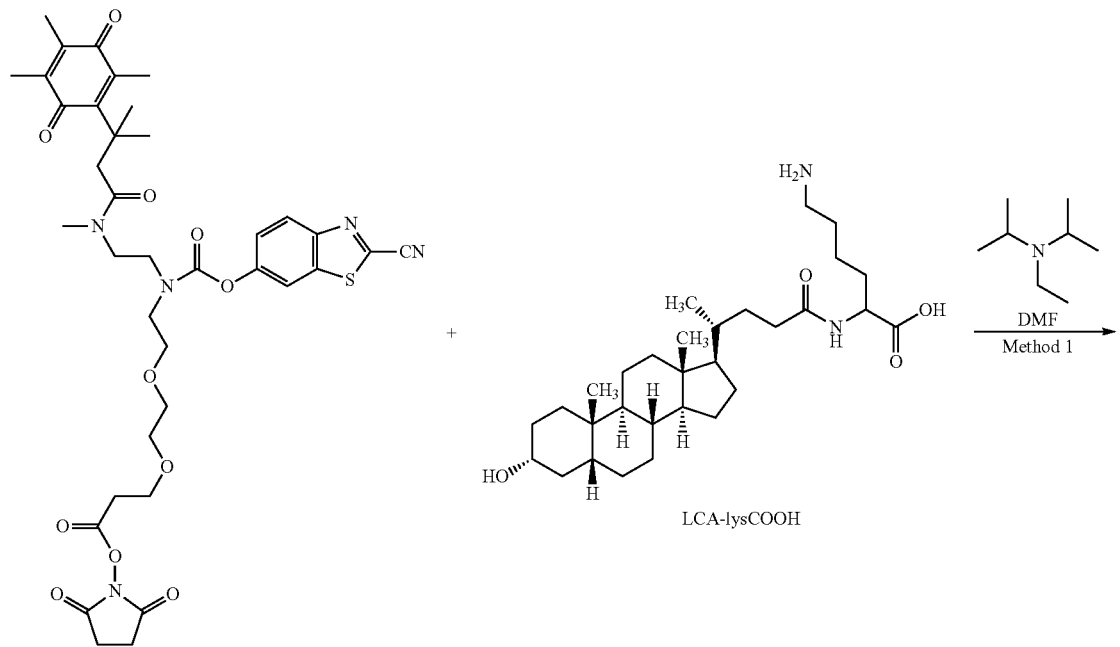
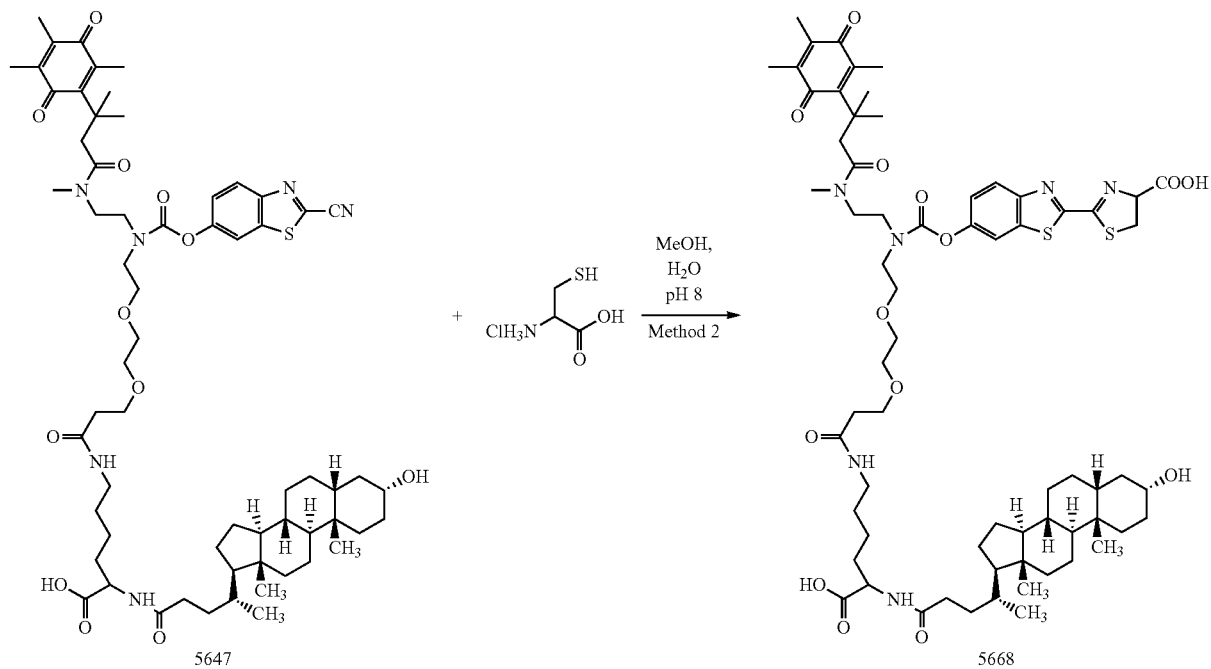

Synthesis of #5647

Method 1 was utilized with slight adjustments. NHS ester (100 mg, 0.130 mmol) was dissolved in 1 mL DMF. LCA-lysCOOH (synthesized by Method 3) (~131 mg, 0.261 mmol) was dissolved in 15 µL of 50% TFA in DMF and then diluted with 4 mL DMF. The pH was increased to 5-6 with 23 uL of DIPEA, and then the solution was added to the dissolved NHS ester, and 55 uL of DIPEA was added. The reaction was stirred at room temperature overnight and then acidified with acetic acid and dried down. The product was extracted into ethyl acetate and then purified by flash column chromatography using a gradient of heptane/ethyl acetate, followed by methylene chloride/methanol to give product in a yield of 45% (68 mg). MS-ESI (m/e): 1155.94 [M+H].

Synthesis of #5668

The luciferin version of #5647 was synthesized using Method 2 to give the product in a yield of 50% (16.20 mg). MS-ESI (m/e): 1260.27 [M+H].

Example 8

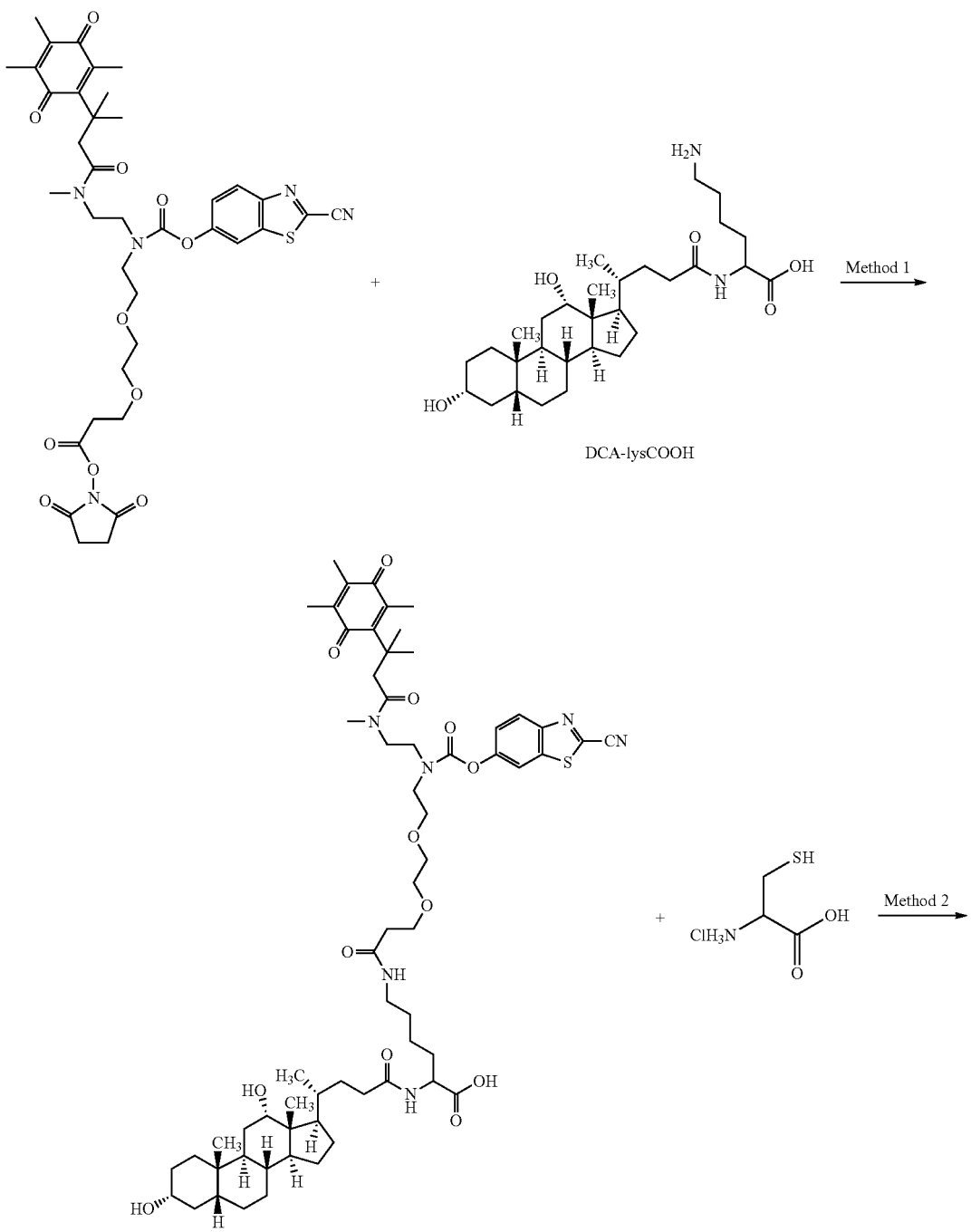

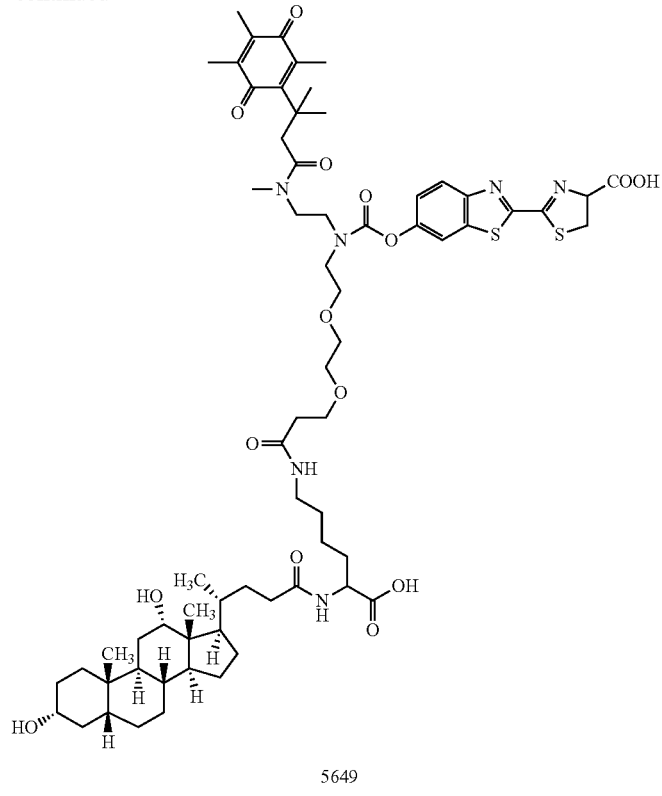
5649
Synthesis of #5625
Utilized Method 1 to couple DCA-lysCOOH (synthesized by Method 3) to the NHS ester to give product in a yield of 15% (26.8 mg). MS-ESI (m/e): 1169.9 [M−H].
Synthesis of #5649
Synthesized the luciferin version of #5625 using Method 2 to to give product in a yield of 69% (12 mg). MS-ESI (m/e): 1176.79 [M+H].
Example 9
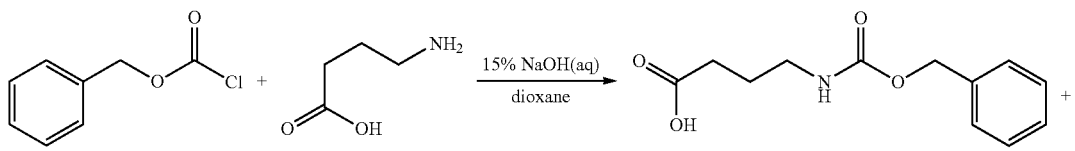
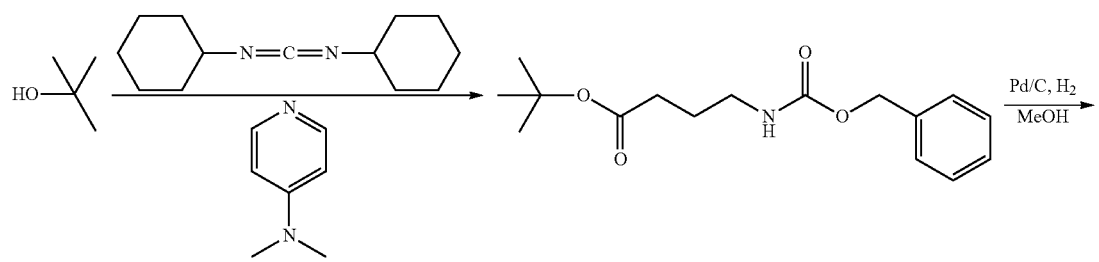

-continued
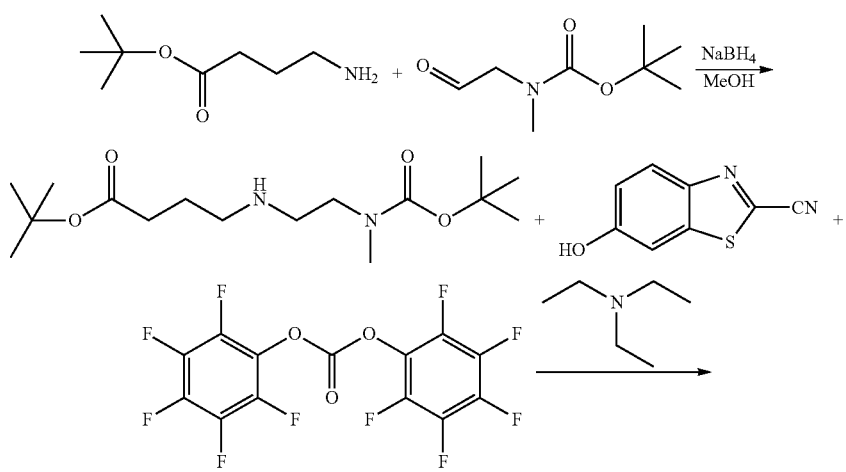
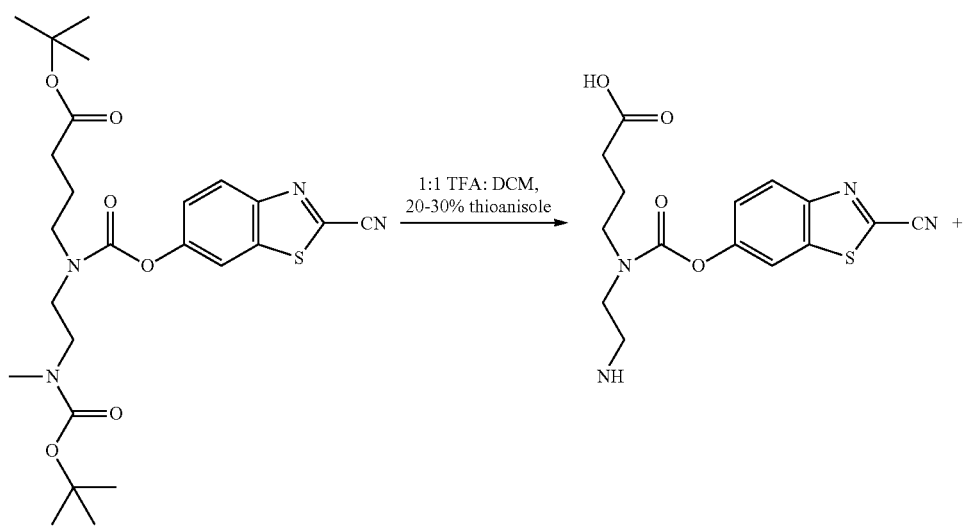
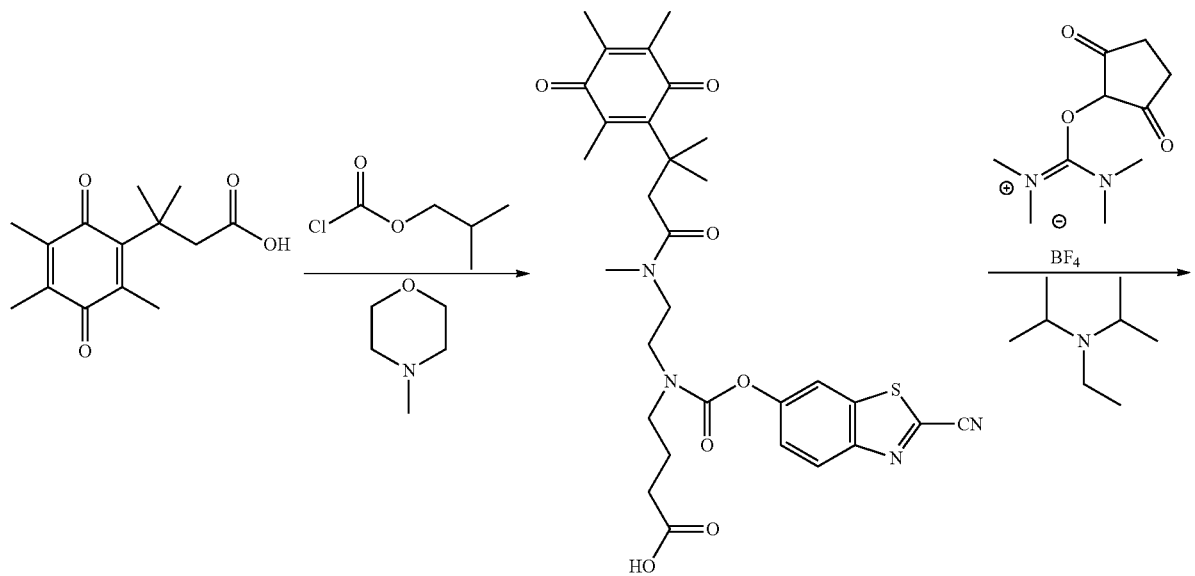

-continued
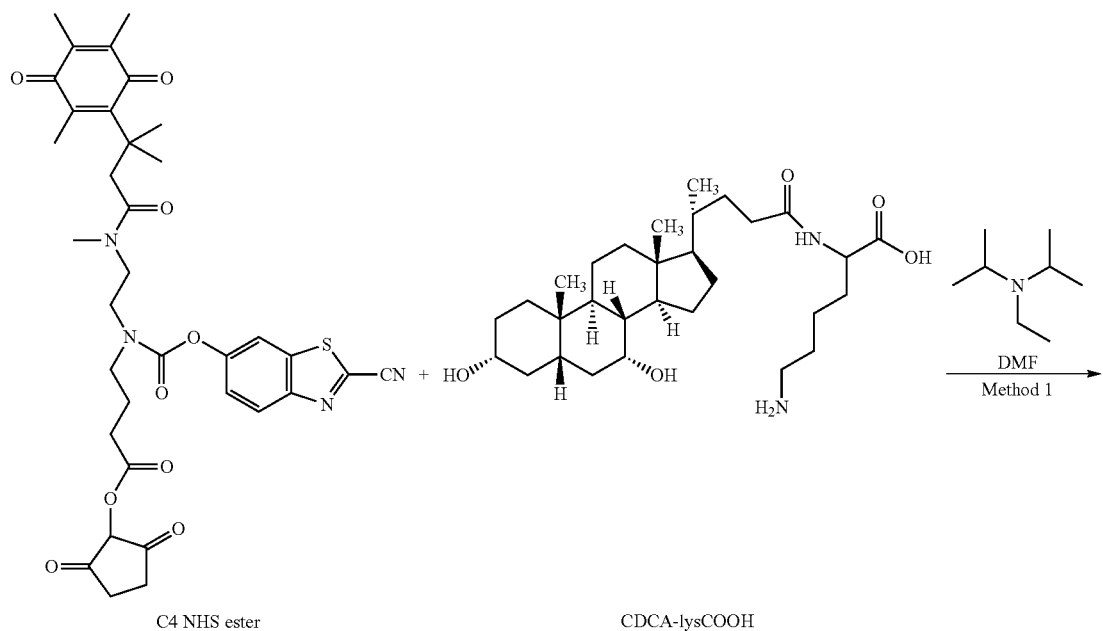
C4 NHS ester     CDCA-lysCOOH
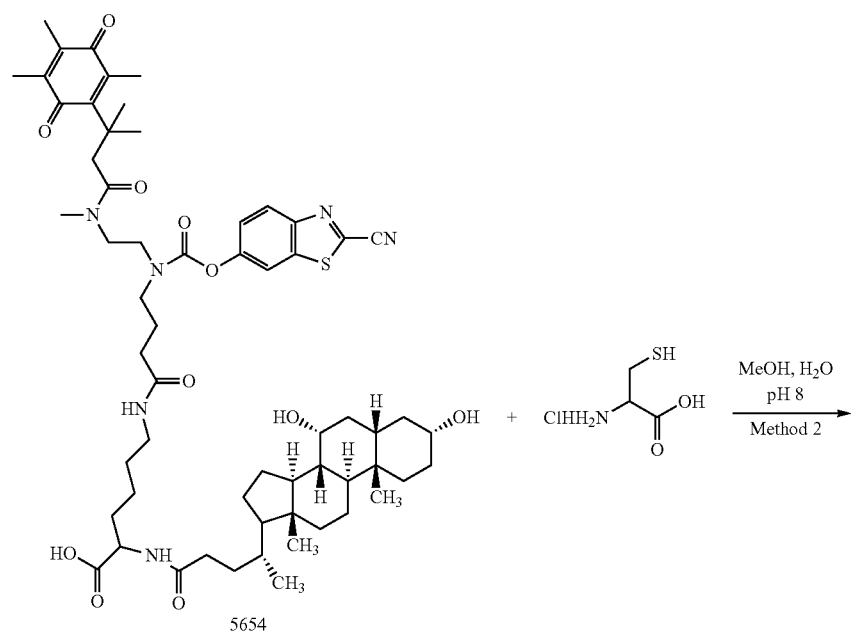

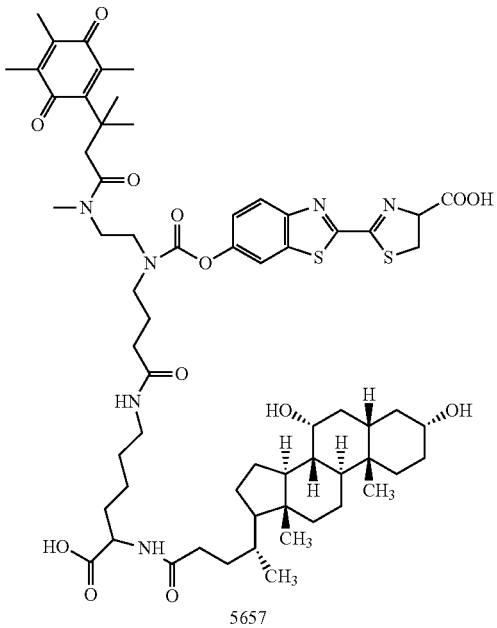

5657

Synthesis of 4-(((benzyloxy)carbonyl)amino)butanoic acid

γ-Amino butyric acid (2.90 g, 28.14 mmol) was dissolved in 15% aqueous NaOH (100 mL) and dioxane (100 mL). After the mixture was cooled to 0° C., benzyl chloroformate (8 mL, 56.27 mmol) was added with vigorous stirring. The mixture was stirred for 3 days at room temperature. The solvent was removed, and the product mixture was dissolved in a small amount of water and acidified with acetic acid. The product was then extracted into methylene chloride (3×100 mL), and the organic layer was dried with sodium sulfate, filtered, and then dried down. The product was purified by flash column chromatography using a gradient of heptane/ethyl acetate to give the product in a 51% yield (3.44 g).

Synthesis of tert-butyl 4-(((benzyloxy)carbonyl)amino)butanoate

To 4-(((Benzyloxy)carbonyl)amino)butanoic acid (3.44 g, 14.50 mmol) in 100 mL methylene chloride, anhydrous t-butanol (4.2 mL, 43.50 mmol) was added, followed by DMAP (1.77 g, 14.50 mmol) and DCC (8.97 g, 43.50 mmol). The reaction mixture was stirred at room temperature for 2 days, after which the precipitate of DCU was filtered, and the solvent was removed. The product was purified by flash column chromatography using heptane/ethyl acetate to give a yield of 49% (2.09 g).

Synthesis of tert-butyl 4-aminobutanoate

A mixture of tert-butyl 4-(((benzyloxy)carbonyl)amino)butanoate (2.09 g, 7.12 mmol) and 10% Pd/C (75.8 mg, 0.712 mmol) in 100 mL methanol was stirred at room temperature under hydrogen for 5 hours. The mixture was then filtered, and the solvent was removed to give a 93% yield (1.06 g) of product.

Synthesis of N—[(CH$_2$)$_3$—COO-t-Bu]-N'—Boc-N'-methyl-ethylenediamine

To the solution of tert-butyl 4-aminobutanoate (1.06 g, 6.66 mmol) in 50 ml of methanol, (N-methyl)-N—BOC acetaldehyde (1.15 g, 6.66 mmol) was added. The mixture was stirred at room temperature for 3 hours. NaBH$_4$ (0.755 g, 19.97 mmol) was added to the mixture at 0° C., and the resultant mixture was stirred at 0° C. for 1 hour and at room temperature for 1 hour. The reaction was quenched by adding 5 ml of water. After removal of solvent, 5 ml of water was added, and the mixture was extracted three times with methylene chloride. The combined organic layer was dried over Na$_2$SO$_4$, and the solvent was removed. The product was purified by flash column chromatography using heptane/ethyl acetate followed by methylene chloride/methanol to give a yield of 105% (2.23 g).

Synthesis of N—[(CH$_2$)$_3$COO-t-Bu]-N'—Boc-N'-methyl-ethylene-diamine 6-hydroxybenzo[d]thiazole-2-carbonitrile-carbamate To the mixture of 2-cyano-6-hydroxybenzothiazole (0.587 g, 3.33 mmol) and bis(pentafluorophenyl) carbonate (1.44 g, 3.66 mmol) in 30 ml of dry THF, TEA (930 µL, 6.66 mmol) was added at room temperature under nitrogen. The mixture was stirred for 30 min minutes, and N—[(CH$_2$)$_3$—COO-t-Bu]-N'—Boc-N'-methyl-ethylenediamine (2.11 g, 6.66 mmol) in 20 mL dry THF was added. The resulting mixture was stirred at room temperature for 2 hours. The reaction mixture was then dried down, and the product mixture was dissolved in methylene chloride and washed with saturated K$_2$CO$_3$ solution 3 times and once with water, then dried over Na$_2$SO$_4$. The solvent was removed, and the compound was purified by flash column chromatography using heptane/ethyl acetate as eluent to give the product in a yield of 86% (1.5 g)

Synthesis of N—[(CH$_2$)$_3$ COO-t-Bu]-N'-methyl-ethylene-diamine-2-cyanobenzothiazole-6-carbamate N—[(CH$_2$)$_3$COO-t-Bu]-N'—Boc-N'-methyl-ethylene-diamine 6-hydroxybenzo[d]thiazole-2-carbonitrile-carbamate was dissolved in 15 mL methylene chloride over ice. Thioanisole (8 mL, 21%) was added, followed by the slow addition of 15 mL TFA over 10-15 min on ice. The mixture was stirred on ice for 30 min, then stirred at room temperature for 4 hours. The TFA was then co-evaporated with toluene, and the product was purified by flash column chromatography using heptane/ethyl acetate, followed by methylene chloride/methanol to elute product the product in a 73% yield (0.765 g).

Synthesis of N—[(CH$_2$)$_3$COOH]—N'-methyl-N'-[3-methyl-3-(2,4,5-trimethyl-3,6-dioxocyclohexa-1,4-dien-1-yl)butanoic amido]-ethylenediamine-2-cyanobenzothiazole-6-carbamate To the solution of 3-methyl-3-(2,4,5-trimethyl-3,6-dioxocyclohexa-1,4-dien-1-yl)butanoic acid (1.59 g, 6.33 mmol) and isobutyl chloroformate (831 uL, 6.33 mmol) in 40 ml dry THF, N-methyl morpholine (1.76 mL, 12.67 mmol) was added at 0° C. The resulting mixture was stirred for 1 hour at 0° C., and then N—[(CH$_2$)$_3$COO-t-Bu]-N'—Boc-N'-methyl-ethylene-diamine 6-hydroxybenzo[d]thiazole-2-carbonitrile-carbamate in 10 ml dry THF was added. The resulting mixture was stirred for 2 hours after which it was acidified with acetic acid then dried down. The product was then purified by flash column chromatography using heptane/ethyl acetate gradient followed by methylene chloride/methanol to give the product in a 142% yield (1.79 g).

Synthesis of N—[(CH$_2$)$_3$COOH]—N'-methyl-N'-[3-methyl-3-(2,4,5-trimethyl-3,6-dioxocyclohexa-1,4-dien-1-yl)butanoic amido]-ethylenediamine-2-cyanobenzothiazole-6-carbamate NHS ester (C4 NHS ester)

TSTU (2.3 g, 7.64 mmol) was added to N-[(CH$_2$)$_3$COOH]—N'-methyl-N'-[3-methyl-3-(2,4,5-trimethyl-3,6-dioxocyclohexa-1,4-dien-1-yl)butanoic amido]-ethylenediamine-2-cyanobenzothiazole-6-carbamate (1.26 g, 2.12 mmol), followed by 70 mL of acetonitrile. DIPEA (2.95 mL, 16.95 mmol) was added, and the mixture was stirred for 1 hour at room temperature. The product mixture was then diluted in a large volume of methylene chloride and washed with 30% citric acid solution twice, then once with water. The organic layer was dried over Na$_2$SO$_4$, filtered, and the solvent was removed. The product was purified by flash column chromatography using heptane/ethyl acetate to give a 70% yield (1.03 g).

Synthesis of #5654

C4 NHS ester was coupled to CDCA-lysineCOOH using Method 1 to give the product in a 41% yield (65 mg). MS-ESI (m/e): 1098.49 [M+H].

Synthesis of #5657

The luciferin version of #5654 was prepared using Method 2 to give a yield of 40% (17.3 mg). MS-ESI (m/e): 1203.37 [M+H].

Synthesis of #5655

C4 NHS ester was coupled to UDCA-lysineCOOH using Method 1 to give the product in a 49% yield (78 mg). MS-ESI (m/e): 1098.40 [M+H].

Synthesis of #5658

The luciferin version of #5655 was prepared using Method 2 to give a yield of 69% (28 mg). MS-ESI (m/e): 1203.14 [M+H].

Synthesis of #5652

C4 NHS ester was coupled to LCA-lysineCOOH using Method 1 to give the product in a 78% yield (172 mg). MS-ESI (m/e): 1079.71 [M−H].

Synthesis of #5669

The luciferin version of #5652 was prepared using Method 2 to give a yield of 24% (6.5 mg). MS-ESI (m/e): 1086.30 [M+H].

Synthesis of #5653

C4 NHS ester was coupled to DCA-lysineCOOH using Method 1 to give the product in a 71% yield (112 mg). MS-ESI (m/e): 1095.59 [M−H].

Synthesis of #5656

The luciferin version of #5653 was prepared using Method 2 to give a yield>99% yield (84 mg). MS-ESI (m/e): 1202.34 [M+H].

Example 10

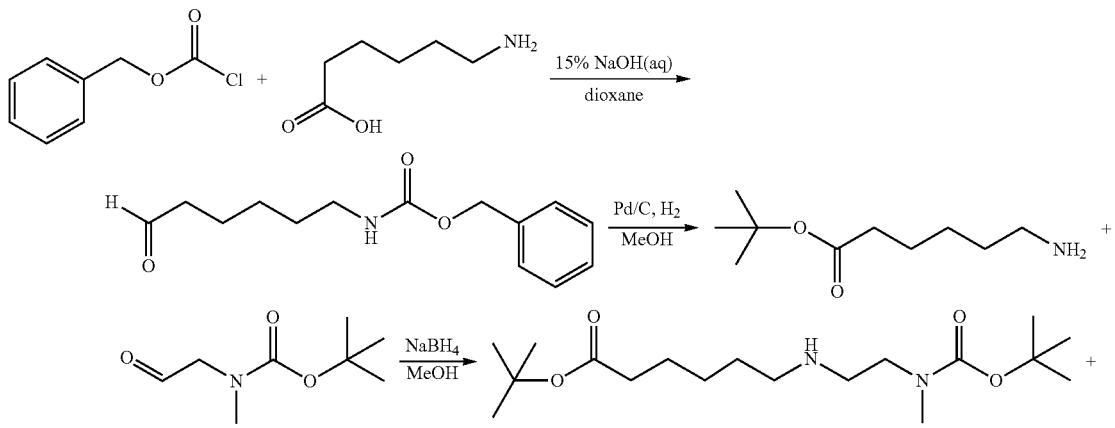

147
-continued
148
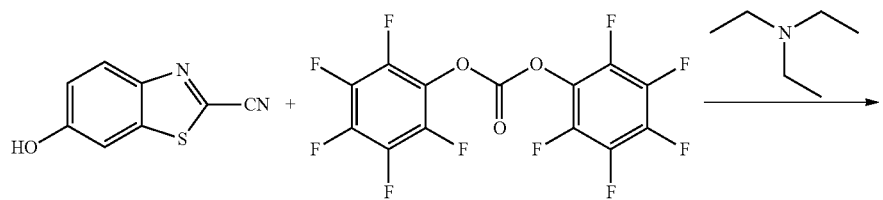
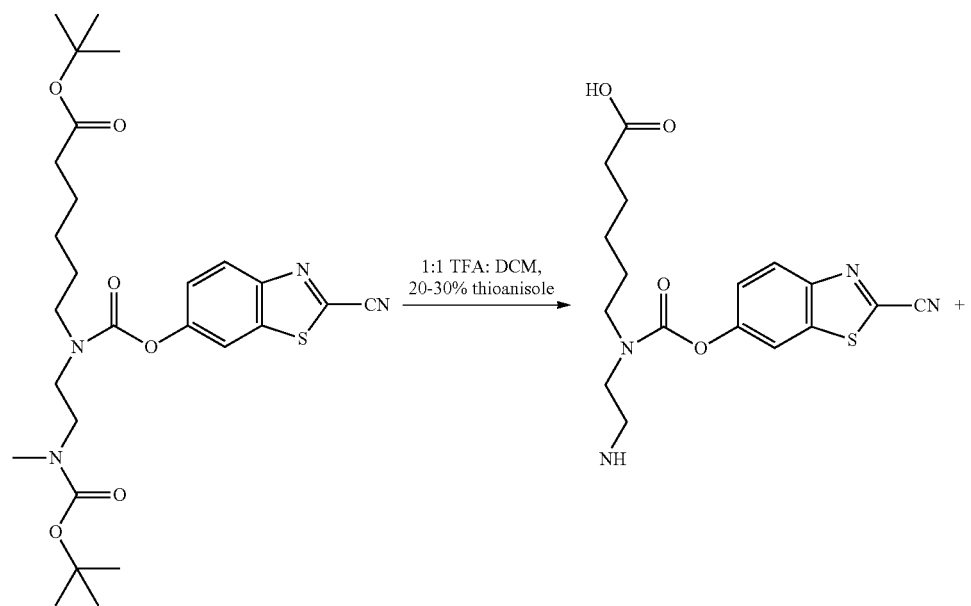
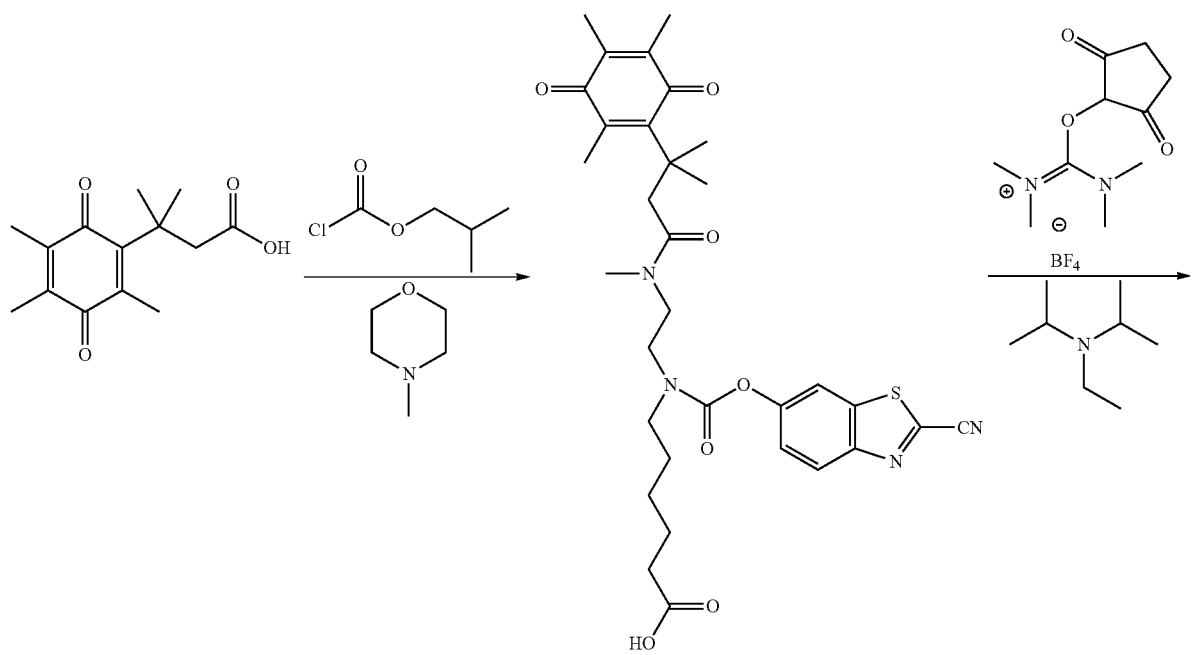

-continued
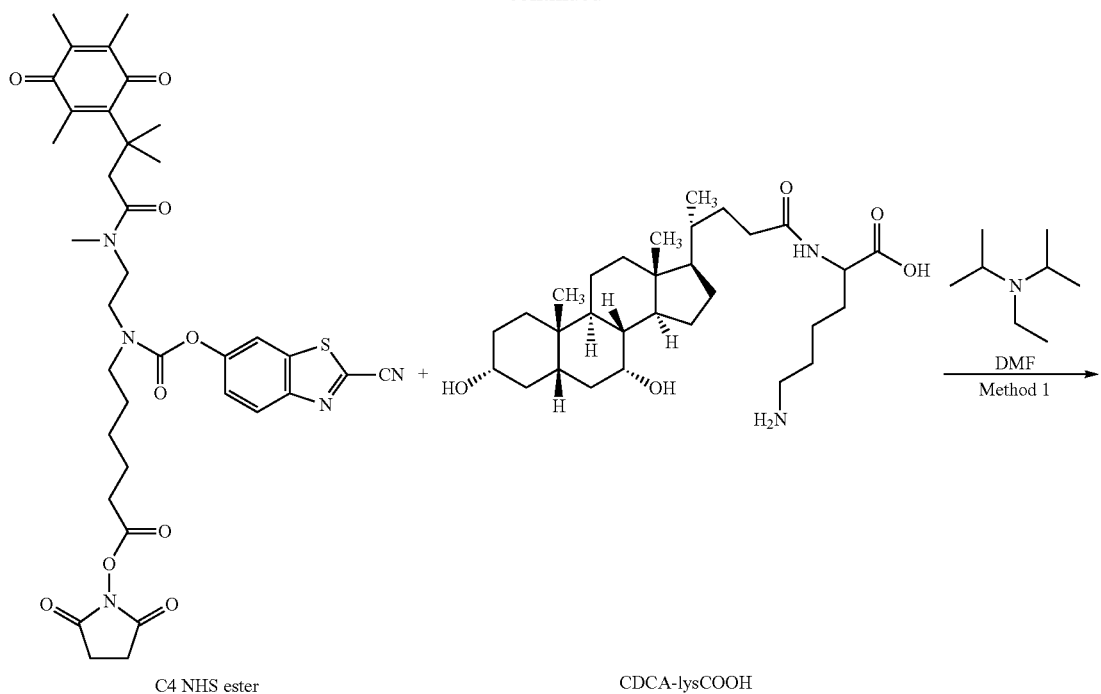
C4 NHS ester
CDCA-lysCOOH
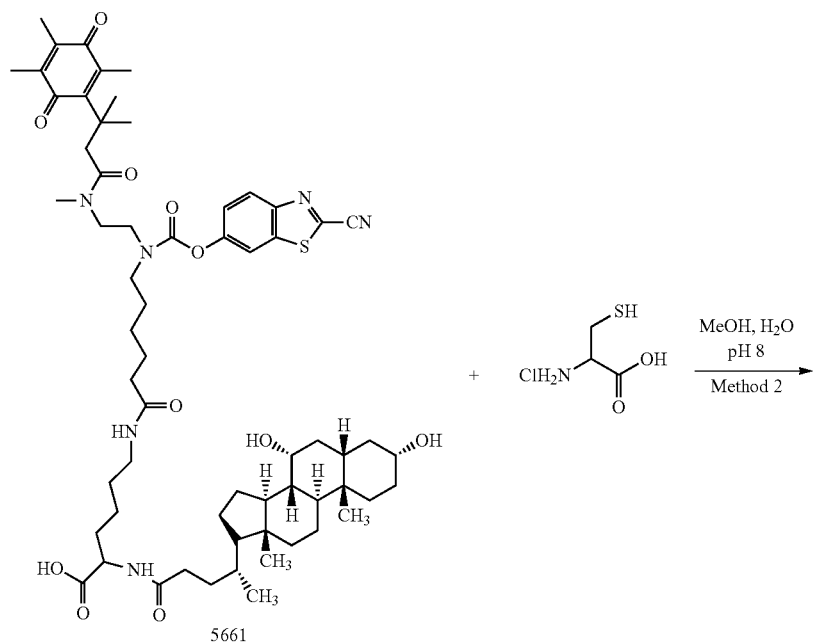
5661

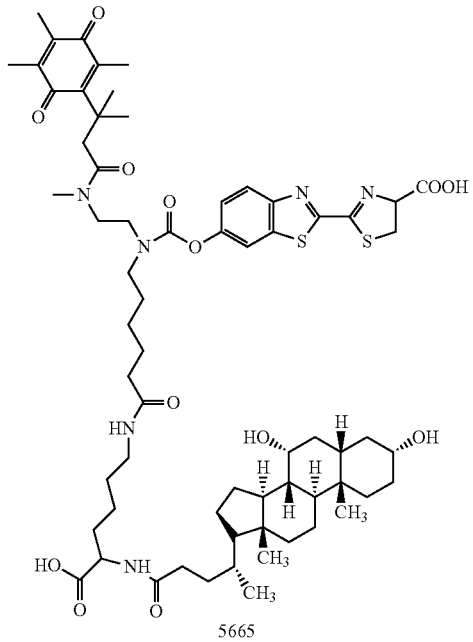

5665

Synthesis of 6-(((benzyloxy)carbonyl)amino)hexanoic acid

6-Aminohexanoic acid (4.61 g, 35.17 mmol) was dissolved in a mixture of 15% aqueous NaOH (100 mL) and dioxane (100 mL). After the mixture was cooled to 0° C., benzyl chloroformate (10 mL, 70.34 mmol) was added with vigorous stirring. The mixture was then stirred at room temperature for 2 days. The solvent was removed, the product mixture dissolved in water and acidified with acetic acid, and the product extracted into methylene chloride. The organic layer was dried with Na2SO4, filtered, and the solvent was removed. The product was purified by flash column chromatography using a gradient of heptane/ethyl acetate to give 81% (7.62 g).

Synthesis of tert-butyl 6-(((benzyloxy)carbonyl)amino)hexanoate 6-(((Benzyloxy)carbonyl)amino)hexanoic acid (7.62 g, 28.72 mmol) was dissolved in 200 mL methylene chloride, and anhydrous t-butanol (8.2 mL, 86.16 mmol) was added, followed by DMAP (3.51 g, 28.72 mmol). DCC (17.78 g, 86.16 mmol) was added, and the mixture was stirred at room temperature for 2 days. The mixture was filtered and then dried down, and the product was purified by flash column chromatography using heptane/ethyl acetate to give a yield of 63% (5.86 g).

Synthesis of tert-butyl 6-aminohexanoate

To a mixture of tert-butyl 6-(((benzyloxy)carbonyl) amino)hexanoate (5.86 g, 18.23 mmol) and 10% Pd/C (194 mg, 1.82 mmol), 250 mL of methanol was added. The mixture was stirred at room temperature for 5 hours under a hydrogen atmosphere, after which it was filtered and the solvent was removed to give the product in 131% yield (4.48 g).

Synthesis of N—[(CH$_2$)$_5$—COO-t-Bu]-N'—Boc-N'-methyl-ethylenediamine

To the solution of tert-butyl 6-aminohexanoate (3.41 g, 18.21 mmol) in 80 mL of methanol, (N-methyl)-N—BOC acetaldehyde (3.15 g, 18.21 mmol) was added. The mixture was stirred at room temperature for 3 hours. NaBH$_4$ (2.07 g, 54.62 mmol) was added to the mixture at 0° C., and the resultant mixture was stirred at 0° C. for 1 hour and at room temperature for 1 hour. The reaction was quenched by adding 10 mL of water. After removal of solvent, 30 mL of water was added, and the mixture was extracted three times with methylene chloride. The combined organic layer was dried over Na$_2$SO$_4$ and dried down. The product was purified by flash column chromatography using heptane/ethyl acetate followed by methylene chloride/methanol.

Synthesis of N—[(CH$_2$)$_5$COO-t-Bu]-N'—Boc-N'-methyl-ethylene-diamine 6-hydroxybenzo[d]thiazole-2-carbonitrile-carbamate To the mixture of 2-cyano-6-hydroxybenzothiazole (0.366 g, 2.08 mmol) and bis(pentafluorophenyl) carbonate (0.902 g, 2.29 mmol) in 20 ml of dry THF, TEA (580 uL, 4.16 mmol) was added at room temperature under nitrogen. The mixture was stirred for 30 min minutes, and N—[(CH$_2$)$_5$—COO-t-Bu]-N'—Boc-N'-methyl-ethylenediamine (1.43 g, 4.16 mmol) in 10 mL dry THF was added. The resulting mixture was stirred at room temperature for over 30 minutes. The solvent was removed, and then the product mixture was dissolved in methylene chloride and washed with saturated K$_2$CO$_3$ solution 3 times and once with water. The organic layer was dried over Na$_2$SO$_4$, and the solvent was removed. The compound was purified by flash column chromatography using heptane/ethyl acetate as eluent to give the product in a yield of 77% (0.875 g).

Synthesis of N—[(CH$_2$)$_5$COO-t-Bu]-N'-methyl-ethylene-diamine-2-cyanobenzothiazole-6-carbamate N—[(CH$_2$)$_5$COO-t-Bu]-N'—Boc-N'-methyl-ethylene-diamine 6-hydroxybenzo[d]thiazole-2-carbonitrile-carbamate was dissolved in 10 mL methylene chloride over ice, and 5 mL (20%)thioanisole was added. 10 mL of TFA were slowly added over ice, after which the reaction mixture was stirred on ice for 30 min, then stirred at room temperature for 5 hours. The solvents were then co-evaporated with toluene, and the product was purified by flash column chromatography using heptane/ethyl acetate followed by methylene chloride/methanol to give the product in a 94% yield (0.589 mg).

Synthesis of N—[(CH$_2$)$_5$COOH]—N'-methyl-N'-[3-methyl-3-(2,4,5-trimethyl-3,6-dioxocyclohexa-1,4-dien-1-yl)butanoic amido]-ethylenediamine-2-cyanobenzothiazole-6-carbamate To the solution of 3-methyl-3-(2,4,5-trimethyl-3,6-dioxocyclohexa-1,4-dien-1-yl)butanoic acid (1.13 g, 4.53 mmol) and isobutyl chloroformate (594 uL, 4.53 mmol) in 35 ml dry THF, N-methyl morpholine (1.26 mL, 9.05 mmol) was added at 0° C. The resultant mixture was stirred for 1 hr at 0° C., after which N—[(CH$_2$)$_5$COO-t-Bu]-N'-methyl-ethylene-diamine-2-cyanobenzothiazole-6-carbamate in 5 ml of dry THF was added, and the resultant mixture was stirred for 2 hours at room temperature. The product mixture was acidified with acetic acid then dried down. The product was purified by flash column chromatography using heptane/ethyl acetate, then methylene chloride/methanol to give a yield of 87% (0.817 g).

Synthesis of N—[(CH$_2$)$_5$COOH]—N'-methyl-N'-[3-methyl-3-(2,4,5-trimethyl-3,6-dioxocyclohexa-1,4-dien-1-yl)butanoic amido]-ethylenediamine-2-cyanobenzothiazole-6-carbamate NHS ester (C6 NHS ester)

To the mixture of TSTU (2.76 g, 9.16 mmol) and N-[(CH$_2$)$_5$COOH]—N'-methyl-N'-[3-methyl-3-(2,4,5-trimethyl-3,6-dioxocyclohexa-1,4-dien-1-yl)butanoic amido]-ethylenediamine-2-cyanobenzothiazole-6-carbamate (0.815 g, 1.31 mmol), 60 mL of acetonitrile was added. DIPEA (1.82 mL, 10.47 mmol) was added, and the reaction mixture was stirred for 1 hour at room temperature. The product mixture was diluted with a large volume of methylene chloride, then washed with 30% citric acid solution twice, then once with water, dried with Na$_2$SO$_4$, filtered, and the solvent was removed. The product was purified by flash column chromatography using heptane/ethyl acetate to give a 76% yield (0.717 g).

Synthesis of #5661

C6 NHS ester and CDCA-lysCOOH were coupled using Method 1 to give product #5661 in a 71% yield (111 mg). MS-ESI (m/e): 1126.48 [M+H].

Synthesis of #5665

The luciferin version of #5661 was prepared using Method 2 to give a 38% yield (21 mg). MS-ESI (m/e): 1230.57 [M+H].

Synthesis of #5662

C6 NHS ester and UDCA-lysCOOH were coupled using Method 1 to give product #5661 in a 78% yield (122 mg). MS-ESI (m/e): 1126.48 [M+H].

Synthesis of #5666

The luciferin version of #5662 was prepared using Method 2 to give a 20% yield (16 mg). MS-ESI (m/e): 1230.57 [M+H].

Synthesis of #5660

C6 NHS ester and DCA-lysCOOH were coupled using Method 1 to give product #5661 in a 38% yield (59 mg). MS-ESI (m/e): 1126.67 [M+H].

Synthesis of #5664

The luciferin version of #5660 was prepared using Method 2 to give a 98% yield (27 mg). MS-ESI (m/e): 1230.62 [M+H].

Synthesis of #5659

C6 NHS ester and LCA-lysCOOH were coupled using Method 1 to give product #5661 in a 33% yield (51 mg). MS-ESI (m/e): 1109.55 [M+H].

Synthesis of #5663

The luciferin version of #5659 was prepared using Method 2 to give a 36% yield (12 mg). MS-ESI (m/e): 1212.30 [M−H].

Example 11

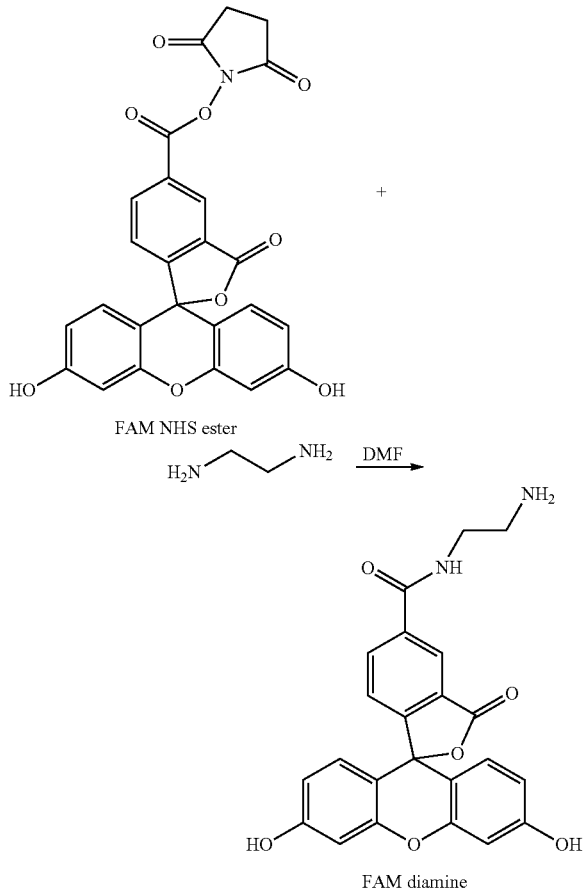

FAM NHS ester

FAM diamine

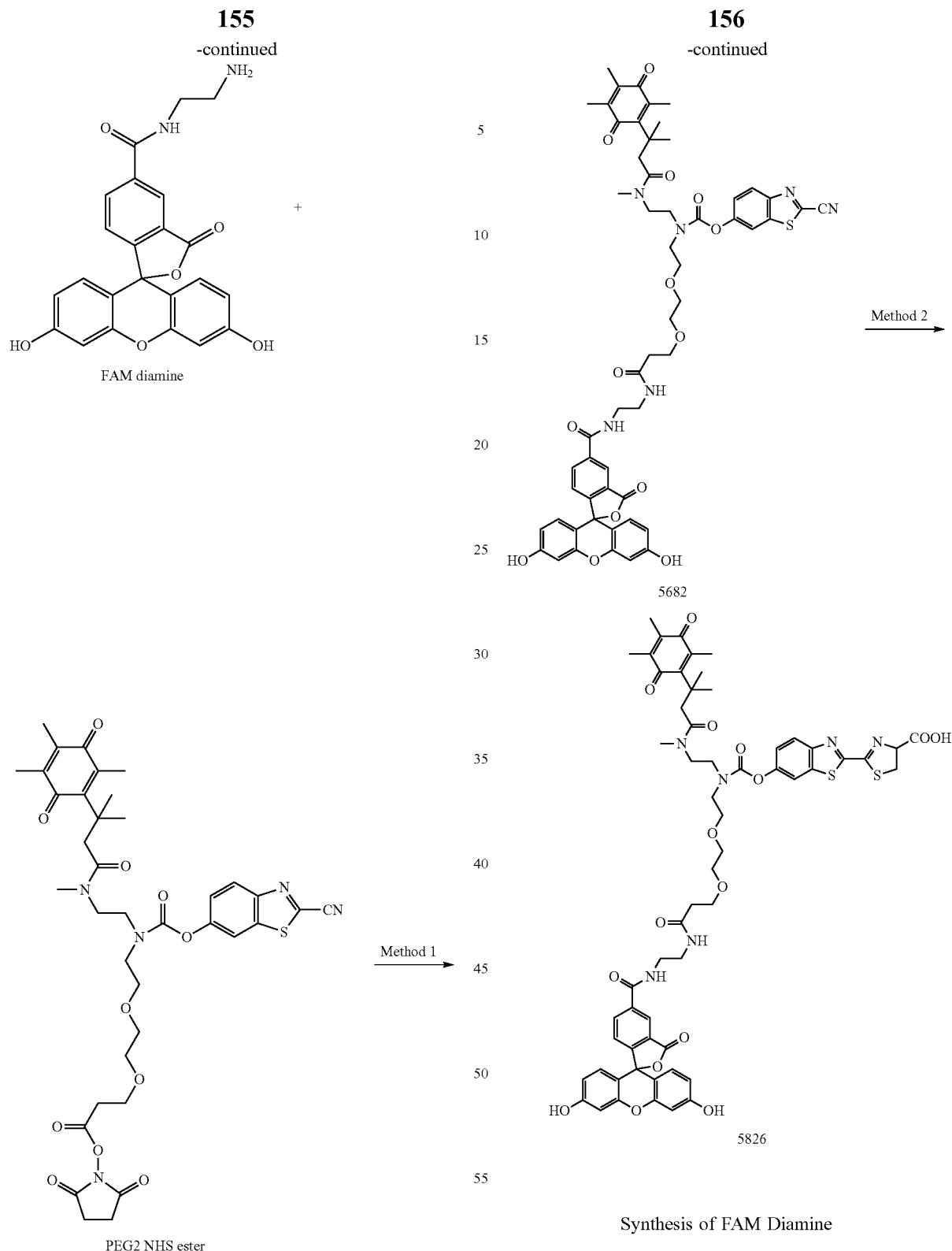

Synthesis of FAM Diamine

Diethyl amine (317 mg, 5.28 mmol) was dissolved in 7 mL DMF, and then 500 mg of FAM NHS ester dissolved in 7 mL DMF was added drop-wise and stirred at room temperature for 30 min. The solvent was then removed, and the product mixture was re-dissolved in methanol and water, and then purified by reverse phase HPLC on a C18 column using 0.1% formic acid and methanol to give FAM diamine in a yield of 77% (342 mg). MS-ESI (m/e): 442.9 [M+H].

Synthesis of #5682

PEG2 NHS ester and FAM diamine were coupled using Method 1 described above. The product was purified by reverse phase HPLC on a C18 column using 0.1% formic acid and acetonitrile to give #5682 in a 47% yield (15 mg). MS-ESI (m/e): 1069.81 [M+H].

Synthesis of #5826

The luciferin version of #5682 was prepared using Method 2 described above. The product was then purified by reverse phase HPLC on a C18 column using 0.1% formic acid and acetonitrile to give #5826 in a 89% yield (42 mg). MS-ESI (m/e): 1175.20 [M+H].

Synthesis of #5684

C4 NHS ester and FAM diamine were coupled using Method 1 described above. The product was purified by reverse phase HPLC on a C18 column using 0.1% formic acid and acetonitrile to give #5682 in a 46% yield (41 mg). MS-ESI (m/e): 995.98 [M+H].

Synthesis of #5824

The luciferin version of #5684 was prepared using Method 2 described above. The product was then purified by reverse phase HPLC on a C18 column using 0.1% formic acid and acetonitrile to give #5824 in >99% yield (67 mg). MS-ESI (m/e): 1099.37 [M+H].

Synthesis of #5683

C6 NHS ester and FAM diamine were coupled using Method 1 described above. The product was purified by reverse phase HPLC on a C18 column using 0.1% formic acid and acetonitrile to give #5682 in a 78% yield (19 mg). MS-ESI (m/e): 1024.38 [M+H].

Synthesis of #5825

The luciferin version of #5683 was prepared using Method 2 described above. The product was then purified by reverse phase HPLC on a C18 column using 0.1% formic acid and acetonitrile to give #5825 in a 67% yield (36 mg). MS-ESI (m/e): 1128.98 [M+H].

Example 12

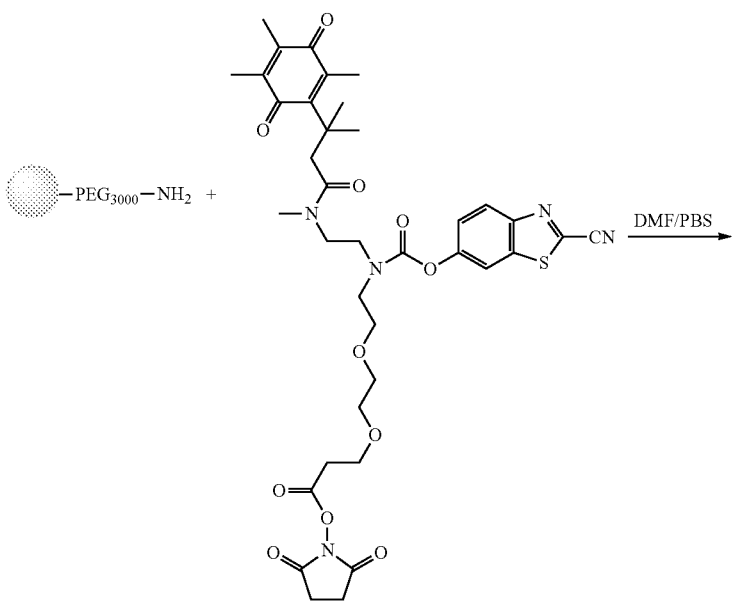

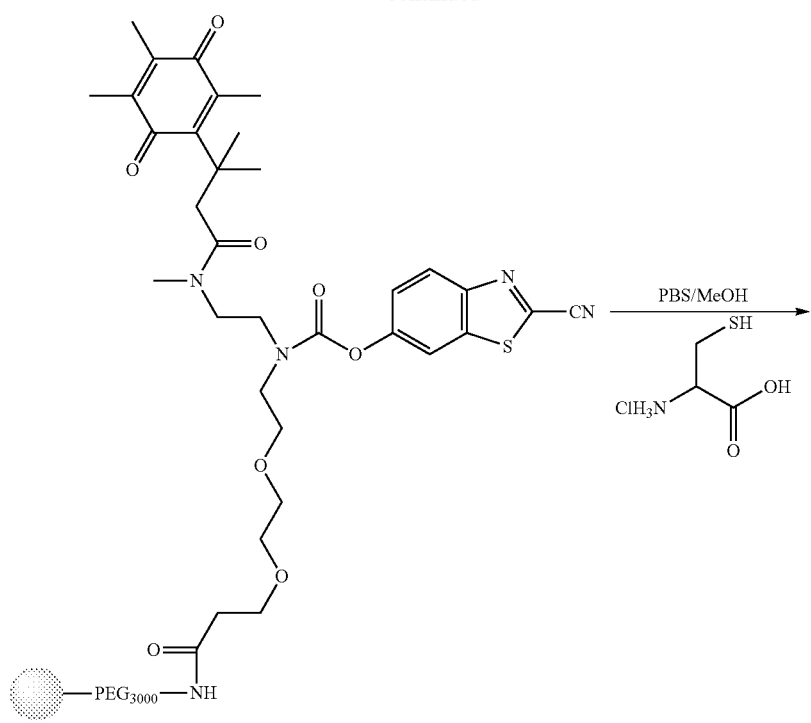
5907
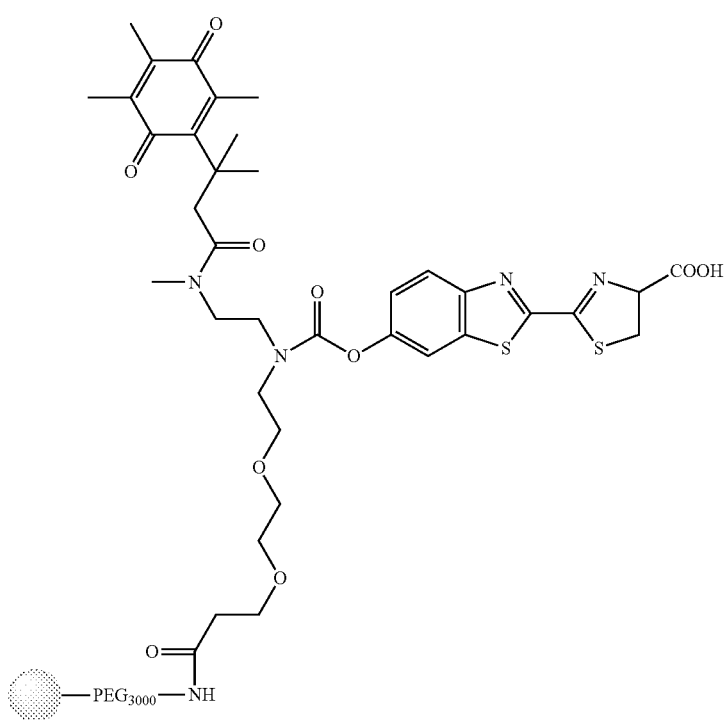
5908

-continued
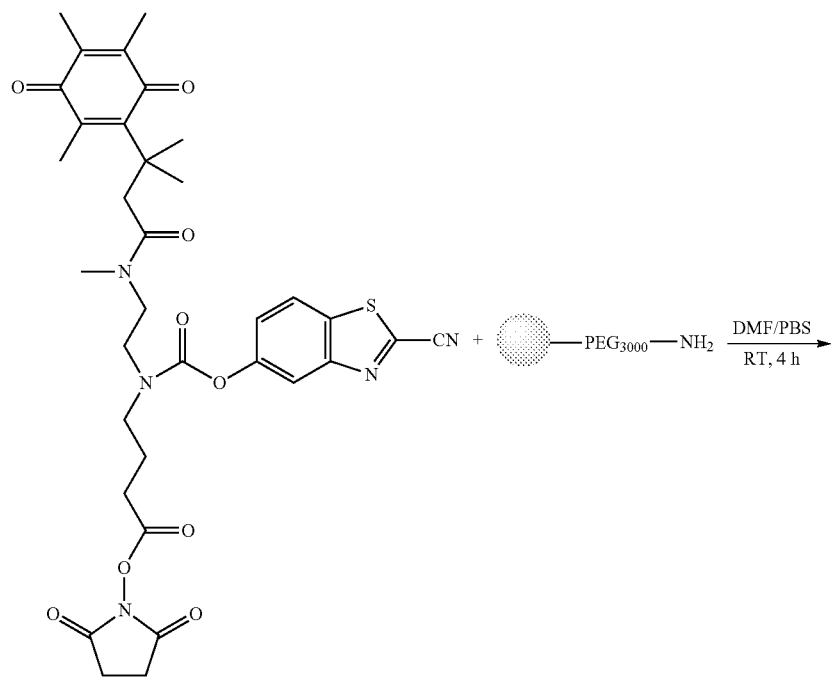
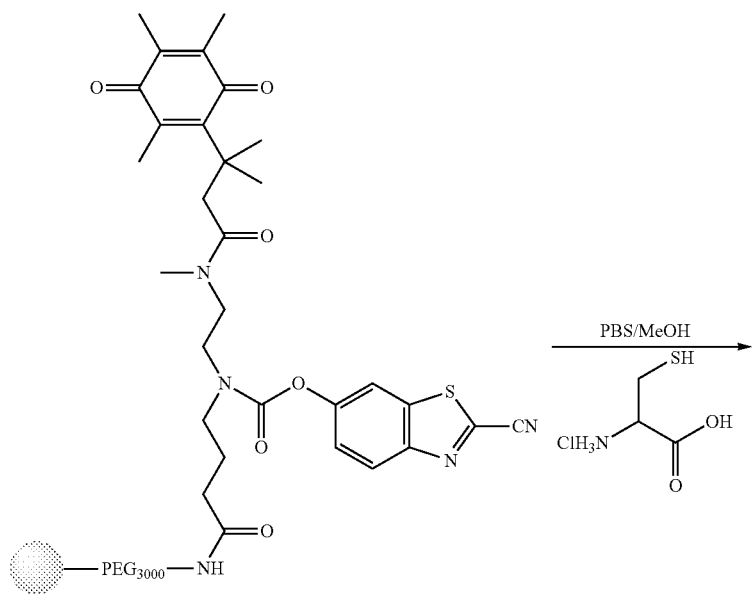
5909

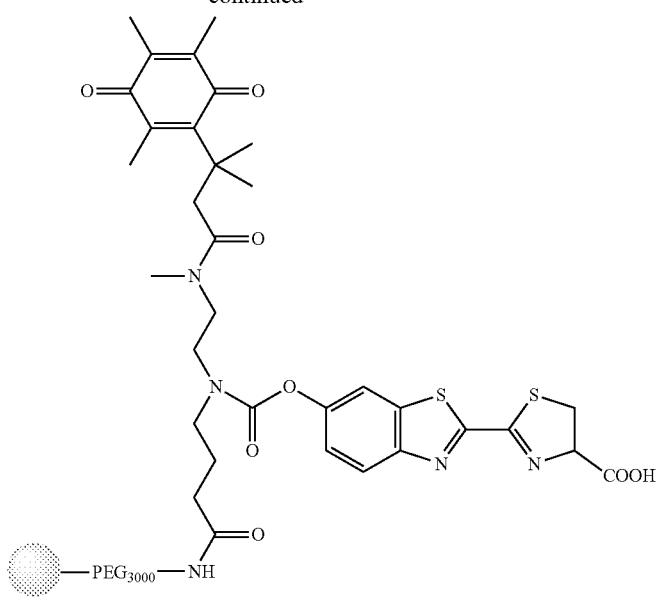
5911
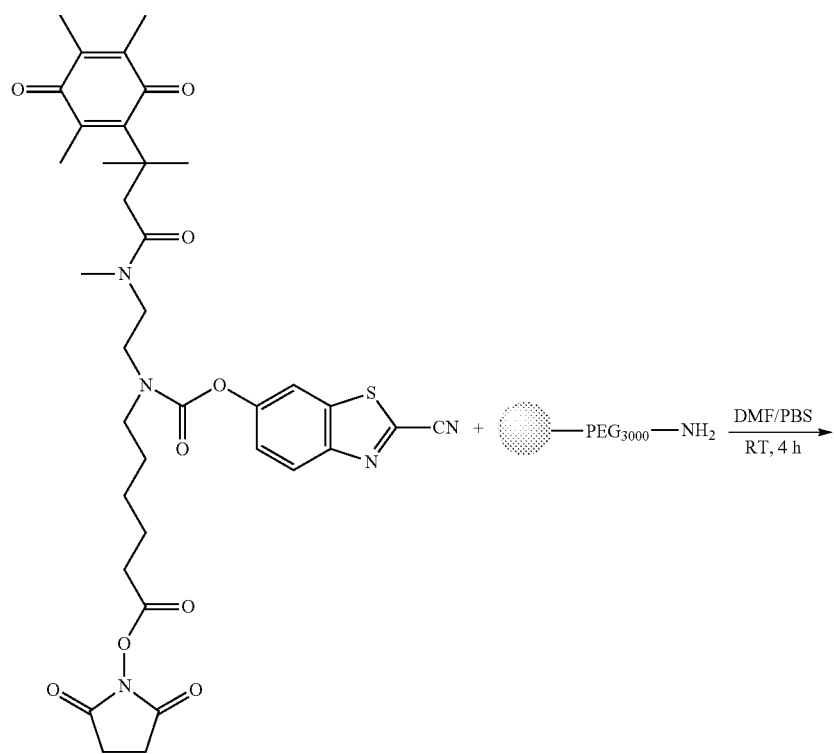

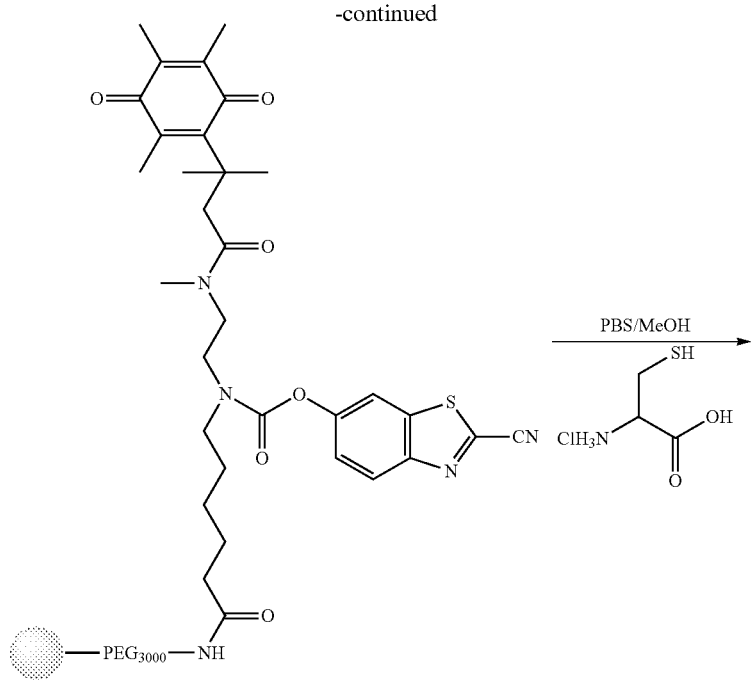

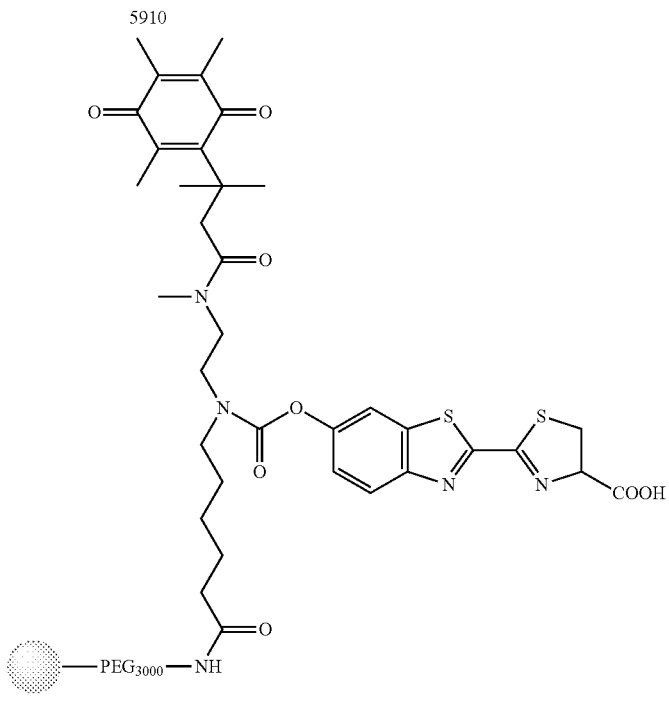

Synthesis of #5907, #5909, and #5910

1 mL of 20 nm gold nanoparticles (GNPs) (OD=50) coated with Peg3000 and functionalized with free amine groups were purchased from Cytodyagnostics Inc. 10 μL of GNP solution was added to a small eppendorf tube, and 1 mg of N-[(PEG)$_2$COOH]—N'-methyl-N'-[3-methyl-3-(2,4,5-trimethyl-3,6-dioxocyclohexa-1,4-dien-1-yl)butanoic amido]-ethylenediamine-2-cyanobenzothiazole-6-carbamate NHS ester dissolved in 10 μL DMF was added. 500 μL of PBS buffer and 500 μL of DMF was added, then sonicated briefly and placed on shaker at room temperature for 4 hours. After the reaction, 1 mL PBST (0.05% Tween80 in PBS buffer) was added and centrifuged at 14,000 rpm for 30 min. The supernatant was removed, and 350 μL methanol added. The pellet was resuspended and then spun down again. The methanol wash was repeated twice, and the pellet washed similarly with DMF three times.

Synthesis of #5908, #5911, and #5912

1 mg of d-cysteine was dissolved in 350 μL PBS buffer and added to eppendorf tube containing modified GNPs

167 from #5907, #5909, or #5910, respectively. 350 μL methanol was added, and then the solution placed on shaker at room temperature for 3 hours. After the reaction, the contents were centrifuged at 14,000 rpm for 30 min, and then most of the supernatant removed. The pellet was washed three times with a 1:1 mixture of water and methanol, and then three times with DMF.

Example 13

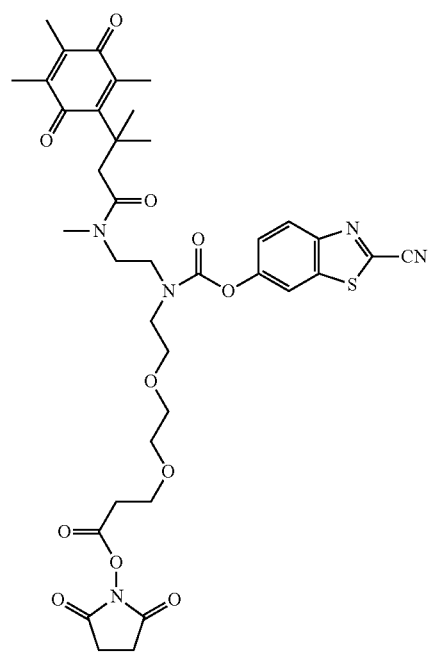

168

-continued

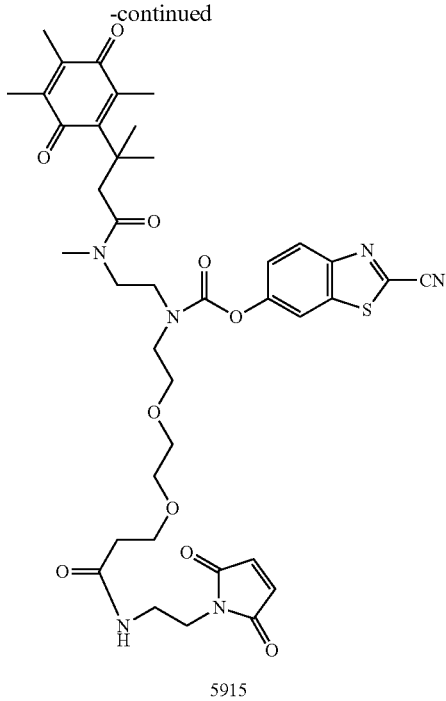

5915

Synthesis of #5915

Approximately 100 mg (392 μmol, 2 equiv.) of maleimide TFA salt was added to a vial together with 2 mL DMF and 150 mg (196 μmol, 1 equiv.) of the respective NHS ester dissolved in 1 mL DMF. 70 μL DIPEA (392 mol, 2 equiv.) was added and then stirred at room temperature for over an hour. The reaction mixture was dried down, and then purified by flash column chromatography using a gradient of methylene chloride/methanol. MS-ESI (m/e): 791.9 [M+H].

Compounds #5916, #5917, and #5918 were synthesized in a similar manner using the corresponding NHS esters.

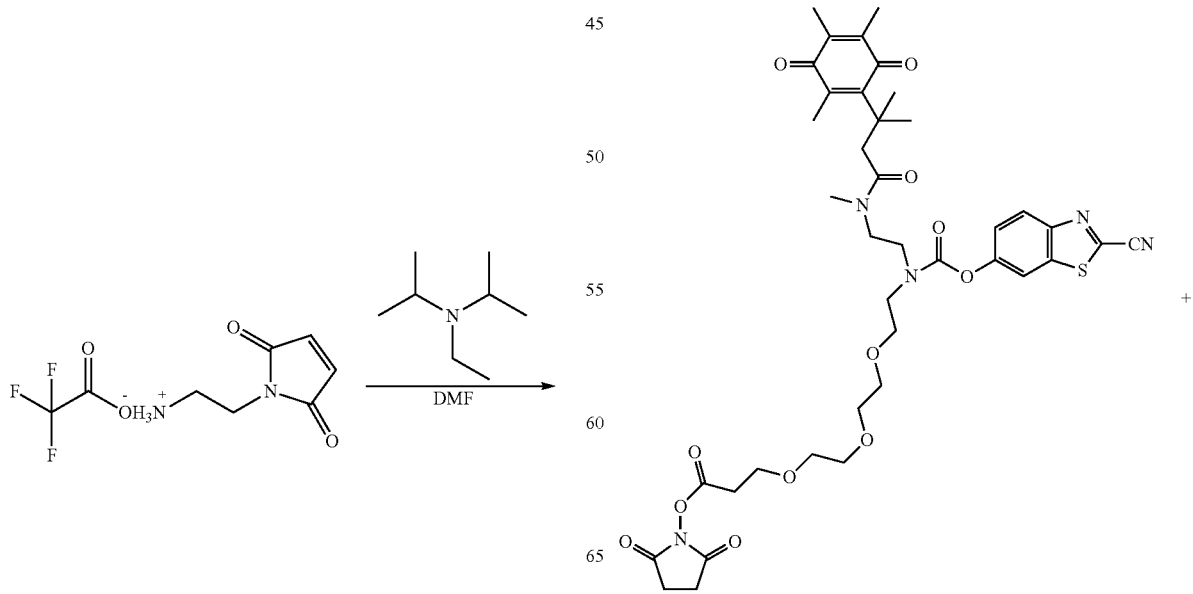

169
-continued
170
-continued
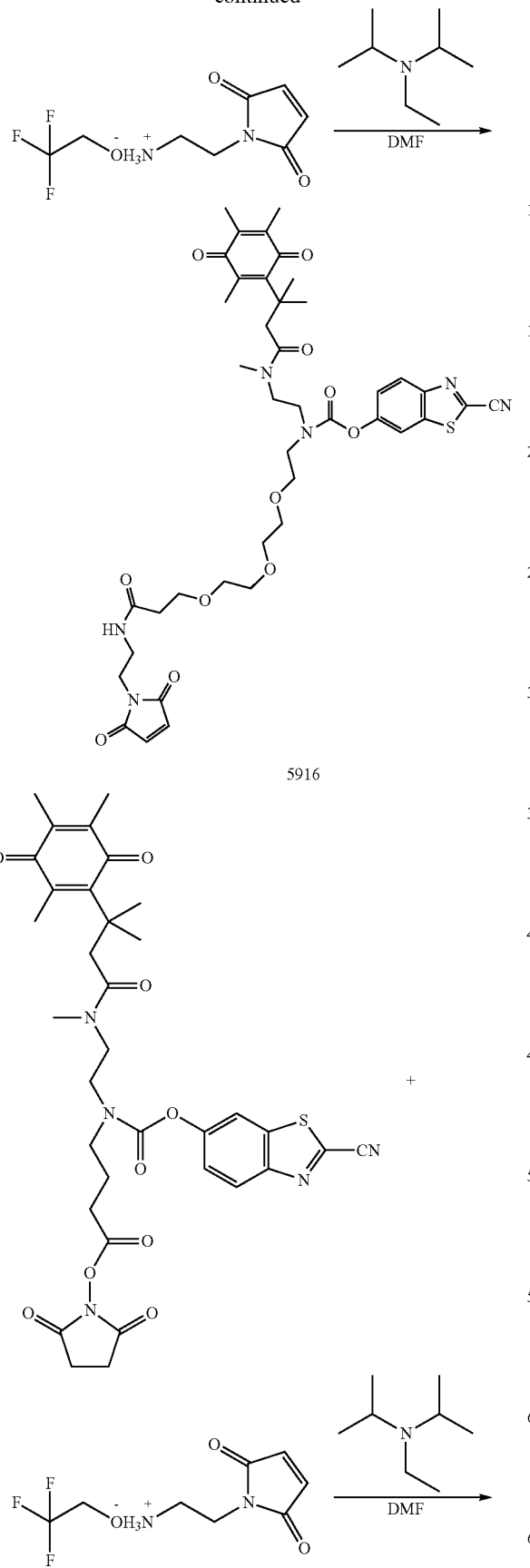
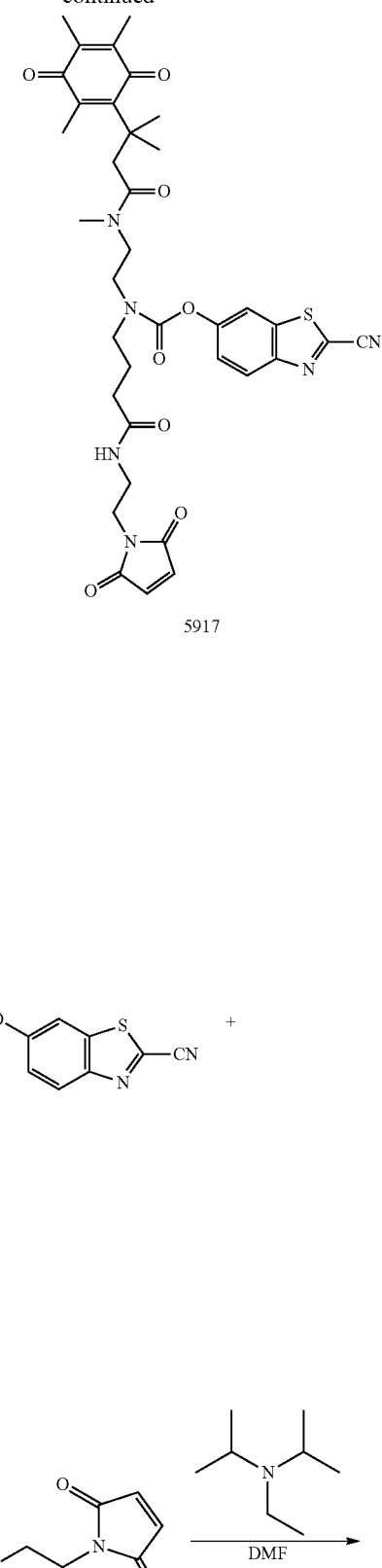

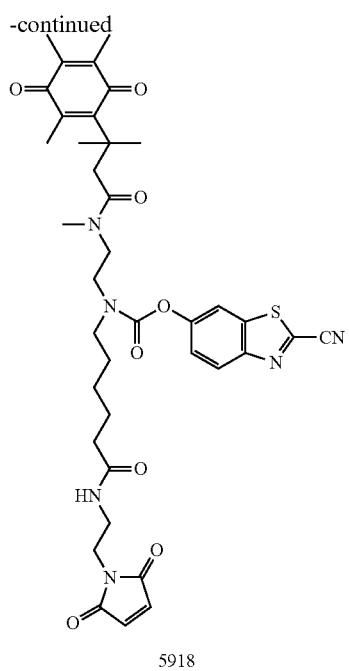

5918

Example 14

Figure 15:
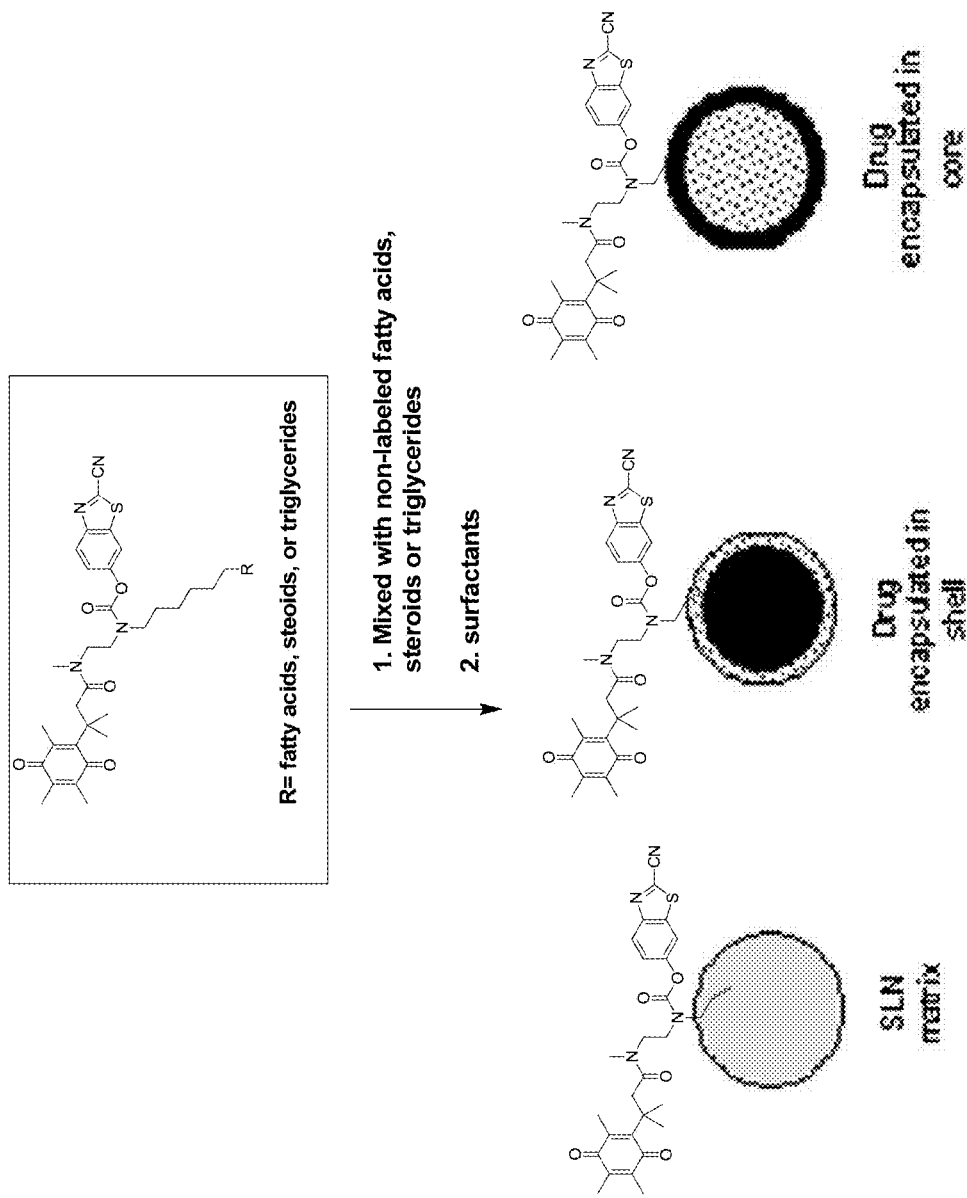
FIG. 15 shows examples of labeled solid-liquid nanoparticles (SLNs).

SLNs may be attached to the quinone probe through the scheme shown in FIG. 15.

Example 15

Antibody Labeling

To demonstrate labeling of an antibody with the compounds of the present invention, the monoclonal antibody, Herceptin, was labeled with PBI-5508 (Example 4). Lyophilized Herceptin was dissolved in 0.1 M Sodium Bicarbonate, pH 8.6 at 10 mg/ml, and then diluted to 1 mg/ml in 100 μl of the same buffer. A 50 mM stock of the pro-luciferin, PBI-5508, was prepared in 100% DMSO. For labeling of the antibody, 3.3 μl of PBI-5508 (3.3 nmol) was added to 100 μl of diluted Herceptin (0.66 nmol) for 5-fold molar excess of PBI-5508. The sample was then covered in foil and incubated for 60 min at room temperature on a tube rotator. To remove free PBI-5508, 100 μl of the labeling reaction was placed onto an equilibrated G-25 Sequencing MicroSpin Column (Amersham, 200 μl resin) and eluted by spinning for 30 sec at 3000 rpm. The labeled Herceptin was contained in the flow-through. Labeling efficiency was determined by spectrophotometry by taking the absorbance of the Herceptin-PBI-5508 molecule at 280 nm and 320 nm. The degree of labeling was 2.3 PBI-5508 molecules per one Herceptin antibody molecule.

Example 16

In a white, 384-well, low volume assay plate, in triplicate, 5 μl of Herceptin:PBI-5508 (Example 15) was plated at varying concentrations, or 5 μl of 0.1 M sodium bicarbonate pH 8.6 buffer was plated as a control. 5 μl of a solution containing Luciferin Detection Reagent (Promega, V859/865), reductase (Promega, NAD(P)H-Glo kit at the recommended concentration), 50 μM NADH and 10 mM D-cysteine was added to the assay wells. The reaction was incubated at room temperature for 45 min, and luminescence (relative light unit, RLU) was measured on a Tecan M1000Pro.

The results in Table 3 show that the Herceptin:PBI-5508 molecule is a substrate for diaphorase.

TABLE 3

|  | Avg RLU | SD |
| --- | --- | --- |
| Herceptin: 5508, 1x | 15513 | 166 |
| Herceptin: 5508, 0.5x | 6526 | 570 |
| Buffer Control | 11 | 5 |

Example 17

In a 384-well assay plate, SKBR3 cells were plated at 10,000 cells/well in 20 μl McCoy media. Other wells received media only as a control. Media and cells were incubated at 37° C./5% $CO_2$ for 2 hours. Herceptin:PBI-5508 was added to a final concentration of 15 ng/μl plus or minus 500 mM sucrose (final concentration) in 20 μl final volume. The reaction was incubated at 37° C./5% $CO_2$ for 6 hours. Then, 40 μl of Luciferin Detection Reagent (Promega, V865/859) plus 10 mM D-cysteine was added to all wells. The reaction was incubated at room temperature for 20 min, and luminescence (RLU) was measured on a Tecan M1000Pro.

The results in Table 4 show that Herceptin:PBI-5508 was reduced in cells after internalization. Sucrose was used to increase the release of molecules from the endosome.

TABLE 4

| Cells | Herceptin: 5508 | Sucrose | Avg RLU at 6 h |
| --- | --- | --- | --- |
| Y | Y | N | 58 |
| Y | Y | Y | 143 |
| N | Y | N | 88 |
| N | Y | Y | 8 |

Example 18

Experiments were conducted during development of embodiments of the present disclosure to demonstrate an uptake transporter assay using a variety of compounds described herein.

Stock solutions of each compound were prepared as 10 mM in methanol. Corning TransportoCells OATP1B1*1a, OATP1B3, and Control Cells were used as cell model for cell-based uptake transporter assay. Cells were cultured according to manufacturer's recommendations. Briefly, cells were thawed from liquid nitrogen storage and cultured in Dulbecco's Modified Eagle's medium supplemented with fetal bovine serum (FBS), MEM non-essential amino acid, and sodium butyrate. Cells were then plated in Corning 96-well, poly-D-Lysine white/clear plate at 100,000 cells/well in 100 μl medium and incubated for 24 hours at 37° C. with 5% $CO_2$.

The uptake transporter assay was carried out by adding 100 μl of Hank's balanced salt solution containing 10 μM of one of the compounds to all the cells and incubated at 37° C. for 30 minutes. For cells treated with PBI-5651, PBI-5657, PBI-5658, PBI-5665, PBI-5666, PBI-5824, PBI-5825, and PBI-5826, an equal volume of Luciferin Detection Reagent (Promega) was added. For cells treated with PBI- 5648, PBI-5682, PBI-5683, and PBI-5684, an equal volume of Luciferin Detection Reagent containing D-cysteine (Promega) was added. After a 20 minute incubation at room temperature (20°-25° C.), luminescence was detected on a GloMax® luminometer.

FIGS. 1-12 demonstrates increased luminescence (RLU) over TransportoCells Control Cells and no-cell control from TransportoCells OATP1B1*1a and OATP1B3 using the compounds of the present invention.

Example 19

Experiments were conducted during development of embodiments of the present invention to demonstrate an uptake transporter assay using different concentrations of PBI-5651.

PBI-5651 stock solution was prepared as 10 mM in methanol. Corning TransportoCells OATP1B1*1a, OATP1B3, and Control Cells were used as cell model for cell-based uptake transporter assay. Cells were cultured according to manufacturer's recommendations. Briefly, cells were thawed from liquid nitrogen storage and cultured in Dulbecco's Modified Eagle's medium supplemented with fetal bovine serum (FBS), MEM non-essential amino acid, and sodium butyrate. Cells were then plated in Corning 96-well, poly-D-Lysine white/clear plate at 100,000 cells/well in 100 μl medium and incubated for 24 hours at 37° C. with 5% $CO_2$.

The uptake transporter assay was carried out by adding 100 μl of Hank's balanced salt solution containing various concentrations (See FIG. 13) of PBI-5651 to all the cells and incubated at 37° C. for 30 minutes. An equal volume of Luciferin Detection Reagent (Promega) was added to the cells. After a 20 minute incubation at room temperature (20°-25° C.), luminescence was detected on a GloMax® luminometer.

Figure 13:
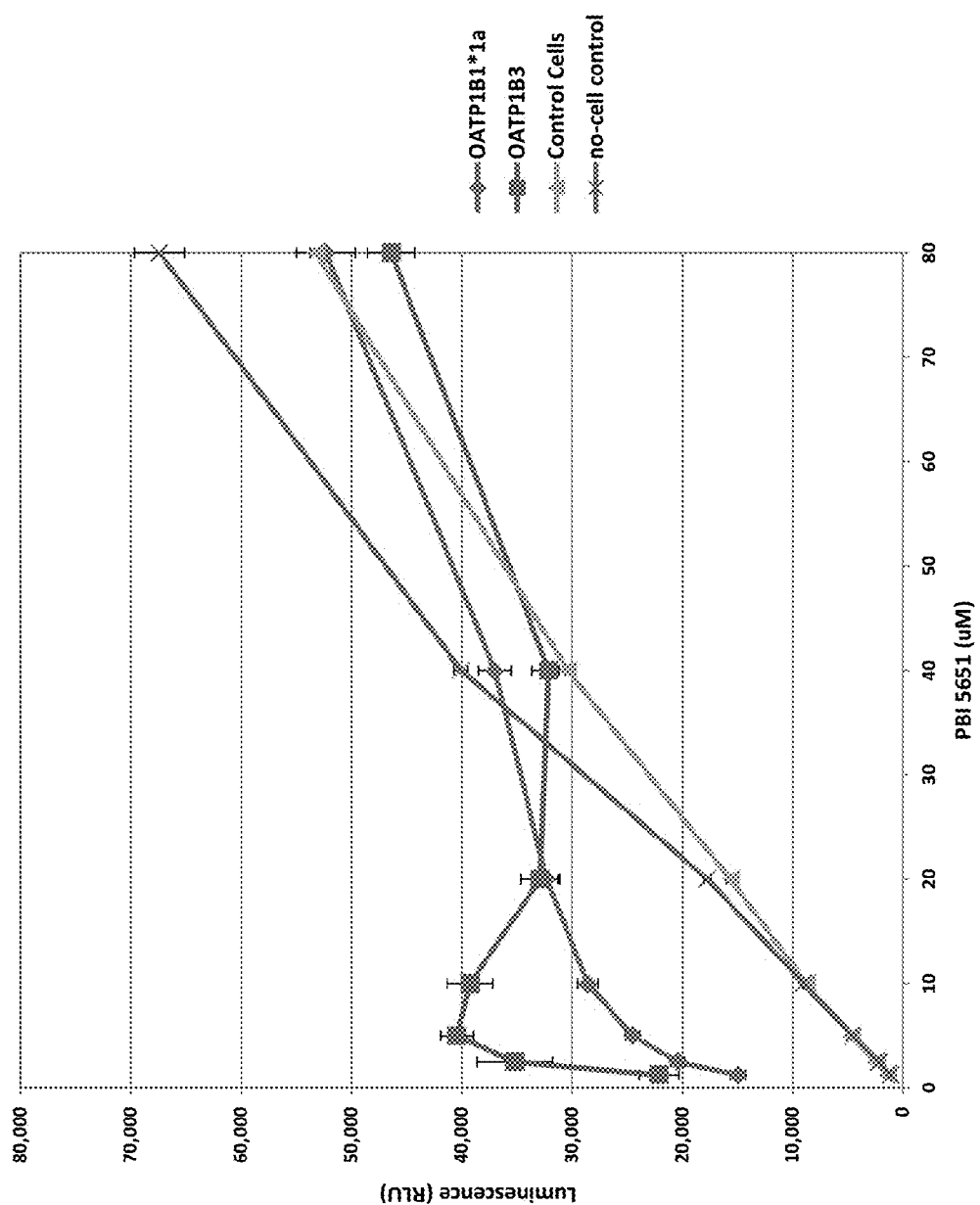
FIG. 13 shows the transporter assay with various amounts of PBI-5651.

FIG. 13 demonstrates dynamic response of luminescence (RLU) from TransportoCells OATP1B1*1a and OATP1B3.

Any ranges given either in absolute terms or in approximate terms are intended to encompass both, and any definitions used herein are intended to be clarifying and not limiting. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges (including all fractional and whole values) subsumed therein.

Furthermore, the invention encompasses any and all possible combinations of some or all of the various embodiments described herein. Any and all patents, patent applications, scientific papers, and other references cited in this application, as well as any references cited therein, are hereby incorporated by reference in their entirety.

For reasons of completeness, various aspects of the present disclosure are set out in the following numbered clauses:

Clause 1. A compound of formula (I), or a salt thereof,

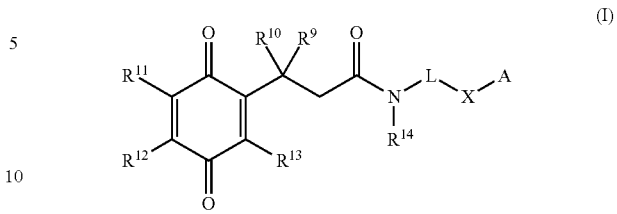

wherein
A is a reporter moiety;
$R^{14}$ is H, alkyl, hydroxyalkyl, alkoxy, carboxyalkyl, or amidoalkyl;
$R^9$ and $R^{10}$ are independently selected from alkyl;
$R^{11}$, $R^{12}$ and $R^{13}$ are independently selected from H, alkyl, alkoxy, bromo, chloro or amino, or $R^{11}$ and $R^{12}$ can form a fused phenyl ring;
X is O;
L is $-(CH_2)_mC(R^{17})_2(CH_2)_n-Y-C(O)-$;
$R^{17}$ is independently H, alkyl or both $R^{17}$ together can form an alkyl ring having from 3-7 carbons;
m is an integer from 0-2;
n is an integer from 0-2;
Y is O or $NR^{15}$;
$R^{15}$ is H, alkyl, hydroxyalkyl, azidoalkyl, cyanoalkyl, haloalkyl, alkenyl, alkynyl, -alkyl-$N(R^{23})C(O)R^{24}$, -alkyl-$SO_3R^{25}$, -alkyl-$SO_2N(R^{26})(R^{27})$, -alkyl-$COR^{28}$, -alkyl-$CO_2R^{29}$, -alkyl-$OC(O)R^{29}$, -alkyl-$OC(O)N(R^{30})(R^{31})$, -alkyl-$CON(R^{30})(R^{31})$, or polyalkoxyalkyl, wherein the polyalkoxyalkyl is unsubstituted or substituted with one or more suitable substituents; and $R^{23}$, $R^{24}$, $R^{25}$, $R^{26}$, $R^{27}$, $R^{28}$, $R^{29}$, $R^{30}$, and $R^{31}$ are each independently selected from hydrogen, alkyl, aryl, heteroaryl, heterocyclyl, and cycloalkyl Clause 2. The compound of claim 1, wherein $R^{15}$ is polyalkoxyalkyl, wherein the polyalkoxyalkyl is $-(C_2-C_6\text{-alkoxy})_x\text{-alkyl}$, $-(C_2-C_6\text{-alkoxy})_x\text{-haloalkyl}$, $-(C_2-C_6\text{-alkoxy})_x\text{-hydroxyalkyl}$, $-(C_2-C_6\text{-alkoxy})_x\text{-aminoalkyl}$, $-(C_2-C_6\text{-alkoxy})_x\text{-alkylaminoalkyl}$, $-(C_2-C_6\text{-alkoxy})_x\text{di(alkyl)aminoalkyl}$, $-(C_2-C_6\text{-alkoxy})_x\text{-azidoalkyl}$, $-(C_2-C_6\text{-alkoxy})_x\text{-cyanoalkyl}$, $-(C_2-C_6\text{-alkoxy})_x\text{-alkenyl}$, $-(C_2-C_6\text{-alkoxy})_x\text{-alkynyl}$, $-(C_2-C_6\text{-alkoxy})_x\text{-}N(R^{23})C(O)R^{24}$, $-(C_2-C_6\text{-alkoxy})_x\text{-}SO_3R^{25}$, $-(C_2-C_6\text{-alkoxy})_x\text{-alkyl-}SO_2N(R^{26})(R^{27})$, $-(C_2-C_6\text{-alkoxy})_x\text{-alkyl-}COR^{28}$, $-(C_2-C_6\text{-alkoxy})_x\text{-alkyl-}OC(O)R^{29}$, $-(C_2-C_6\text{-alkoxy})_x\text{-alkyl-}OC(O)N(R^{30})(R^{31})$, $-(C_2-C_6\text{-alkoxy})_x\text{-alkyl-}CO_2R^{29}$, and $-(C_2-C_6\text{-alkoxy})_x\text{-alkyl-}CON(R^{30})(R^31)$, wherein $R^{23}$, $R^{24}$, $R^{25}$, $R^{26}$, $R^{27}$, $R^{28}$, $R^{29}$, $R^{30}$, and $R^{31}$ are each independently selected from hydrogen, alkyl, aryl, heteroaryl, heterocyclyl, and cycloalkyl; and x is an integer selected from 1 to 20.

Clause 3. The compound of clause 1, wherein $R^{15}$ is polyalkoxyalkyl, wherein the polyalkoxyalkyl is unsubstituted or substituted with 1 to 3 substituents independently selected from the group consisting of alkyl, alkoxyalkyl, haloalkyl, haloalkoxyalkyl, hydroxyalkyl, aminoalkyl, alkylaminoalkyl, di(alkyl)aminoalkyl, azidoalkyl, cyanoalkyl, alkoxy, haloalkoxy, alkoxyalkoxy, alkenyl, alkynyl, $-N(R^{23})C(O)R^{24}$, $-SO_3R^{25}$, $-SO_2N(R^{26})(R^{27})$, $-COR^{28}$, $-CO_2R^{29}$, and $-CON(R^{30})(R^{31})$, wherein $R^{23}$, $R^{24}$, $R^{25}$, $R^{26}$, $R^{27}$, $R^{28}$, $R^{29}$, $R^{30}$, and $R^{31}$ are each independently selected from hydrogen, alkyl, aryl, heteroaryl, heterocyclyl, and cycloalkyl.

Clause 4. The compound of clause 1, wherein $R^{15}$ is

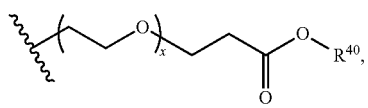

wherein $R^{40}$ is selected from the group consisting of hydrogen, alkyl, alkenyl, alkynyl, aryl, heteroaryl, heterocyclyl, and cycloalkyl, wherein said aryl, heteroaryl, heterocyclyl, and cycloalkyl are unsubstituted or substituted with one or more suitable substituents; and x is an integer selected from 1 to 20.

Clause 5. The compound of clause 4, wherein $R^{40}$ is hydrogen.

Clause 6. The compound of clause 4, wherein $R^{40}$ is a 5- or 6-membered heterocyclyl, having 1, 2, or 3 heteroatoms independently selected from the group consisting of N, O, and S.

Clause 7. The compound of clause 4, wherein $R^{40}$ is

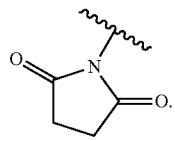

Clause 8. The compound of clause 4, wherein x is 2, 3, or 4.

Clause 9. The compound of clause 4, having formula (I-vi), or a salt thereof,

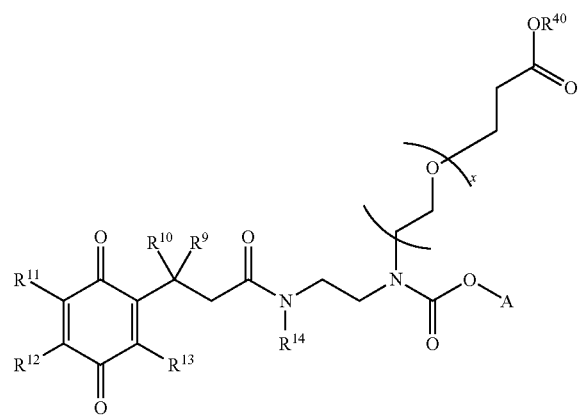

(I-vi)

wherein $R^9$, $R^{10}$, $R^{11}$, $R^{12}$, $R^{13}$, $R^{14}$, $R^{40}$, x, and A are as defined above.

Clause 10. The compound of clause 1, selected from the group consisting of:

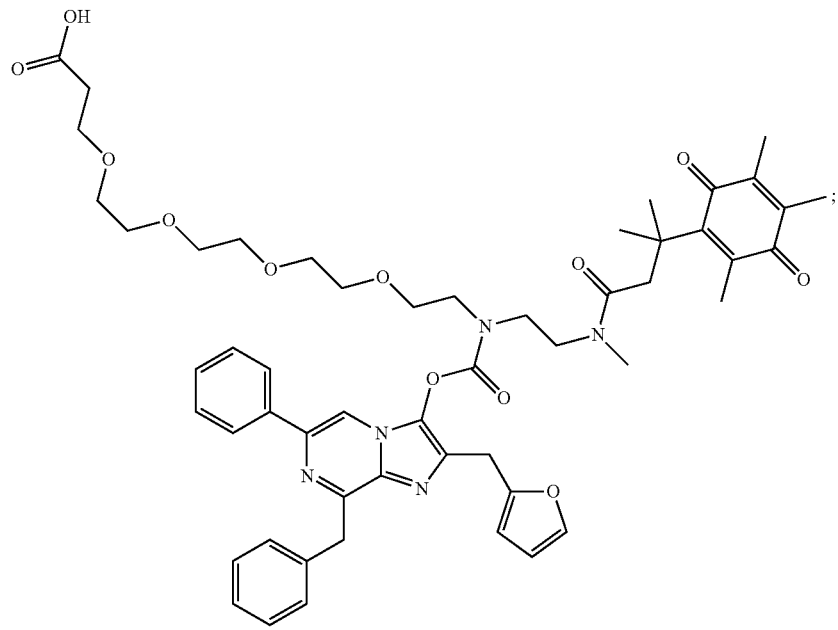

PBI 5463

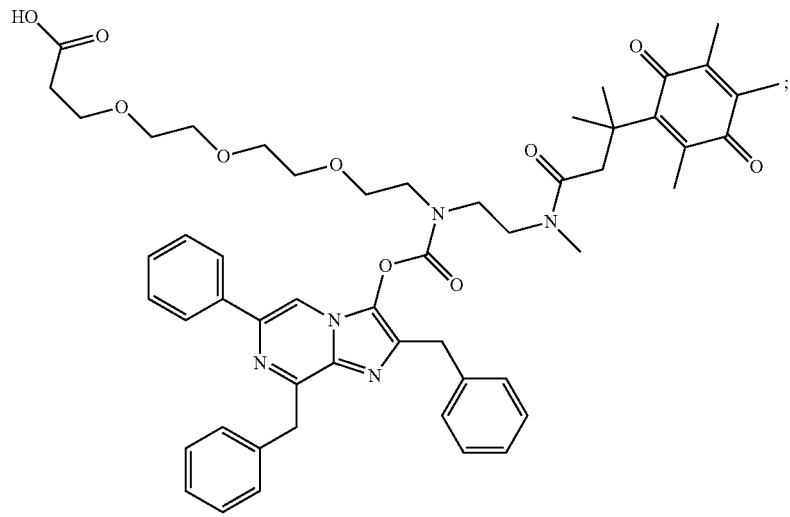
PBI 5470
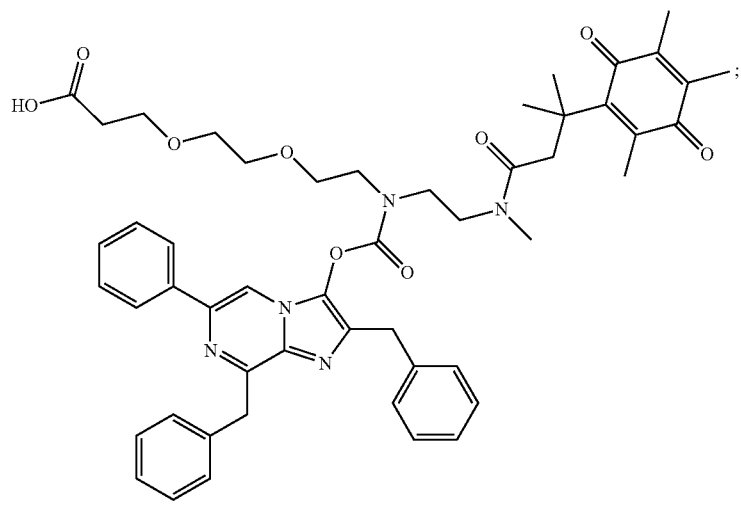
PB 5471
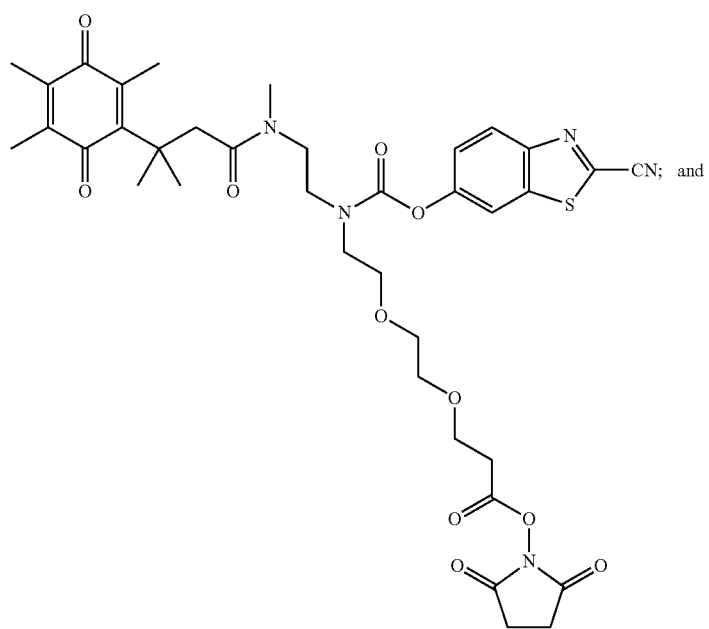
PBI 5508 and

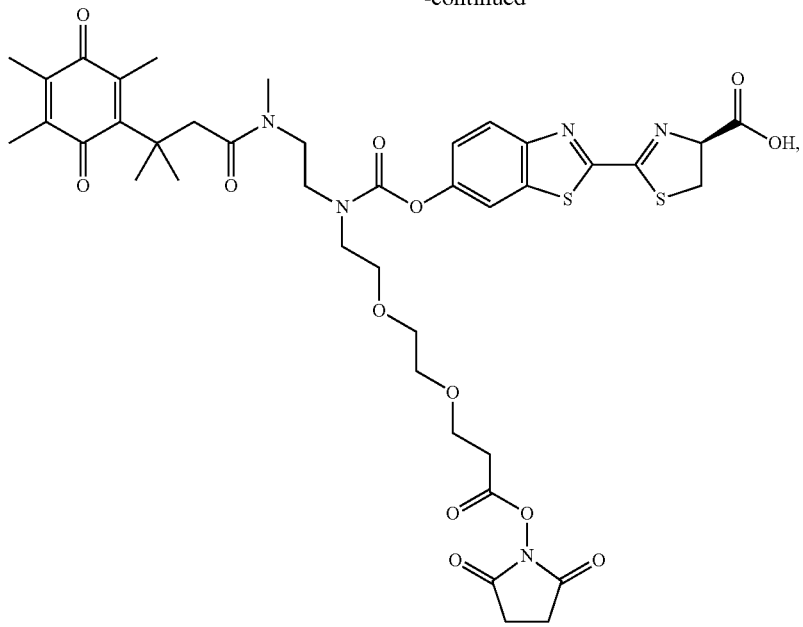

or a salt thereof.

Clause 11. The compound of clause 1, wherein the reporter moiety comprises a bioluminescent reporter moiety or fluorescent reporter moiety.

Clause 12. The compound of clause 11, wherein the bioluminescent reporter moiety comprises a substrate for a luciferase.

Clause 13. The compound of clause 12, wherein the substrate comprises luciferin, a luciferin derivative or analog, a preluciferin or a preluciferin analog, a coelenterazine or a coelenterazine derivative or analog.

Clause 14. The compound of clause 12, wherein the substrate is furimazine, coelenterazine H,H, or luciferin.

Clause 15. The compound of clause 12, wherein the luciferase is a beetle luciferase, a *Renilla* luciferase, an *Oplophorus* luciferase or a variant thereof.

Clause 16. The compound of clause 11, wherein the reporter moiety comprises a fluorescent reporter moiety.

Clause 17. The compound of clause 16, wherein the fluorescent reporter moiety comprises a fluorophore.

Clause 18. The compound of clause 17, wherein the fluorophore is coumarin, R110, fluoroscein, DDAO, resorufin, cresyl violet, silyl xanthene or carbopyronine.

Clause 19. A method for evaluating cellular uptake of an agent, the method comprising:
a) contacting a sample with a labeled agent, wherein the labeled agent comprises an agent and a compound of any one of clauses 1 to 18, wherein the sample comprises a cell; and
b) detecting light emission,
whereby the detection of light emission indicates cellular uptake of the agent.

Clause 20. The method of clause 19, wherein the cellular uptake of the agent results in the reduction of the compound and the release of the reporter moiety, thereby generating a released reporter moiety.

Clause 21. The method of clause 20, wherein the reporter moiety comprises a fluorescent reporter moiety.

Clause 22. The method of clause 21, wherein detecting light emission comprises exposing the sample to a wavelength of light to generate fluorescence and detecting light emission comprises detecting the fluorescence level of the sample, wherein an increase in fluorescence level or a change in fluorescence wavelength as compared to the fluorescence level of a control sample indicates cellular uptake of the agent.

Clause 23. The method of clause 22, wherein the control sample is a sample that is not contacted with a labeled agent.

Clause 24. The method of clause 22, wherein the fluorescence level is detected inside the cell.

Clause 25. The method of clause 22, wherein the fluorescence level is detected outside the cell.

Clause 26. The method of clause 20, wherein the reporter moiety comprises a bioluminescent reporter moiety.

Clause 27. The method of clause 26, wherein the bioluminescent reporter moiety comprises a substrate for a luciferase.

Clause 28. The method of clause 27, wherein the cell comprises a luciferase.

Clause 29. The method of clause 28, wherein the cell expresses the luciferase.

Clause 30. The method of clause 28, wherein detecting light emission comprises detecting the luminescence level produced by the luciferase and the released reporter moiety.

Clause 31. The method of clause 27, further comprising contacting the sample with a luciferase and wherein detecting light emission comprises detecting luminescence level produced by the luciferase and the released reporter moiety.

Clause 32. The method of clause 30 or 31, wherein the light emission is detected inside the cell or detected outside the cell.

Clause 33. A method for evaluating cellular uptake of an agent, the method comprising:
(a) contacting a sample with a labeled agent, wherein the labeled agent comprises an agent and a compound of any one of clause 1 to 11, wherein the sample comprises a cell, wherein the cellular uptake of the agent results in the reduction of the compound and the release of the reporter moiety, thereby generating a released reporter moiety;

(b) exposing the sample to a wavelength of light to generate fluorescence, (c) detecting the fluorescence level of the sample, and (d) comparing the fluorescence level of the sample to a fluorescence level of a control sample, wherein an increase in fluorescence level or a change in fluorescence wavelength as compared to the fluorescence level of the control sample indicates cellular uptake of the agent.

Clause 34. The method of clause 33, wherein the reporter moiety comprises a fluorescent reporter moiety.

Clause 35. The method of clause 34, wherein the fluorescent reporter moiety comprises a fluorophore.

Clause 36. The method of clause 35, wherein the fluorophore is coumarin, R110, fluoroscein, DDAO, resorufin, cresyl violet, silyl xanthen or carbopyronine.

Clause 37. The method of clause 33, wherein the fluorescence level is detected inside the cell.

Clause 38. The method of clause 33, wherein the fluorescence level is detected in the sample.

Clause 39. The method of clause 33, wherein the control sample is sample medium with labeled agent but without cells, a sample with labeled agent and cells but without experimental treatment, or a sample not contacted with labeled agent.

Clause 40. A method for evaluating cellular uptake of an agent, the method comprising:

a) contacting a sample with a labeled agent, wherein the labeled agent comprises an agent and a compound of any one of clause 1 to 11, wherein the sample comprises a cell, wherein the cell comprises luciferase, wherein the cellular uptake of the agent results in the reduction of the compound and the release of the reporter moiety, thereby generating a released reporter moiety;

b) detecting a luminescence level of the sample; and c) comparing the luminescence level of the sample to a luminescence level of a control sample, wherein cellular uptake of the agent is indicated if the luminescence level of the sample is higher or lower than the luminescence level of the control sample.

Clause 41. The method of clause 40, wherein the luminescence level is produced by the luciferase and the released reporter moiety.

Clause 42. The method of clause 40, wherein the luminescence is detected inside the cell or detected outside in the cell medium.

Clause 43. The method of clause 40, wherein the control sample is a sample that is not contacted with a labeled agent.

Clause 44. A method for evaluating cellular uptake of an agent, the method comprising:

a) contacting a sample with a labeled agent, wherein the labeled agent comprises an agent and a compound of any one of clause 1 to 11, wherein the sample comprises a cell and a cell medium, wherein the cellular uptake of the agent results in the reduction of the compound and the release of the reporter moiety, thereby generating a released reporter moiety;

b) contacting the sample with a luciferase;

c) detecting a luminescence level of the sample; and d) comparing the luminescence level of the sample to a luminescence level of a control sample, wherein cellular uptake of the agent is indicated if the luminescence level of the sample is higher or lower than the luminescence level of the control sample.

Clause 45. The method of clause 44, wherein the luminescence level is produced by the luciferase and the release reporter moiety.

Clause 46. The method of clause 44, wherein the luminescence is detected in the cell or detected in the cell medium.

Clause 47. The method of clause 44, wherein the control sample is sample medium with labeled agent but without cells, a sample with labeled agent and cells but without experimental treatment, or a sample not contacted with labeled agent.

Clause 48. The method of any one of clauses 19-47, wherein the agent is a biological agent.

Clause 49. The method of clause 48, wherein the biological agent is selected from the group consisting of a protein, a nucleic acid, a lipid, and a sugar.

Clause 50. The method of clause 49, wherein the protein is an antibody or a lipoprotein.

Clause 51. The method of clause 50, wherein the antibody is Herceptin.

Clause 52. The method of any one of clauses 19-47, wherein the agent is a non-biological agent.

Clause 53. The method of clause 52, wherein the non-biological agent is selected from the group consisting of a therapeutic drug, a small molecule, and a nanoparticle, or any combination thereof.

Clause 54. The method of any one of clauses 19-53, wherein the cell is a eukaryotic cell or a prokaryotic cell.

Clause 55. The method of clause 54, wherein the cell is in an animal.

Clause 56. The method of clause 54, wherein the cell is growing in culture medium.

Clause 57. A labeled agent derived from an agent and a compound according to any one of clauses 1 to 10.

Clause 58. The labeled agent of clause 57, wherein the agent is a biological agent.

Clause 59. The labeled agent of clause 58, wherein the biological agent is selected from the group consisting of a protein, a nucleic acid, a lipid, and a sugar.

Clause 60. The labeled agent of clause 59, wherein the protein is an antibody or a lipoprotein.

Clause 61. The labeled agent of clause 60, wherein the antibody is Herceptin.

Clause 62. The labeled agent of clause 57, wherein the reporter moiety comprises a bioluminescent reporter moiety or fluorescent reporter moiety.

Clause 63. The labeled agent of any one of clauses 57, wherein the agent is a non-biological agent.

Clause 64. The labeled agent of clause 63, wherein the non-biological agent is selected from the group consisting of a therapeutic drug, a small molecule, and a nanoparticle, or any combination thereof.

Clause 65. The labeled agent of clause 62, wherein the bioluminescent reporter moiety comprises a substrate for a luciferase.

Clause 66. The labeled agent of clause 65, wherein the substrate comprises luciferin, a luciferin derivative, a coelenterazine or a coelenterazine derivative.

Clause 67. The labeled agent of clause 66, wherein the substrate is furimazine, coelenterazine H,H, lucifeirn, or pre-luciferin.

Clause 68. The labeled agent of clause 66, wherein the luciferase is a beetle luciferase, a *Renilla* luciferase, or an *Oplophorus* luciferase.

Clause 69. The labeled agent of clause 62, wherein the reporter moiety comprises a fluorescent reporter moiety.

Clause 70. The labeled agent of clause 69, wherein the fluorescent reporter moiety comprises a fluorophore.

Clause 71. The labeled agent of clause 70, wherein the fluorophore is coumarin, a rhodamine, R110, fluoroscein, DDAO, resorufin or cresyl violet.

Clause 72. A kit comprising a compound according to any one of clauses 1 to 18, an agent, or any combination thereof.

Clause 73. A kit comprising a labeled agent comprising an agent and a compound according to any one of clauses 1 to 18.

Clause 74. The kit of clause 72 or 73, wherein the agent is a biological agent.

Clause 75. The kit of clause 74, wherein the biological agent is selected from the group consisting of a protein, a nucleic acid, a lipid, and a sugar.

Clause 76. The kit of clause 75, wherein the protein is an antibody or a lipoprotein.

Clause 77. The kit of clause 72 or 73, wherein the agent is a non-biological agent.

Clause 78. The kit of clause 77, wherein the non-biological agent is selected from the group consisting of a therapeutic drug, a small molecule, and a nanoparticle, or any combination thereof.

Clause 79. The kit of clause 72 or 73, wherein the compound is a substrate for luciferase.

Clause 80. The kit of clause 79, further comprising a detection reagent.

Clause 81. The kit of clause 80, wherein the detection reagent comprises a luciferase enzyme.

Clause 82. A compound of formula (I), or a salt thereof,

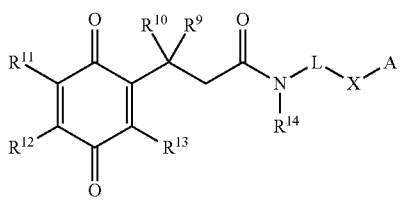

(I)

wherein
A is a reporter moiety;
$R^{14}$ is H, alkyl, hydroxyalkyl, alkoxy, carboxyalkyl, or amidoalkyl;
$R^9$ and $R^{10}$ are independently selected from alkyl;
$R^{11}$, $R^{12}$ and $R^{13}$ are independently selected from H, alkyl, alkoxy, bromo, chloro or amino, or $R^{11}$ and $R^{12}$ can form a fused phenyl ring;
X is O;
L is $-(CH_2)_m C(R^{17})_2 (CH_2)_n - Y - C(O) -$;
$R^{17}$ is independently H, alkyl or both $R^{17}$ together can form an alkyl ring having from 3-7 carbons;
m is an integer from 0-2;
n is an integer from 0-2;
Y is O or $NR^{15}$;
$R^{15}$ is H, alkyl, hydroxyalkyl, azidoalkyl, cyanoalkyl, haloalkyl, alkenyl, alkynyl, -alkyl-$N(R^{23})C(O)R^{24}$, -alkyl-$SO_3R^{25}$, -alkyl-$SO_2N(R^{26})(R^{27})$, -alkyl-$COR^{28}$, -alkyl-$CO_2R^{29}$, -alkyl-$OC(O)R^{29}$, -alkyl-$OC(O)N(R^{30})(R^{31})$, -alkyl-amide, or polyalkoxyalkyl, wherein the polyalkoxyalkyl and -alkyl-amide are unsubstituted or substituted with one or more suitable substituents; and
$R^{23}$, $R^{24}$, $R^{25}$, $R^{26}$, $R^{27}$, $R^{28}$, $R^{29}$, $R^{30}$, and $R^{31}$ are each independently selected from hydrogen, alkyl, aryl, heteroaryl, heterocyclyl, and cycloalkyl.

Clause 83. The compound of clause 82, wherein $R^{15}$ is polyalkoxyalkyl, wherein the polyalkoxyalkyl is selected from the group consisting of $-(C_2-C_6\text{-alkoxy})_x$-alkyl, $-(C_2-C_6\text{-alkoxy})_x$-haloalkyl, $-(C_2-C_6\text{-alkoxy})_x$-hydroxyalkyl, $-(C_2-C_6\text{-alkoxy})_x$-aminoalkyl, $-(C_2-C_6\text{-alkoxy})_x$-alkylaminoalkyl, $-(C_2-C_6\text{-alkoxy})_x$di(alkyl)aminoalkyl, $-(C_2-C_6\text{-alkoxy})_x$-azidoalkyl, $-(C_2-C_6\text{-alkoxy})_x$-cyanoalkyl, $-(C_2-C_6\text{-alkoxy})_x$-alkenyl, $-(C_2-C_6\text{-alkoxy})_x$-alkynyl, $-(C_2-C_6\text{-alkoxy})_x$-$N(R^{23})C(O)R^{24}$, $-(C_2-C_6\text{-alkoxy})_x$-$SO_3R^{25}$, $-(C_2-C_6\text{-alkoxy})_x$-alkyl-$SO_2N(R^{26})(R^{27})$, $-(C_2-C_6\text{-alkoxy})_x$-alkyl-$COR^{28}$, $-(C_2-C_6\text{-alkoxy})_x$-alkyl-$OC(O)R^{29}$, $-(C_2-C_6\text{-alkoxy})_x$-alkyl-$OC(O)N(R^{30})(R^{31})$, $-(C_2-C_6\text{-alkoxy})_x$-alkyl-$CO_2R^{29}$, $-(C_2-C_6\text{-alkoxy})_x$-alkyl-$CON(R^{32})(R^{33})$ and $-(C_2-C_6\text{-alkoxy})_x$-alkyl-$(CO)-NR^{34}-(CR^a R^b)_p-NR^{35}(CO)$-T, wherein
$R^{23}$, $R^{24}$, $R^{25}$, $R^{26}$, $R^{27}$, $R^{28}$, $R^{29}$, $R^{30}$, and $R^{31}$ are each independently selected from hydrogen, alkyl, aryl, heteroaryl, heterocyclyl, and cycloalkyl;
x is an integer selected from 1 to 20;
$R^{32}$ and $R^{33}$ are each independently selected from hydrogen, alkyl, carboxy, a peptide, a drug, a biologically active moiety, and a dye;
$R^{34}$ and $R^{35}$ are each independently selected from hydrogen, and alkyl;
$R^a$ and $R^b$ are each independently selected from hydrogen, alkyl, and carboxy;
p is 0 to 6; and
T is selected from aryl, arylalkyl, cycloalkylalkyl, heteroaryl, heteroarylalkyl, heterocycle, hydroxyalkyl, protein, polypeptide, polypeptide-based toxin, amino acid, nucleotide, polynucleotide, lipid, sugar, carbohydrate, enzyme substrate, drug, derivative of a drug, polymer-linked nanoparticle, antibody, detergent, and a dye, or a combination thereof.

Clause 84. The compound of clause 82, wherein $R^5$ is polyalkoxyalkyl, wherein the polyalkoxyalkyl is $-(C_2-C_6\text{-alkoxy})_x$-alkyl-$CON(R^{32})(R^{33})$ or $-(C_2-C_6\text{-alkoxy})_x$-alkyl-$(CO)-NR^{34}-(CR^a R^b)_p-NR^{35}(CO)$-T;
x is an integer selected from 1 to 20;
$R^{32}$ and $R^{33}$ are each independently selected from hydrogen, alkyl, carboxy, aryl, arylalkyl, cycloalkylalkyl, heteroaryl, heteroarylalkyl, heterocycle, hydroxyalkyl, protein, polypeptide, polypeptide-based toxin, amino acid, nucleotide, polynucleotide, lipid, sugar, carbohydrate, enzyme substrate, drug, derivative of a drug, polymer-linked nanoparticle, antibody, detergent, and a dye, or a combination thereof;
$R^{34}$ and $R^{35}$ are each independently selected from hydrogen, and alkyl;
$R^a$ and $R^b$ are each independently selected from hydrogen, alkyl, and carboxy;
p is 0 to 6; and
T is selected from aryl, arylalkyl, cycloalkylalkyl, heteroaryl, heteroarylalkyl, heterocycle, hydroxyalkyl, protein, polypeptide, polypeptide-based toxin, amino acid, nucleotide, polynucleotide, lipid, sugar, carbohydrate, enzyme substrate, drug, derivative of a drug, polymer-linked nanoparticle, antibody, detergent, and a dye, or a combination thereof.

Clause 85. The compound of clause 82, wherein $R^{15}$ is

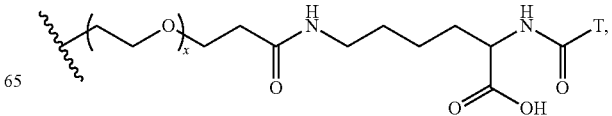

-continued

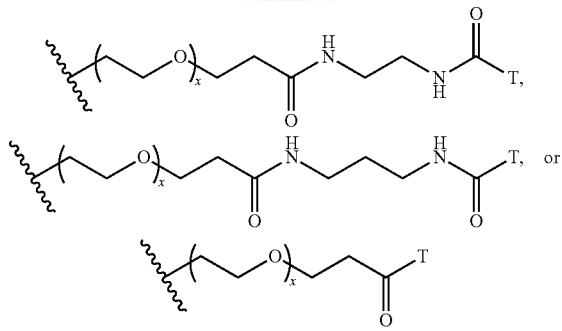

wherein

T is selected from aryl, arylalkyl, cycloalkylalkyl, heteroaryl, heteroarylalkyl, heterocycle, hydroxyalkyl, protein, polypeptide, polypeptide-based toxin, amino acid, nucleotide, polynucleotide, lipid, sugar, carbohydrate, enzyme substrate, drug, derivative of a drug, polymer-linked nanoparticle, antibody, detergent, and a dye, or a combination thereof; and x is an integer selected from 1 to 20.

Clause 86. The compound of clause 82, wherein $R^{15}$ is -alkyl-amide, wherein the -alkyl-amide is -alkyl-CON($R^{32}$)($R^{33}$) or -alkyl-(CO)—$NR^{34}$—$(CR^aR^b)_p$—$NR^{35}$(CO)-T, wherein $R^{32}$ and $R^{33}$ are each independently selected from hydrogen, alkyl, carboxy, aryl, arylalkyl, cycloalkylalkyl, heteroaryl, heterocycle, alkene, polyol, alkenylpolylol, a peptide, a drug, a derivative of a drug, a biologically active moiety, and a dye;

$R^{34}$ and $R^{35}$ are each independently selected from hydrogen, and alkyl;

$R^a$ and $R^b$ are each independently selected from hydrogen, alkyl, and carboxy;

p is 0 to 6; and

T is selected from aryl, arylalkyl, cycloalkylalkyl, heteroaryl, heteroarylalkyl, heterocycle, hydroxyalkyl, protein, polypeptide, polypeptide-based toxin, amino acid, nucleotide, polynucleotide, lipid, sugar, carbohydrate, enzyme substrate, drug, derivative of a drug, polymer-linked nanoparticle, antibody, detergent, and a dye, or a combination thereof.

Clause 87. The compound of clause 82, wherein $R^{15}$ is

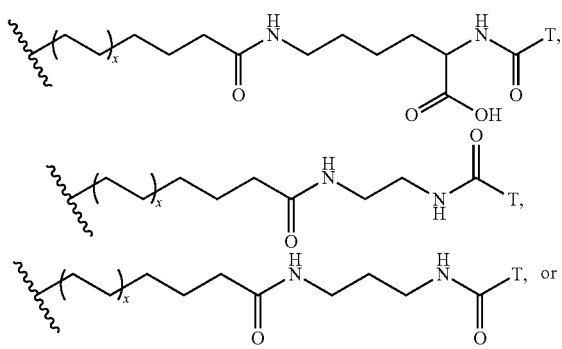

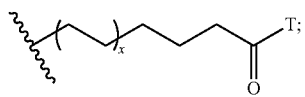

wherein

T is selected from aryl, arylalkyl, cycloalkylalkyl, heteroaryl, heterocycle, hydroxyalkyl, protein, polypeptide, polypeptide-based toxin, amino acid, nucleotide, polynucleotide, lipid, sugar, carbohydrate, enzyme substrate, drug, derivative of a drug, polymer-linked nanoparticle, antibody, detergent, and a dye, or a combination thereof; and x is 0 to 20.

Clause 88. The compound of clause 82, wherein $R^{15}$ is polyalkoxyalkyl, wherein the polyalkoxyalkyl is unsubstituted or substituted with 1 to 3 substituents independently selected from the group consisting of alkyl, alkoxyalkyl, haloalkyl, haloalkoxyalkyl, hydroxyalkyl, aminoalkyl, alkylaminoalkyl, di(alkyl)aminoalkyl, azidoalkyl, cyanoalkyl, alkoxy, haloalkoxy, alkoxyalkoxy, alkenyl, alkynyl, —N($R^{23}$)C(O)$R^{24}$, —SO$_3R^{25}$, —SO$_2$N($R^{26}$)($R^{27}$), —COR$^{28}$, —CO$_2R^{29}$ and —CON($R^{30}$)($R^{31}$), wherein $R^{23}$, $R^{24}$, $R^{25}$, $R^{26}$, $R^{27}$, $R^{28}$, $R^{29}$, $R^{30}$, and $R^{31}$ are each independently selected from hydrogen, alkyl, aryl, heteroaryl, heterocyclyl, and cycloalkyl.

Clause 89. The compound of clause 82, wherein $R^{15}$ is

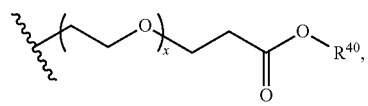

wherein $R^{40}$ is selected from the group consisting of hydrogen, alkyl, alkenyl, alkynyl, aryl, heteroaryl, heterocyclyl, and cycloalkyl, wherein said aryl, heteroaryl, heterocyclyl, and cycloalkyl are unsubstituted or substituted with one or more suitable substituents; and x is an integer selected from 1 to 20.

Clause 90. The compound of clause 89, wherein $R^{40}$ is hydrogen.

Clause 91. The compound of clause 89, wherein $R^{40}$ is a 5- or 6-membered heterocyclyl, having 1, 2, or 3 heteroatoms independently selected from the group consisting of N, O, and S.

Clause 92. The compound of clause 89, wherein $R^{40}$ is

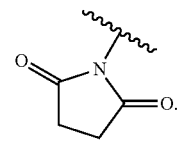 [SMILES: *N1C(=O)CCC1=O]

Clause 93. The compound of clause 89, wherein x is 2, 3, or 4.

Clause 94. The compound of clause 89, having formula (I-vi), or a salt thereof, (I-vi)
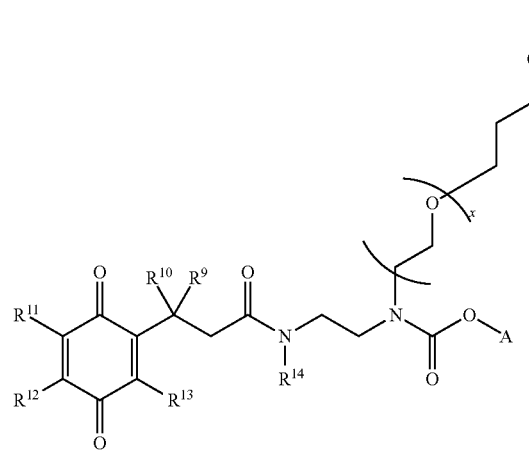
Clause 95. The compound of clause 82, wherein $R^{15}$ is
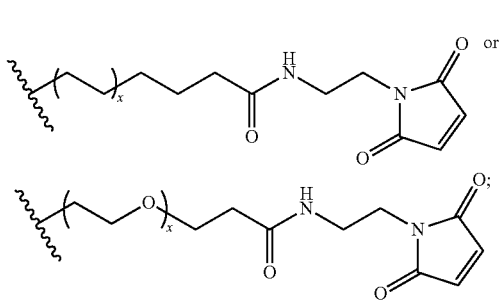
and
each x is independently 0 to 20.
Clause 96. The compound of clause 82, selected from the group consisting of:
PBI 5463
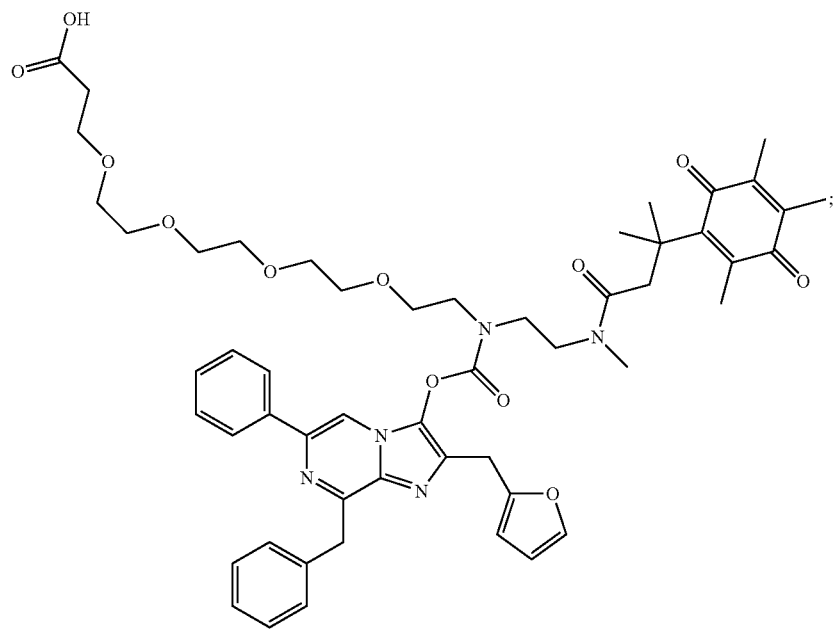
PBI 5470
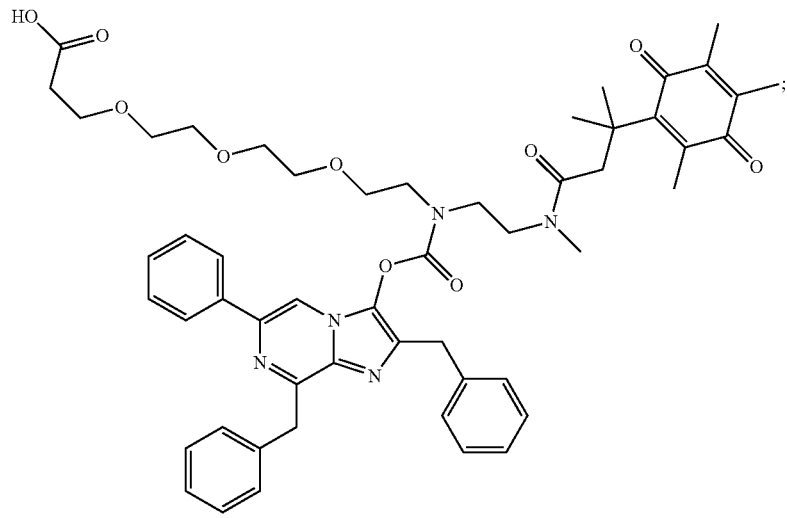

-continued
PBI 5471
PBI 5508
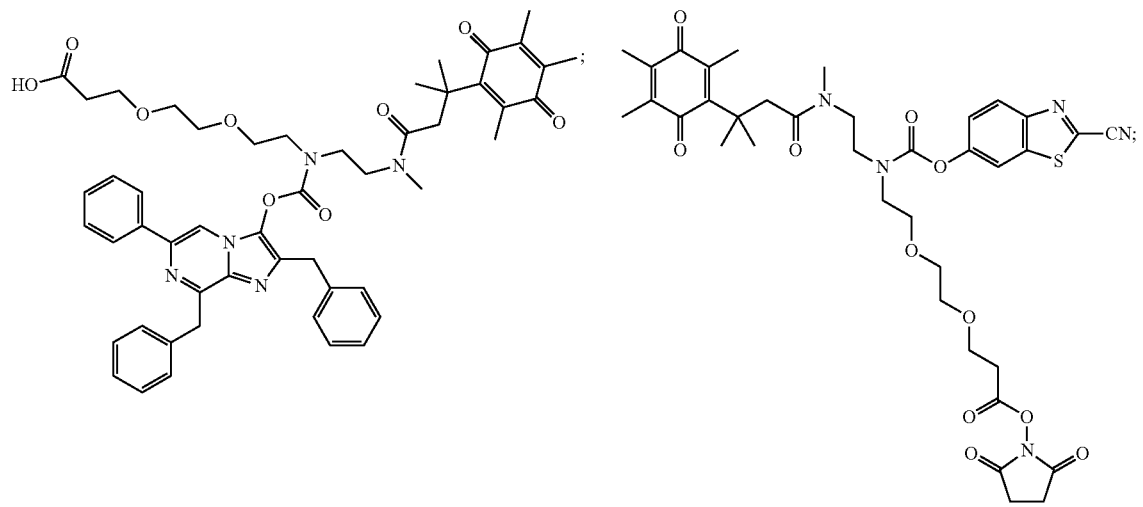
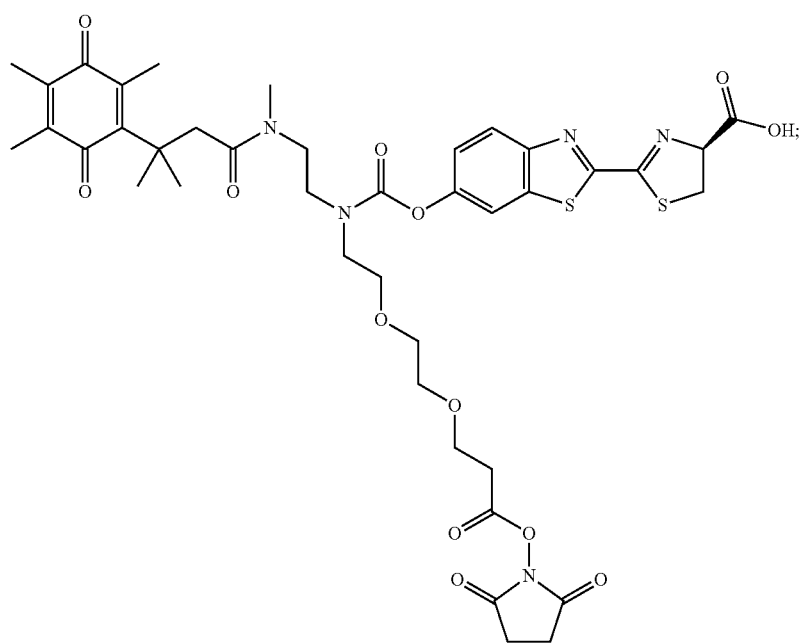

191 192
-continued
PBI 5915
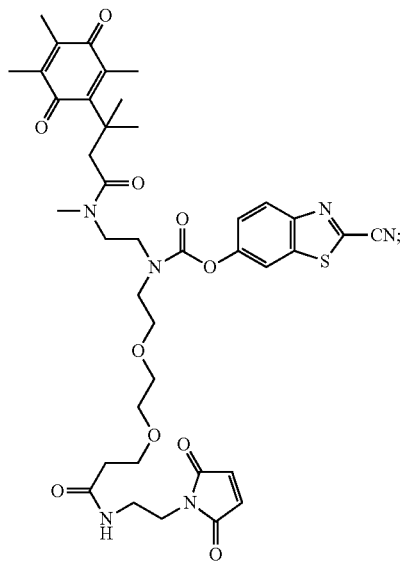
PBI 5916
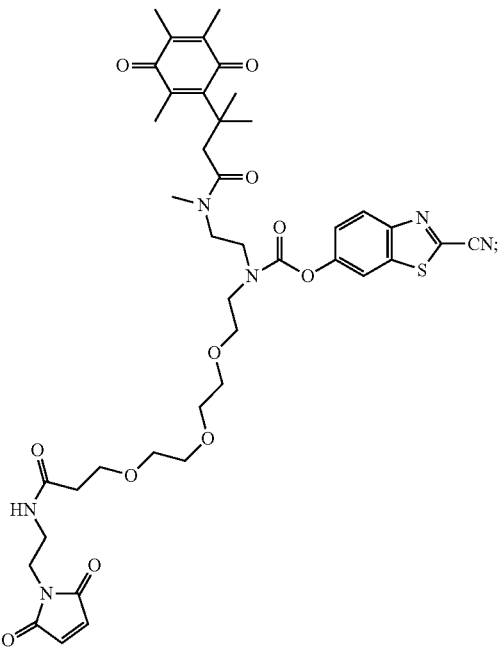
PBI 5917
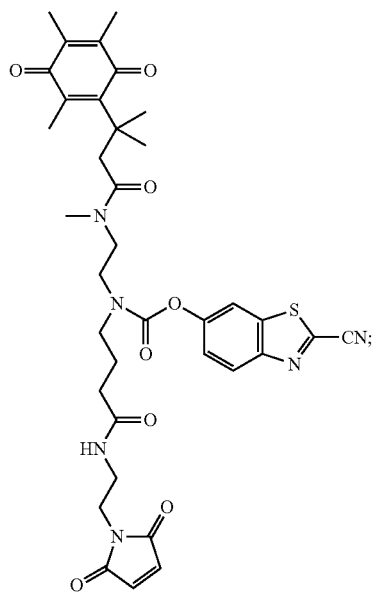
PBI 5918
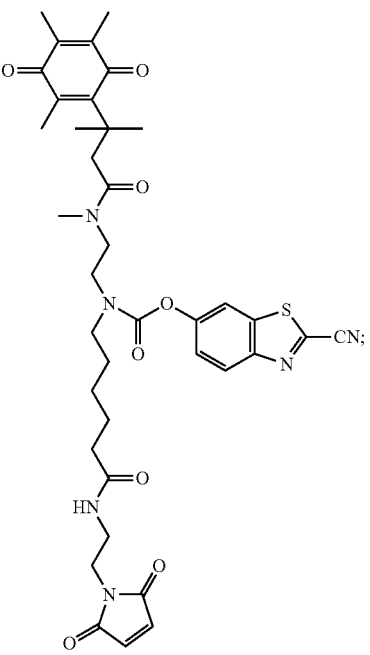

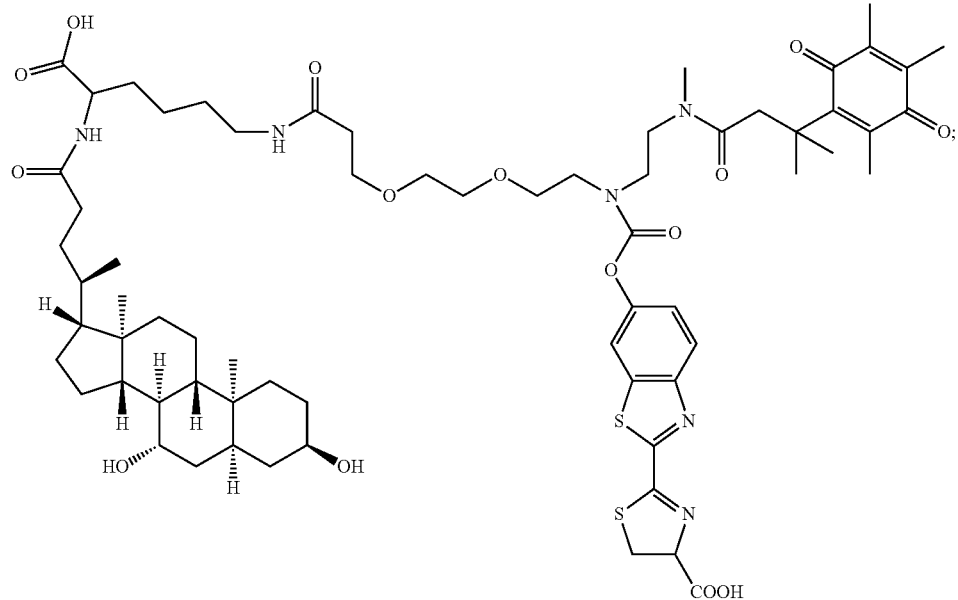
PBI 5651
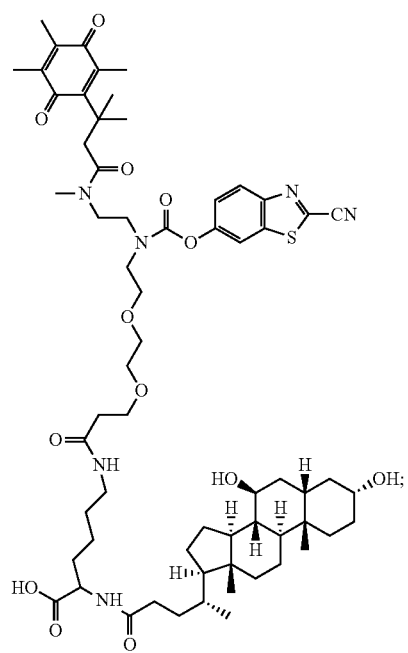
PBI 5648

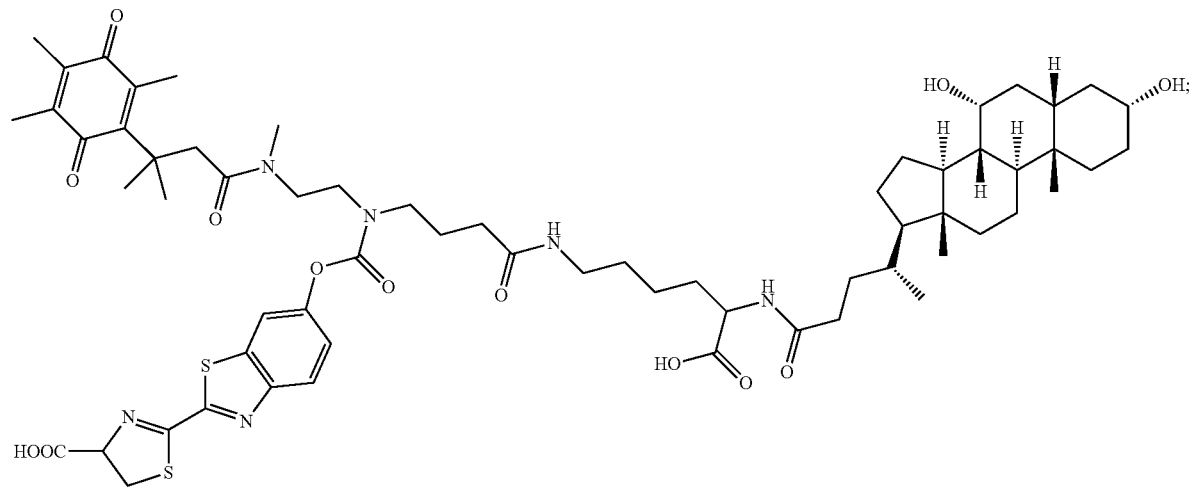
PBI 5657
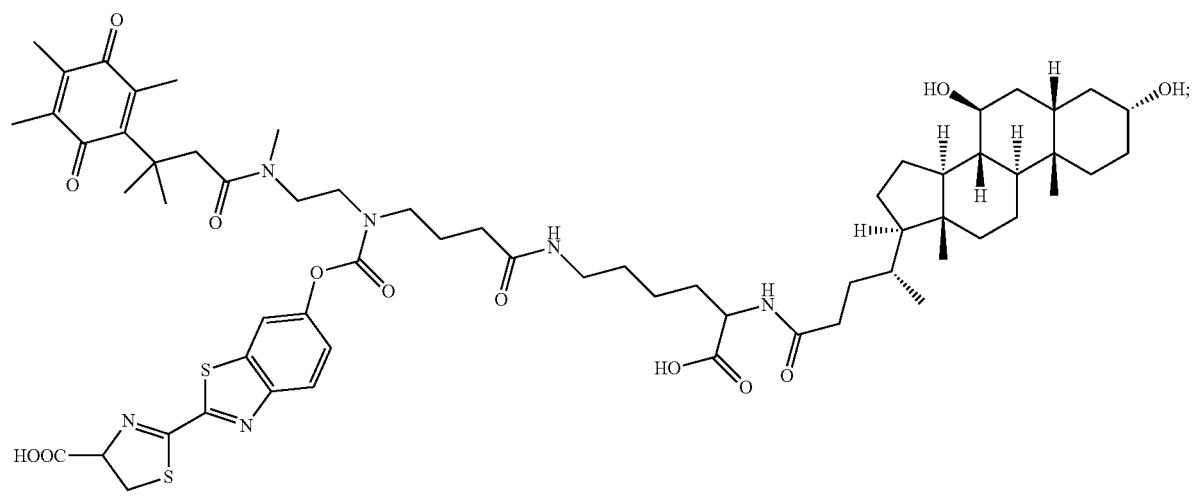
PBI 5658
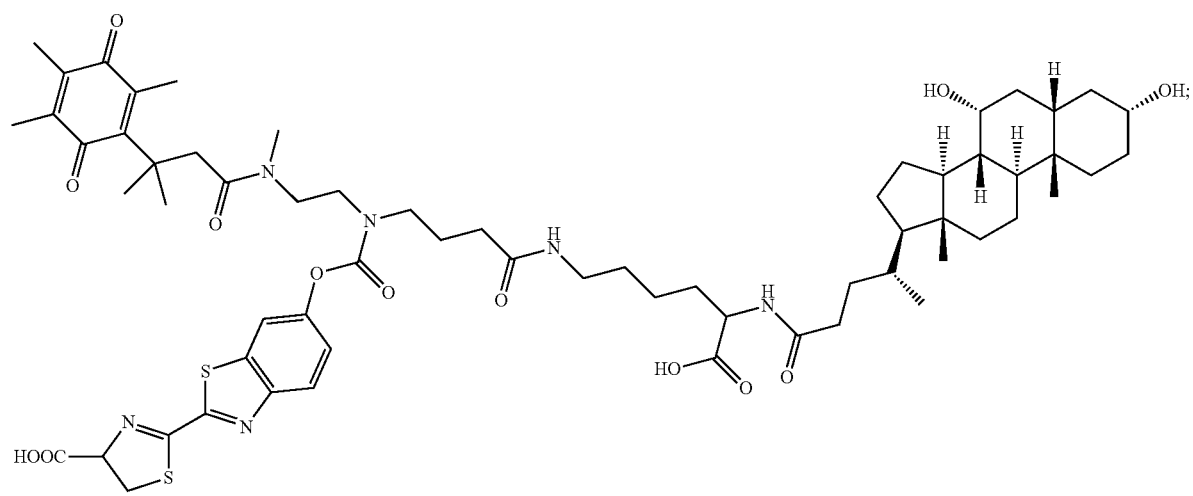
PBI 5665

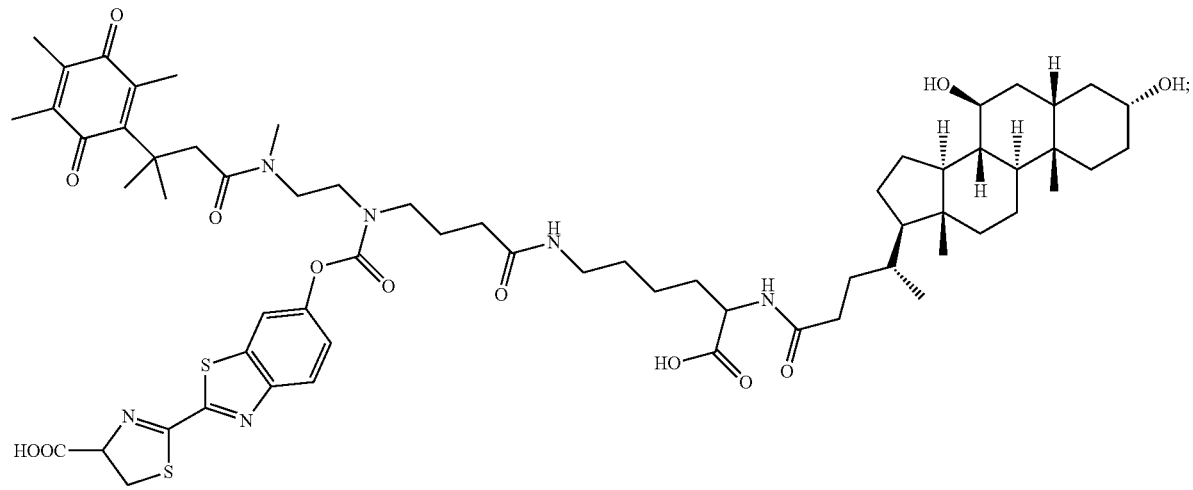
PBI 5666
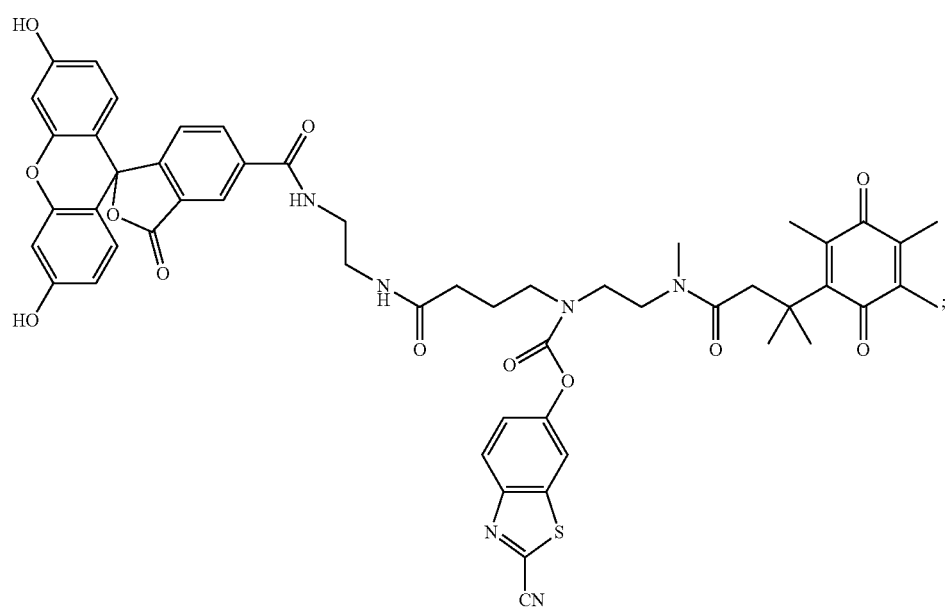
PBI 5684

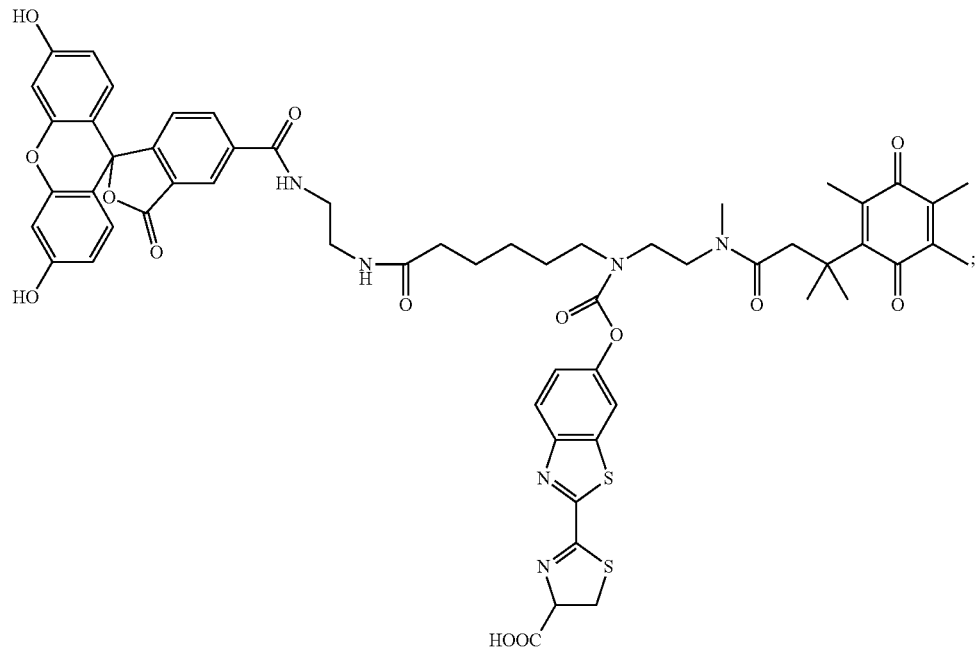
PBI 5825
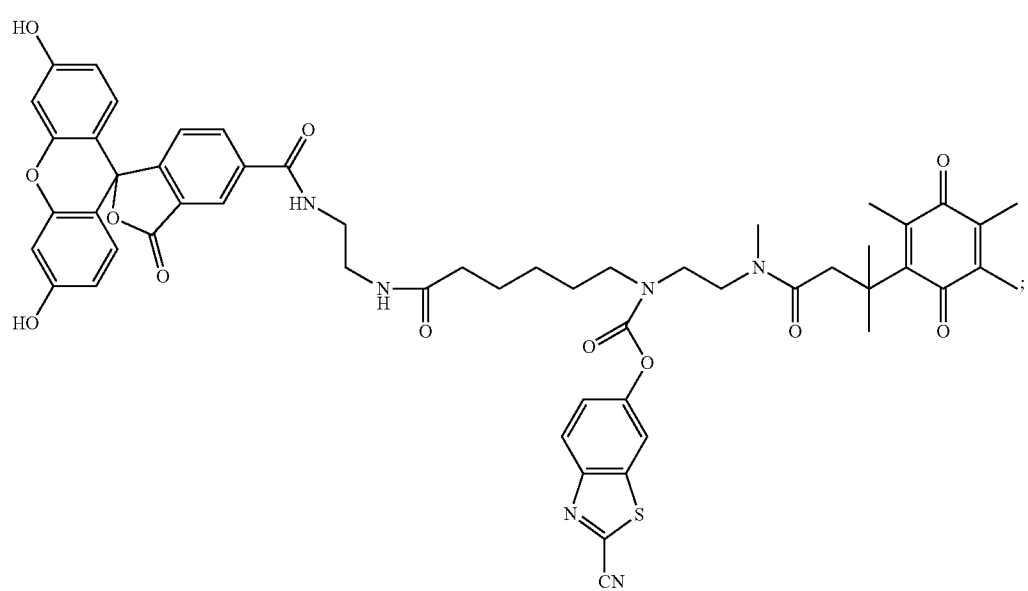
PBI 5683

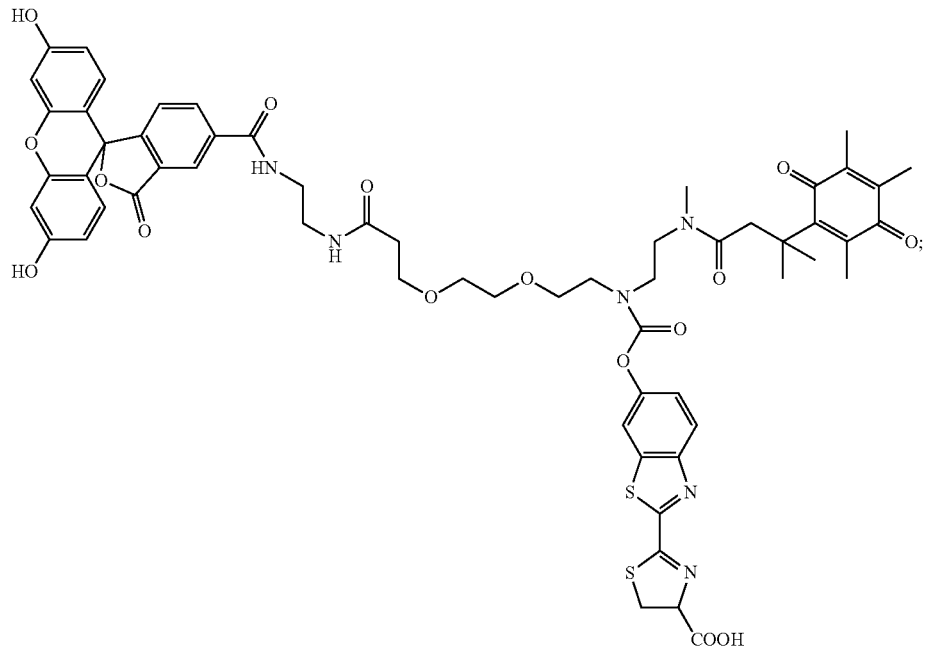
PBI 5826
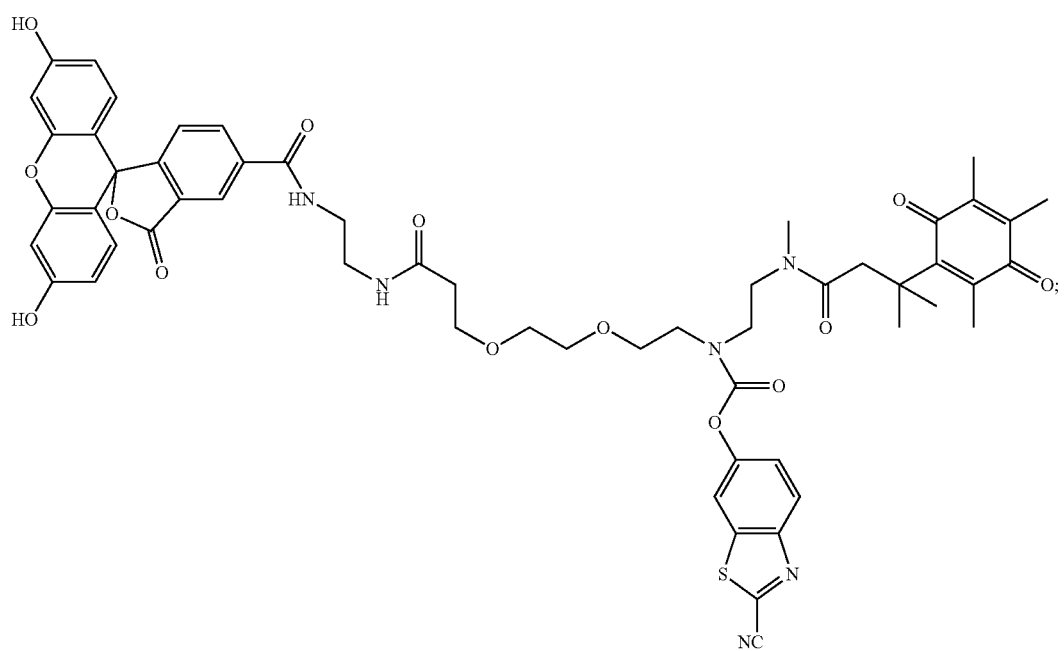
PBI 5682

-continued
PBI 5647
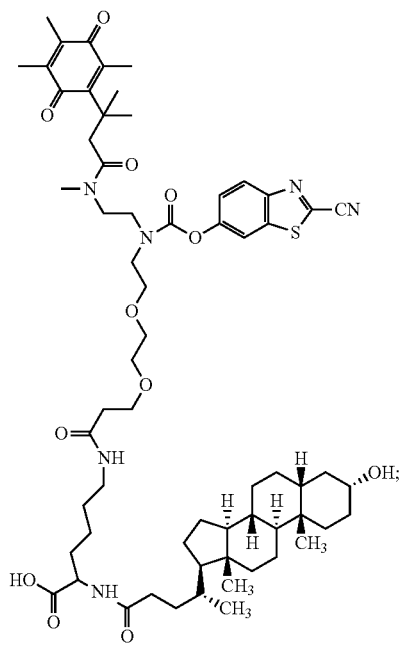
PBI 5668
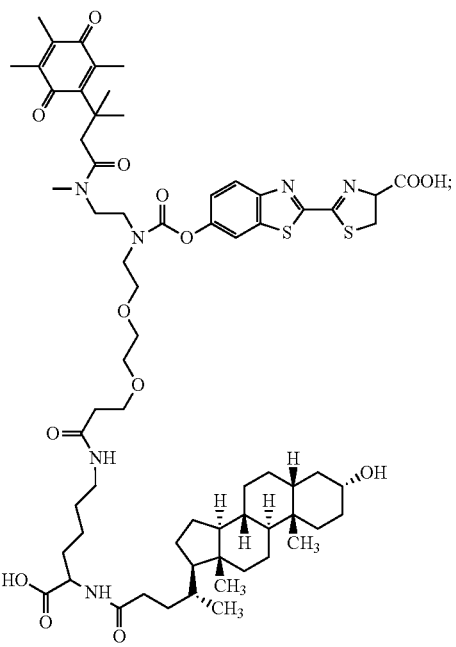
PBI 5625
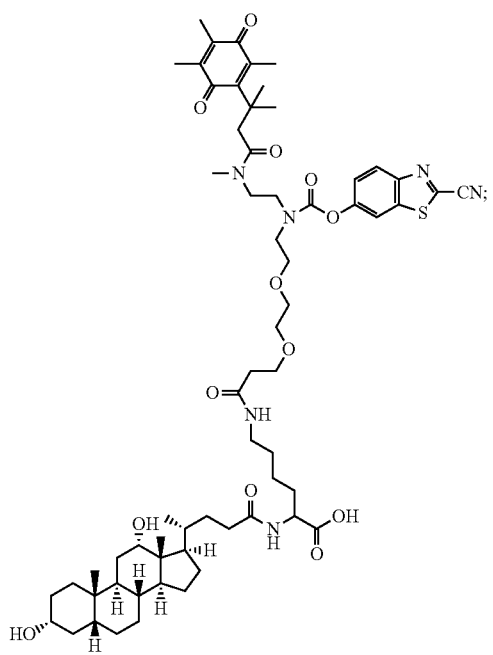
PBI 5649

205
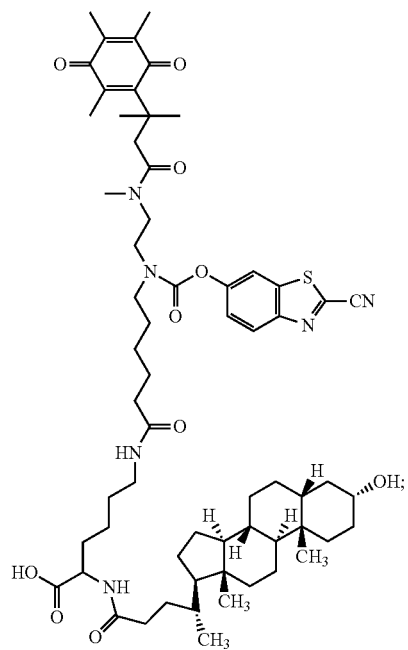
PBI 5659
206
-continued
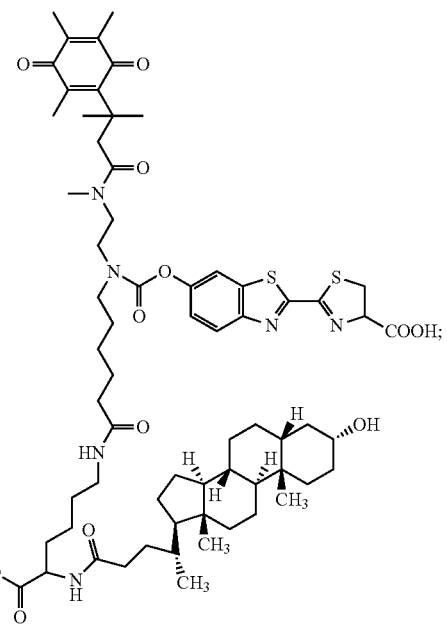
PBI 5663
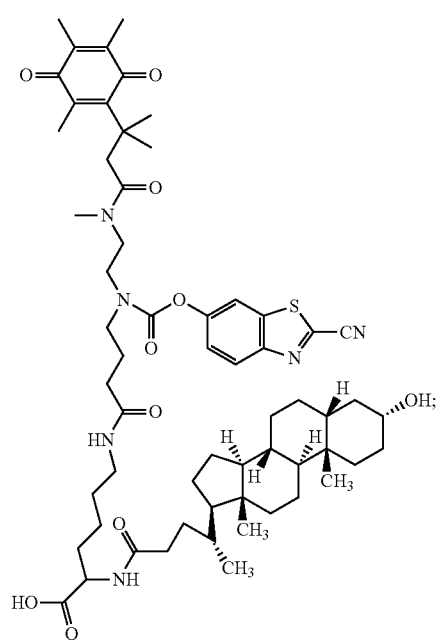
PBI 5652
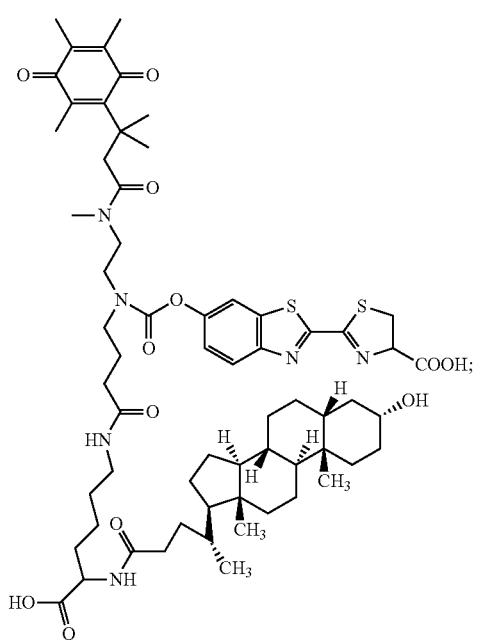
PBI 5669

207
-continued
PBI 5653
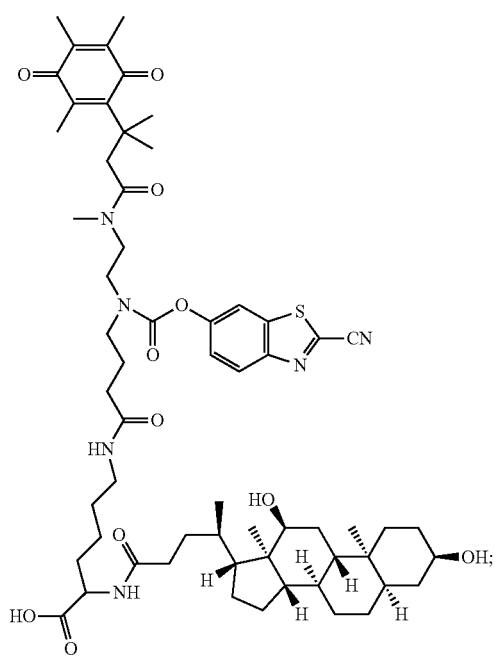
208
PBI 5656
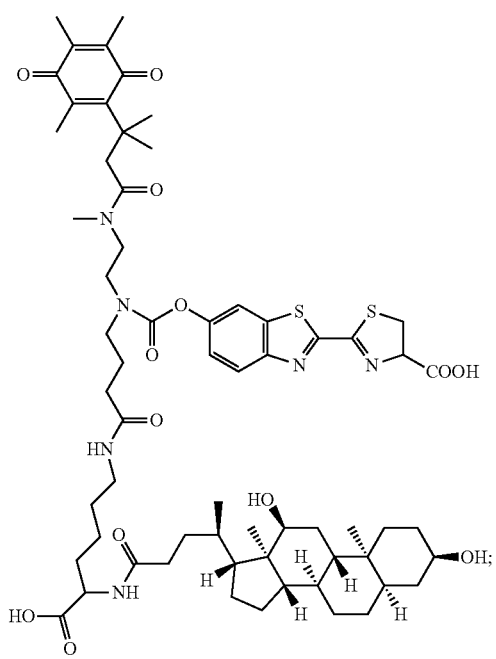
PBI 5660
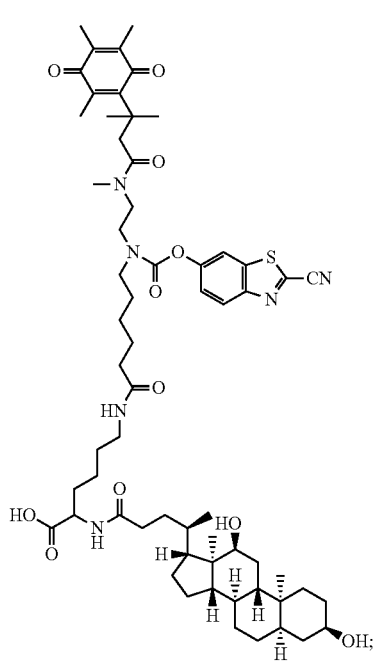
PBI 5664
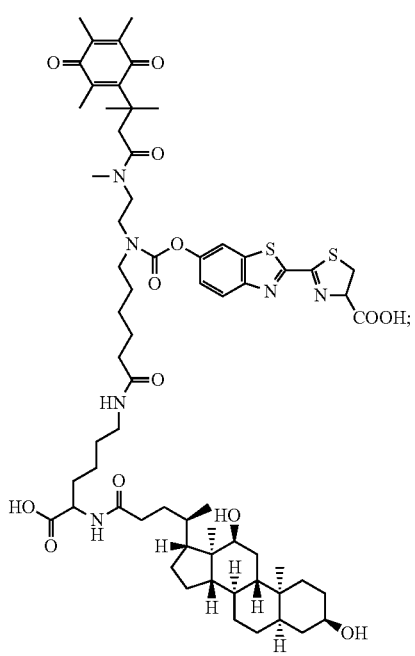

209
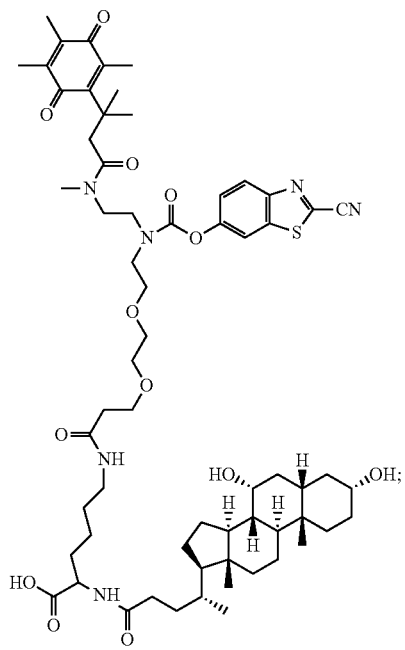
PBI 5667
210
-continued
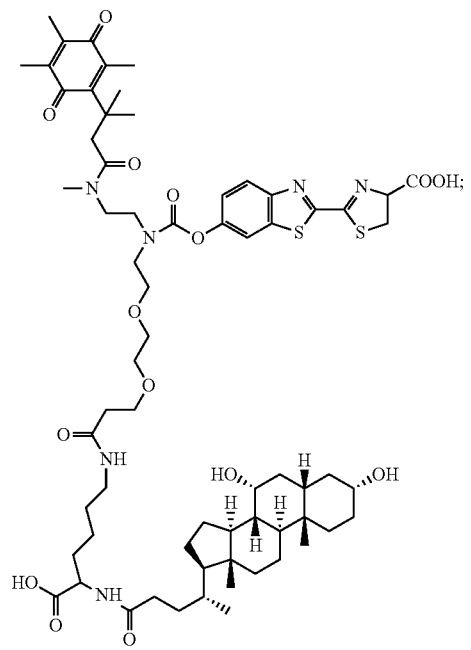
PBI 5650
PBI 5654
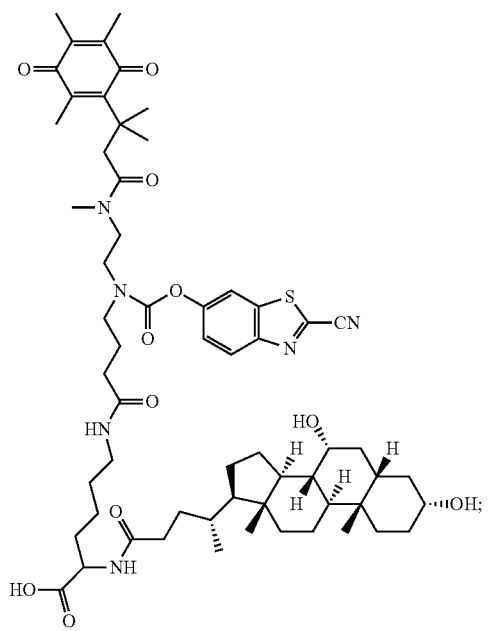
PBI 5655
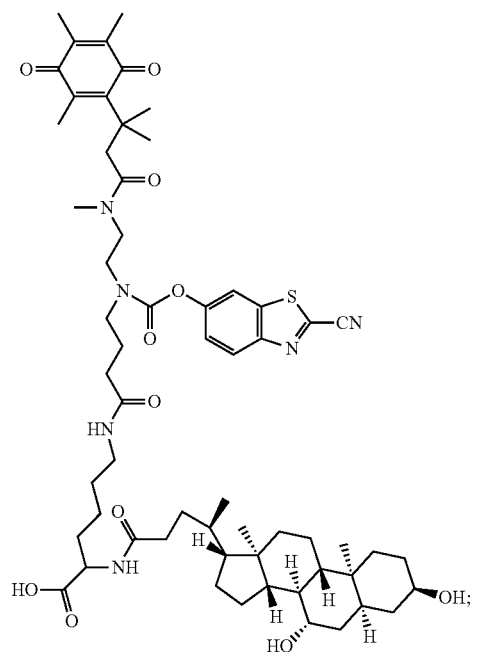

211
-continued
PBI 5661
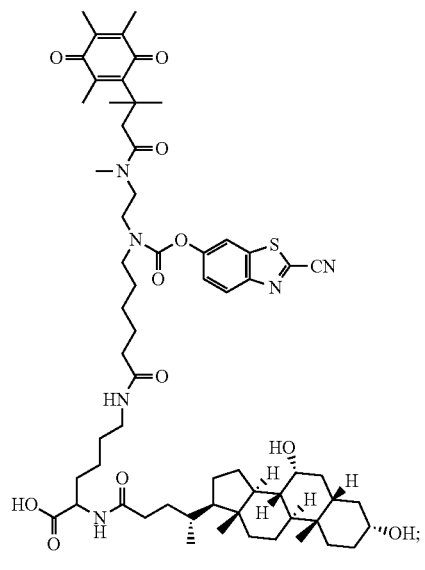
212
PBI 5662
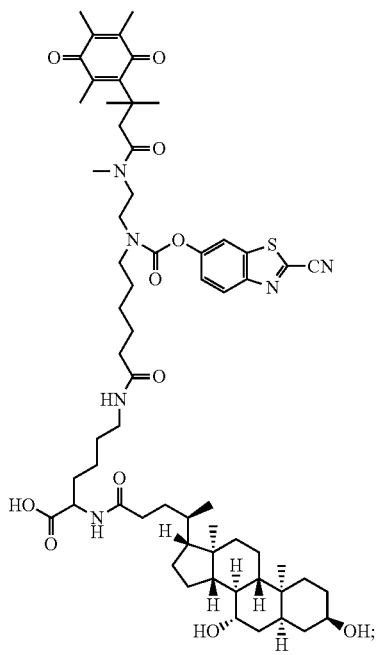
PBI 5824
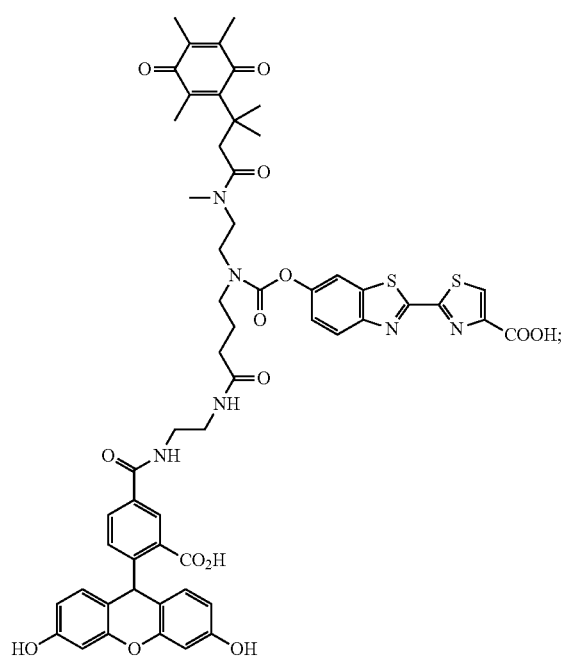
PBI 5830
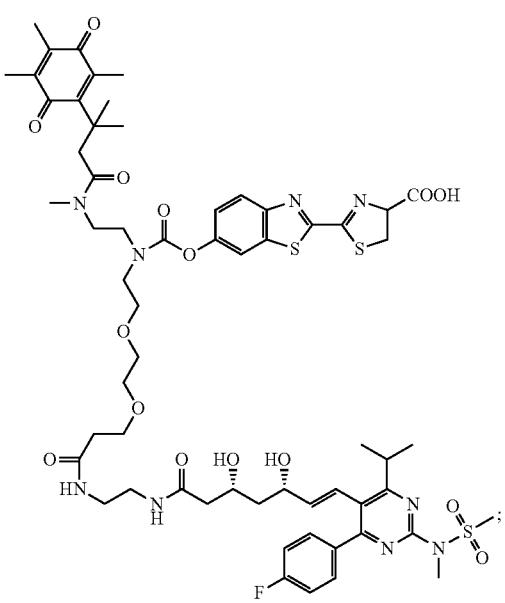

213
PBI 5831
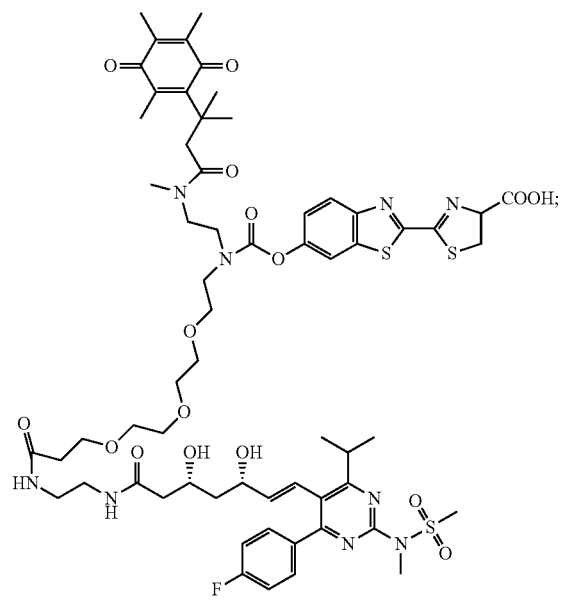
214
PBI 5827
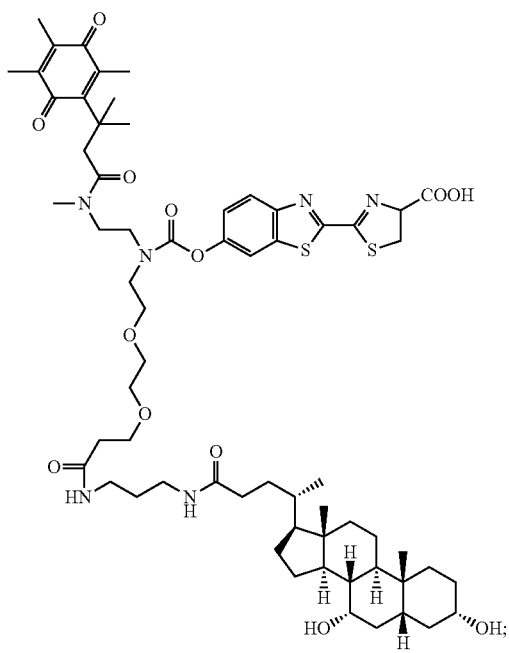
PBI 5828
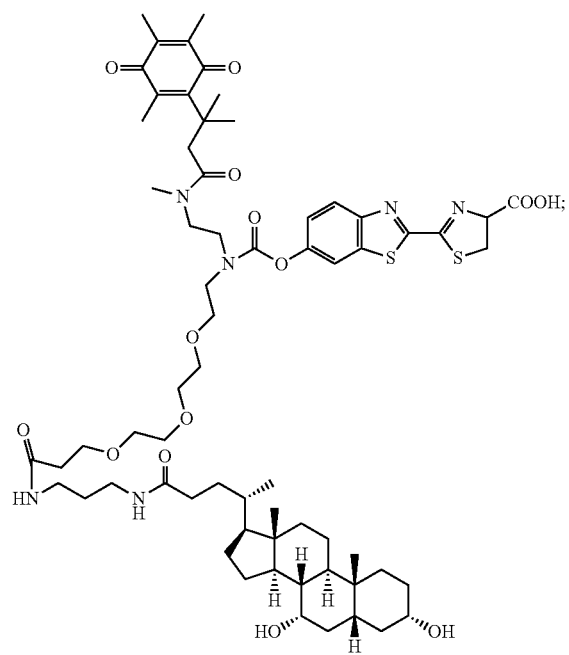

-continued
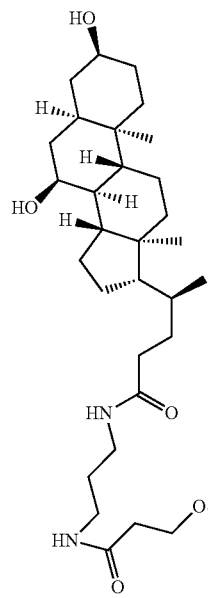 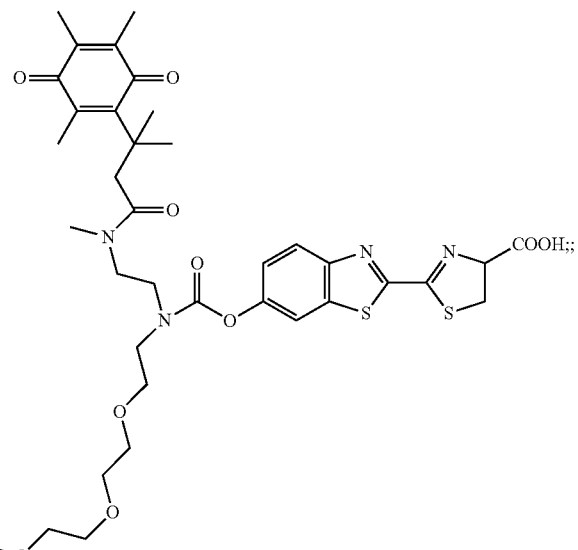
PBI 5829
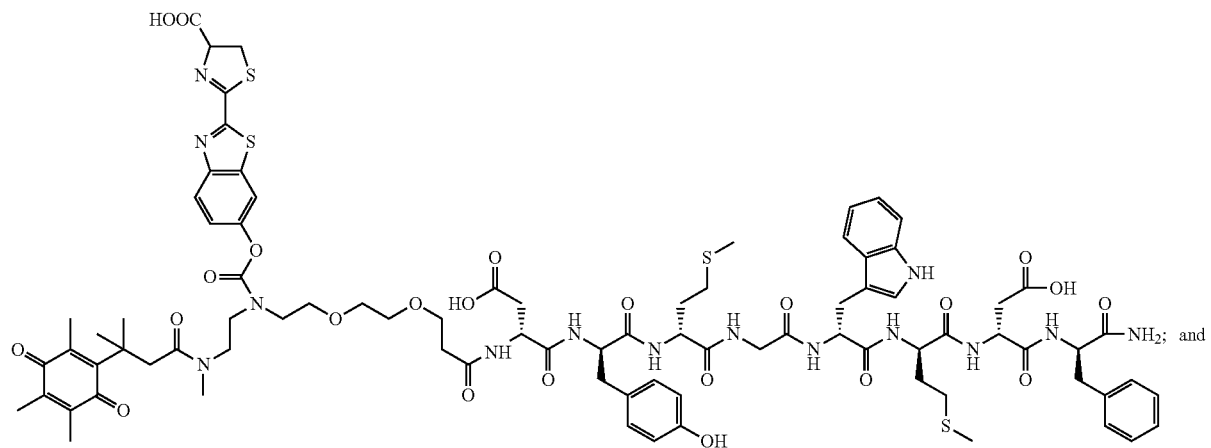
PBI 5832

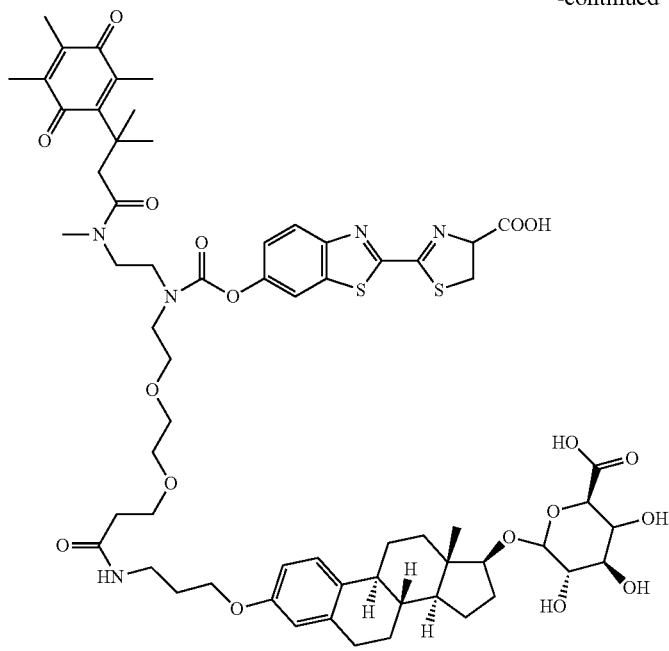

or a salt thereof.

Clause 97. The compound of any one of clauses 83-87, wherein T is a protein, a polypeptide, a oligonucleotide, a protein-oligonucleotide conjugate, a lipid, a therapeutic drug, a small molecule, a fluorescent molecule, a polymer-linked nanoparticle, a detergent, or a sugar.

Clause 98. The compound of clause 97, wherein T is a protein.

Clause 99. The compound of clause 98, wherein the protein is an antibody.

Clause 100. The compound of clause 97, wherein T is a polypeptide.

Clause 101. The compound of clause 100, wherein the polypeptide is a polypeptide toxin.

Clause 102. The compound of clause 97, wherein T is a therapeutic drug.

Clause 103. The compound of clause 102, wherein the compound is PBI-5651, PBI-5658, PBI-5666, PBI-5648, PBI-5655, PBI-5662, PBI-5657, PBI-5665, PBI-5667, PBI-5650, PBI-5654, PBI-5661, PBI-5827, PBI-5828, PBI-5829, PBI-5647, PBI-5668, PBI-5659, PBI-5663, PBI-5652, PBI-5669, PBI-5625, PBI-5649, PBI-5653, PBI-5656, PBI-5660, PBI-5664, PBI-5830, PBI-5831 or

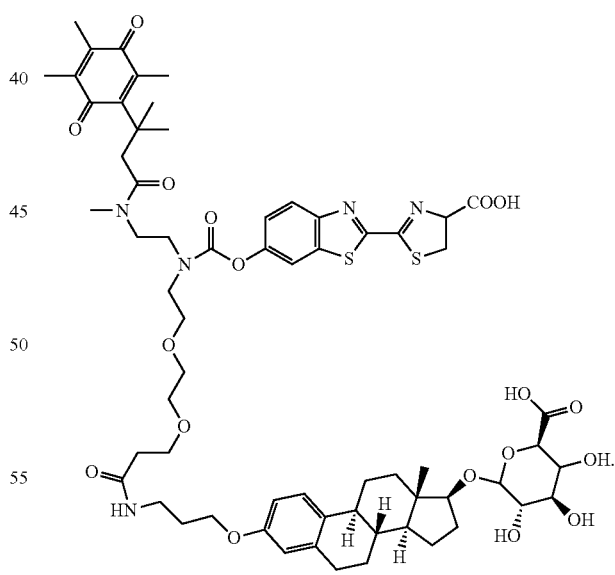

Clause 104. The compound of clause 97, wherein T is a fluorescent molecule.

Clause 105. The compound of clause 104, wherein the fluorescent molecule is FAM diamine.

Clause 106. The compound of clause 105, wherein the compound is PBI-5683, PBI-5826, PBI-5682, PBI-5684, PBI-5824, or PBI-5825.

Clause 107. The compound of clause 97, wherein T is a polymer-linked nanoparticle or a detergent.

Clause 108. The compound of clause 107, wherein the nanoparticle is a gold nanoparticle.

Clause 109. The compound of clause 108, wherein the compound is PBI-5907, PBI-5908, PBI-5909, PBI-5910, PBI-5911, or PBI-5912.

Clause 110. The compound of clause 82, wherein the reporter moiety comprises a bioluminescent reporter moiety or fluorescent reporter moiety.

Clause 111. The compound of clause 110, wherein the bioluminescent reporter moiety comprises a substrate for a luciferase.

Clause 112. The compound of clause 111, wherein the substrate comprises luciferin, a luciferin derivative or analog, a preluciferin or a preluciferin analog, a coelenterazine or a coelenterazine derivative or analog.

Clause 113. The compound of clause 111, wherein the substrate is furimazine, coelenterazine H,H, or luciferin.

Clause 114. The compound of clause 111, wherein the luciferase is a beetle luciferase, a *Renilla* luciferase, an *Oplophorus* luciferase, or a variant thereof.

Clause 115. The compound of clause 110, wherein the reporter moiety comprises a fluorescent reporter moiety.

Clause 116. The compound of clause 115, wherein the fluorescent reporter moiety comprises a fluorophore.

Clause 117. The compound of clause 116, wherein the fluorophore is coumarin, R110, fluoroscein, DDAO, resorufin, cresyl violet, silyl xanthene or carbopyronine.

Clause 118. A method for evaluating cellular uptake of an agent, the method comprising:
a) contacting a sample with a labeled agent, wherein the labeled agent comprises i) an agent and a compound of any one of clauses 82-117 or ii) a compound of any one of clauses 82-117, wherein the sample comprises a cell; and
b) detecting light emission,
whereby the detection of light emission indicates cellular uptake of the agent.

Clause 119. The method of clause 118, wherein the cellular uptake of the agent results in the reduction of the compound and the generation of a released reporter moiety.

Clause 120. The method of clause 119, wherein the reporter moiety comprises a fluorescent reporter moiety.

Clause 121. The method of clause 120, wherein detecting light emission comprises exposing the sample to a wavelength of light and detecting fluorescence level in the sample, wherein an increase in fluorescence or a change in fluorescence wavelength as compared to the fluorescence or fluorescence wavelength of a control sample indicates cellular uptake of the agent.

Clause 122. The method of clause 121, wherein the control sample is a sample that is not contacted with a labeled agent.

Clause 123. The method of clause 121, wherein fluorescence is detected inside the cell.

Clause 124. The method of clause 121, wherein fluorescence is detected outside the cell.

Clause 125. The method of clause 119, wherein the reporter moiety comprises a bioluminescent reporter moiety.

Clause 126. The method of clause 125, wherein the bioluminescent reporter moiety comprises a substrate for a luciferase.

Clause 127. The method of clause 126, wherein the cell comprises a luciferase.

Clause 128. The method of clause 127, wherein the cell expresses the luciferase.

Clause 129 The method of clause 127, wherein detecting light emission comprises detecting the luminescence produced by the luciferase utilizing the released reporter moiety.

Clause 130. The method of clause 126, further comprising contacting the sample with a luciferase and wherein detecting light emission comprises detecting the luminescence produced by the luciferase utilizing the released reporter moiety.

Clause 131. The method of clause 129 or 130, wherein the light emission is detected inside or outside the cell.

Clause 132. A method for evaluating cellular uptake of an agent, the method comprising:
(a) contacting a sample with a labeled agent, wherein the labeled agent comprises i) an agent and a compound of any one of clauses 82-96, 110, or 115-117 or ii) a compound of any one of clauses 82-96, 110, or 115-117, wherein the sample comprises a cell, wherein the cellular uptake of the agent results in the reduction of the compound and the generation of a released fluorescent reporter moiety;
(b) exposing the sample to a wavelength of light to generate fluorescence,
(c) detecting fluorescence in the sample, and
(d) comparing the fluorescence or fluorescent wavelength of the sample to the fluorescence of a control sample, wherein an increase in fluorescence or a change in the fluorescent wavelength as compared to fluorescence or fluorescent wavelength of the control sample indicates cellular uptake of the agent.

Clause 133. The method of clause 132, wherein the fluorescent reporter moiety comprises a fluorophore.

Clause 134. The method of clause 133, wherein the fluorophore is coumarin, R110, fluoroscein, DDAO, resorufin, cresyl violet, silyl xanthen or carbopyronine.

Clause 135. The method of clause 132, wherein the fluorescence level is detected inside the cell.

Clause 136. The method of clause 132, wherein the fluorescence level is detected in the sample.

Clause 137. The method of clause 132, wherein the control sample is sample medium only with labeled agent, a sample with labeled agent and cells but without experimental treatment, or a sample not contacted with labeled agent.

Clause 137. A method for evaluating cellular uptake of an agent, the method comprising:
a) contacting a sample with a labeled agent, wherein the labeled agent comprises i) an agent and a compound of any one of clause 82-96, or ii) a compound of any one of clauses 82-96, wherein the sample comprises a cell, wherein the cell comprises luciferase, wherein the cellular uptake of the agent results in the reduction of the compound and the generation of a released bioluminescent reporter moiety;
b) detecting luminescence in the sample; and
c) comparing the luminescence of the sample to luminescence of a control sample, wherein cellular uptake of the agent is indicated if the luminescence of the sample is changed compared to the luminescence of the control sample.

Clause 149. The method of clause 138, wherein the luminescence level is produced by the luciferase utilizing the released bioluminescent reporter moiety.

Clause 140. The method of clause 139, wherein the bioluminescent reporter moiety comprises a substrate for a luciferase.

Clause 141. The method of clause 140, wherein the substrate comprises luciferin, a luciferin derivative, a coelenterazine or a coelenterazine derivative.

Clause 142. The method of clause 141, wherein the substrate is furimazine, coelenterazine H,H, luciferin, or pre-luciferin.

Clause 143. The method of clause 141, wherein the luciferase is a beetle luciferase, a *Renilla* luciferase, an *Oplophorus* luciferase, or a variant thereof.

Clause 14482. The method of clause 138, wherein the luminescence is detected inside the cell or detected outside in the cell medium.

Clause 145. The method of clause 138, wherein the control sample is a sample that is not contacted with a labeled agent.

Clause 146. A method for evaluating cellular uptake of an agent, the method comprising:
 a) contacting a sample with a labeled agent, wherein the labeled agent comprises i) an agent and a compound of any one of clauses 82-96 or ii) a compound of any one of clauses 82-96, wherein the sample comprises a cell and cell medium, wherein the cellular uptake of the agent results in the reduction of the compound and the generation of a released bioluminescent reporter moiety;
 b) contacting the sample with a luciferase;
 c) detecting luminescence in the sample; and
 d) comparing the luminescence of the sample to luminescence in a control sample, wherein cellular uptake of the agent is indicated if the luminescence in the sample is changed compared to the luminescence of the control sample.

Clause 147. The method of clause 146, wherein the luminescence level is produced by the luciferase utilizing the released bioluminescent reporter moiety.

Clause 148. The method of clause 147, wherein the bioluminescent reporter moiety comprises a substrate for a luciferase.

Clause 149. The method of clause 148, wherein the substrate comprises luciferin, a luciferin derivative, a coelenterazine or a coelenterazine derivative.

Clause 150. The method of clause 149, wherein the substrate is furimazine, coelenterazine H,H, luciferin, or pre-luciferin.

Clause 151. The method of clause 149, wherein the luciferase is a beetle luciferase, a *Renilla* luciferase, an *Oplophorus* luciferase, or a variant thereof.

Clause 152. The method of clause 146, wherein the luminescence is detected in the cell or detected in the cell medium.

Clause 153. The method of clause 146, wherein the control sample is sample medium with labeled agent but without cells, a sample with labeled agent and cells but without experimental treatment, or a sample not contacted with labeled agent.

Clause 154. The method of any one of clauses 118-153, wherein the agent is a biological agent.

Clause 155. The method of clause 154, wherein the biological agent is selected from the group consisting of a protein, a polypeptide, a oligonucleotide, a protein-oligonucleotide conjugate, a lipid, a therapeutic drug, small molecule, a fluorescent molecule, and a sugar.

Clause 156. The method of clause 155, wherein the protein is an antibody or a lipoprotein.

Clause 157. The method of any one of clauses 118-153, wherein the agent is a non-biological agent.

Clause 158. The method of clause 157, wherein the non-biological agent is a polymer-linked nanoparticle or a detergent.

Clause 159. The method of any one of clauses 118-158, wherein the cell is a eukaryotic cell or a prokaryotic cell.

Clause 160. The method of clause 159, wherein the cell is in an animal.

Clause 161. The method of clause 159, wherein the cell is growing in culture medium.

Clause 162. A labeled agent derived from i) an agent and a compound according to any one of clauses 82-96 or ii) a compound according to any one of clauses 82-117.

Clause 163. The labeled agent of clause 162, wherein the agent is a biological agent.

Clause 164. The labeled agent of clause 163, wherein the biological agent is selected from the group consisting of a protein, a polypeptide, a oligonucleotide, a protein-oligonucleotide conjugate, a lipid, a therapeutic drug, small molecule, a fluorescent molecule, and a sugar.

Clause 165. The labeled agent of clause 164, wherein the protein is an antibody or a lipoprotein.

Clause 166. The labeled agent of clause 164, wherein the polypeptide is a polypeptide toxin.

Clause 167. The labeled agent of clause 164, wherein the fluorescent molecule is FAM diamine.

Clause 168. The labeled agent of clause 162, wherein the reporter moiety comprises a bioluminescent reporter moiety or fluorescent reporter moiety.

Clause 169. The labeled agent of any one of clauses 162, wherein the agent is a non-biological agent.

Clause 170. The labeled agent of clause 169, wherein the non-biological agent is a polymer-linked nanoparticle or detergent.

Clause 171. The labeled agent of clause 170, wherein the nanoparticle is a gold nanoparticle.

Clause 172. The labeled agent of clause 168, wherein the bioluminescent reporter moiety comprises a substrate for a luciferase.

Clause 173. The labeled agent of clause 172, wherein the substrate comprises luciferin, a luciferin derivative, a coelenterazine or a coelenterazine derivative.

Clause 174. The labeled agent of clause 173, wherein the substrate is furimazine, coelenterazine H,H, luciferin, or pre-luciferin.

Clause 175. The labeled agent of clause 174, wherein the luciferase is a beetle luciferase, a *Renilla* luciferase, an *Oplophorus* luciferase, or a variant thereof.

Clause 176. The labeled agent of clause 168, wherein the reporter moiety comprises a fluorescent reporter moiety.

Clause 177. The labeled agent of clause 176, wherein the fluorescent reporter moiety comprises a fluorophore.

Clause 178. The labeled agent of clause 177, wherein the fluorophore is coumarin, a rhodamine, R110, fluoroscein, DDAO, resorufin or cresyl violet.

Clause 179. A kit comprising a compound according to any one of clauses 82-117, an agent, or any combination thereof.

Clause 180. A kit comprising a labeled agent comprising an agent and a compound according to any one of clauses 82-117.

Clause 181. The kit of clause 179 or 180, wherein the agent is a biological agent.

Clause 182. The kit of clause 181, wherein the biological agent is selected from the group consisting of a protein, a polypeptide, a oligonucleotide, a protein-oligonucleotide conjugate, a lipid, a therapeutic drug, small molecule, a fluorescent molecule, and a sugar.

Clause 183. The kit of clause 182, wherein the protein is an antibody or a lipoprotein.

Clause 184. The kit of clause 179 or 180, wherein the agent is a non-biological agent.

Clause 185. The kit of clause 184, wherein the non-biological agent is a polymer-linked nanoparticle or detergent.

Clause 186. The kit of clause 185, wherein the nanoparticle is a gold nanoparticle.

Clause 187. The kit of clause 179 or 180, wherein the compound is a substrate for luciferase.

Clause 188. The kit of clause 187, further comprising a detection reagent.

Clause 189. The kit of clause 188, wherein the detection reagent comprises a luciferase enzyme.

What is claimed is:

1. A compound of formula (I), or a salt thereof,

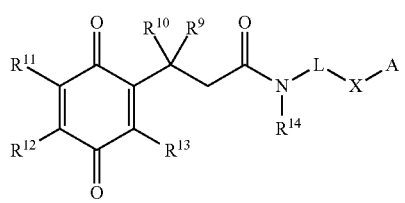

wherein

A is a reporter moiety;

$R^{14}$ is H, alkyl, hydroxyalkyl, alkoxy, carboxyalkyl, or amidoalkyl;

$R^9$ and $R^{10}$ are independently selected from alkyl;

$R^{11}$, $R^{12}$ and $R^{13}$ are independently selected from alkyl;

X is O;

L is $-(CH_2)_m C(R^{17})_2 (CH_2)_n - Y - C(O) -$;

$R^{17}$ is independently H, alkyl or both $R^{17}$ together can form an alkyl ring having from 3-7 carbons;

m is an integer from 0-2;

n is an integer from 0-2;

Y is O or $NR^{15}$;

$R^5$ is -alkyl-amide, wherein the -alkyl-amide is -alkyl-$CON(R^{32})(R^{33})$ or -alkyl-(CO)—$NR^{34}$—$(CR^a R^b)_p$—$NR^{35}$(CO)-T, wherein $R^{32}$ and $R^{33}$ are each independently selected from hydrogen, alkyl, carboxy, aryl, arylalkyl, cycloalkylalkyl, heteroaryl, heteroarylalkyl, heterocycle, alkene, polyol, alkenylpolyol, a peptide, a drug, a derivative of a drug, a biologically active moiety, and a dye;

$R^{34}$ and $R^{35}$ are each independently selected from hydrogen, and alkyl;

$R^a$ and $R^b$ are each independently selected from hydrogen, alkyl, and carboxy;

p is 0 to 6; and

T is selected from aryl, arylalkyl, cycloalkylalkyl, heteroaryl, heteroarylalkyl, heterocycle, hydroxyalkyl, protein, polypeptide, polypeptide-based toxin, amino acid, nucleotide, polynucleotide, lipid, sugar, carbohydrate, enzyme substrate, drug, derivative of a drug, polymer-linked nanoparticle, antibody, detergent, and a dye, or a combination thereof;

or $R^{15}$ is polyalkoxyalkyl, wherein the polyalkoxyalkyl is $-(C_2-C_6\text{-alkoxy})_x\text{-alkyl-CON}(R^{32})(R^{33})$ or $-(C_2-C_6\text{-alkoxy})_x\text{-alkyl-(CO)}-NR^{34}-(CR^a R^b)_p-NR^{35}(CO)\text{-T}$;

x is an integer selected from 1 to 20;

$R^{32}$ and $R^{33}$ are each independently selected from hydrogen, alkyl, carboxy, aryl, arylalkyl, cycloalkylalkyl, heteroaryl, heteroarylalkyl, heterocycle, hydroxyalkyl, protein, polypeptide, polypeptide-based toxin, amino acid, nucleotide, polynucleotide, lipid, sugar, carbohydrate, enzyme substrate, drug, derivative of a drug, polymer-linked nanoparticle, antibody, detergent, and a dye, or a combination thereof;

$R^{34}$ and $R^{35}$ are each independently selected from hydrogen, and alkyl;

$R^a$ and $R^b$ are each independently selected from hydrogen, alkyl, and carboxy;

p is 0 to 6; and

T is selected from aryl, arylalkyl, cycloalkylalkyl, heteroaryl, heteroarylalkyl, heterocycle, hydroxyalkyl, protein, polypeptide, polypeptide-based toxin, amino acid, nucleotide, polynucleotide, lipid, sugar, carbohydrate, enzyme substrate, drug, derivative of a drug, polymer-linked nanoparticle, antibody, detergent, and a dye, or a combination thereof;

or $R^{15}$ is

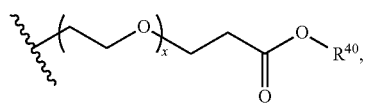

wherein $R^{40}$ is selected from the group consisting of hydrogen, alkyl, alkenyl, alkynyl, aryl, heteroaryl, heterocyclyl, and cycloalkyl, wherein said aryl, heteroaryl, heterocyclyl, and cycloalkyl are unsubstituted or substituted with one or more suitable substituents; and x is an integer selected from 1 to 20.

2. The compound of claim 1, wherein $R^{15}$ is polyalkoxyalkyl, wherein the polyalkoxyalkyl is —($C_2$-$C_6$-alkoxy)$_x$-alkyl-CON($R^{32}$)($R^{33}$) or —($C_2$-$C_6$-alkoxy)$_x$-alkyl-(CO)—NR$^{34}$—(CR$^a$R$^b$)$_p$—NR$^{35}$(CO)-T;

x is an integer selected from 1 to 20;

$R^{32}$ and $R^{33}$ are each independently selected from hydrogen, alkyl, carboxy, aryl, arylalkyl, cycloalkylalkyl, heteroaryl, heteroarylalkyl, heterocycle, hydroxyalkyl, protein, polypeptide, polypeptide-based toxin, amino acid, nucleotide, polynucleotide, lipid, sugar, carbohydrate, enzyme substrate, drug, derivative of a drug, polymer-linked nanoparticle, antibody, detergent, and a dye, or a combination thereof;

$R^{34}$ and $R^{35}$ are each independently selected from hydrogen, and alkyl;

$R^a$ and $R^b$ are each independently selected from hydrogen, alkyl, and carboxy;

p is 0 to 6; and

T is selected from aryl, arylalkyl, cycloalkylalkyl, heteroaryl, heteroarylalkyl, heterocycle, hydroxyalkyl, protein, polypeptide, polypeptide-based toxin, amino acid, nucleotide, polynucleotide, lipid, sugar, carbohydrate, enzyme substrate, drug, derivative of a drug, polymer-linked nanoparticle, antibody, detergent, and a dye, or a combination thereof.

3. The compound of claim 1, wherein $R^{15}$ is

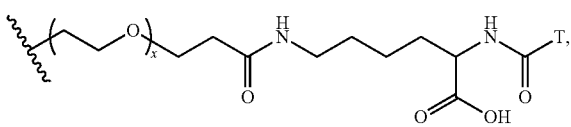

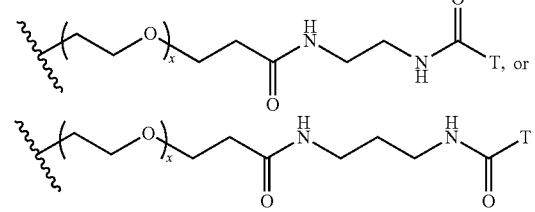

wherein

T is selected from aryl, arylalkyl, cycloalkylalkyl, heteroaryl, heteroarylalkyl, heterocycle, hydroxyalkyl, protein, polypeptide, polypeptide-based toxin, amino acid, nucleotide, polynucleotide, lipid, sugar, carbohydrate, enzyme substrate, drug, derivative of a drug, polymer-linked nanoparticle, antibody, detergent, and a dye, or a combination thereof; and x is an integer selected from 1 to 20.

4. The compound of claim 1, wherein $R^{15}$ is -alkyl-amide, wherein the -alkyl-amide is -alkyl-CON($R^{32}$)($R^{33}$) or -alkyl-(CO)—NR$^{34}$—(CR$^a$R$^b$)$_p$—NR$^{35}$(CO)-T, wherein $R^{32}$ and $R^{33}$ are each independently selected from hydrogen, alkyl, carboxy, aryl, arylalkyl, cycloalkylalkyl, heteroaryl, heterocycle, alkene, polyol, alkenylpolylol, a peptide, a drug, a derivative of a drug, a biologically active moiety, and a dye;

$R^{34}$ and $R^{35}$ are each independently selected from hydrogen, and alkyl;

$R^a$ and $R^b$ are each independently selected from hydrogen, alkyl, and carboxy;

p is 0 to 6; and

T is selected from aryl, arylalkyl, cycloalkylalkyl, heteroaryl, heteroarylalkyl, heterocycle, hydroxyalkyl, protein, polypeptide, polypeptide-based toxin, amino acid, nucleotide, polynucleotide, lipid, sugar, carbohydrate, enzyme substrate, drug, derivative of a drug, polymer-linked nanoparticle, antibody, detergent, and a dye, or a combination thereof.

5. The compound of claim 1, wherein $R^5$ is

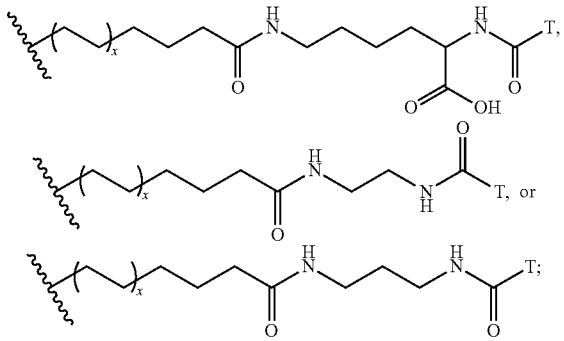

wherein

T is selected from aryl, arylalkyl, cycloalkylalkyl, heteroaryl, heterocycle, hydroxyalkyl, protein, polypeptide, polypeptide-based toxin, amino acid, nucleotide, polynucleotide, lipid, sugar, carbohydrate, enzyme substrate, drug, derivative of a drug, polymer-linked nanoparticle, antibody, detergent, and a dye, or a combination thereof; and x is 0 to 20.

6. The compound of claim 1, wherein $R^{15}$ is

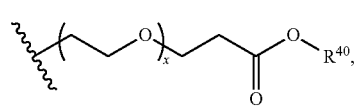

wherein $R^{40}$ is selected from the group consisting of hydrogen, alkyl, alkenyl, alkynyl, aryl, heteroaryl, heterocyclyl, and cycloalkyl, wherein said aryl, heteroaryl, heterocyclyl, and cycloalkyl are unsubstituted or substituted with one or more suitable substituents; and x is an integer selected from 1 to 20.

7. The compound of claim 6, wherein $R^{40}$ is a 5- or 6-membered heterocyclyl, having 1, 2, or 3 heteroatoms independently selected from the group consisting of N, O, and S.

8. The compound of claim 6, having formula (I-vi), or a salt thereof,

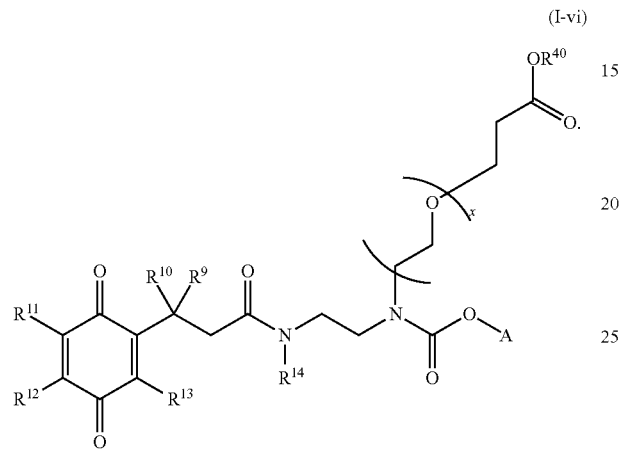

9. The compound of claim 8, wherein $R^9$, $R^{10}$, $R^{11}$, $R^{12}$, $R^{13}$, and $R^{14}$ are methyl;

x is 3;

$R^{40}$ is hydrogen; and

A is

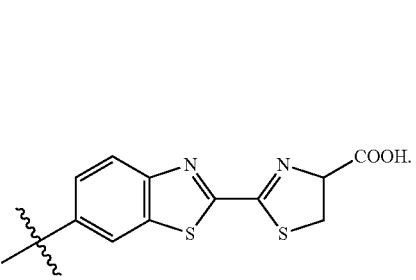 [SMILES: *c1ccc2nc(C3=NC(C(=O)O)CS3)sc2c1]

10. The compound of claim 1, selected from the group consisting of:

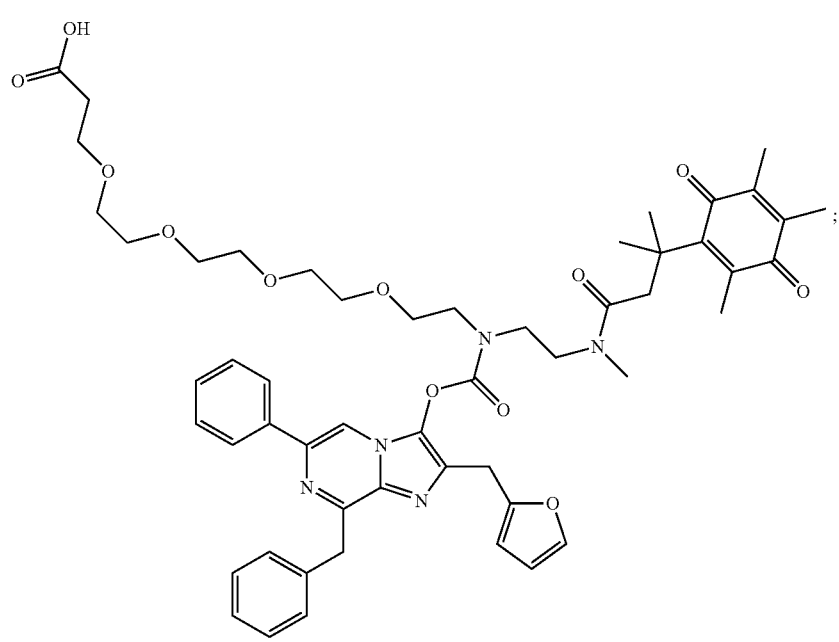

-continued
PBI 5470
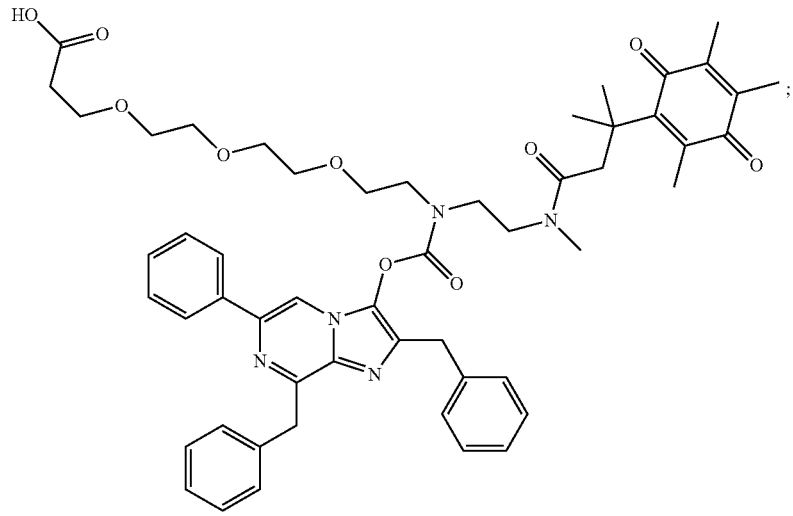
PBI 5471
PBI 5508
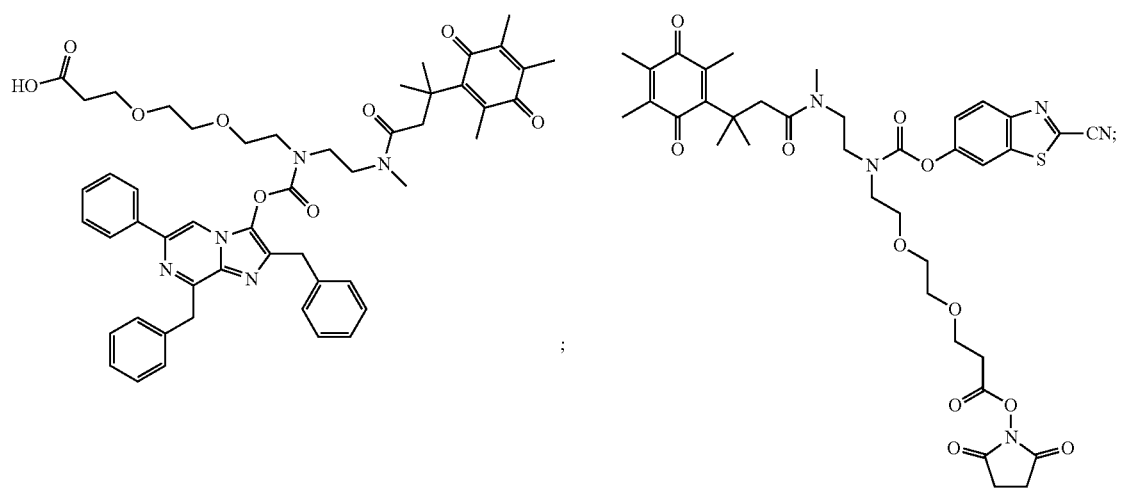
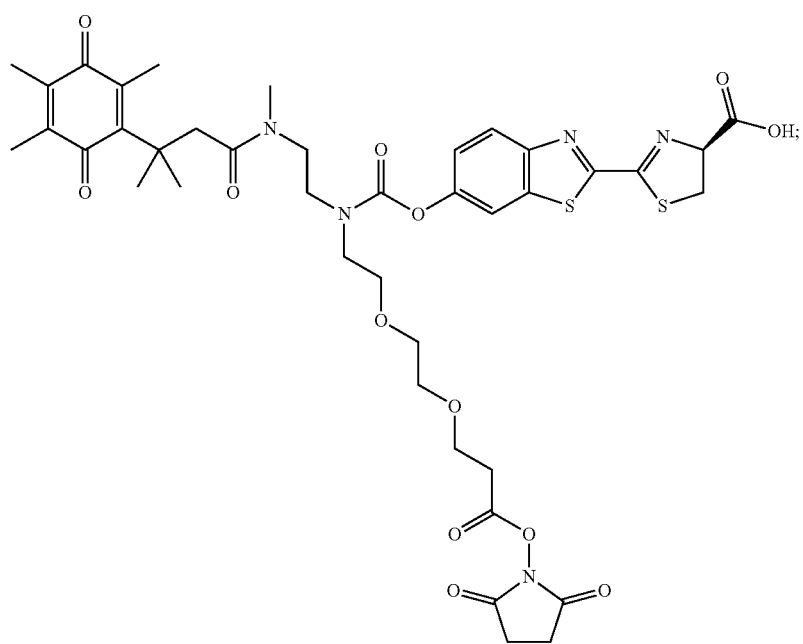

-continued
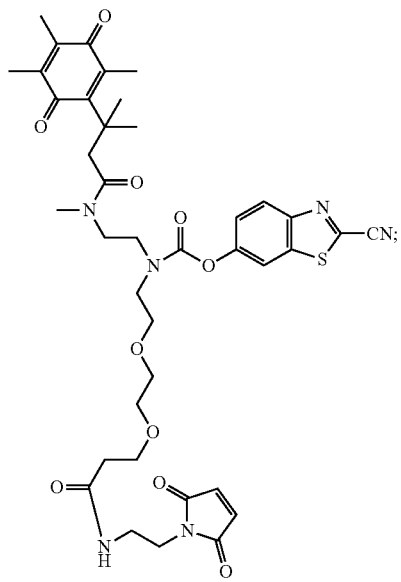
PBI 5915
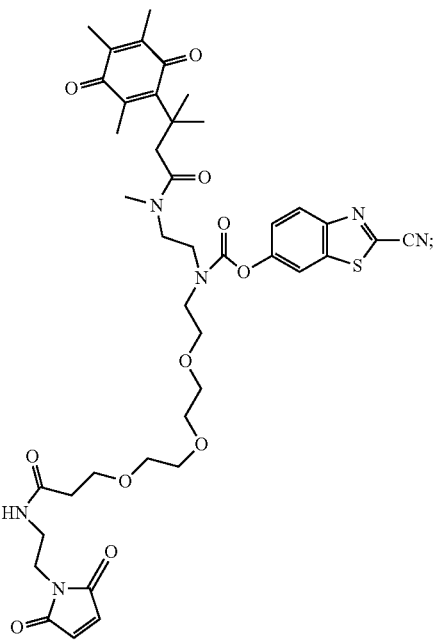
PBI 5916
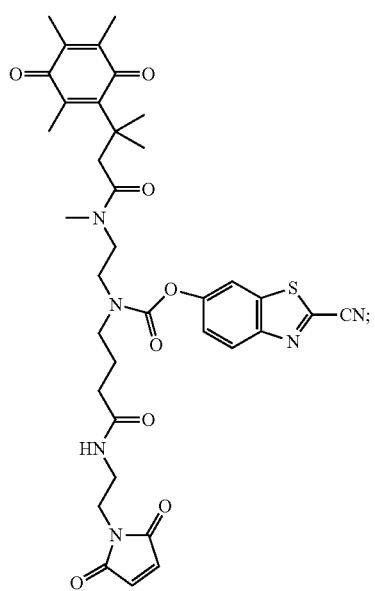
PBI 5917
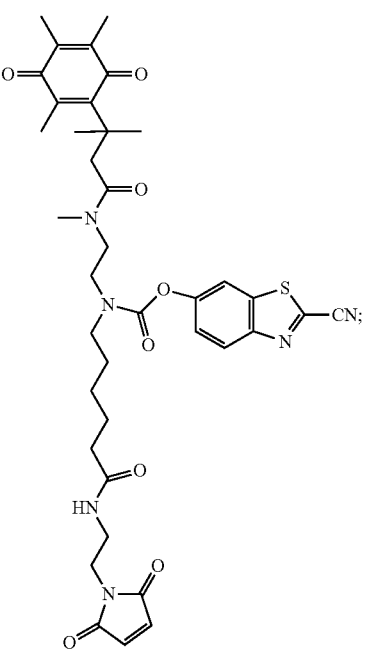
PBI 5918

-continued
PBI 5651
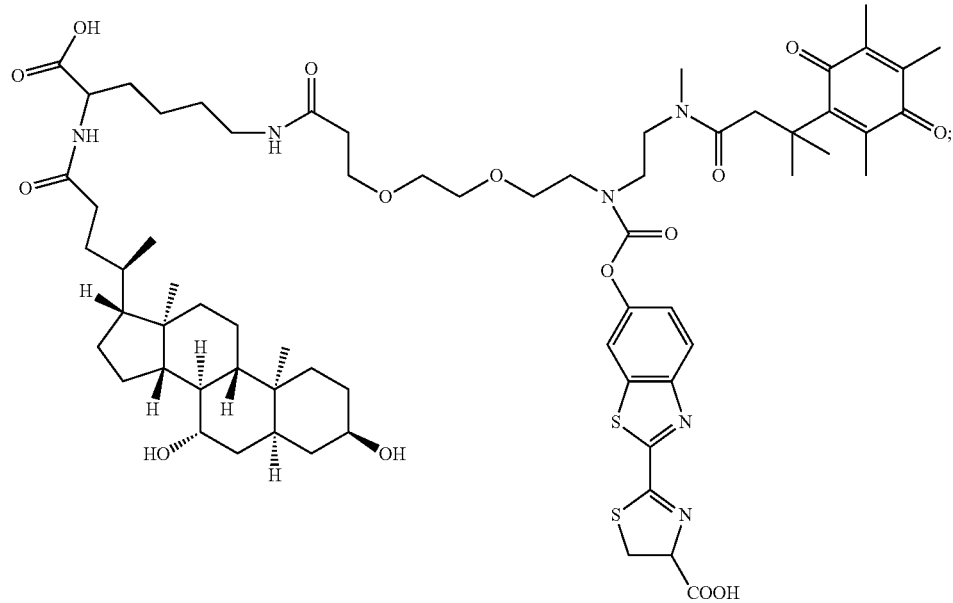
PBI 5648
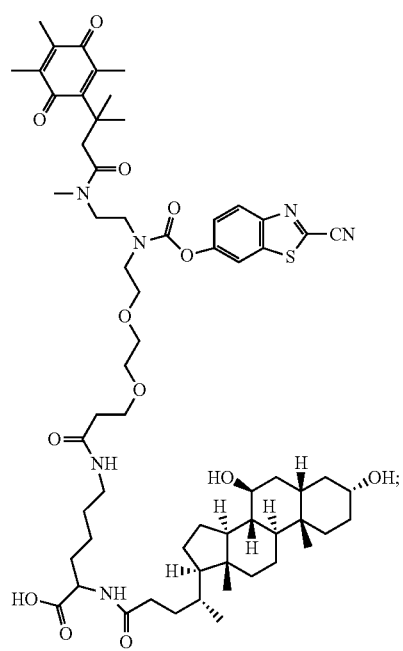

PBI 5657
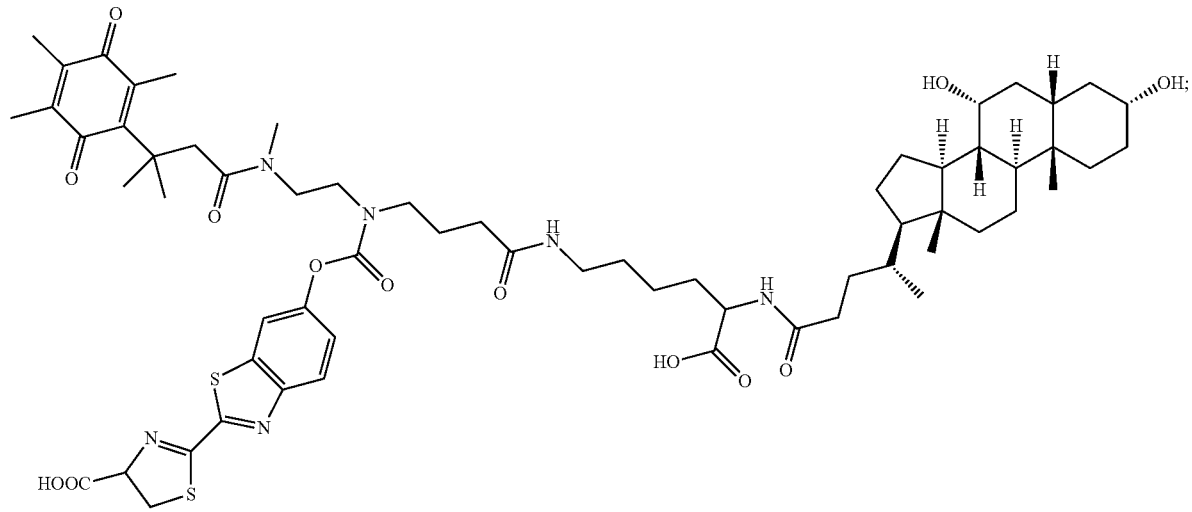
PBI 5658
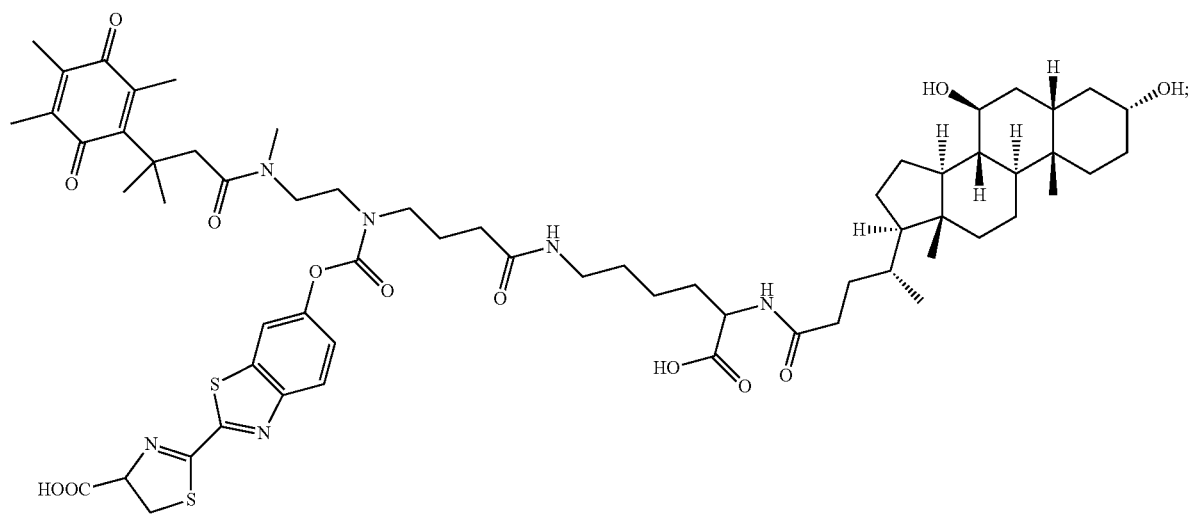
PBI 5665
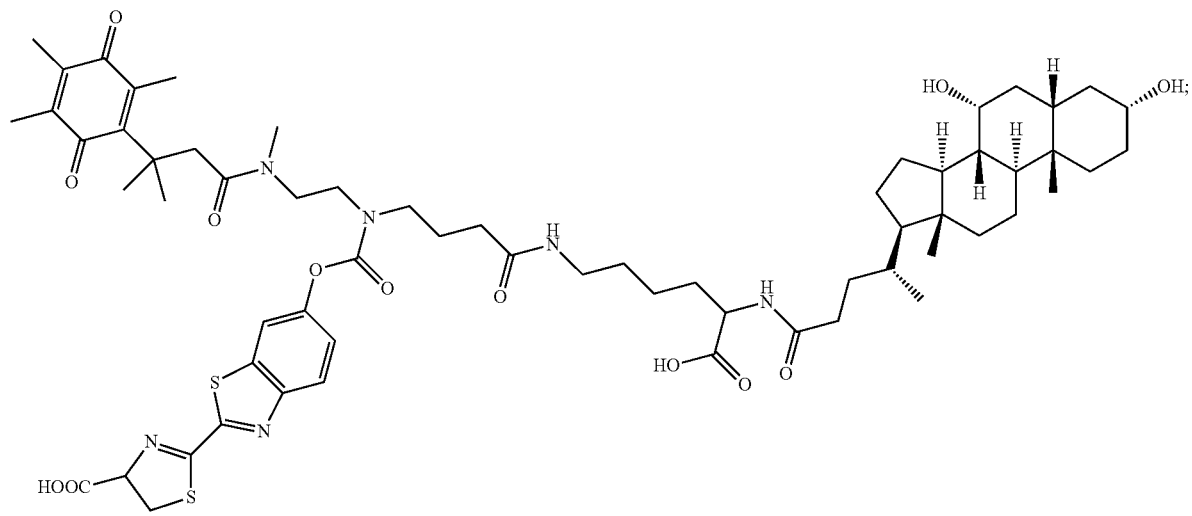

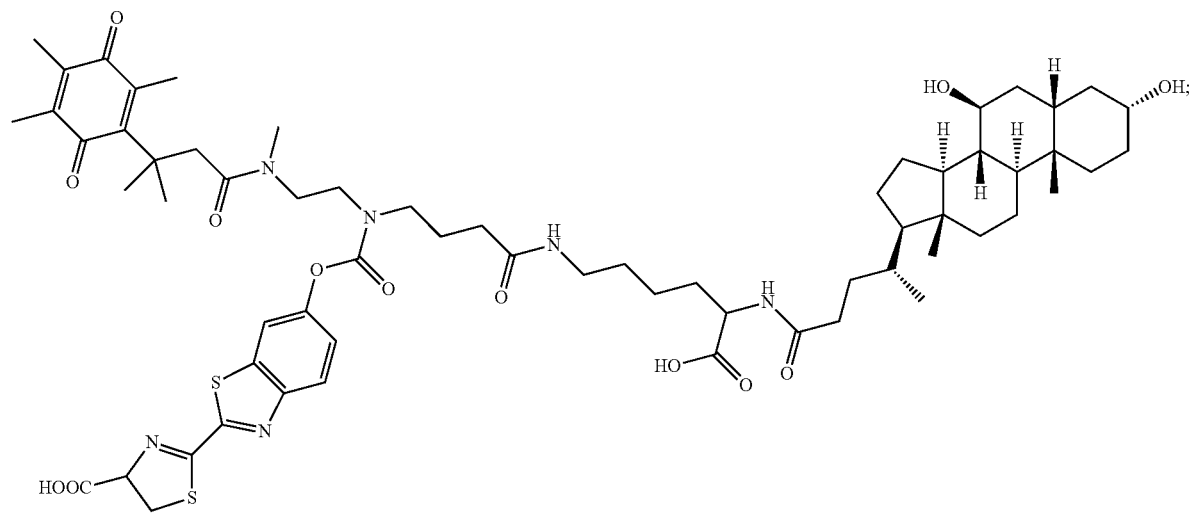
PBI 5666
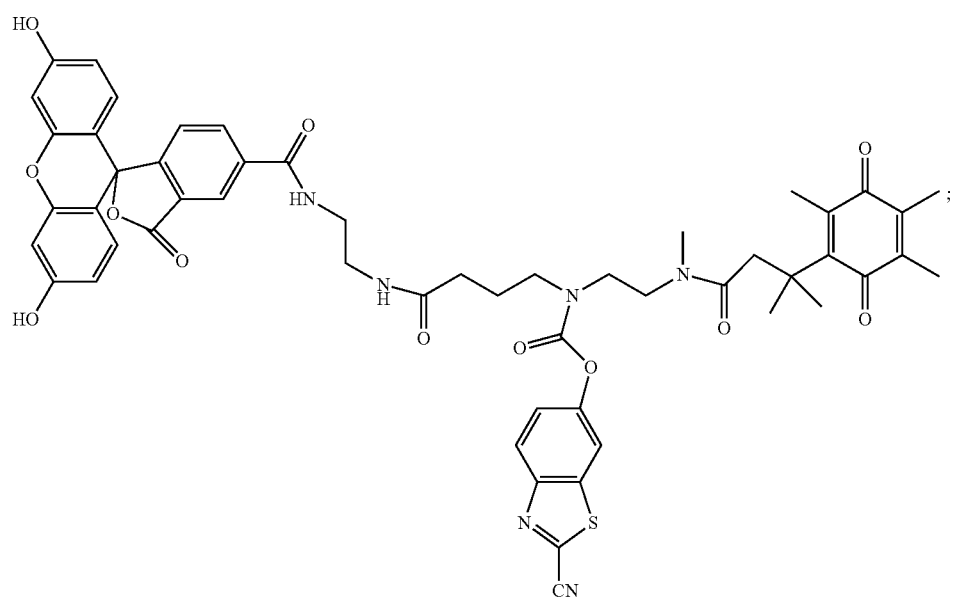
PBI 5684

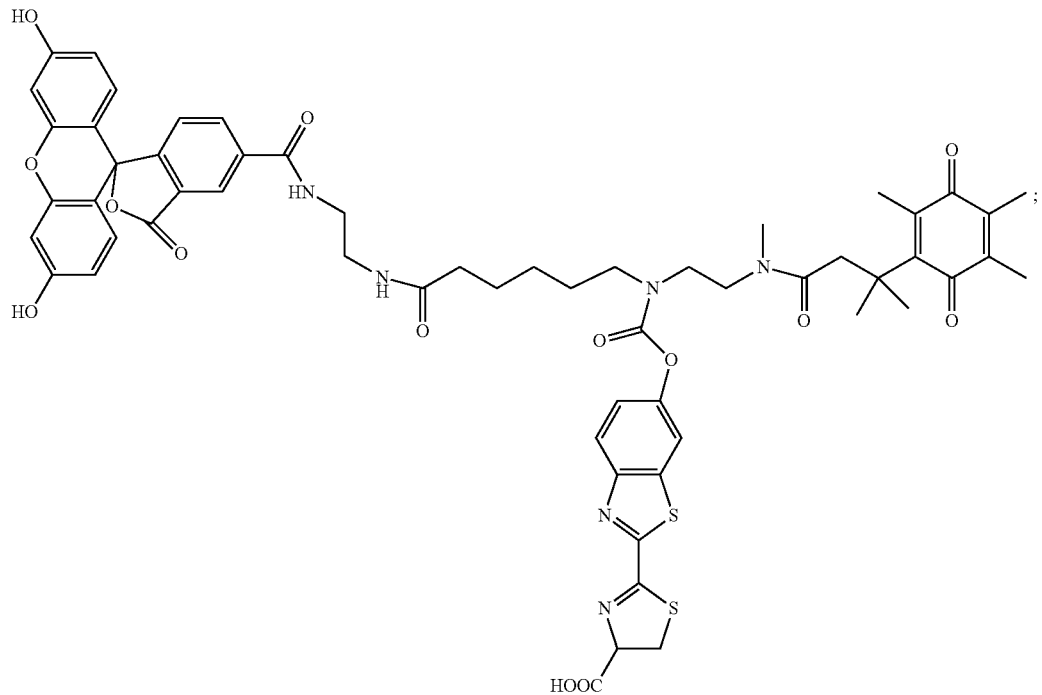
PBI 5825
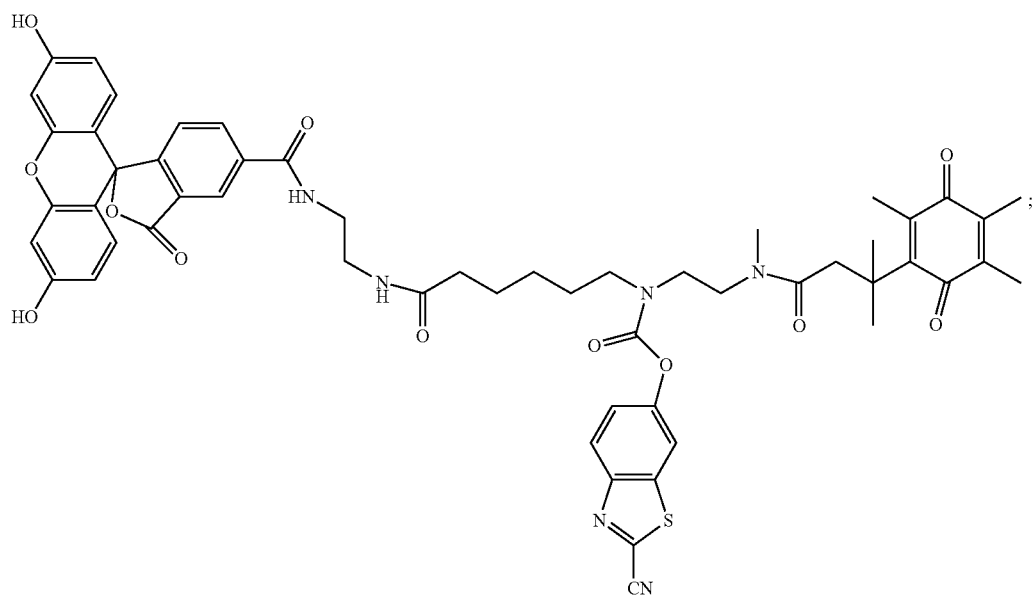
PBI 5683

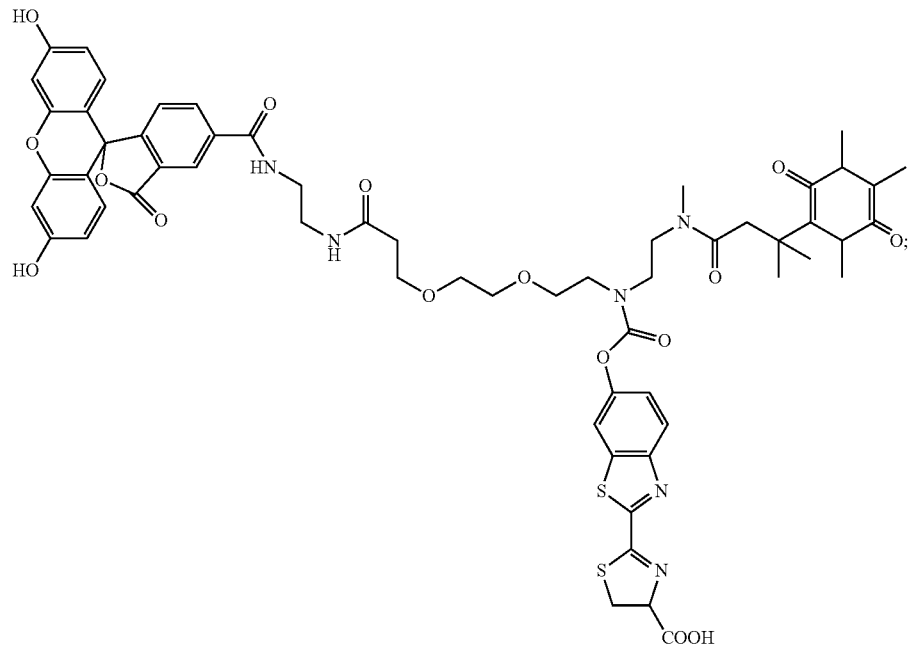
PBI 5826
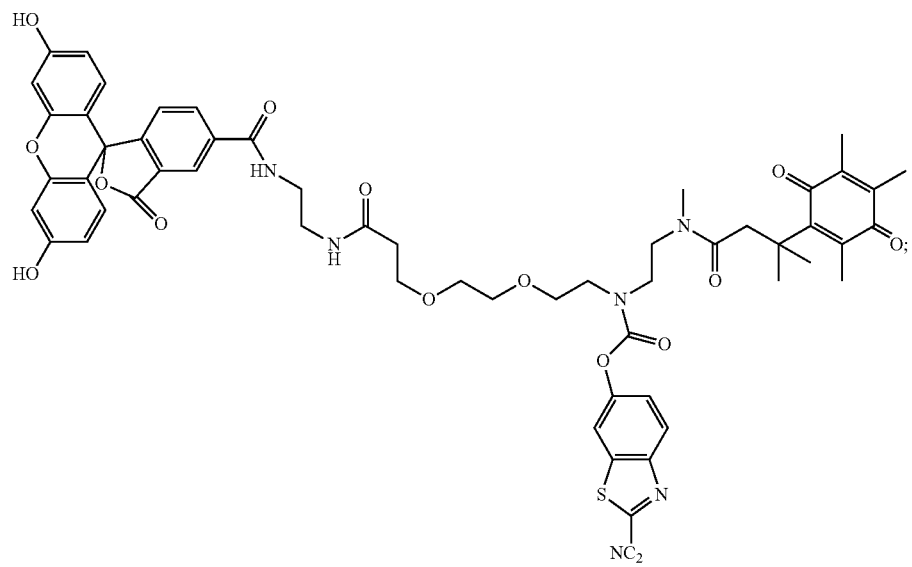
PBI 5682

247 248
-continued
PBI 5647
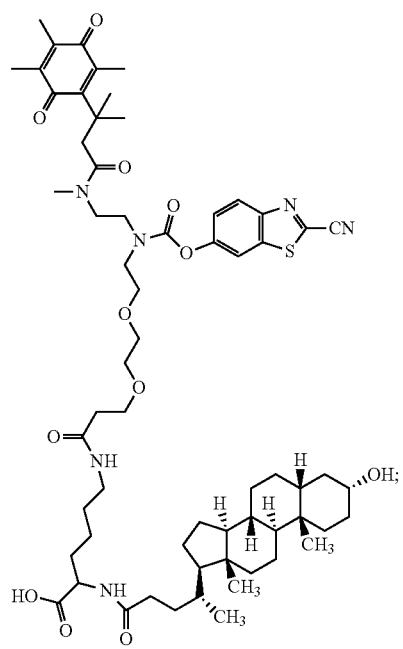
PBI 5668
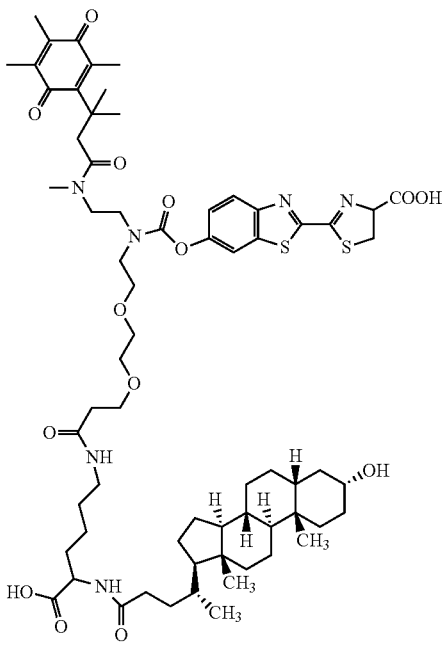
PBI 5625
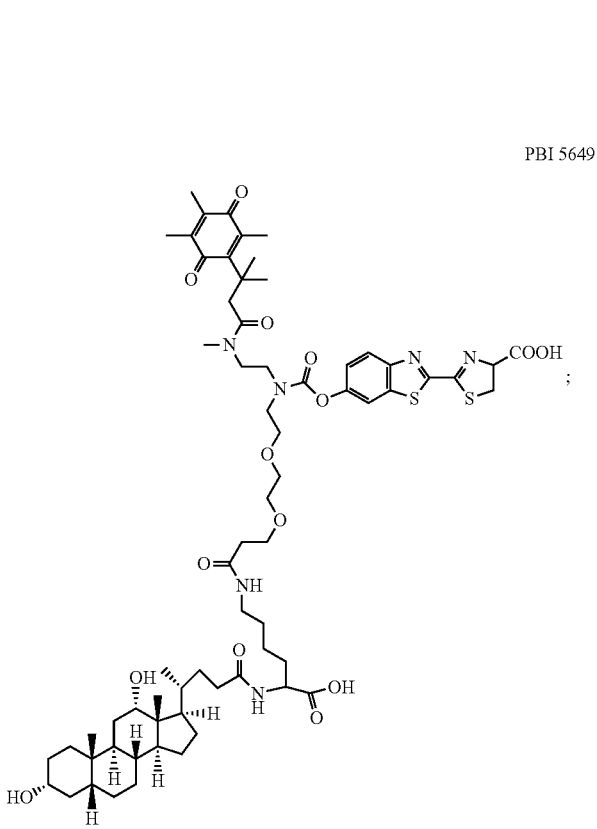
PBI 5649

-continued
PBI 5659
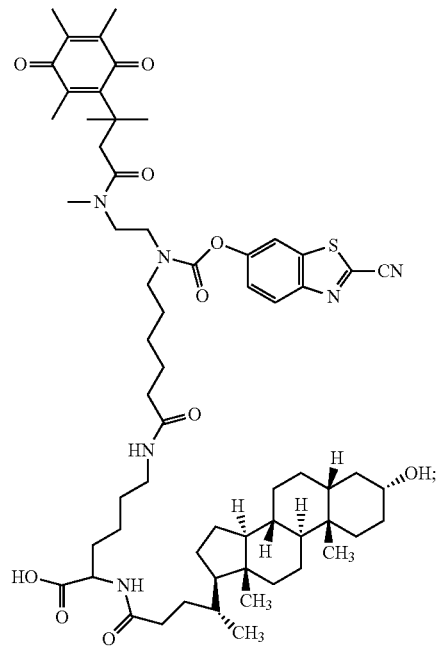
PBI 5663
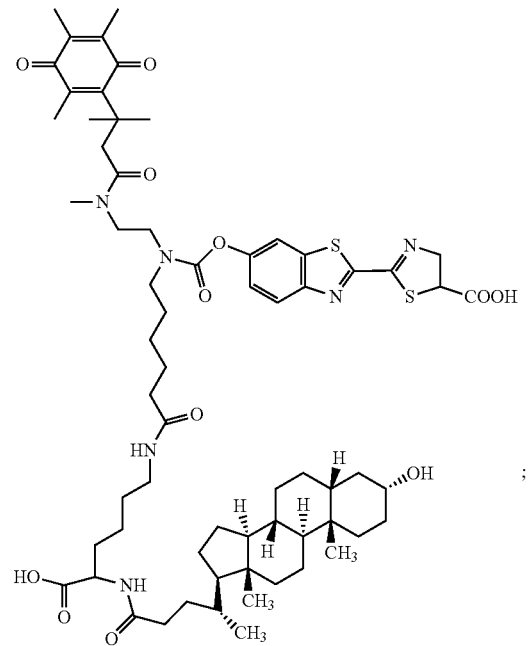
;
PBI 5652
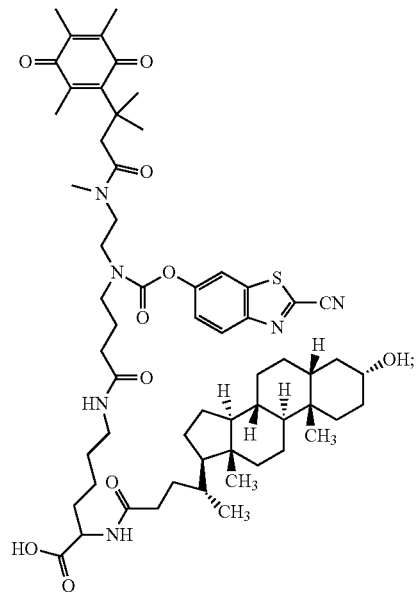
PBI 5669
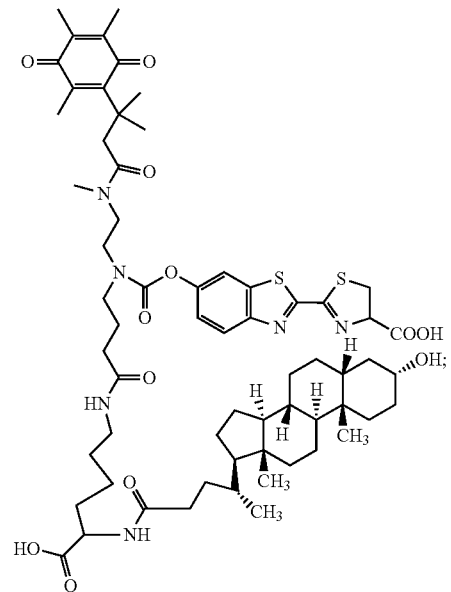

251
-continued
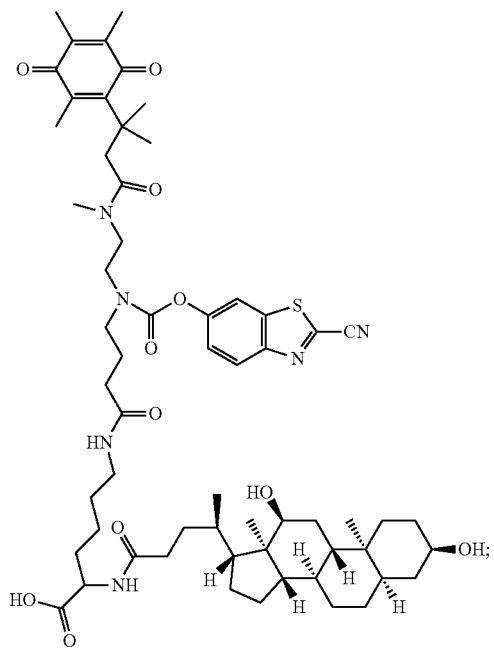
PBI 5653
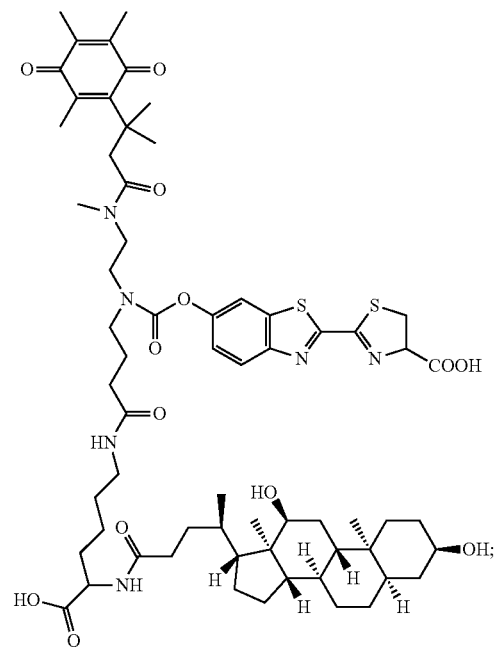
PBI 5656
252
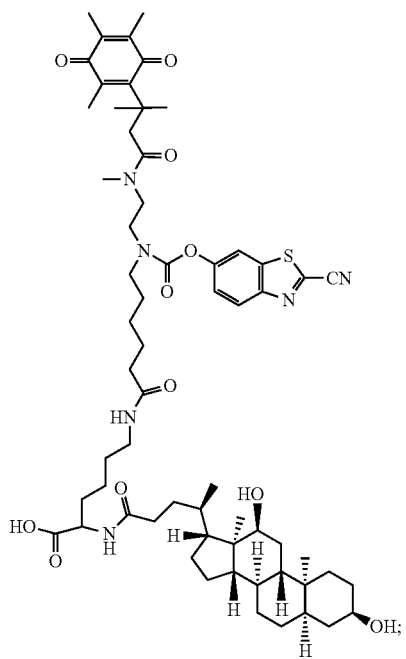
PBI 5660
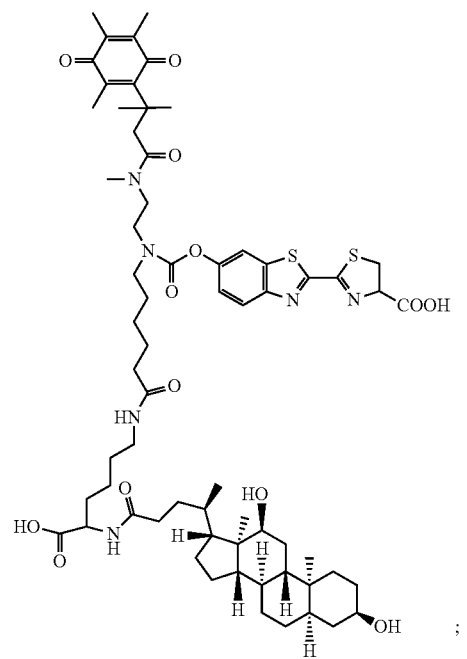
PBI 5664

253
254
-continued
PBI 5667
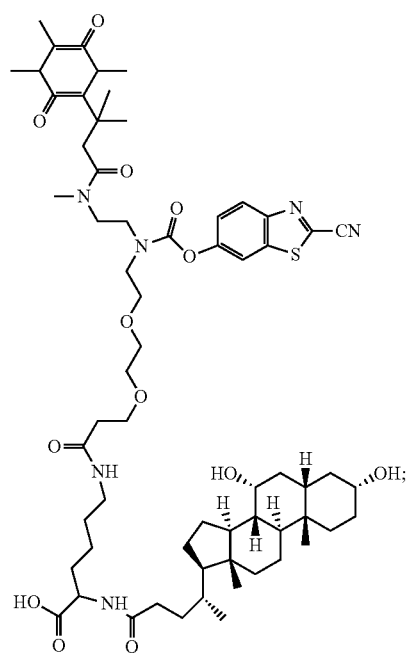
PBI 5650
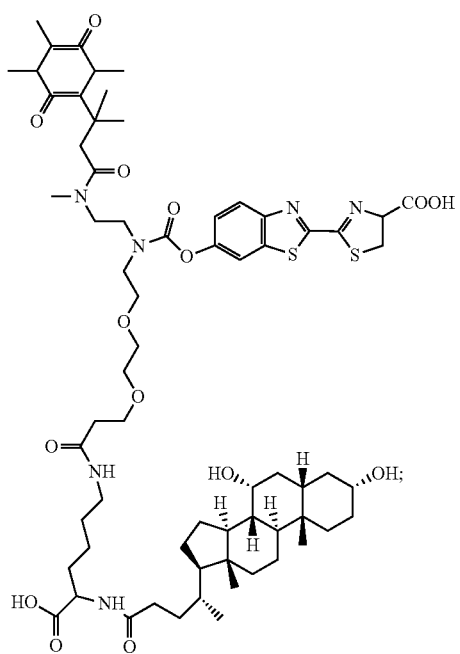
PBI 5654
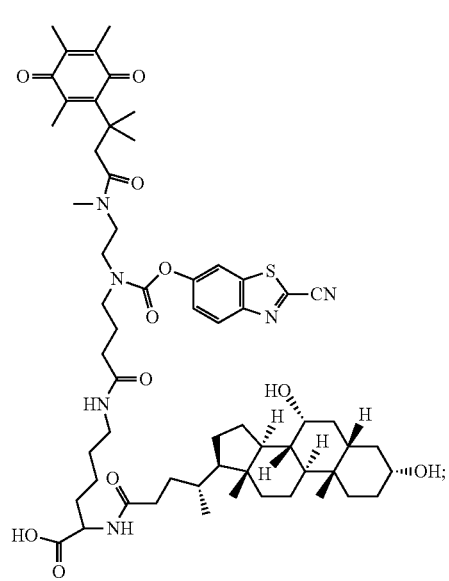
PBI 5655
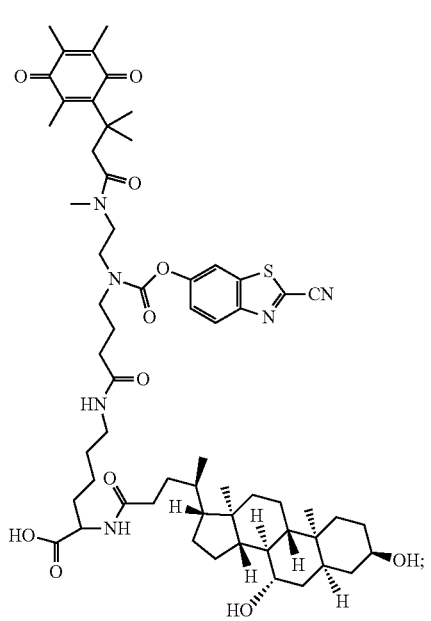

-continued
PBI 5661
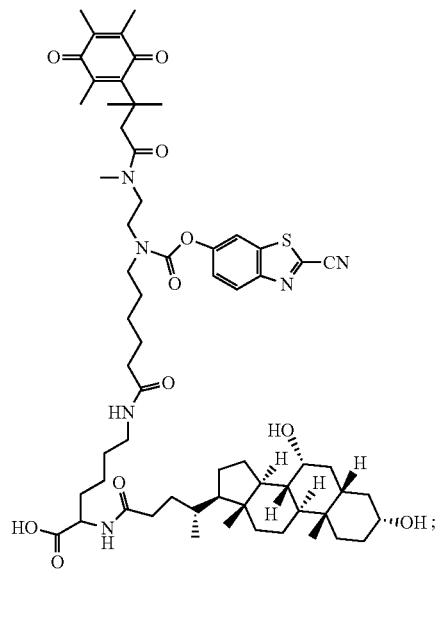
PBI 5662
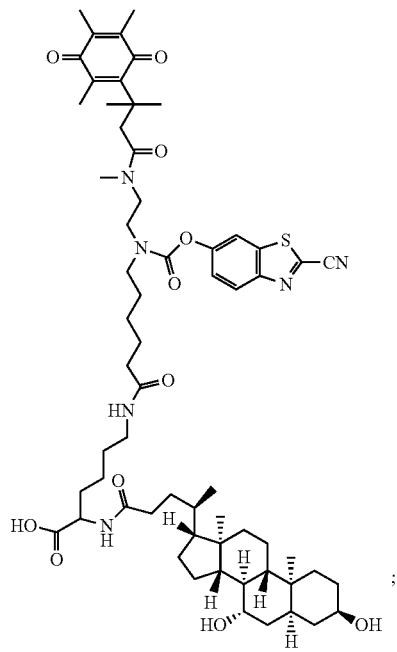
PBI 5824
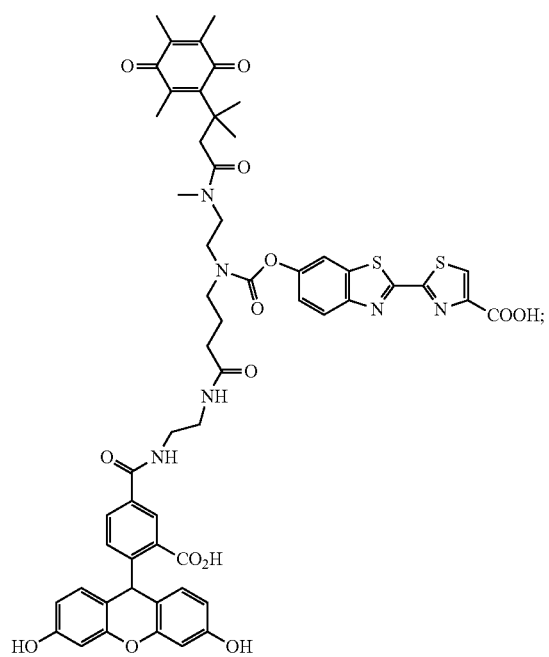
PBI 5830
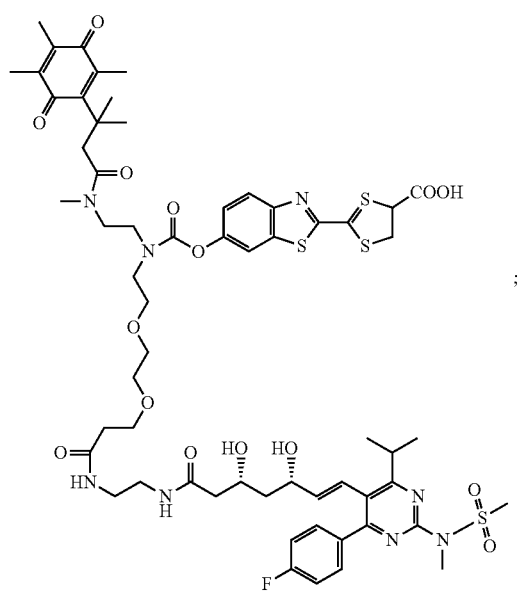

PBI 5831
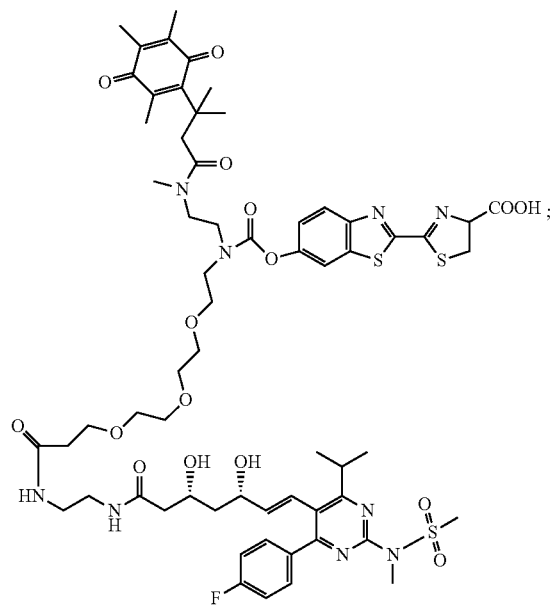
PBI 5827
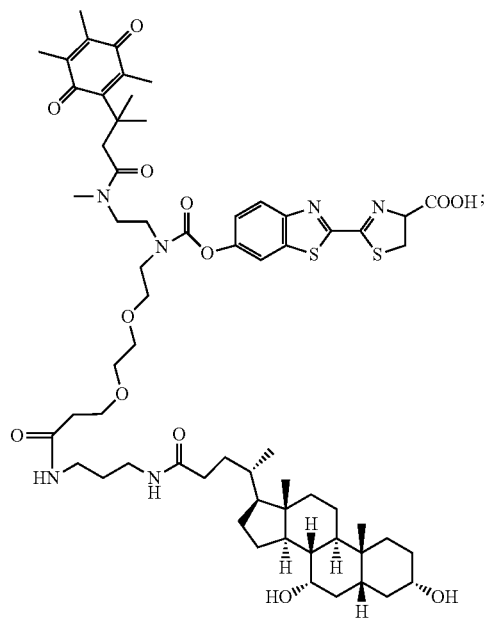
PBI 5828
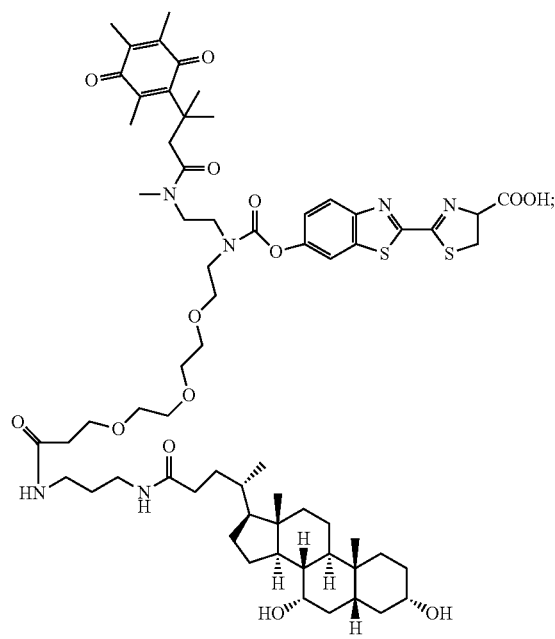

-continued
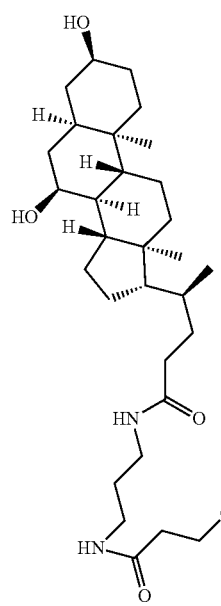
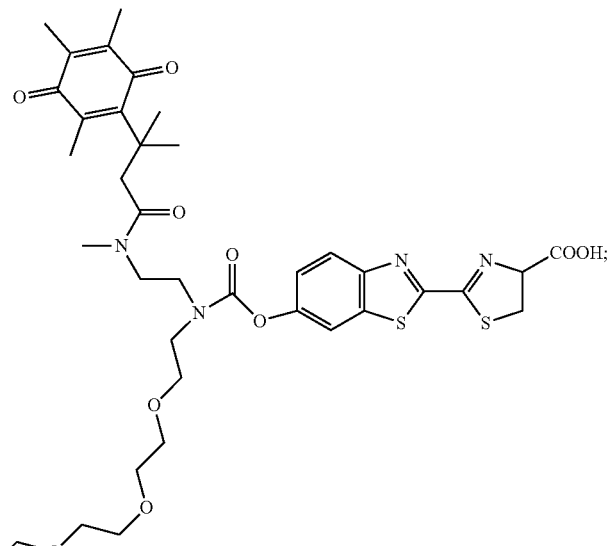
PBI 5829
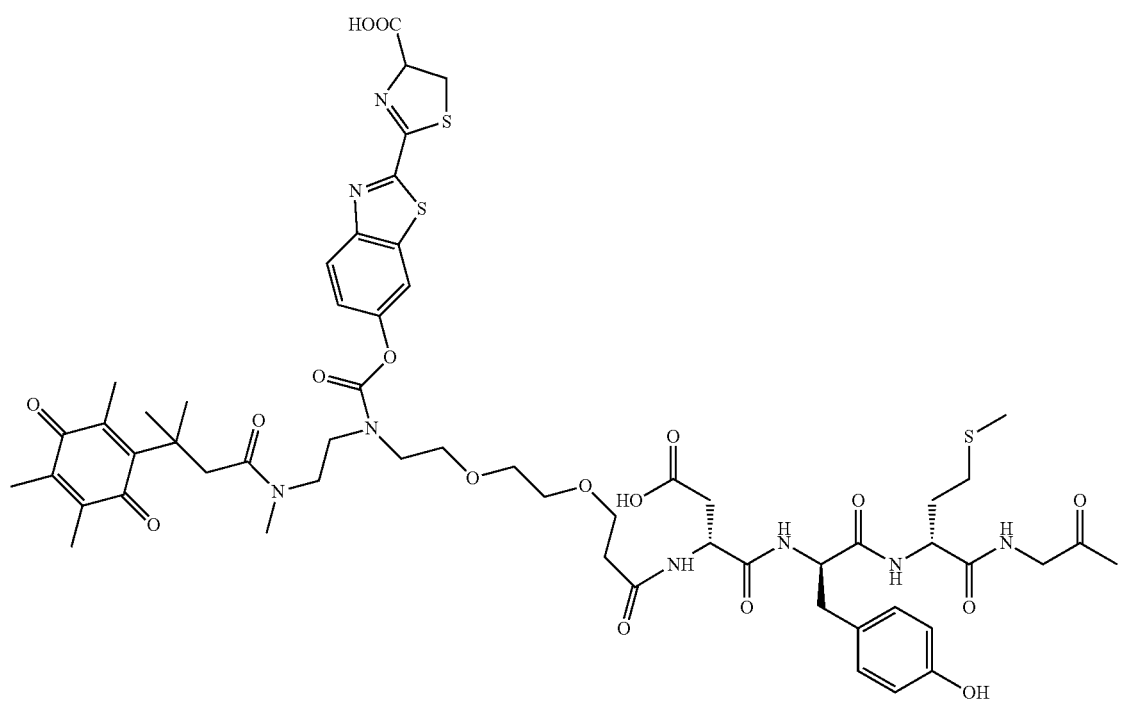
PBI 5832
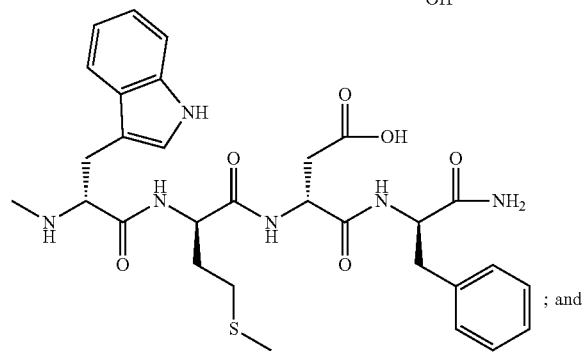
; and

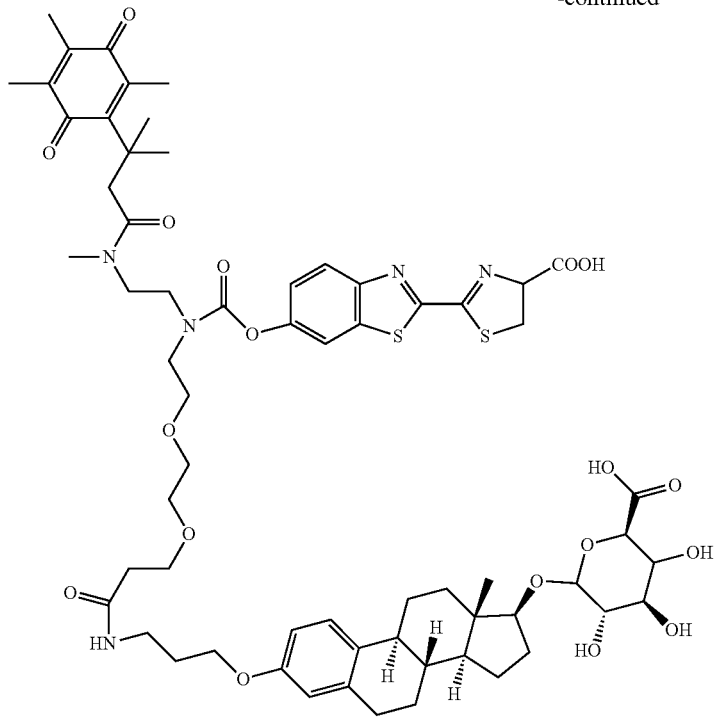

or a salt thereof.

11. The compound of claim 1, wherein the reporter moiety comprises a bioluminescent reporter moiety or fluorescent reporter moiety.

12. The compound of claim 11, wherein the bioluminescent reporter moiety comprises a substrate for a luciferase.

13. The compound of claim 11, wherein the fluorescent reporter moiety comprises a fluorophore.

14. A method for evaluating cellular uptake of an agent, the method comprising:
   a) contacting a sample with a labeled agent, wherein the labeled agent comprises a compound of claim 1, wherein the sample comprises a cell; and
   b) detecting light emission,
   whereby the detection of light emission indicates cellular uptake of the agent.

15. The method of claim 14, wherein the cellular uptake of the agent results in the reduction of the compound and the generation of a released reporter moiety.

16. The method of claim 15, wherein the reporter moiety comprises a fluorescent reporter moiety.

17. The method of claim 16, wherein detecting light emission comprises exposing the sample to a wavelength of light and detecting fluorescence level in the sample, wherein an increase in fluorescence or a change in fluorescence wavelength as compared to the fluorescence or fluorescence wavelength of a control sample indicates cellular uptake of the agent.

18. The method of claim 15, wherein the reporter moiety comprises a bioluminescent reporter moiety.

19. The method of claim 18, wherein the bioluminescent reporter moiety comprises a substrate for a luciferase.

20. The method of claim 19, further comprising contacting the sample with a luciferase and wherein detecting light emission comprises detecting the luminescence produced by the luciferase utilizing the released reporter moiety.

21. The method of claim 14, wherein the cell is a eukaryotic cell or a prokaryotic cell.

22. A labeled agent comprising a compound according to claim 1 conjugated to an agent.

23. The labeled agent of claim 22, wherein the agent is selected from the group consisting of a nucleoside, a nucleotide, a polynucleotide, a polypeptide, a polypeptide-based toxin, an amino acid, a lipid, a carbohydrate, an enzyme substrate, and combinations thereof.

24. The labeled agent of claim 22, wherein the agent is selected from the group consisting of a peptide, an antibody, a lipoprotein, a sugar, a fatty acid, and a detergent.

25. The labeled agent of claim 22, wherein the agent is selected from the group consisting of a therapeutic drug, a small molecule, and a nanoparticle, and combinations thereof.

26. A kit comprising the compound of claim 1, an agent, or any combination thereof.

27. The kit of claim 26, further comprising a detection reagent.

28. The kit of claim 27, wherein the detection reagent comprises a luciferase enzyme.

29. A kit comprising a labeled agent according to claim 22 and at least one additional component.

30. The kit of claim 29, wherein the at least one additional component comprises a detection reagent.

31. The kit of claim 30, wherein the detection reagent comprises a luciferase enzyme.

* * * * *